(12) United States Patent
Ducry et al.

(10) Patent No.: US 10,294,270 B2
(45) Date of Patent: May 21, 2019

(54) BRANCHED LINKER FOR PROTEIN DRUG CONJUGATES

(75) Inventors: Laurent Ducry, Sierre (CH); Bernhard Stump, Brig (CH); Heilam Wong, Guangzhou (CN); Jin She, Guangzhou (CN); Gayle Allway, Brig-Glis (CH)

(73) Assignees: LONZA LTD, Visp (CH); Lonza Guangzhou Nansha Ltd., Guangzhou (CN)

( * ) Notice: Subject to any disclaimer, the term of this patent is extended or adjusted under 35 U.S.C. 154(b) by 0 days.

(21) Appl. No.: 14/001,237

(22) PCT Filed: Feb. 23, 2012

(86) PCT No.: PCT/EP2012/053039
§ 371 (c)(1),
(2), (4) Date: Aug. 23, 2013

(87) PCT Pub. No.: WO2012/113847
PCT Pub. Date: Aug. 30, 2012

(65) Prior Publication Data
US 2013/0324706 A1  Dec. 5, 2013

(30) Foreign Application Priority Data

Feb. 25, 2011  (WO) ............... PCT/CN2011/071287
Aug. 1, 2011   (WO) ............... PCT/CN2011/077863
Nov. 7, 2011   (WO) ............... PCT/CN2011/081857

(51) Int. Cl.
| | |
|---|---|
| *A61K 47/60* | (2017.01) |
| *A61K 47/64* | (2017.01) |
| *A61K 47/65* | (2017.01) |
| *A61K 47/68* | (2017.01) |
| *C07K 5/062* | (2006.01) |

(52) U.S. Cl.
CPC .......... *C07K 5/06043* (2013.01); *A61K 47/60* (2017.08); *A61K 47/64* (2017.08); *A61K 47/65* (2017.08); *A61K 47/6809* (2017.08); *A61K 47/6845* (2017.08)

(58) Field of Classification Search
None
See application file for complete search history.

(56) References Cited

U.S. PATENT DOCUMENTS

| 6,214,345 B1 | 4/2001 | Firestone et al. |
|---|---|---|
| 6,759,509 B1 | 7/2004 | King et al. |
| 6,897,289 B1 | 5/2005 | Obiols et al. |
| 2010/0260786 A1 | 10/2010 | Doronina et al. |

FOREIGN PATENT DOCUMENTS

| EP | 0624377 | 11/1994 |
|---|---|---|
| WO | WO 2007/011968 | 1/2007 |
| WO | WO 2008/053479 | 5/2008 |

OTHER PUBLICATIONS

Claude Mazuel et al. HPLC-MS/MS determination of a peptide conjugate prodrug of doxorubicin, and its active metabolites, leucine-doxorubicin and doxorubicin, in dog and rat plasma, Journal of Pharmaceutical and Biomedical Analysis, 2003, vol. 33, 1093-1102.
PCT/CN2011/071287 Written Opinion and International Search report dated Dec. 1, 2011.
International Search Report for PCT/EP2012/053039; dated Nov. 5, 2012.
Guzmán, et al., "Peptide synthesis: chemical or enzymatic"; *Electronic Journal of Biotechnology*; vol. 10, No. 2, Issue of Apr. 15, 2007.
Okada, Yoshio; "Synthesis of Peptides by Solution Methods"; *Current Organic Chemistry*, 2001, 5, 1-43.
George Tsatsas, et al., "The Synthesis and Evaluation of the Local Anesthetic Activity of a Series of 4-(ω-Alkylaminoacylamino)salicylate Esters", Journal of Medical Chemistry, 1967, p. 235-242.

*Primary Examiner* — Thomas S Heard
(74) *Attorney, Agent, or Firm* — Dority & Manning, P.A.

(57) ABSTRACT

The present invention relates to method for connecting a protein and a drug to a protein drug conjugate, wherein the drug is linked to the protein through a specific branched linker, said branched linker comprises a peptide chain and is derived from o-hydroxy p-amino benzylic alcohol, wherein the peptide chain is connected to the phenyl ring via the p-amino group, the drug is connected to the phenyl ring via the benzylic alcohol moiety, and the protein is connected to the phenyl ring via the o-hydroxy group; further to a process for the preparation of said protein-drug-conjugates via various intermediates, to the pharmaceutical use of such protein drug conjugates, such as methods of controlling the growth of undesirable cells, to pharmaceutical compositions comprising such protein drug conjugates, and to intermediates of the preparation of the protein drug conjugates.

19 Claims, 1 Drawing Sheet
Specification includes a Sequence Listing.

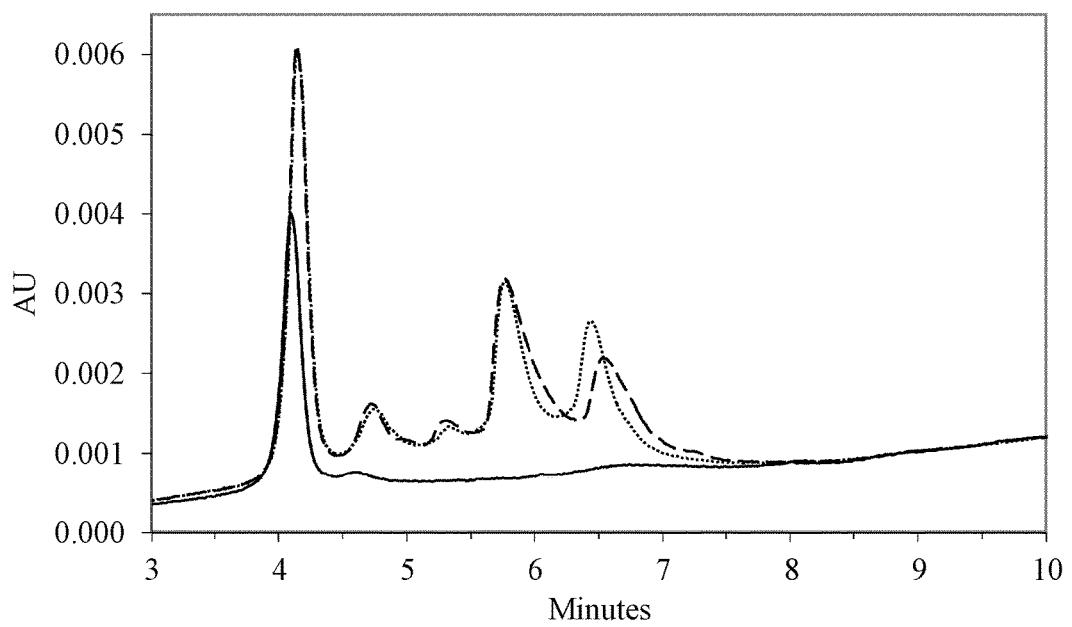

```
                            SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Leu Ala Leu
1
```

BRANCHED LINKER FOR PROTEIN DRUG CONJUGATES

RELATED APPLICATION

This application is the national stage entry of International Patent Application No. PCT/EP2012/053039 having a filing date of Feb. 23, 2012, which claims filing benefit of International Patent Application PCT/CN2011/071287 having a filing date of Feb. 25, 2011; PCT/CN2011/077863 having a filing date of Aug. 1, 2011; PCT/CN20211/081857 having a filing date of Nov. 7, 2011,which are incorporated herein by reference in their entirety.

SEQUENCE LISTING

The instant application contains Sequence Listing which has been submitted electronically in ASCII format and is hereby incorporated by reference in its entirety. Said ASCII copy, created on Jul. 23, 2014, is named LZA-47-PCT-US_SL.txt and is 862 bytes in size.

The present invention relates to method for connecting a protein and a drug to a protein drug conjugate, wherein the drug is linked to the protein through a specific branched linker, said branched linker comprises a peptide chain and is derived from o-hydroxy p-amino benzylic alcohol, wherein the peptide chain is connected to the phenyl ring via the p-amino group, the drug is connected to the phenyl ring via the benzylic alcohol moiety, and the protein is connected to the phenyl ring via the o-hydroxy group;

further to a process for the preparation of said protein-drug-conjugates via various intermediates, to the pharmaceutical use of such protein drug conjugates, such as methods of controlling the growth of undesirable cells, to pharmaceutical compositions comprising such protein drug conjugates, and to intermediates of the preparation of the protein drug conjugates.

Most drugs used for chemotherapy have severe side-effects which limit their efficacy and use. Linking such payloads, i.e. pharmaceutically active compounds, such as drugs, to targeting agents, in particular monoclonal antibodies, affords novel antibody drug conjugates (ADC) for e.g. cancer therapy. Tissue-specificity is typically governed by the monoclonal antibody (mAb) component, while the drug provides the therapeutic effect. The efficiency and tolerability of ADCs is dependent on the interplay between the target antigen, drug potency and conjugation technology. In particular, linker chemistry strongly influences the ADC specificity and safety.

Instead of chemically labile linkers, which have limited stability in physiological extracellular conditions, such as hydrazone- and disulfide-based linkers, linkers, which are stable in physiological extracellular conditions, especially which have high plasma stability, are desired for improving the therapeutic applicability, because the drug should be released only within the cell, which is targeted by the protein, to which the drug is linked, and not outside of the cell.

Non cleavable linkers have disadvantages: ADC internalization followed by complete hydrolysis of the polypeptide backbone of the mAb is required for payload release, and reduced efficacy may be encountered when ADC internalization is poor. Thus, ADCs bearing non-cleavable linkers are highly dependent on the biology of the target cell. Also, not all payloads retain their biological activity when attached to the last amino acid of the mAb as is the case after mAb degradation.

In order to allow the ADC to deliver the payload not only to tumor cells but also to adjacent antigen-negative cells, i.e. bystander effect, the released payload must readily diffuse through hydrophobic cell membranes, which is not the case, when ADCs with non-cleavable linkers release their payloads in form of an amino acid bearing drug with the amino acid being in a zwitterionic state, i.e. having a positively charged ammonium and a negatively charged carboxylate.

Therefore it is desired to have a linker which shows high plasma stability, and which releases the drug without the drug being chemically modified after its release.

Furthermore it is desired to have protein drug conjugates, which show reduced agglomeration or aggregation, which would impair their performance.

EP 624377 A discloses a drug ligand conjugate, wherein the linker comprises a linear peptide.

Fanny Guzman et al, Electronic Journal of Biotechnology, 2007, 10, 279-314; Yoshio Okada, Current Organic Chemistry, 2001, 5, 1-43; U.S. Pat. No. 6,897,289 B and the text books "Houben-Weyl Synthesis of Peptides and Peptidomimetics (Methods in Organic Chemistry)", Murray Goodman et al., Thieme Publishing Group, 2001, in particular Volumes E22a and E22b; disclose protecting groups, peptide bond formation, the synthesis of peptides and proteins detailing general and specific methods, and analytical techniques used to determine the structure and composition of peptides.

Known linkers comprising linear peptide chains still show deficiencies. There was a need for linkers and for protein drug conjugates based on such linkers, which show improved performance. Surprisingly, specific branched linkers derived from o-hydroxy p-amino benzylic alcohol show the desired performance.

In the following text, the following abbreviations are used, if not otherwise stated:
DCC N,N'-dicyclohexylcarbodiimide
EDC N-(3-dimethylaminopropyl)-N'-ethylcarbodiimide
Fmoc 9-fluorenylmethoxycarbonyl
Boc tert-butoxycarbonyl
Boc2O di-tert-butyl dicarbonate
Cit citrulline
NBS N-bromosuccinimide
NHS compound of formula (HOSu), N-hydroxysuccinimide
NIS N-iodosuccinimide
-OTs tosylate
-OMs mesylate
-OTf triflate
PBS phosphate buffered saline
Red-Al sodium bis(2-methoxyethoxy)aluminium hydride
TCEP tris(2-carboxyethyl)phosphine hydrochloride
Tos or Ts Tosyl or p-toluenesulfonyl
TsCl Tosyl chloride or p-toluenesulfonyl chloride
Z or Cbz benzyloxycarbonyl Subject of the invention is a method (MI) for connecting a ligand LI with a drug DR,
LI is selected from the group consisting of amino acids LI-AA, mono- or polyclonal antibodies LI-Ab, antibody fragments LI-AbFrag, proteins LI-Prot and peptides LI-Pep;
DR is a pharmaceutically active drug;
characterized that a linker LIN is used to covalently connect LI with DR;
LIN comprises a connecting group CG2;
CG2 is derived from o-hydroxy p-amino benzylic alcohol and is a connecting group of formula (CG2-1);

(CG2-1)

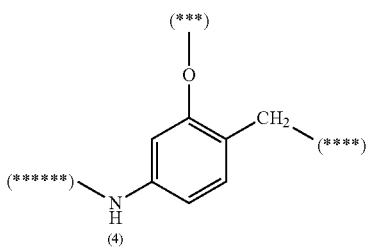

(***) denotes the connecting site which is used to connect LI;

(****) denotes the connecting site which is used to connect DR;

(******) denotes the connecting site to which a linear peptide is connected, said peptide has 2 to 8 amino acid residues;

(4) denotes the p-amino group of the o-hydroxy p-amino benzylic alcohol from which CG2 is derived.

Further subject of the invention is a method (MI), with the method (MI) as defined herein, also with all its preferred embodiments, wherein LI is covalently connected with DR in form of a compound of formula (I);

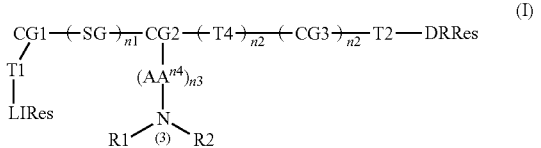

CG2 is as defined herein, also with all its preferred embodiments;

CG1 is a connecting group selected from the group consisting of connecting group of formula (CG1-I), connecting group of formula (CG1-II), connecting group of formula (CG1-III) and connecting group of formula (CG1-IV);

(CG1-I)

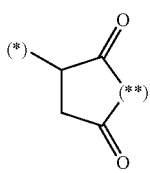

(CG1-II)

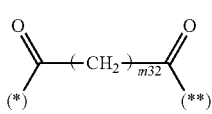

(CG1-III)

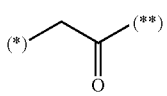

(CG1-IV)

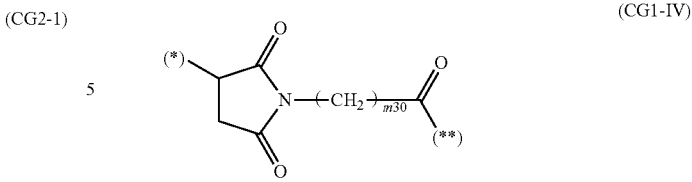

m30 and m32 are identical or different and independently from each other 1, 2, 3, 4, 5, 6, 7, 8, 9 or 10;

(*) in the formulae of CG1 denotes the bond between T1 and CG1, the covalently connected LI forms in compound of formula (I) a ligand residue LIRes, which is covalently connected to CG1 via T1;

LI is as defined herein, also with all its preferred embodiments, and is a compound of formula (LIRes-T1-H);

LIRes-T1-H            (LIRes-H)

LIRes is selected from the group consisting of amino acid residue LIRes-AA, mono- or polyclonal antibody residue LIRes-Ab, antibody fragment residue LIRes-AbFrag, protein residue LIRes-Prot and peptide residue LIRes-Pep;

LI has a functional group selected from the group consisting of SH, OH or $NH_2$, which forms in formula (I) the T1, the T1 is bonded to CG1 via the bond (*);

T1 is —S—, —O— or —NH—;

n1 is 0 or 1;

SG is a spacer group selected from the group consisting of spacer group of formula (SG-II) and spacer group of formula (SG-III);

(SG-II)

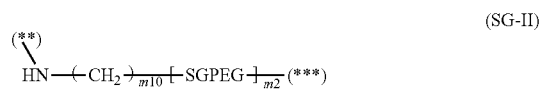

(SG-III)

m1 and m2 are identical or different and independently from each other 0 or 1;

m10, m11 and m12 are identical or different and independently from each other 0, 1, 2, 3, 4, 5, 6, 7, 8, 9 or 10;

with the proviso, that m2 and m10 are not simultaneously 0;

with the proviso, that m1, m11 and m12 are not simultaneously 0;

SGPEG is a connecting group of formula (SGPEG-I);

(SGPEG-I)

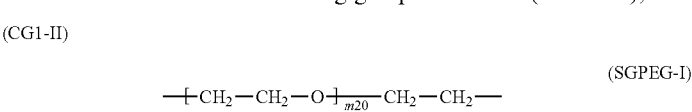

m20 is 1, 2, 3, 4, 5 or 6;

n2 is 0 or 1;

T4 is —O—;

CG3 is selected from the group consisting of connecting group of formula (CG3-I) and connecting group of formula (CG3-II);

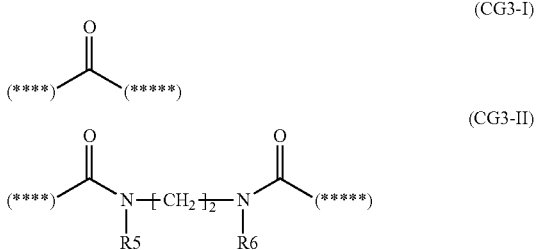

(CG3-I)

(CG3-II)

R5 and R6 are identical or different and independently from each other $C_{1-4}$ alkyl;

for n1 being 1, the () in the formulae of CG1 and in the formulae of SG denote the bond between to CG1 and SG, and the (*) in the formula of SG and in the formula of CG2 denote the bond between SG and CG2; in case that CG1 is a connecting group of formula (CG1-I), the nitrogen atom denoted with (**) in SG forms an endocyclic nitrogen atom, thereby replacing the hydrogen atom of said nitrogen atom by an endocyclic bond;

for n1 being 0, the () in the formulae of CG1 and the (*) in the formula of CG2 denote the bond between CG1 and CG2;

with the proviso, that in case that n1 is 0, then CG1 is not a connecting group of formula (CG1-I);

for n2 being 1, the (**) in the formula of CG2 and in the formula of CG3 denote the bonds, with which CG2 and CG3 are bonded to T4; and the (***) in the formula of CG3 denotes the bond between CG3 and T2;

for n2 being 0, the (****) in the formula of CG2 denotes the bond between CG2 and T2;

the (******) in the formula of CG2 denotes the bond between CG2 and $AA^{n4}$;

the covalently connected DR forms in compound of formula (I) a drug residue DRRes, which is covalently connected to CG2 via T2;

DR is as defined herein, also with all its preferred embodiments, and is a compound of formula (DRRes-T2-H);

H-T2-DRRes  (DRRes-T2-H)

DRRes is a drug residue derived from DR;

DR has a functional group selected from the group consisting of —N(R4)H, —OH or —SH, which forms in formula (I) the T2;

T2 is —N(R4)-, —O— or —S—;

R4 is H or $C_{1-4}$ alkyl;

n3 is 2, 3, 4, 5, 6, 7 or 8;

n4 is an integer from 1 to n3;

$AA^{n4}$ is an amino acid residue, with n4 being the index of said amino acid residue, and $(AA^{n4})_{n3}$ is a linear peptide with n3 amino acid residues $AA^{n4}$ and with n4 denoting the position of the amino acid residue $AA^{n4}$ in the peptide starting from CG2, in which peptide the individual amino acid residues are connected to each other via a peptide bond, with $AA^1$ being the first amino acid residue in the chain and being connected to CG2 via the bond (****), with the bond (****) being an amid bond of the carboxylic acid group of $AA^1$ with the amino group denoted with (4) of CG2, and with $AA^{n3}$ being the last amino acid residue in the chain, and with the individual $AA^{n4}$ being independently from each other identical or different;

(3) denotes the N-terminal amino group of $AA^{n3}$;

R1 and R2 are identical or different and independently from each other selected from the group consisting of hydrogen, $C_{1-4}$ alkyl, $C(O)$—$(CH_2$—$O$—$)_{m5}$-$(GRPEG)_{m4}$-R3 and PGN;

R3 is $C_{1-4}$ alkyl;

m4 is 0 or 1;

m5 is 0 or 1;

PGN is a protecting group;

GRPEG is a connecting group of formula (GRPEG-I);

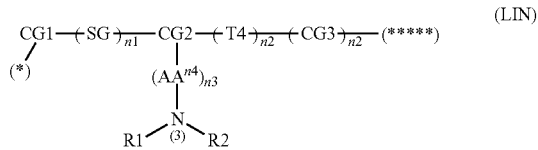

(GRPEG-I)

m21 is 1, 2, 3, 4, 5 or 6;

LI, DR and CG2 are as defined herein, also with all their preferred embodiments.

Preferably, LIN is compound of formula (LIN).

$$CG1-(SG)_{n1}-CG2-(T4)_{n2}-(CG3)_{n2}-(*****)$$
$$(*) \quad (AA^{n4})_{n3}$$
$$R1^{(3)}N_{R2}$$

(LIN)

Preferably, the drug DR is selected from group consisting of cytotoxic agents, other chemotherapeutic and antimetastatic agents.

Preferably, the other chemotherapeutic and antimetastatic agents are selected from the group consisting of tyrosine kinase inhibitors and Rac1 inhibitors.

Preferably, tyrosine kinase inhibitors are selected from the group of active pharmaceutical ingredients (API) consisting of Imatinib, Lapatibim, Sunitimib, Nilotimib and Dasatimib.

Preferably, Rac1 inhibitors is NSC 23766.

Preferable cytotoxic agents are those used for cancer therapy.

Preferable classes of cytotoxic agents include, for example, the enzyme inhibitors such as the anthracycline family of drugs, the bleomycins, the cytotoxic nucleosides, dihydrofolate reductase inhibitors, differentiation inducers, DNA cleavers, DNA intercalators, diynenes, the mitomycins, the podophyllotoxins, the pteridine family of drugs, taxols, thymidylate synthase inhibitors, topoisomerase inhibitors, and the vinca drugs.

Preferable useful members of various classes of cytotoxic agents are selected from the group consisting of N8-acetyl spermidine, actinomycin, 9-amino camptothecin, aminopterin, anguidine, anthracycline, auristatin, bleomycin, calicheamycin, camptothecin (lactone or ring-opened form of the lactone), caminomycin, CC-1065, clofaribine, 1-(2-chloroethyl)-1,2-dimethanesulfonyl hydrazide, cyclopropabenzindol-4-one (CBI), cytarabine, cytosine arabinoside, daunorubicin, dichloromethotrexate, n-(5,5-diacetoxy-pentyl) doxorubicin, 1,8-dihydroxy-bicyclo[7.3.1]trideca-4-9-diene-2,6-diyne-13-one, difluoronucleosides, doxorubicin, duocarmycin, epirubicin, esperamicin, etoposide, 5-fluorouracil, irinotecan, leurosideine, leurosine, maytansine, melphalan, 6-mercaptopurine, methopterin, methotrexate, mitomycin A, mitomycin C, morpholine-doxorubicin, nemorubicin, podophyllotoxin and podophyllotoxin derivatives such as etoposide or etoposide phosphate, retinoic acid, saporin, tallysomycin, vinblastine, vincristine, vindesine, taxane, such as taxol or paclitaxel, taxotere or docetaxel, and taxotere retinoic acid, and analogues and derivatives thereof.

More preferable cytotoxic agents are selected from the group consisting of anthracycline, auristatin, calicheamycin, cyclopropabenzindol-4-one (CBI), doxorubicin, duocarmycin, maytansine, mitomycin C, taxol, and analogues and derivatives of these substances.

Preferably, R4 is H.

Preferably, T1 is —NH— or —S—.

Preferably, n2 is 1 and T2 is —NH—, —O— or —S— and is connected via the bond (*****) with CG3; more preferably, T2 is —NH— or —S—.

Doxorubicin has the CAS number 23214-92-8 and is the compound of formula (DOXO).

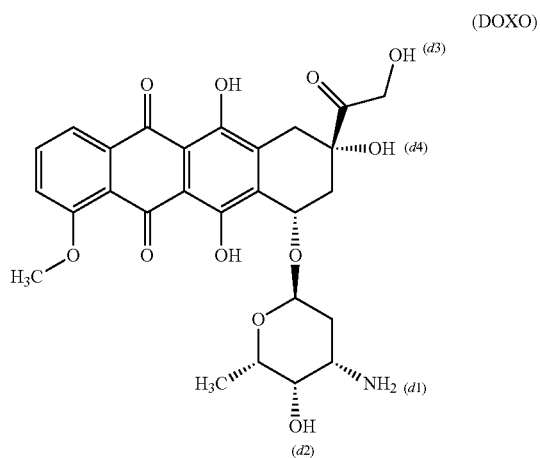 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

(DOXO)

Compound of formula (DOXO) is also used in form of its hydrochloride salt.

Doxorubicin can be connected to CG3 or CG2 respectively via one of its functional groups, e.g. via one of the functional groups denoted with (d1), (d2), (d3) and (d4) in formula (DOXO).

The functional groups denoted with (d1), (d2), (d3) and (d4) function then as the T2 in formula (I).

Preferably doxorubicin is connected via the amino group denoted with (d1) in formula (DOXO) with CG3 via the bond (*****).

Maytansine has the CAS number 35846-53-8 and the formula (MAYT).

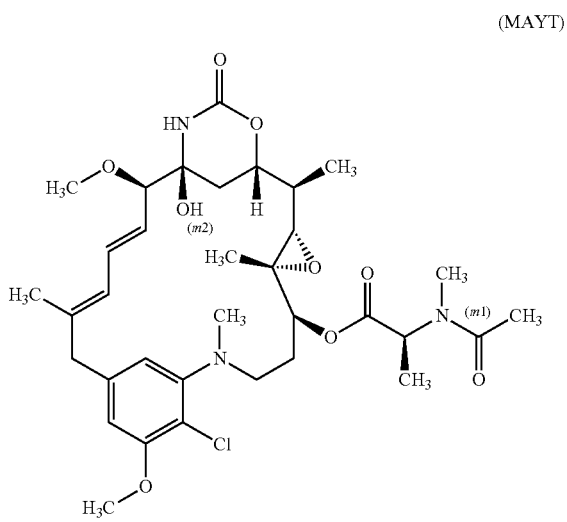 [SMILES: COc1cc2cc(c1Cl)N(C)CC[C@H](OC(=O)[C@H](C)N(C)C(C)=O)[C@]1(C)O[C@H]1[C@H](C)[C@@H]1C[C@@](O)(NC(=O)O1)[C@H](OC)/C=C/C=C(\C)C2]

(MAYT)

Maytansine can be connected to CG3 or CG2 respectively via the —OH denoted with (m2) in formula (MAYT).

Or the —C(O)—CH₃ group denoted with (m1) in the formula (MAYT) is exchanged against an acyl group, said acyl group has a nucleophilic group —SH, —NH₂ or —OH, which again is the connected to CG3 or CG2 respectively.

The —OH denoted with (m2) or said nucleophilic group of the acyl group function then as the T2 in formula (I).

A preferred taxane is taxol with the CAS number 33069-62-4 and the formula (TAXO).

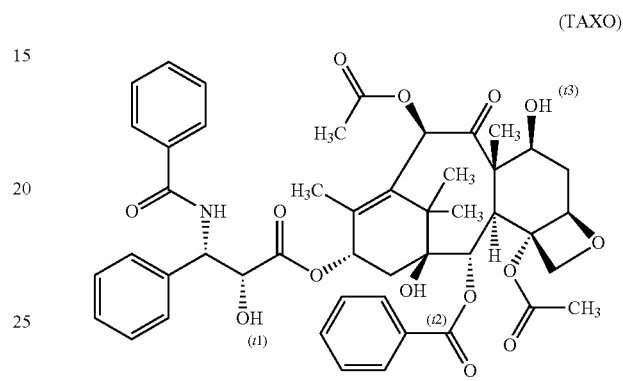

(TAXO)

Taxol can be connected to CG3 or CG2 respectively via one of the —OH denoted with (t1), (t2) and (t3) in formula (TAXO). Said —OH functions then as the T2 in formula (I).

In one preferred embodiment, n2 is 0, T2 is —O— and is connected via the bond (****) with CG2, and DRRes is derived from DR, with DR being compound of formula (TAXO).

In another preferred embodiment, n2 is 1, T2 is —O— and is connected via the bond (*****) with CG3, CG3 is the connecting group of formula (CG3-II) and DRRes is derived from DR, with DR being compound of formula (TAXO), one possible Taxol intermediate for this embodiment is the compound of formula (TAXO-t1-1).

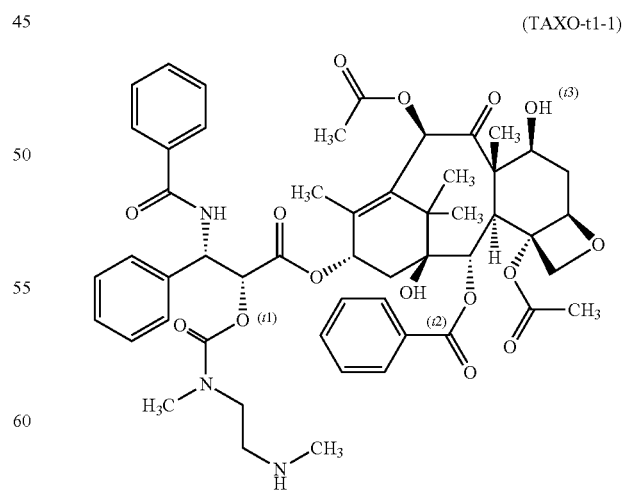

(TAXO-t1-1)

A Camptothecin is (S)-(+)-camptothecin, which has the CAS number 7689-03-4 and is the compound of formula (CAMPTO).

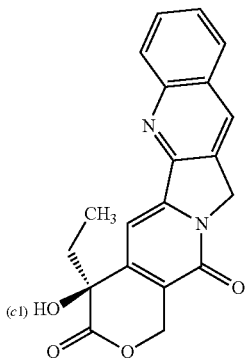

(CAMPTO)

Camptothecin can be connected to CG3 or the CG2 respectively via the functional group denoted with (c1) in formula (CAMPTO).

The functional group denoted with (c1) functions then as the T2 in formula (I).

In one preferred embodiment, n2 is 0, T2 is —O— and is connected via the bond (****) with CG2, and DRRes is derived from DR, with DR being compound of formula (CAMPTO).

In another preferred embodiment, n2 is 1, T2 is —O— and is connected via the bond (*****) with CG3, CG3 is the connecting group of formula (CG3-II) and DRRes is derived from DR, with DR being compound of formula (CAMPTO).

In one preferred embodiment, CG1 is the connecting group of formula (CG1-I), (CG1-III) or (CG1-IV) and the sulphur atom of the side chain of a Cys residue of LIRes is T1 and is connected via the bond (*) to CG1.

In another preferred embodiment, CG1 is the connecting group of formula (CG1-II), and T1 is —N— or —O— of LIRes and is connected to CG1 via the bond (*). This amino or hydroxyl group of LIRes connected to CG1 is preferably the N-terminal amino group of LIRes or an amino or hydroxy group of a side chain of an amino acid residue of LIRes. Preferably, in case T1 is an amino group of a side chain of an amino acid residue of LIRes connected to CG1, said amino acid residue of LIRes is preferably a Lys; in case T1 is an hydroxyl group of a side chain of an amino acid residue of LIRes connected to CG1, said amino acid residue of LIRes is preferably a Tyr, Ser or Thr.

Preferably, LI is selected from the group consisting of mono- or polyclonal antibodies LI-Ab, antibody fragments LI-AbFrag, proteins LI-Prot and peptides LI-Pep; and LIRes is selected from the group consisting of mono- or polyclonal antibody residue LIRes-Ab, antibody fragment residue LIRes-AbFrag, protein residue LIRes-Prot and peptide residue LIRes-Pep.

In the case that LIRes is LIRes-AA, LIRes is preferably an alpha amino acid residue.

LIRes can be preferably connected to CG1 via one of two possible functional groups of LIRes: via a N-terminal amino group or via a functional group of a side chain of LIRes, if LIRes has such a side chain with a functional group. This functional group, which connects LIRes with CG1, is the T1. In case that LIRes is connected via a functional group of a side chain of LIRes, said side chain is preferably a side chain of a Cys, Lys, Tyr, Ser or Thr residue of LIRes.

In case of LIRes being LIRes-AA, the remaining functional groups of LIAARes-AA, which are not connected to CG1, can be protected by a protecting group commonly used in peptide chemistry, e.g. a non-connected amino group can carry a acetate, a non-connected carboxy group can be esterified with a $C_{1-4}$ alkohol, a non-connected functional group of a side chain can carry a side chain protecting group conventionally used in peptide chemistry.

More preferably, LIRes-AA is an alpha amino acid residue with a side chain having a functional group and is connected via this functional group with CG1, even more preferably LIRes-AA is derived from Cys, Lys, Tyr, Ser or Thr.

Preferably, in the case, that LIRes is connected via the side chain of a Cys residue of LIRes, T1 is formed by the sulfur atom of the side chain of said Cys residue and is connected through the bond (*) with CG1, preferably with CG1 being the connecting group of formula (CG1-I), (CG1-III) or (CG1-IV); or in the case, that LIRes is connected via the side chain of a Lys, Tyr, Ser or Thr residue of LIRes, T1 is formed by the nitrogen or oxygen atom of the side chain of said Lys, Tyr, Ser or Thr residue and is connected through the bond (*) with CG1, preferably with CG1 being the connecting group of formula (CG1-II).

LIRes-Pep can be derived from a cell-penetrating peptide.

LIRes-AB and LIRes-ABFrag are preferably derived from antibodies and antibody fragments used in treatment of diseases, preferably in cancer treatment.

Preferably, m30 and m32 are identical or different and independently from each other 2, 3, 4, 5 or 6.

Preferably, m30 is 2 when CG1 is a connecting group of formula (CG1-IV).

Preferably, m32 is 2 when CG1 is a connecting group of formula (CG1-II).

Preferably, n1 is 1.

Preferably, m1 and m2 are 0 or 1.

Preferably, m10, m11 and m12 are identical or different and independently from each other 0, 1, 2, 3, 4, 5 or 6.

Preferably, m20 is 1, 2, 3 or 4.

More preferably,
m10 is 6 and m2 is 0; or
m2 is 1, m10 is 0 and m20 is 1; or
m1 is 1, m11 is 1, m12 is 1 and m20 is 3; or
m1 is 0, m11 is 3, m12 is 0.

Preferably, R5 and R6 are $CH_3$.

In a particular embodiment, CG1 is a connecting group of formula (CG1-I), SG is a spacer group of formula (SG-II), m10 is 6 and m2 is 0.

In another particular embodiment, CG1 is a connecting group of formula (CG1-II) with m32 being 2 or a connecting group of formula (CG1-III), or a connecting group of formula (CG1-IV) with m30 being 2, and SG is a spacer group of formula (SG-II), m10 is 0, m2 is 1 and m20 is 1.

In another particular embodiment, CG1 is a connecting group of formula (CG1-II) with m32 being 2 or a connecting group of formula (CG1-III), or a connecting group of formula (CG1-IV) with m30 being 2, and SG is a spacer group of formula (SG-III) with m1 being 1, m11 being 1, m12 being 1 and m20 being 3, or SG is a spacer group of formula (SG-III) with m1 being 0, m11 being 3 and m12 being 0.

Preferably, n3 is 2, 3, 4, 5 or 6; more preferably 2, 3 or 4; even more preferably, n3 is 2 or 3.

Preferably, $AA^{n4}$ is an alpha amino acid residue.

More preferably, $AA^{n4}$ is selected from the group consisting of alanine, valine, leucine, isoleucine, methionine, phenylalanine, tryptophan, proline, lysine, lysine side chain protected with acetyl or formyl, arginine, arginine side chain protected, preferably protected with tosyl or nitro groups, histidine, ornithine, ornithine side chain protected, preferably protected with acetyl or formyl, and citrulline.

Even more preferably, $AA^{n4}$ is alanine, glycine, phenylalanine, valine, lysine, leucine, tryptophan, arginine, side-chain protected arginine or citrulline, especially alanine, glycine, phenylalanine, valine, lysine or citrulline.

In case that $AA^{n4}$ has a side chain with a functional group, this functional group can be protected by a protecting group commonly used for protecting functional groups of side chains of amino acids.

In case of Lys, the side chain is preferably protected with acetyl or formyl

Examples of peptides for the $(AA^{n4})_{n3}$ peptide chain are Phe-Lys, Val-Lys, Phe-Phe-Lys, D-Phe-Phe-Lys, Gly-Phe-Lys, Ala-Lys, Val-Cit, Phe-Cit, Leu-Cit, Trp-Cit, Phe-Ala, Gly-Phe-Leu-Gly (SEQ ID: 1), Ala-Leu-Ala-Leu(SEQ ID: 2), Phe-N9-tosyl-Arg and Phe-N9-Nitro-Arg, preferably Phe-Lys, Val-Lys, Val-Cit and D-Phe-L-Phe-Lys; any Lys side chain being optionally protected, preferably with acetyl.

Especially preferably, n3 is 2 or 3, and $AA^{n4}$ is alanine, glycine, valine or citrulline; more especially,
n3 is 2 and $AA^1$ is citrulline and $AA^2$ is valine or alanine; or
n3 is 3 and $AA^1$ is citrulline, $AA^2$ is valine and $AA^3$ is glycine.

Preferably, m4 is 1.
Preferably, R3 is methyl.
Preferably, R1 and R2 are identical or different and independently from each other selected from the group consisting of hydrogen, methyl, $C(O)-(CH_2-O-)_{m5}$-$(GRPEG)_{m4}$-$CH_3$ and PGN.

Preferably, m21 is 2, 3 or 4.
Preferably, PGN is a protecting group commonly used in peptide chemistry for protecting the N-terminus of a peptide or for protecting the alpha amino group of an alpha amino acid used as building block in peptide synthesis.

More preferably, PGN is selected from group consisting of Boc, Fmoc and Z.

Even more preferably, R1 is hydrogen, methyl, acetyl or $C(O)-(CH_2-O-)_{m5}$-$(GRPEG)_{m4}$-$CH_3$ with m4 being 1 and m21 being 3, and R2 is hydrogen or methyl.

Especially,
R1 is acetyl and R2 is hydrogen; or
R1 and R2 are methyl; or
R1 is $C(O)-(CH_2-O-)_{m5}$-$(GRPEG)_{m4}$-$CH_3$ with m5 being 0, m4 being 1 and m21 being 3, and R2 is hydrogen; or
R1 is $C(O)-(CH_2-O-)_{m5}$-$(GRPEG)_{m4}$-$CH_3$ with m5 being 1, m4 being 1 and m21 being 2, and R2 is hydrogen.

Further subject of the invention is a method (MI);
wherein compound of formula (I) is prepared in a step (MI); step (MI) comprises a reaction (MI), wherein a compound of formula (II) is reacted with a compound of formula (LIRes-T1-H);

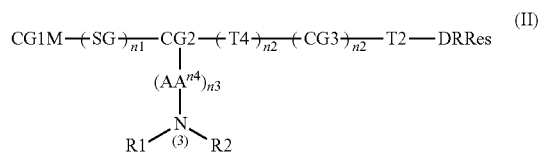

(II)

CG1M is a connecting group selected from the group consisting of connecting group of formula (CG1M-I), connecting group of formula (CG1M-II), connecting group of formula (CG1M-III) and connecting group of formula (CG1M-IV);

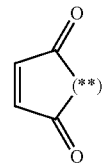
(CG1M-I)

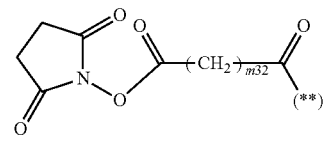
(CG1M-II)

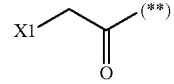
(CG1M-III)

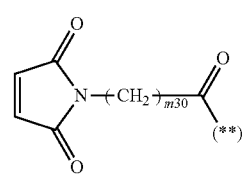
(CG1M-IV)

X1 is Cl, Br or I;
SG, n1, n4, n3, $AA^{n4}$, (3), R1, R2, T4, CG3, n2, T2, DRRes, m30 and m32 are as defined herein, also with all their preferred embodiments;
CG2 is as defined herein, also with all its preferred embodiments.

Preferably, X1 is Cl or Br, more preferably X1 is Br.
Preferably, CG1M is a connecting group of formula (CG1M-IV).
More preferably, CG1M is a connecting group of formula (CG1M-IV) and m30 is 2.

In a particular embodiment, CG1M is a connecting group of formula (CG1M-I), SG is a spacer group of formula (SG-II), m10 is 6 and m2 is 0.

In another particular embodiment, CG1M is a connecting group of formula (CG1M-II) with m32 being 2 or a connecting group of formula (CG1M-III) or a connecting group of formula (CG1M-IV) with m30 being 2, and SG is a spacer group of formula (SG-II), m10 is 0, m2 is 1 and m20 is 1.

In another particular embodiment, CG1M is a connecting group of formula (CG1-II) with m32 being 2 or a connecting group of formula (CG1-III), or a connecting group of formula (CG1M-IV) with m30 being 2, and SG is a spacer group of formula (SG-III) with m1 being 1, m11 being 1, m12 being 1 and m20 being 3, or SG is a spacer group of formula (SG-III) with m1 being 0, m11 being 3 and m12 being 0.

Preferably, the reaction temperature of reaction (MI) is from 0 to 150° C., more preferably from 5 to 50° C., even more preferably from 10 to 40° C.

Preferably, the reaction time of reaction (MI) is from 1 min to 168 h, more preferably from 10 min to 24 h, even more preferably from 15 min to 3 h.

Reaction (MI) is usually done in a solvent (MI).
Preferably, solvent (MI) is selected from the group consisting of water, N,N-dimethylacetamide, N,N-dimethylformamide, N,N-dimethylsulfoxide and mixtures thereof.

In case of water, the water can comprise a buffer (MI), preferably the buffer (MI) is a buffer conventionally used in protein chemistry, more preferably buffer (MI) is derived from a buffering substance selected from the group consisting of acetic acid, citric acid, dithiothreitol (DTT), ethylenediaminetetraacetic acid (EDTA), glycine, histidine, phosphoric acid (incl. phosphate buffered saline, PBS), polysorbate 20, polysorbate 80, saccharose, sodium chloride, succinic acid, trehalose, tris-(hydroxymethyl)-aminomethane, mixtures thereof and salts thereof.

The salts of said buffering substance are preferably sodium salt, potassium salts or HCl salts.

Preferably, the amount of solvent (MI) is from 5 to 10000 fold, more preferably from 10 to 5000 fold, even more preferably from 50 to 500 fold, of the weight of compound of (LIRes-T1-H).

Preferably, in reaction (MI), from 1 to 100 mol equivalents, more preferably from 2 to 20 mol equivalents, even more preferably from 3 to 10 mol equivalents, of compound of formula (II) are used, the mol equivalents being based the mol of compound of formula (LIRes-T1-H).

Reaction (MI) can be done in the presence of TCEP.

TCEP is preferably used, when LI is a mono- or polyclonal antibodies LI-Ab or an antibody fragments LI-Ab-Frag.

Preferably, in reaction (MI), from 0.5 to 20 mol equivalents, more preferably from 1 to 10 mol equivalents, even more preferably from 1.5 to 5 mol equivalents, of TCEP are used, the mol equivalents being based the mol of compound of formula (LIRes-T1-H)

After the reaction (MI), compound of formula (I) can be isolated by standard methods such as washing, extraction, filtration, concentration and drying. The compound of formula (I) can be purified before or after isolation, preferably by chromatography or crystallization from an appropriate solvent.

Alternatively, compound of formula (I) can be purified by standard methods such as filtration, ultrafiltration, diafiltration and chromatography, and can be stored or further used as a solution.

Further subject of the invention is a method (MII) for the preparation of compound of formula (II), with the compound of formula (II) as defined herein, also with all its preferred embodiments,
wherein
in case that n2 is 1 and CG3 is a connecting group of formula (CG3-I), then method (MII) comprises a step (MIIa) and a step (MIIb);
in case that n2 is 1 and CG3 is a connecting group of formula (CG3-II), then method (MII) comprises the step (MIIa), a step (MIIc), a step (MIId) and a step (MIIe);
in case that n2 is 0 and CG1M is a connecting group of formula (CG1M-IV) then method (MII) comprises one step, a step (MII0-IV), or two steps, a step (MII0-I-IVa) and a step (MII0-I-IVb);
in case that n2 is 0 and CG1M is a connecting group of formula (CG1M-III) then method (MII) comprises a step (MII0-III);
in case that n2 is 0 and CG1M is a connecting group of formula (CG1M-II) then method (MII) comprises two steps, a step (MII0-IIa) and a step (MII0-IIb), or one step, a step (MII0-IIc);
in case that n2 is 0 and CG1M is a connecting group of formula (CG1M-I) then method (MII) comprises one step, a step (MII0-I), or two steps, a step (MII0-I-IVa) and a step (MII0-I-IVb);

step (MIIa) comprises a reaction (MIIa), wherein a compound of formula (III) is reacted with a compound (II-I);

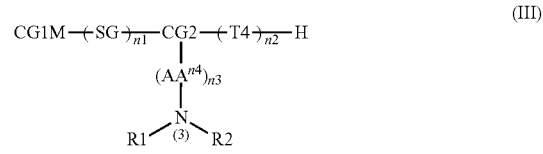
(III)

n2 in formula (III) is as defined herein, also with all its preferred embodiment;
compound (II-I) is selected from the group consisting of compound of formula (II-1), 1,1'-carbonyldiimidazole, 4-nitrophenylchloroformate, phosgene, diphosgene, triphosgene and mixtures thereof;

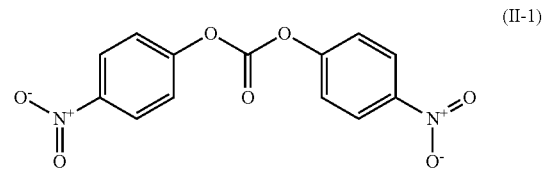 [SMILES: O=C(Oc1ccc([N+](=O)[O-])cc1)Oc1ccc([N+](=O)[O-])cc1]
(II-1)

step (MIIb) comprises a reaction (MIIb), wherein the reaction product from the reaction (MIIa) is reacted with a compound of formula (DRRes-T2-H);
step (MIIc) comprises a reaction (MIIc), wherein the reaction product from the reaction (MIIa) is reacted with a compound of formula (CG3M-II) to provide a compound of formula (IIc);

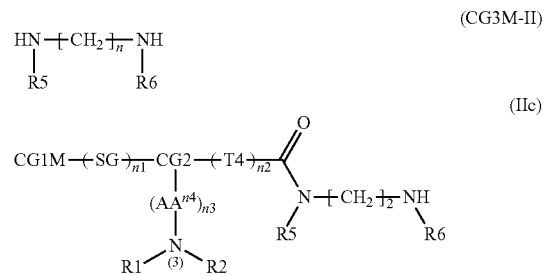
(CG3M-II)

(IIc)

n2 in formula (IIc) is as defined in claim 2;
step (MIId) comprises a reaction (MIId), wherein compound of formula (IIc), prepared in reaction (MIIc), is reacted with the compound (II-I);
step (MIIe) comprises a reaction (MIIe), wherein the reaction product from the reaction (MIId) is reacted with a compound of formula (DRRes-T2-H);
step (MII0-I-IVa) comprises a reaction (MII0-I-IVa), wherein a compound of formula (III) is reacted with a compound (II0-I-IVa) to provide a compound of formula (III0-I-IVa);

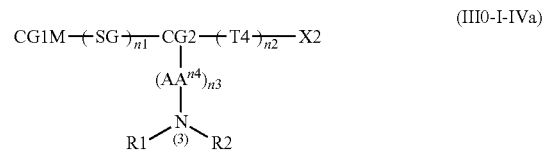
(III0-I-IVa)

n2 is 0 in formula (III0-I-IVa);

compound (II0-I-IVa) is selected from the group consisting of p-toluenesulfonyl chloride, p-toluenesulfonic anhydride, methanesulfonyl chloride, methanesulfonic anhydride, trifluoromethanesulfonyl chloride and trifluoromethanesulfonic anhydride and mixtures thereof;

X2 is selected from the group consisting of —OTs, —OMs and -OTf;

step (MII0-I-IVb) comprises a reaction (MII0-I-IVb), wherein compound of formula (III0-I-IVa), prepared in reaction (MII0-I-IVa), is reacted with compound of formula (DRRes-T2-H);

compound of formula (III) is prepared in a step (MIII-IV) for the case that CG1M is a connecting group of formula (CG1M-IV); or in a step (MIII-III) for the case that CG1M is a connecting group of formula (CG1M-III); or in two steps, a step (MIII-IIa) and a step (MIII-IIb), or in one step, a step (MIII-IIc), for the case that CG1M is a connecting group of formula (CG1M-II); or a step (MIII-I) for the case that CG1M is a connecting group of formula (CG1M-I);

step (MIII-IV) comprises a reaction (MIII-IV) of a compound of formula (IV),

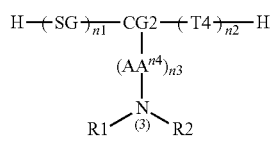
(IV)

n2 in formula (IV) is as defined herein, also with all its preferred embodiments;

with a compound of formula (CG1MR-IV);

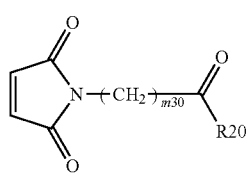
(CG1MR-IV)

m30 is as defined herein, also with all its preferred embodiments;

R20 is a residue of formula (R20-1);

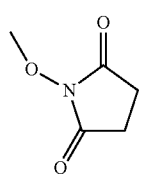
(R20-1)

step (MIII-III) comprises a reaction (MIII-III) of a compound of formula (IV) with a compound of formula (CG1MR-III);

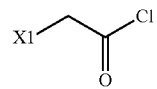
(CG1MR-III)

with X1 as defined herein, also with all its preferred embodiments;

step (MIII-IIa) comprises a reaction (MIII-IIa) of the compound of formula (IV) with a compound of formula (CG1MR-IIa) to provide a compound of formula (IV-IIa);

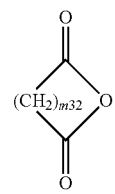
(CG1MR-IIa)

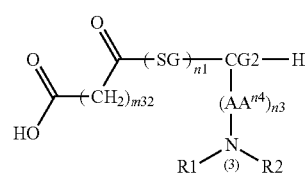
(IV-IIa)

with m32 as defined herein, also with all its preferred embodiments;

step (MIII-IIb) comprises a reaction (MIII-IIb) of compound of formula (IV-IIa) prepared in step (MIII-IIa) with a compound of formula (HOSu);

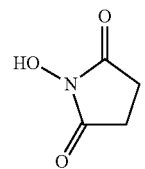
(HOSu)

step (MIII-IIc) comprises a reaction (MIII-IIc) of the compound of formula (IV) with a compound of formula (CG1MR-IIc);

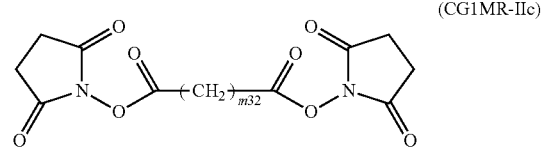 [SMILES: O=C(CC(=O)ON1C(=O)CCC1=O)ON1C(=O)CCC1=O]
(CG1MR-IIc)

with m32 as defined herein, also with all its preferred embodiments;

step (MIII-I) comprises a reaction (MIII-I) of a compound of formula (IV) with a compound of formula (MA);

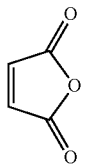

(MA)

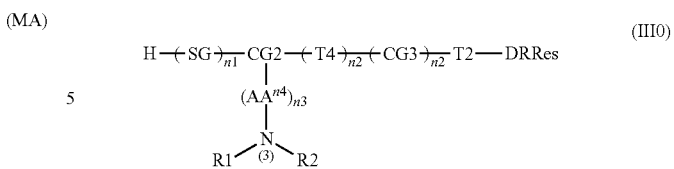

(III0)

with

SG, CG2, n1, AA, n4, n3, (3), R1, R2, T2 and DRRes as defined herein, also with all their preferred embodiments, and n2 is 0 in formula (III0);

step (MII0-III) comprises a reaction (MII0-III) of a compound of formula (III0) with a compound of formula (CG1MR-III);

step (MII0-IIa) comprises a reaction (MII0-IIa) of the compound of formula (III0) with a compound of formula (CG1MR-IIa) to provide a compound of formula (III0-IIa);

compound of formula (IV) is prepared in a step (MIV);

step (MIV) comprises a reaction (MIV), reaction (MIV) is a reduction of a compound of formula (V) with a compound (IV);

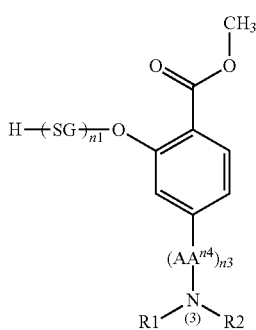

(V)

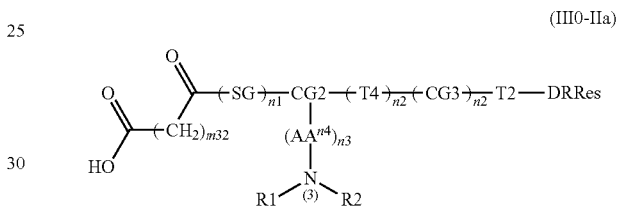

(III0-IIa)

with

SG, CG2, n1, AA, n4, n3, (3), R1, R2, T2 and DRRes and m32 as defined herein, also with all their preferred embodiments, and n2 is 0 in formula (III0-IIa);

step (MII0-IIb) comprises a reaction (MII0-IIb) of compound of formula (III0-IIa) prepared in step (MII0-IIa) with a compound of formula (HOSu);

step (MII0-IIc) comprises a reaction (MII0-IIc) of the compound of formula (III0) with a compound of formula (CG1MR-IIc);

step (MII0-I) comprises a reaction (MII0-I) of a compound of formula (III0) with a compound of formula (MA);

compound of formula (III0) is prepared in a step (MIII0), step (MIII0) comprises a reaction (MIII0), wherein R30 is cleaved off from compound of formula (IV0) with HCl;

compound (IV) is selected from the group consisting of NaBH$_4$, BH$_3$, DIBAL-H, sodium bis(2-methoxyethoxy) aluminium hydride and mixtures thereof;

SG, n1, AA, n4, n3, (3), R1 and R2 have the same definition as above, also with all their preferred embodiments;

compound of formula (V) is prepared in a step (MVb);

step (MVb) comprises a reaction (MVb), wherein R30 is cleaved off from compound of formula (Va) with HCl;

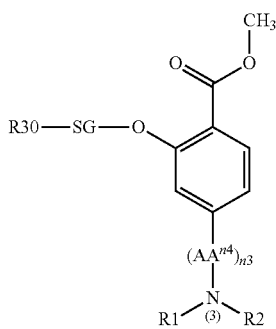

(Va)

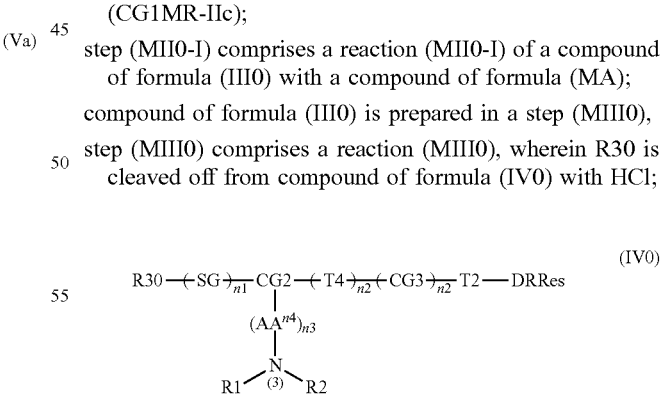

(IV0)

n2 is 0 in formula (IV0);

compound of formula (IV0) is prepared in a step (MIV0a) and a step (MIV0b), step (MIV0a) comprises a reaction (MIV0a), wherein a compound of formula (V0) is reacted with a compound (RIV0a) to provide a compound of formula (IV0a);

R30 is connected to SG via the bond denoted with (**) in the formulae of SG and is Boc;

step (MII0-IV) comprises a reaction (MII0-IV) of a compound of formula (III0) with a compound of formula (CG1MR-IV);

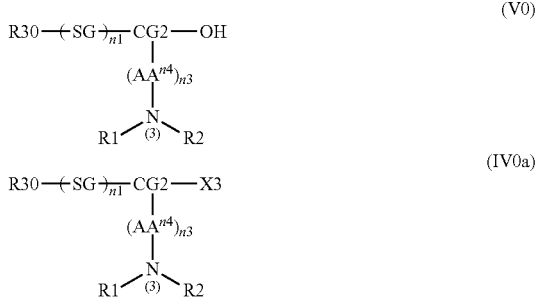

with
R30, SG, CG2, n1, AA, n4, n3, (3), R1 and R2 as defined herein, also with all their preferred embodiments;
compound (RIV0a) is selected from the group consisting of p-toluenesulfonyl chloride, p-toluenesulfonic anhydride, methanesulfonyl chloride, methanesulfonic anhydride, trifluoromethanesulfonyl chloride and trifluoromethanesulfonic anhydride, $SOCl_2$, $(COCl)_2$, $POCl_3$, $PCl_3$, $PCl_5$, $POBr_3$, $PBr_3$, $PBr_5$, N-bromosuccinimide, N-iodosuccinimide, HCl, HBr, HI and mixtures thereof;
X3 is selected from the group consisting of —OTs, —OMs, —OTf, —Cl, —Br and —I;
step (MIV0b) comprises a reaction (MIV0b), wherein compound of formula (IV0a), prepared in reaction (MIV0), is reacted with compound of formula (DRRes-T2-H);
compound of formula (V0) is prepared in a step (MV0),
step (MV0) comprises a reaction (MV0), reaction (MV0) is a reduction of a compound of formula (Va) with a compound (IV);
CG1M and X1 are as defined herein, also with all its preferred embodiments;
SG, n1, n4, n3, $AA^{n4}$, (3), R1, R2, T4, CG3, n2, T2, DRRes, compound of formula (DRRes-T2-H), m30, m32, R5 and R6 are as defined herein, also with all its preferred embodiments; CG2 is as defined herein, also with all its preferred embodiments.

The compounds (II-I) and of formula (CG3M-II) are known compounds and can be prepared according to known methods, often they are even commercially available.

Reaction (MIIa) and reaction (MIId) are similar reactions and can be done under similar reaction parameters ranges as defined herein, with the individual reaction parameters for each of said two reactions being selected independently from each other.

Preferably, compound (II-I) is compound of formula (II-1).

Reaction (MIIa) and reaction (MIId) are usually done in a solvent (MIIa).

Preferably, solvent (MIIa) is selected from the group consisting of N,N-dimethylformamide, N,N-dimethylacetamide, N,N-dimethylsulfoxide, acetonitrile, acetone, 1,4-dioxane, THF and mixtures thereof.

Preferably, the amount of solvent (MIIa) is from 1 to 500 fold, more preferably from 5 to 50 fold, even more preferably from 10 to 30 fold, of the weight of compound of formula (III).

Preferably, in the reaction (MIIa) and in the reaction (MIId), from 0.5 to 20 mol equivalents, more preferably from 1 to 10 mol equivalents, even more preferably from 1 to 2 mol equivalents, of compound (II-I) are used, the mol equivalents being based the mol of compound of formula (III).

Reaction (MIIa) and reaction (MIId) can be done in the presence of a base (MIIa).

Preferably, the base (MIIa) is selected from the group consisting of $K_2CO_3$, $Na_2CO_3$, diisopropylethylamine, triethylamine, pyridine, 4-dimethylaminopyridine and mixtures thereof.

Preferably, in the reaction (MIIa) and in the reaction (MIId), from 0.5 to 50 mol equivalents, more preferably from 1 to 20 mol equivalents, even more preferably from 2 to 10 mol equivalents, of base (MIIa) are used, the mol equivalents being based the mol of compound of formula (III).

Preferably, the reaction (MIIa) and the reaction (MIId) are done under inert atmosphere.

After the reaction (MIIa) and the reaction (MIId), the reaction product of reaction (MIIa) and of reaction (MIId) can be isolated by standard methods such as washing, extraction, filtration, concentration and drying. Any of the compounds can be purified before or after isolation, preferably by chromatography or crystallization from an appropriate solvent.

The crude reaction mixture from reaction (MIIa) and from reaction (MIId) can also be directly used in reaction (MIIb) or reaction (MIIe).

More preferably, reaction (MIIa) and reaction (MIIb) as well as reaction (MIId) and reaction (MIIe) are done consecutively in the same solvent and in one pot.

Reaction (MIIb) and reaction (MIIe) are similar reactions and can be done under similar reaction parameters ranges as defined herein, with the individual reaction parameters for each of said two reactions being selected independently from each other.

Reaction (MIIb) and reaction (MIIe) are usually done in a solvent (MIIb).

Preferably, solvent (MIIb) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIIb) is from 1 to 500 fold, more preferably from 5 to 50 fold, even more preferably from 10 to 30 fold, of the weight of the reaction product of reaction (MIIa) or of reaction product of reaction (MIId) respectively.

Preferably, in reaction (MIIb) and in reaction (MIIe), from 0.2 to 10 mol equivalents, more preferably from 0.5 to 5 mol equivalents, even more preferably from 0.8 to 2 mol equivalents, of compound of formula (DRRes-T2-H) are used, the mol equivalents being based the mol of the reaction product of reaction (MIIa) or of the reaction product of reaction (MIId) respectively.

Preferably, reaction (MIIb) and reaction (MIIe) are done under inert atmosphere.

Reaction (MII0-I-IVb) and reaction (MIV0b) are similar reactions and can be done under similar reaction parameters ranges as defined herein, with the individual reaction parameters for each of said two reactions being selected independently from each other.

Reaction (MII0-I-IVb) and reaction (MIV0b) are usually done in a solvent (MIV0b).

Preferably, solvent (MIV0b) is selected from the group consisting of N,N-dimethylformamide, N,N-dimethylacetamide, N,N-dimethylsulfoxide, acetonitrile, acetone, 1,4-dioxane, THF and mixtures thereof.

Preferably, the amount of solvent (MIV0b) is from 1 to 500 fold, more preferably from 5 to 50 fold, even more preferably from 10 to 30 fold, of the weight of compound of formula (III0-I-IVb) or of formula (IV0a) respectively.

Preferably, in reaction (MII0-I-IVb) and in reaction (MIV0b), from 0.2 to 10 mol equivalents, more preferably from 0.5 to 5 mol equivalents, even more preferably from 0.8 to 2 mol equivalents, of compound of formula (DRRes-T2-H) are used, the mol equivalents being based the mol of compound of formula (III0-I-IVb) or of formula (IV0a) respectively.

Preferably, reaction (MII0-I-IVb) and reaction (MIV0b) are done under inert atmosphere.

Reaction (MIIc) is usually done in a solvent (MIIc).

Preferably, solvent (MIIc) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIIc) is from 1 to 500 fold, more preferably from 5 to 50 fold, even more preferably from 10 to 30 fold, of the weight of reaction product of reaction (MIIa).

Preferably, in the reaction (MIIc) from 0.2 to 20 mol equivalents, more preferably from 0.5 to 10 mol equivalents, even more preferably from 0.8 to 5 mol equivalents, of compound of formula (CG3M-II) are used, the mol equivalents being based the mol of the reaction product of reaction (MIIa).

Preferably, the reaction (MIIc) is done under inert atmosphere.

After the reaction (MIIc), the reaction product of the reaction (MIIc) can be isolated by standard methods such as washing, extraction, filtration, concentration and drying. Any of the compounds can be purified before or after isolation, preferably by chromatography or crystallization from an appropriate solvent.

After reaction (MIIb), reaction (MIIe), reaction (MII0-I-IVb) and reaction (MIV0b), compound of formula (II) or compound of formula (IV0) respectively can be isolated by standard methods such as washing, extraction, filtration, concentration and drying. Any of the compounds can be purified before or after isolation, preferably by chromatography or crystallization from an appropriate solvent.

Preferably, CG1M is a connecting group of formula (CG1M-IV);

more preferably, CG1M is a connecting group of formula (CG1M-IV) and m30 is 2.

Compound of formula (V) and compound of formula (III0) can be used in unprotonated form or in protonated form as a salt in reaction (MIV), reaction (MII0-I), reaction (MII0-IIa), reaction (MII0-III) and reaction (MII0-IV)

Reaction (MIII-IV) and reaction (MII0-IV) are similar reactions and can be done under similar reaction parameters ranges as defined herein, with the individual reaction parameters for each of said two reactions being selected independently from each other.

Reaction (MIII-IV) and reaction (MII0-IV) are usually done in a solvent (MIII-IV).

Preferably, solvent (MIII-IV) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIII-IV) is from 1 to 500 fold, more preferably from 5 to 50 fold, even more preferably from 10 to 30 fold, of the weight of compound of formula (IV).

Preferably, in the reaction (MIII-IV) and in the reaction (MII0-IV), from 1 to 20 mol equivalents, more preferably from 1 to 10 mol equivalents, even more preferably from 1 to 5 mol equivalents, of compound (CG1MR-IV) are used, the mol equivalents being based the mol of compound of formula (IV) or of formula (III0) respectively.

Preferably, reaction (MIII-IV) and reaction (MII0-IV) are done under inert atmosphere.

Reaction (MIII-IV) and reaction (MII0-IV) is usually done in the presence of a base (MIII-IV).

Preferably, the base (MIII-IV) is selected from the group consisting of $K_2CO_3$, $Na_2CO_3$, diisopropylethylamine, triethylamine, pyridine, 4-dimethylaminopyridine and mixtures thereof.

Preferably, in the reaction (MIII-IV) and in reaction (MII0-IV), from 0.5 to 50 mol equivalents, more preferably from 1 to 20 mol equivalents, even more preferably from 2 to 10 mol equivalents, of base (MIII-IV) are used, the mol equivalents being based the mol of compound of formula (IV) or of formula (III0) respectively.

After reaction (MIII-IV) and reaction (MII0-IV), the compound of formula (III) or of formula (II) respectively can be isolated by standard methods such as washing, extraction, filtration, concentration and drying. The compound of formula (III) or of formula (II) respectively can be purified before or after isolation, preferably by chromatography or crystallization from an appropriate solvent.

Reaction (MIII-III) and reaction (MII0-III) are similar reactions and can be done under similar reaction parameters ranges as defined herein, with the individual reaction parameters for each of said two reactions being selected independently from each other.

Reaction (MIII-III) and reaction (MII0-III) are usually done in a solvent (MIII-III).

Preferably, solvent (MIII-III) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIII-III) is from 1 to 500 fold, more preferably from 5 to 50 fold, even more preferably from 10 to 30 fold, of the weight of compound of formula (IV).

Preferably, in reaction (MIII-III) and in reaction (MII0-III), from 1 to 20 mol equivalents, more preferably from 1 to 10 mol equivalents, even more preferably from 1 to 5 mol equivalents, of compound (CG1MR-III) are used, the mol equivalents being based the mol of compound of formula (IV) or of formula (III0) respectively.

Preferably, reaction (MIII-III) and reaction (MII0-III) are done under inert atmosphere.

After reaction (MIII-III) and reaction (MII0-III), the compound of formula (III) or of formula (II) respectively can be isolated by standard methods such as washing, extraction, filtration, concentration and drying. The compound of formula (III) or of formula (II) respectively can be purified before or after isolation, preferably by chromatography or crystallization from an appropriate solvent.

Reaction (MIII-IIa) and reaction (MII0-IIa) are similar reactions and can be done under similar reaction parameters ranges as defined herein, with the individual reaction parameters for each of said two reactions being selected independently from each other.

Reaction (MIII-IIa) and reaction (MII0-IIa) are usually done in a solvent (MIII-IIa).

Preferably, solvent (MIII-IIa) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIII-IIa) is from 1 to 500 fold, more preferably from 5 to 50 fold, even more preferably from 10 to 30 fold, of the weight of compound of formula (IV).

Preferably, in reaction (MIII-IIa) and in reaction (MII0-IIa), from 1 to 20 mol equivalents, more preferably from 1 to 10 mol equivalents, even more preferably from 1 to 5 mol equivalents, of compound (CG1MR-IIa) are used, the mol equivalents being based the mol of compound of formula (IV) or of formula (III0).

Preferably, reaction (MIII-IIa) and reaction (MII0-IIa) done under inert atmosphere.

After reaction (MIII-IIa) and reaction (MII0-IIa), the compound of formula (IV-IIa) or of formula (III0-IIa) respectively can be isolated by standard methods such as washing, extraction, filtration, concentration and drying. The compound of formula (IV-IIa) or of formula (III0-IIa) respectively can be purified before or after isolation, preferably by chromatography or crystallization from an appropriate solvent.

Reaction (MIII-IIb) and reaction (MII0-IIb) are similar reactions and can be done under similar reaction parameters ranges as defined herein, with the individual reaction parameters for each of said two reactions being selected independently from each other.

Preferably, reaction (MIII-IIb) and reaction (MII0-IIb) are done in the presence of a compound (COUPADD).

Compound (COUPADD) is a coupling additive conventionally used in peptide chemistry for the coupling reaction of amino acid to peptides by amide bond formation. Preferably, compound (COUPADD) is selected from the group consisting of DCC, EDC and mixtures thereof.

Preferably, in reaction (MIII-IIb) and in reaction (MII0-IIb), from 1 to 20 mol equivalents, more preferably from 1 to 10 mol equivalents, even more preferably from 1 to 5 mol equivalents, of compound (COUPADD) are used, the mol equivalents being based the mol of compound of formula (IV-IIa) or of formula (III0-IIa) respectively.

Reaction (MIII-IIb) and reaction (MII0-IIb) are usually done in a solvent (MIII-IIb).

Preferably, solvent (MIII-IIb) is selected from the group consisting of N,N-dimethylformamide, N,N-dimethylacetamide, N,N-dimethylsulfoxide, acetonitrile, acetone, 1,4-dioxane, THF and mixtures thereof.

Preferably, the amount of solvent (MIII-IIb) is from 1 to 500 fold, more preferably from 5 to 50 fold, even more preferably from 10 to 30 fold, of the weight of compound of formula (IV-IIa).

Preferably, in reaction (MIII-IIb) and in reaction (MII0-IIb), from 1 to 20 mol equivalents, more preferably from 1 to 10 mol equivalents, even more preferably from 1 to 5 mol equivalents, of compound of formula (HOSu) are used, the mol equivalents being based the mol of compound of formula (IV-IIa) or of formula (III0-IIa) respectively.

Preferably, reaction (MIII-IIb) and reaction (MII0-IIb) are done under inert atmosphere.

After reaction (MIII-IIb) and reaction (MII0-IIb), the compound of formula (III) or of formula (II) respectively can be isolated by standard methods such as washing, extraction, filtration, concentration and drying. The compound of formula (III) or of formula (II) respectively can be purified before or after isolation, preferably by chromatography or crystallization from an appropriate solvent.

Reaction (MIII-IIc) and reaction (MII0-IIc) are similar reactions and can be done under similar reaction parameters ranges as defined herein, with the individual reaction parameters for each of said two reactions being selected independently from each other.

Reaction (MIII-IIc) and reaction (MII0-IIc) are usually done in a solvent (MIII-IIc).

Preferably, solvent (MIII-IIc) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIII-IIc) is from 1 to 500 fold, more preferably from 5 to 50 fold, even more preferably from 10 to 30 fold, of the weight of compound of formula (IV).

Preferably, in reaction (MIII-IIc) and in reaction (MII0-IIc), from 1 to 20 mol equivalents, more preferably from 1 to 10 mol equivalents, even more preferably from 1 to 5 mol equivalents, of compound (CG1MR-IIa) are used, the mol equivalents being based the mol of compound of formula (IV) or of formula (III0) respectively.

Preferably, reaction (MIII-IIc) and reaction (MII0-IIc) are done under inert atmosphere.

Reaction (MIII-IIc) and reaction (MII0-IIc) are usually done in the presence of a base (MIII-IIc).

Preferably, the base (MIII-IIc) is selected from the group consisting of $K_2CO_3$, $Na_2CO_3$, diisopropylethylamine, triethylamine, pyridine, 4-dimethylaminopyridine and mixtures thereof.

Preferably, in the reaction (MIII-IIc) and reaction (MII0-IIc), from 0.5 to 50 mol equivalents, more preferably from 1 to 20 mol equivalents, even more preferably from 2 to 10 mol equivalents, of base (MIII-IIc) are used, the mol equivalents being based the mol of compound of formula (IV) or of formula (III0) respectively.

After reaction (MIII-IIc) and reaction (MII0-IIc), the compound of formula (III) or of formula (II) respectively can be isolated by standard methods such as washing, extraction, filtration, concentration and drying. The compound of formula (III) or of formula (II) respectively can be purified before or after isolation, preferably by chromatography or crystallization from an appropriate solvent.

Reaction (MIII-I) and reaction (MII0-I) are similar reactions and can be done under similar reaction parameters ranges as defined herein, with the individual reaction parameters for each of said two reactions being selected independently from each other.

Preferably, the reaction time of reaction (MIII-I) and of reaction (MII0-I) is from 1 min to 168 h, more preferably from 2 to 144 h, even more preferably from 12 to 120 h.

Reaction (MIII-I) and reaction (MII0-I) are usually done in a solvent (MIII-I).

Preferably, solvent (MIII-I) is selected from the group consisting of N,N-dimethylformamide, N,N-dimethylacetamide, N,N-dimethylsulfoxide, acetonitrile, acetone, 1,4-dioxane, THF and mixtures thereof.

Preferably, the amount of solvent (MIII-I) is from 1 to 500 fold, more preferably from 5 to 50 fold, even more preferably from 10 to 30 fold, of the weight of compound of formula (IV) or of formula (III0) respectively.

Preferably, in reaction (MIII-I) and in reaction (MII0-I), from 1 to 20 mol equivalents, more preferably from 1 to 10 mol equivalents, even more preferably from 1 to 5 mol equivalents, of compound of formula (MA) are used, the mol equivalents being based the mol of compound of formula (IV) or of formula (III0) respectively.

Preferably, reaction (MIII-I) and reaction (MII0-I) are done under inert atmosphere.

Preferably, reaction (MIII-I) and reaction (MII0-I) are done in the presence of compound (COUPADD).

Preferably, in reaction (MIII-I) and reaction (MII0-I), from 1 to 20 mol equivalents, more preferably from 1 to 10 mol equivalents, even more preferably from 1 to 5 mol equivalents, of compound (COUPADD) are used, the mol equivalents being based the mol of compound of formula (IV) or of formula (III0) respectively.

Preferably, reaction (MIII-I) and reaction (MII0-I) are done in the presence of compound of formula (HOSu).

Preferably, reaction (MIII-I) and reaction (MII0-I) are done in the presence of compound (COUPADD) and compound of formula (HOSu).

Preferably, in reaction (MIII-I) and reaction (MII0-I), from 1 to 20 mol equivalents, more preferably from 1 to 10 mol equivalents, even more preferably from 1 to 5 mol equivalents, of compound of formula (HOSu) are used, the mol equivalents being based the mol of compound of formula (IV) or of formula (III0) respectively.

After reaction (MIII-I) and reaction (MII0-I), the compound of formula (III) or of formula (II) respectively can be isolated by standard methods such as washing, extraction, filtration, concentration and drying. The compound of formula (III) or of formula (II) respectively can be purified before or after isolation, preferably by chromatography or crystallization from an appropriate solvent.

Reaction (MIV) and reaction (MV0) are similar reactions and can be done under similar reaction parameters ranges as defined herein, with the individual reaction parameters for each of said two reactions being selected independently from each other.

Preferably, the reaction time of reaction (MIV) and of reaction (MV0) is from 1 min to 168 h, more preferably from 1 to 120 h, even more preferably from 6 to 48 h.

Reaction (MIV) and reaction (MV0) are usually done in a solvent (MIV).

Preferably, solvent (MIV) is selected from the group consisting of water, methanol, ethanol, N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIV) is from 1 to 500 fold, more preferably from 5 to 50 fold, even more preferably from 10 to 30 fold, of the weight of compound of formula (V) or of formula (Va) respectively.

Preferably, reaction (MIV) and reaction (MV0) are done under inert atmosphere.

Preferably, compound (IV) is selected from the group consisting of $NaBH_4$, DIBAL-H and mixtures thereof.

Compound (IV) used in reaction (MIV) and compound (IV) used in reaction (MV0) can be independently from each identical or different.

Preferably, in the reaction (MIV) and in reaction (MV0), from 1 to 50 mol equivalents, more preferably from 1 to 20 mol equivalents, even more preferably from 2 to 10 mol equivalents, of compound (IV) are used, the mol equivalents being based the mol of compound of formula (V) or of formula (Va).

Reaction (MIV) and reaction (MV0) can be done in the presence of a salt (MIV), salt (MIV) is selected from the group consisting of LiCl, $CaCl_2$, $AlCl_3$, $ZnCl_2$ and mixtures thereof.

Preferably, if salt (MIV) is used in the reaction (MIV) and in reaction (MV0), from 1 to 20 mol equivalents, more preferably from 1 to 10 mol equivalents, even more preferably from 1.5 to 5 mol equivalents, of salt (MIV) are used, the mol equivalents being based the mol of compound of formula (V) or of formula (Va).

After reaction (MIV) and reaction (MV0), the compound of formula (IV) or of formula (V0) respectively can be isolated by standard methods such as washing, extraction, filtration, concentration and drying. The compound of formula (IV) or of formula (V0) respectively can be purified before or after isolation, preferably by chromatography or crystallization from an appropriate solvent.

Reaction (MII0-I-IVa) and reaction (MIV0a) are similar reactions and can be done under similar reaction parameters ranges as defined herein, with the individual reaction parameters for each of said two reactions being selected independently from each other.

Preferably, the reaction time of reaction (MII0-I-IVa) and of reaction (MIV0a) is from 1 min to 168 h, more preferably from 2 to 144 h, even more preferably from 12 to 120 h.

Reaction (MII0-I-IVa) and reaction (MIV0a) are usually done in a solvent (MIV0a).

Preferably, solvent (MIV0a) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MIV0a) is from 1 to 500 fold, more preferably from 5 to 50 fold, even more preferably from 10 to 30 fold, of the weight of compound of formula (V0).

Preferably, in reaction (MII0-I-IVa) and in reaction (MIV0a), from 1 to 20 mol equivalents, more preferably from 1 to 10 mol equivalents, even more preferably from 1 to 5 mol equivalents, of compound (II0-I-IVa) or of compound (RIV0a) respectively are used, the mol equivalents being based the mol of compound of formula (V0).

Preferably, reaction (MII0-I-IVa) and reaction (MIV0a) are done under inert atmosphere.

Preferably, reaction (MII0-I-IVa) and reaction (MIV0a) are done in the presence of compound of formula (HOSu).

Preferably, in reaction (MII0-I-IVa) and reaction (MIV0a), from 1 to 20 mol equivalents, more preferably from 1 to 10 mol equivalents, even more preferably from 1 to 5 mol equivalents, of compound of formula (HOSu) are used, the mol equivalents being based the mol of compound (II0-I-IVa) or of compound (RIV0a) respectively.

After reaction (MII0-I-IVa) and reaction (MIV0a), compound of formula (III0-I-IVa) or of formula (IV0a) respectively can be isolated by standard methods such as washing, extraction, filtration, concentration and drying. Any of the compounds can be purified before or after isolation, preferably by chromatography or crystallization from an appropriate solvent.

Further subject of the invention is a method (MVa) for the preparation of compound of formula (Va), with the compound of formula (Va) as defined herein, also with all its preferred embodiments;

method (MVa) comprises a step (MVa);

step (MVa) comprises a reaction (MVa), wherein a compound of formula (VI) is reacted with a compound of formula (SGM);

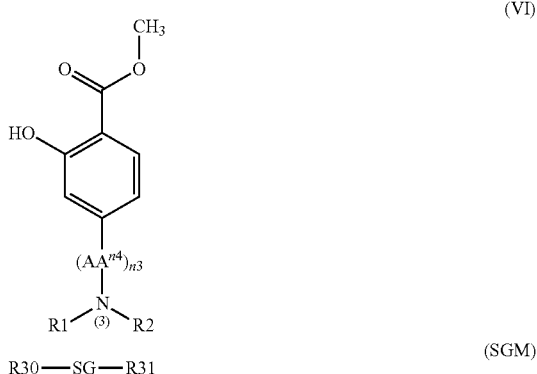

(VI)

(SGM)

R31 is connected to SG via the bond denoted with (***) in the formulae of SG and is —OTs, —OMs, —OTf, —Br, —Cl or —I;

R30 is as defined herein, also with all its preferred embodiments;

SG, n4, n3, AA$^{n4}$, (3), R1, R2 are as defined herein, also with all their preferred embodiments.

Preferably, method (MII) comprises as a further step the step (MVa), wherein compound of formula (Va) is prepared.

Preferably, the reaction temperature of reaction (MVa) is from 0 to 150° C., more preferably from 20 to 100° C., even more preferably from 30 to 60° C.

Preferably, the reaction time of reaction (MVa) is from 1 min to 168 h, more preferably from 1 to 144 h, even more preferably from 12 to 120 h.

Reaction (MVa) is usually done in a solvent (MVa).

Preferably, solvent (MVa) is selected from the group consisting of N,N-dimethylformamide, N,N-dimethylacetamide, N,N-dimethylsulfoxide, acetonitrile, acetone, 1,4-dioxane, THF and mixtures thereof.

Preferably, the amount of solvent (MVa) is from 1 to 500 fold, more preferably from 5 to 50 fold, even more preferably from 10 to 30 fold, of the weight of compound of formula (VI).

Preferably, in the reaction (MVa), from 1 to 20 mol equivalents, more preferably from 1 to 10 mol equivalents, even more preferably from 1.5 to 5 mol equivalents, of compound (SGM) are used, the mol equivalents being based the mol of compound of formula (VI).

Preferably, the reaction (MVa) is done under inert atmosphere.

Reaction (MVa) are usually done in the presence of a base (MVa).

Preferably, base (MVa) is selected from the group consisting of $K_2CO_3$, $Na_2CO_3$, diisopropylethylamine, triethylamine, pyridine, 4-dimethylaminopyridine and mixtures thereof.

Preferably, in the reaction (MVa), from 1 to 20 mol equivalents, more preferably from 1 to 10 mol equivalents, even more preferably from 1.5 to 5 mol equivalents, of base (MVa) are used, the mol equivalents being based the mol of compound of formula (VI).

After the reaction (MVa), compound of formula (Va) can be isolated by standard methods such as washing, extraction, filtration, concentration and drying. Any of the compounds can be purified before or after isolation, preferably by chromatography or crystallization from an appropriate solvent.

Reaction (MVb) and reaction (MIII0) are similar reactions and can be done under similar reaction parameters ranges as defined herein, with the individual reaction parameters for each of said two reactions being selected independently from each other.

Preferably, in reaction (MVb) and in reaction (MIII0), from 1 to 500 mol equivalents, more preferably from 5 to 100 mol equivalents, even more preferably from 10 to 50 mol equivalents, of HCl are used, the mol equivalents being based the mol of compound of formula (Va) or of formula (IV0) respectively.

Preferably, the reaction time of reaction (MVb) and of reaction (MIII0) is from 1 min to 168 h, more preferably from 1 to 48 h, even more preferably from 2 to 24 h.

Reaction (MVb) and reaction (MIII0) is usually done in a solvent (MVb).

Preferably, solvent (MVb) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MVb) is from 1 to 500 fold, more preferably from 5 to 50 fold, even more preferably from 10 to 30 fold, of the weight of compound of formula (Va) or of formula (IV0).

Preferably, the reaction (MVb) and reaction (MIII0) is done under inert atmosphere.

After reaction (MVb) and reaction (MIII0), compound of formula (V) or of formula (III0) respectively can be isolated by standard methods such as washing, extraction, filtration, concentration and drying. They can be isolated in protonated form of their salts or in unprotonated form.

Any of the compounds can be purified before or after isolation, preferably by chromatography or crystallization from an appropriate solvent.

Further subject of the invention is a method (MVI) for the preparation of compound of formula (VI), with the compound of formula (VI) being as defined herein, also with all its preferred embodiments;

method (MVI) comprises a step (MVIa) and optionally a step (MVIb);

in step (MVIa) the n3 AA$^{n4}$ are consecutively connected to a compound of formula (VII-1) by peptide coupling reactions and then to the respective products of the preceding peptide coupling reactions;

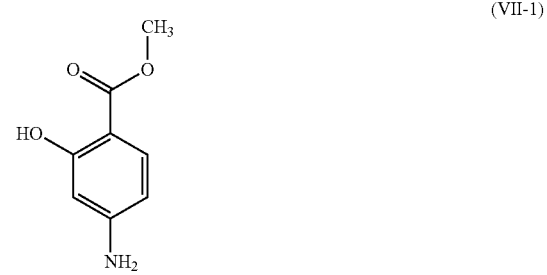

(VII-1)

step (MVIb) comprises a reaction (MVIb), wherein the N-terminal amino group of AA$^{n3}$ denoted with (3) in formula (VI) is reacted with a compound NTermProt;

NTermProt is selected from the group consisting of $C_{1-4}$ alkyl iodide, $C_{1-4}$ alkyl bromide, Cl—C(O)-(GRPEG)$_{m4}$-R3, R3-C(O)—O—C(O)—R3 and PGNPrec;

PGNPrec is a reagent which provides for the introduction of PGN on the N-terminal amino group of AA$^{n3}$ denoted with (3) in formula (VI);

GRPEG, m4, R3 and PGN have the same definition as above, also with all their preferred embodiments;

n4, n3, AA$^{n4}$ and (3) are as defined herein, also with all their preferred embodiments.

Preferably, method (MII) comprises as further steps the step (MVa), wherein compound of formula (Va) is prepared, and the step (MVIa) and optionally the step (MVIb), wherein compound of formula (VI) is prepared.

Compound of formula (VII-1) is a known compound and can be prepared by known methods.

For simplicity sake, AA$^{n4}$ in this text is used both for the covalently bonded amino acid residue, e.g. in formula (II), and for the amino acid used in method (MVIa).

In case that AA$^{n4}$ has a side chain with a functional group, this functional group can be protected by a protecting group commonly used for protecting functional groups of side chains of amino acids.

Preferably, NTermProt is Ac$_2$O.

Preferably, PGNPrec is Boc$_2$O, FmocCl or CbzCl.

Method (MVIa) is done using methodology, parameters and reagents commonly used in peptide synthesis, and which are known to the skilled person. Above cited references give the necessary information.

Preferably, the reaction time of reaction (MVIb) is from 1 min to 168 h, more preferably from 1 to 48 h, even more preferably from 2 to 24 h.

Reaction (MVIb) is usually done in a solvent (MVIb).

Preferably, solvent (MVIb) is selected from the group consisting of N,N-dimethylformamide, N,N-dimethylacetamide, N,N-dimethylsulfoxide, acetonitrile, acetone, 1,4-dioxane, THF, water, methanol, ethanol and mixtures thereof.

Preferably, the amount of solvent (MVIb) is from 1 to 500 fold, more preferably from 2 to 50 fold, even more preferably from 5 to 20 fold, of the weight of compound of formula (VII-1).

More preferably, method (MVIa) and reaction (MVIb) are done consecutively in the same solvent.

More preferably, method (MVIa) and reaction (MVIb) are done consecutively in the same solvent and in one pot.

Preferably, in the method (MVIa), from 1 to 20 mol equivalents, more preferably from 1 to 10 mol equivalents, even more preferably from 1 to 5 mol equivalents, of NTermProt are used, the mol equivalents being based the mol of compound of formula (VII-1).

Preferably, the reaction (MVIb) is done under inert atmosphere.

After the method (MVIa) or reaction (MVIb), the reaction product of the method (MVIa) or of the reaction (MVIb), each of which is a respective compound of formula (VI), can be isolated by standard methods such as washing, extraction, filtration, concentration and drying. Any of the compounds can be purified before or after isolation, preferably by chromatography or crystallization from an appropriate solvent.

Compound of formula (SGM) is a known compound and can be prepared according to known methods.

Preferably, compound of formula (SGM) is selected from the group consisting of compound SGM-II and compound SGM-III.

Preferably, compound SGM-II is prepared by reacting a compound of formula (HSGH-II) first with Boc$_2$O and then with compound (SGM-II-R31).

Compound (SGM-II-R31) is selected from the group consisting of p-toluenesulfonyl chloride, p-toluenesulfonic anhydride, methanesulfonyl chloride, methanesulfonic anhydride, trifluoromethanesulfonyl chloride and trifluoromethanesulfonic anhydride, SOCl$_2$, (COCl)$_2$, POCl$_3$, PCl$_3$, PCl$_5$, POBr$_3$, PBr$_3$, PBr$_5$, N-bromosuccinimide, N-iodosuccinimide, HCl, HBr, HI and mixtures thereof.

Preferably, compound (SGM-II-R31) is TsCl.

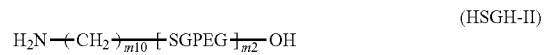

(HSGH-II)

Preferably, compound SGM-III is prepared by reacting a compound of formula (HSGH-III) first with Boc$_2$O and then with a compound of formula (HSGHReac-1).

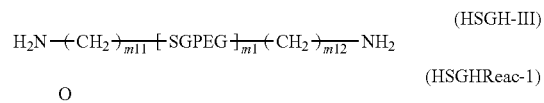

(HSGH-III)

(HSGHReac-1)

Compound of formula (HSGH-II) is preferably a compound of formula (HSGH-II-1) or a compound of formula (HSGH-II-2).

(HSGH-II-1)

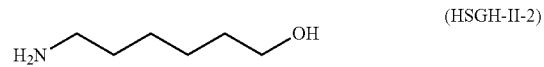

(HSGH-II-2)

Compound SGM-II is preferably a compound of formula (SGM-II-1) or a compound of formula (SGM-II-2).

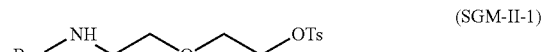

(SGM-II-1)

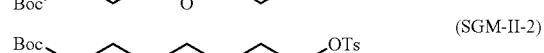

(SGM-II-2)

Compound of formula (HSGH-III) is preferably a compound of formula (HSGH-III-1) or a compound of formula (HSGH-III-2).

(HSGH-III-1)

(HSGH-III-2)

Compound SGM-III is preferably a compound of formula (SGM-III-1) or a compound of formula (SGM-III-2).

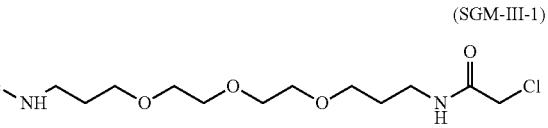

(SGM-III-1)

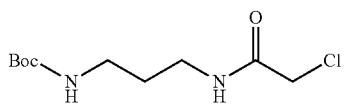
(SMG-III-2)

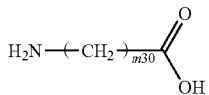
(AC)

Compound of formula (HSGH-II) and compound of formula (HSGH-III) are a known compound, can be prepared according to known methods, and are often even commercially available.

Compounds of formulae (CG1MR-IV), (CG1MR-III), (CG1MR-IIa), (HOSu) and compound (COUPADD) are known compounds, can be prepared by known methods and are often even commercially available.

Preferably, compound of formula (CG1MR-IV) is prepared by reacting a compound of formula (CG1MR-IV-OH) with a compound of formula (HOSu);

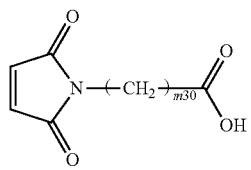
(CG1MR-IV-OH)

with the compound of formula (HOSu) as defined herein; preferably, compound of formula (CG1MR-IV-OH) is prepared by reacting compound of formula (MA) with compound of formula (AC);

with compound of formula (MA) and m30 as defined herein, also with all their preferred embodiments.

Any of the above defined reactions can be done under similar reaction conditions with the individual reaction parameters for each of these reactions being selected independently from each other:

with respect to pressure: any of the above defined reactions can be done under vacuum, at atmospheric pressure or even under pressure, the pressure can for example be up to 10 bar, preferably they are done under atmospheric pressure;

with respect to temperature: preferably, the reaction temperature of any of the above defined reactions is from −20 to 100° C., more preferably from 0 to 75° C., even more preferably from 10 to 50° C.;

with respect to reaction time: the reaction time of any of the above defined reactions is from 1 min to 168 h, more preferably from 0.5 to 24 h, even more preferably from 1 to 12 h;

if not stated otherwise for any of the above defined reactions.

In particular, compound of formula (I) is selected from the group consisting of compound of formula (10), compound of formula (11), compound of formula (12), compound of formula (12-101), compound of formula (13), compound of formula (14), compound of formula (15), compound of formula (15-102) and compound of formula (16);

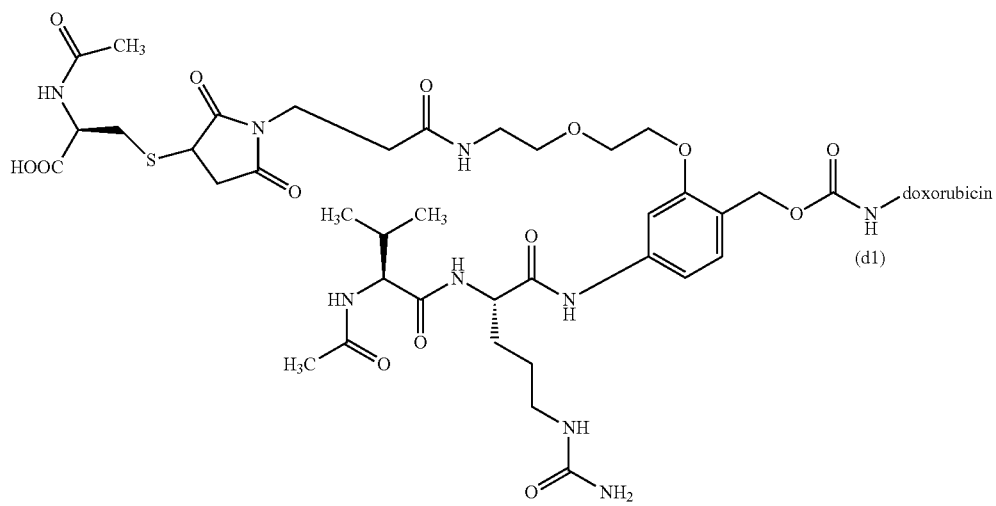
(10)

(11)
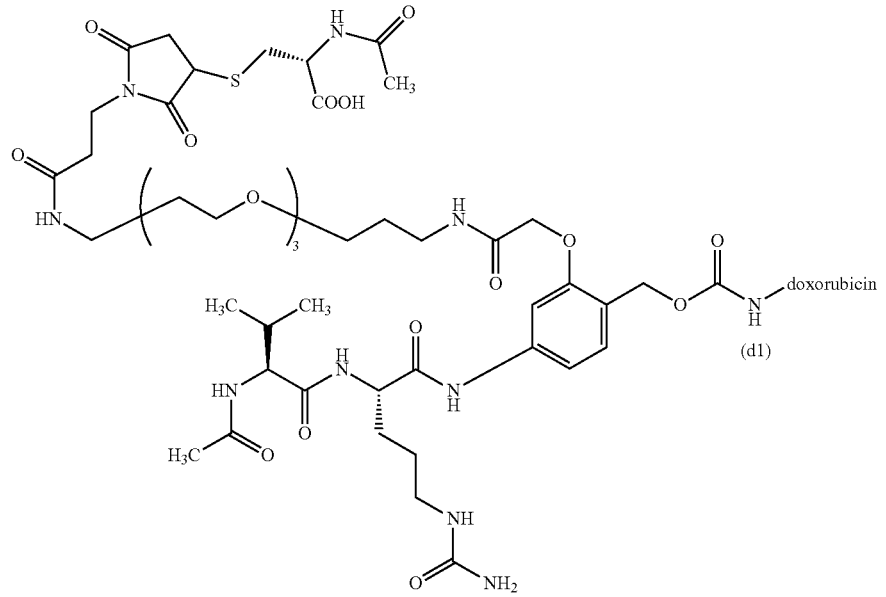
(d1)
(12)
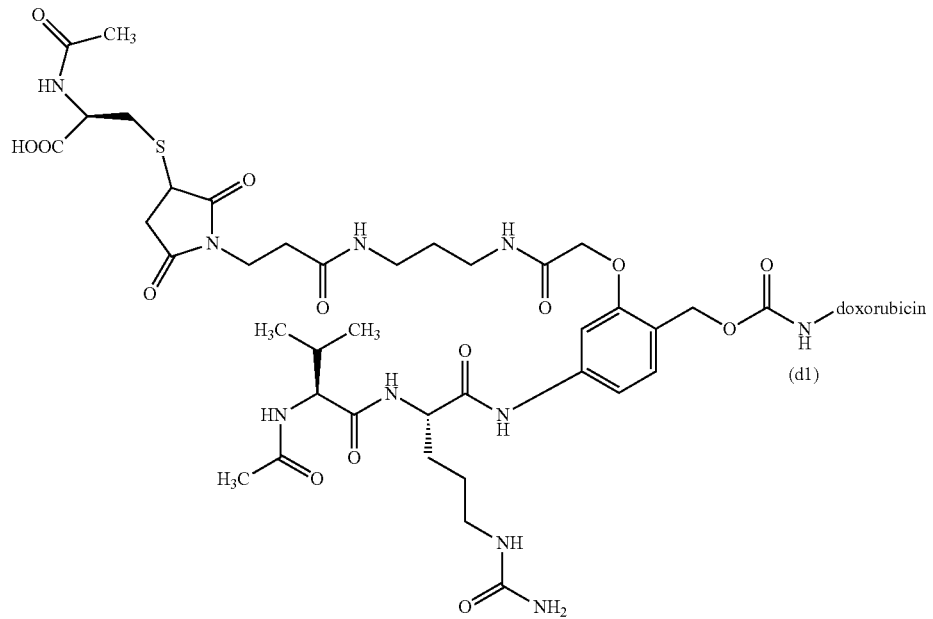
(d1)

(12-101)
Monoclonal anti-interleukin-1b antibody produced in mouse
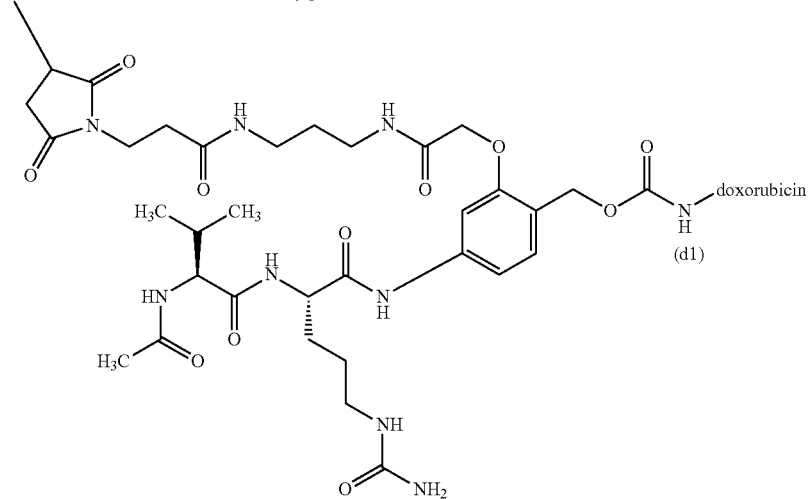
(13)
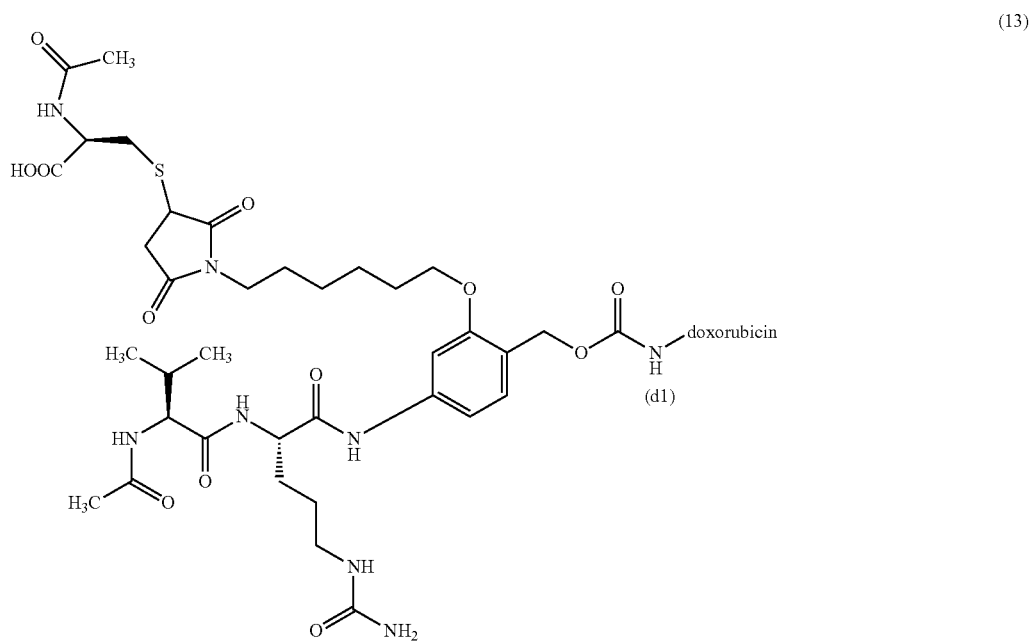
(14)
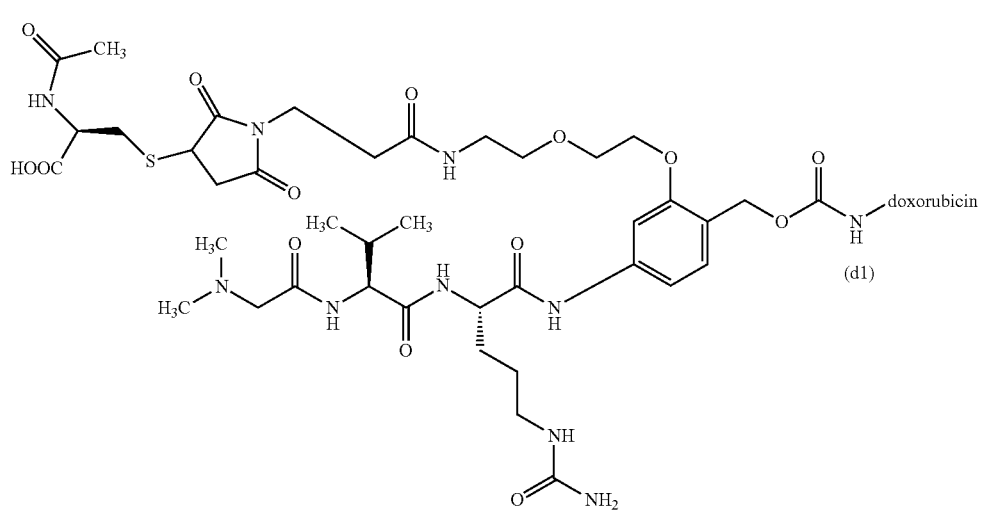

(15)
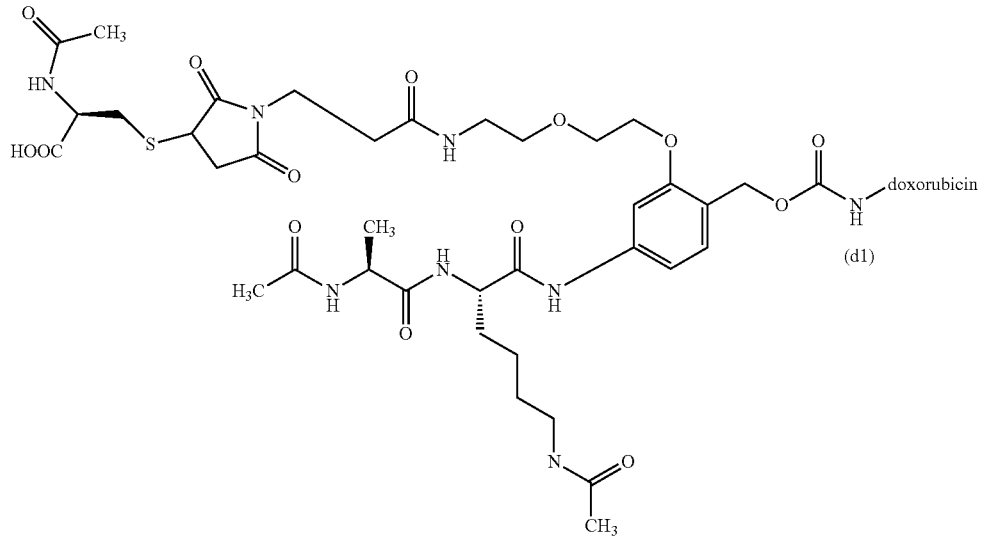
(15-102)
Monoclonal anti-interleukin-1b antibody produced in mouse
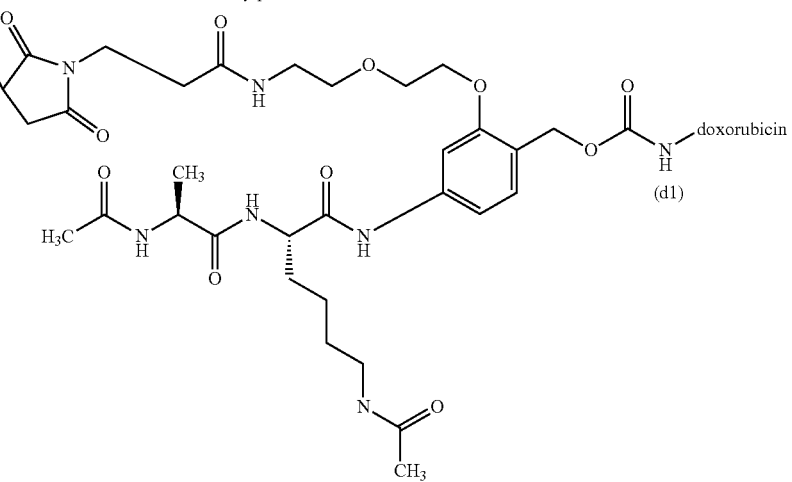
(16)
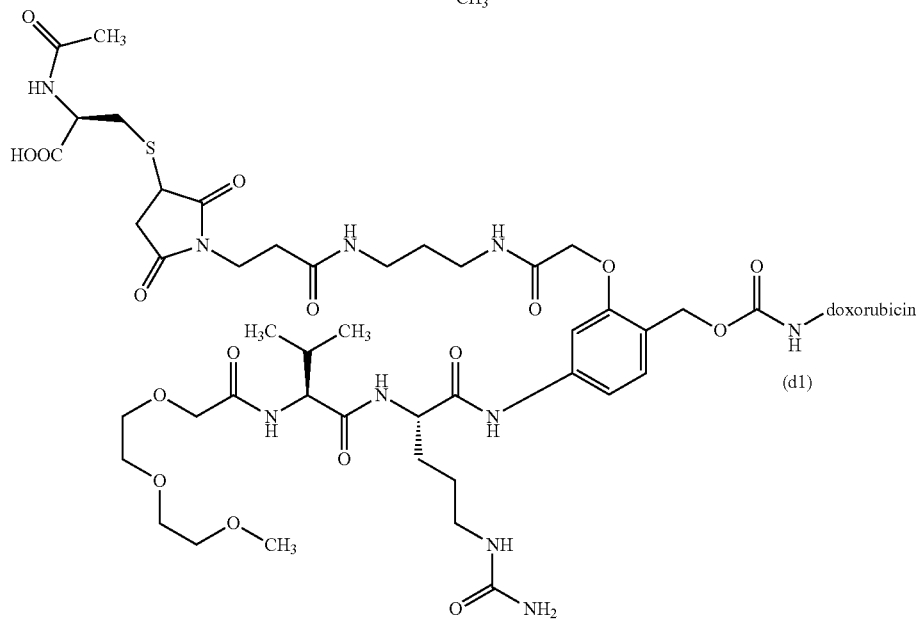

wherein doxorubicin is the compound of formula (DOXO), which is connected via the amino group denoted with (d1) in formula (10), (11), (12), (12-101), (13), (14), (15), (15-102) and (16) respectively and in formula (DOXO).

In particular, compound of formula (II) is selected from the group consisting of compound of formula (20), compound of formula (21), compound of formula (22), compound of formula (23), compound of formula (24), compound of formula (25), compound of formula (26), compound of formula (20-CAMPTO), compound of formula (21-CAMPTO), compound of formula (22-CAMPTO), compound of formula (23-CAMPTO) and compound of formula (21-TAXO-t1-1);

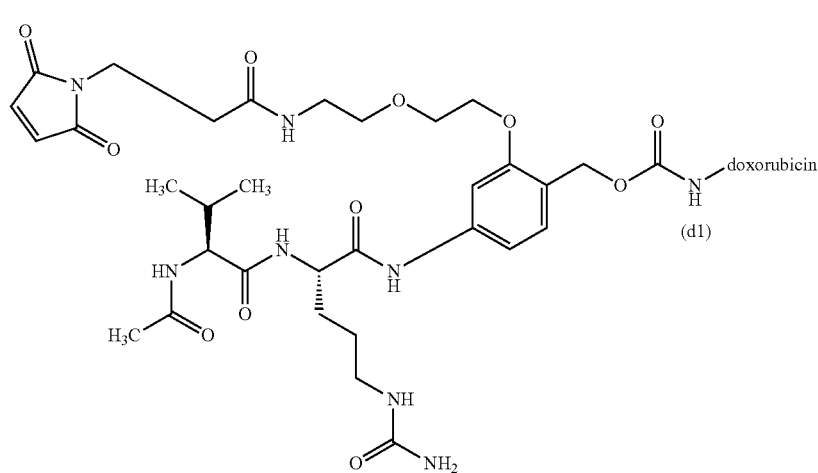

(20)

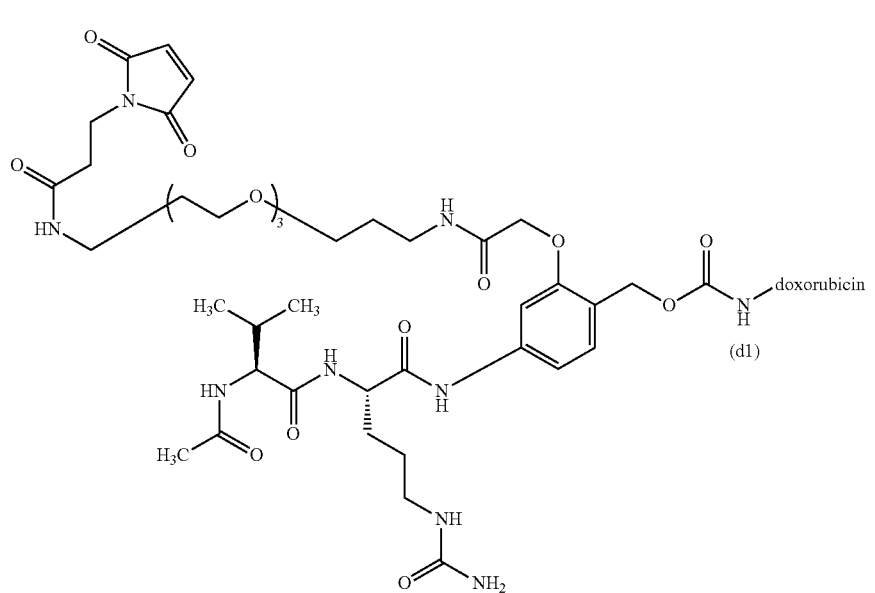

(21)

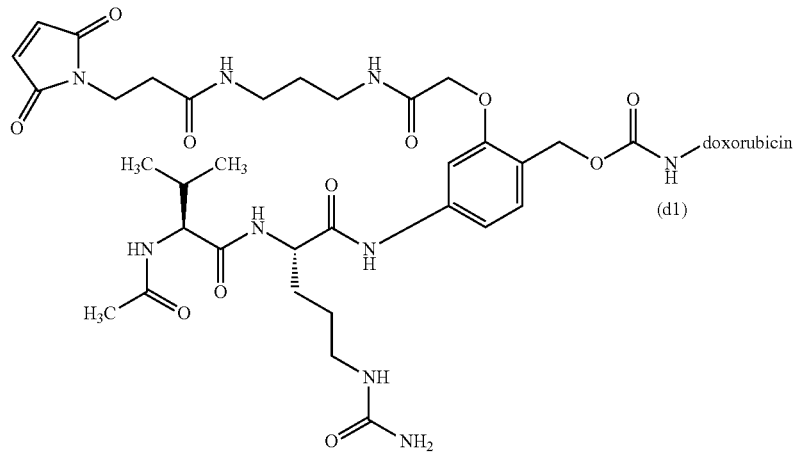
(22)
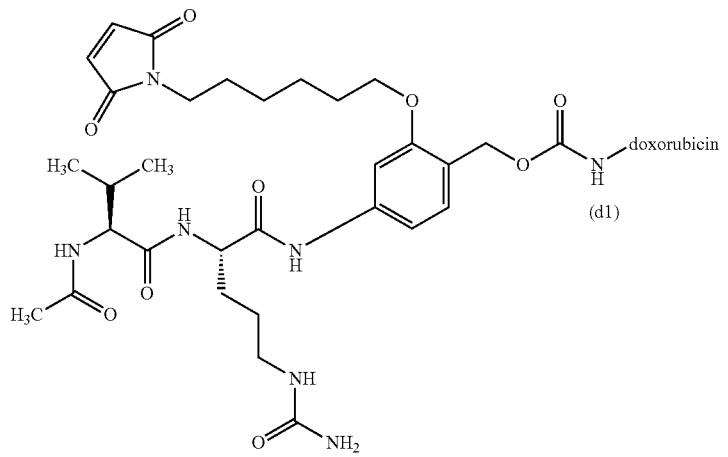
(23)
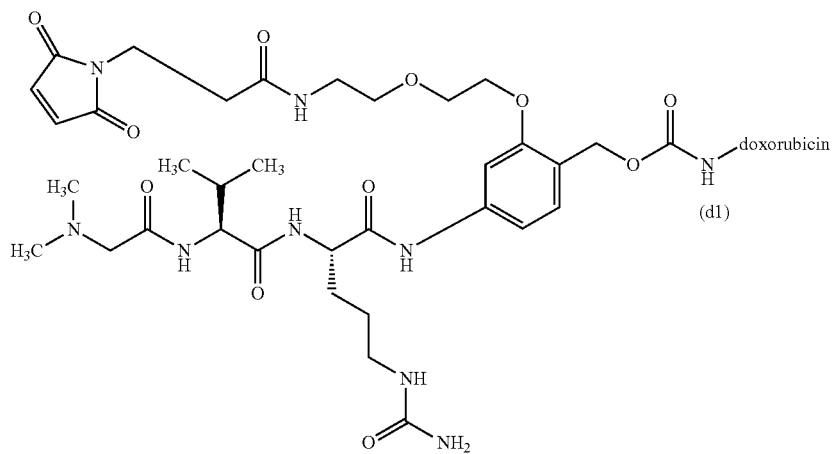
(24)

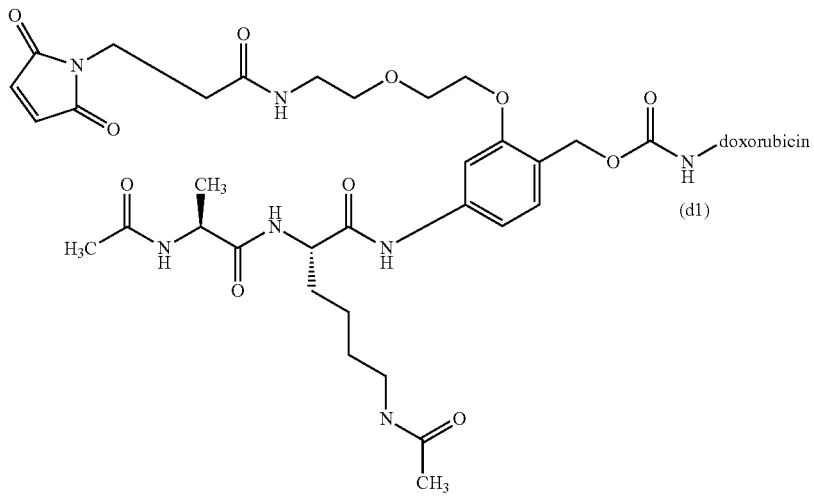
(25)
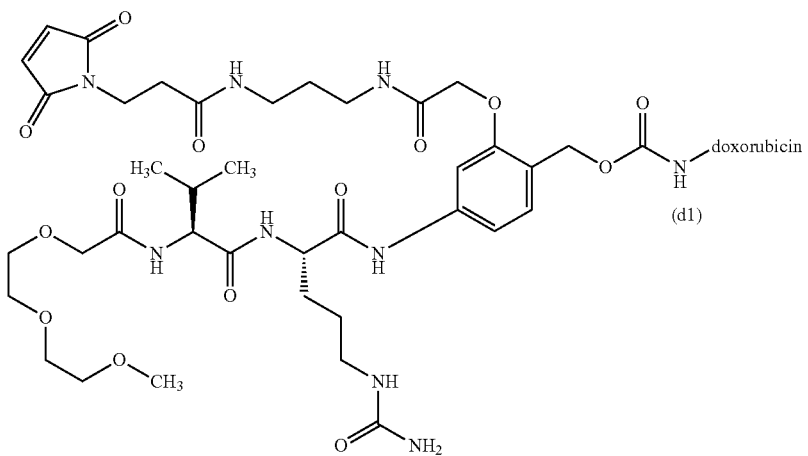
(26)
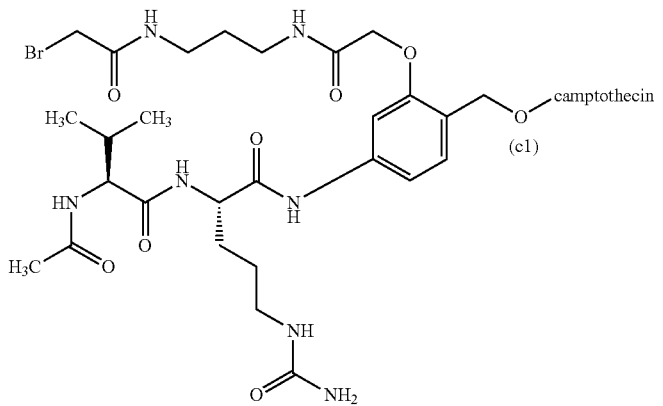
(20-CAMPTO)

(21-CAMPTO)
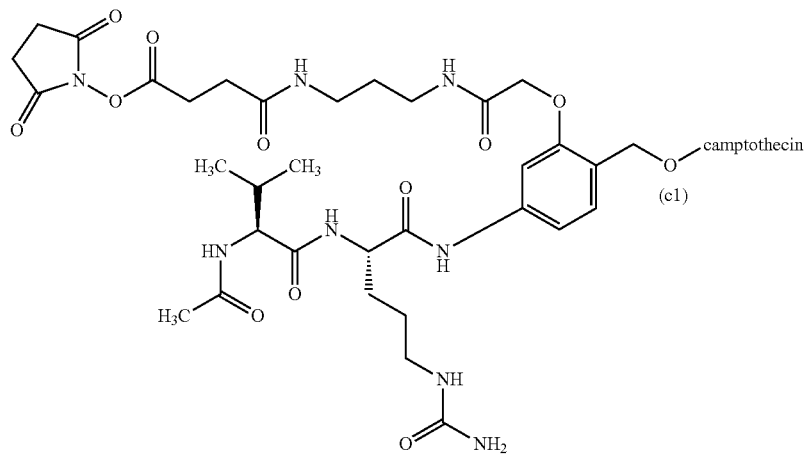
(22-CAMPTO)
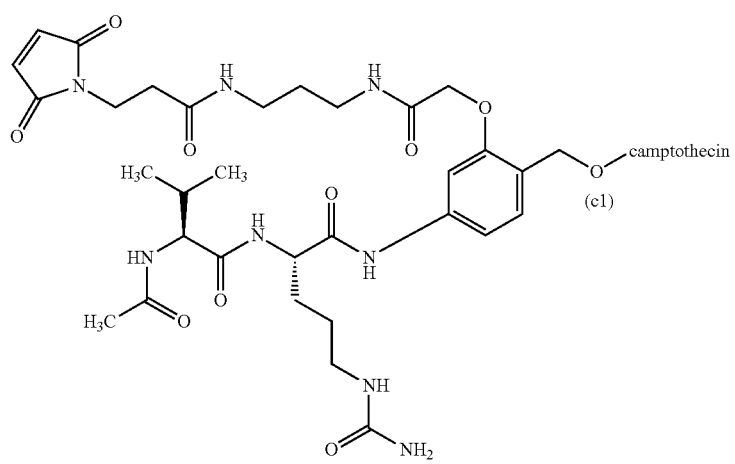
(23-CAMPTO)
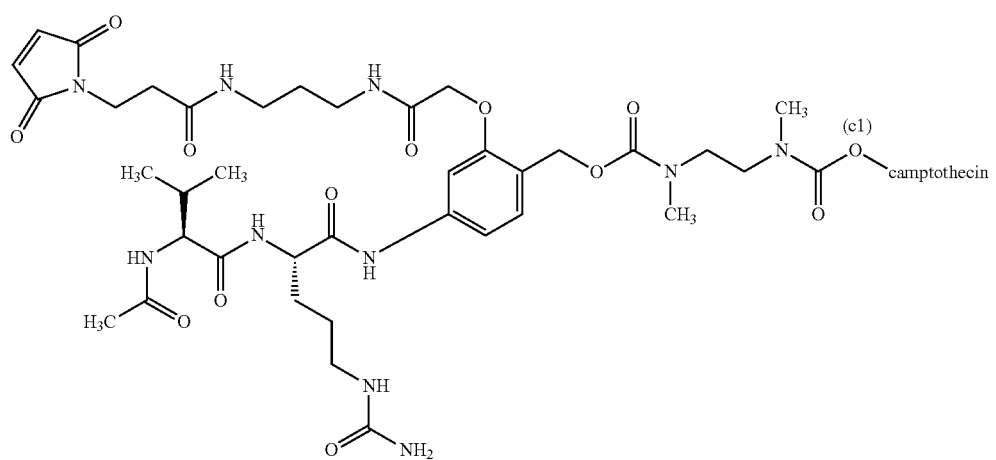

(21-TAXO-t1-1)

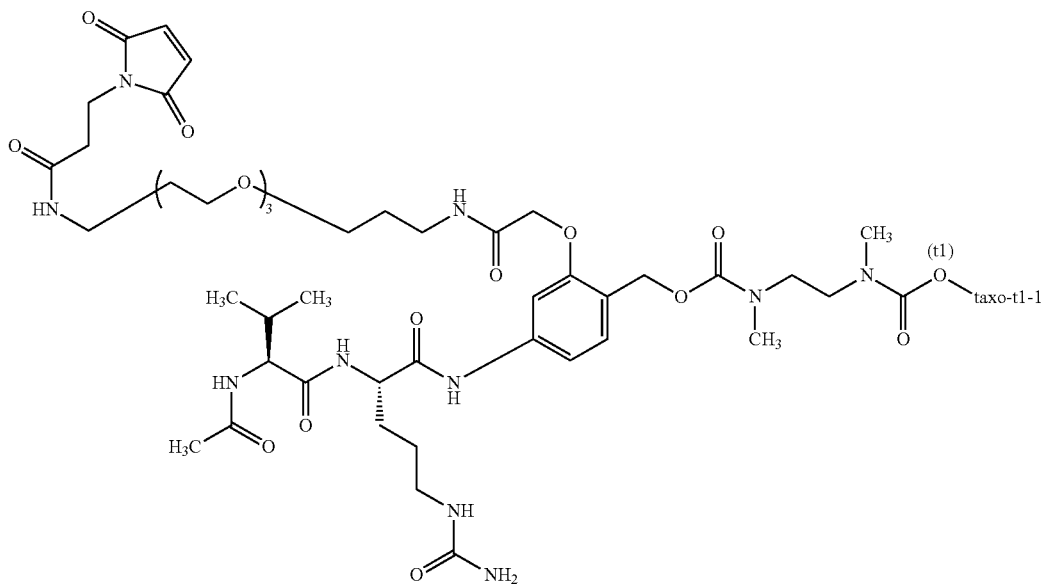

wherein
doxorubicin is the compound of formula (DOXO), which is connected via the amino group denoted with (d1) in formula (20), (21), (22), (23), (24), (25) and (26) respectively and in formula (DOXO);
camptothecin is the compound of formula (CAMPTO), which is connected via the hydroxy group denoted with (c1) in formula (20-CAMPTO), (21-CAMPTO), (22-CAMPTO) and (23-CAMPTO) respectively and in formula (CAMPTO);
taxo-t1-1 is the compound of formula (TAXO), which is connected via the hydroxy group denoted with (t1) in formula (21-TAXO-t1-1), in formula (TAXO-t1-1) and in formula (TAXO).

In particular, compound of formula (IIc) is compound of formula (20c).

(20c)

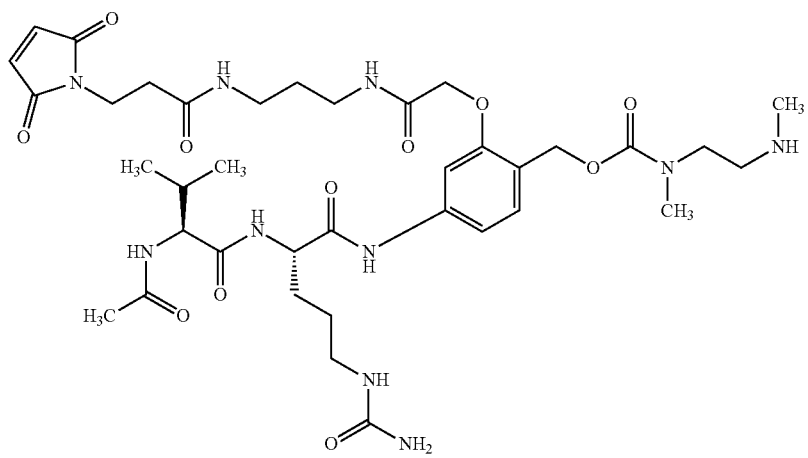

In particular, compound of formula (III) is selected from the group consisting of compound of formula (30), compound of formula (31), compound of formula (32), compound of formula (33), compound of formula (34), compound of formula (35) and compound of formula (36).
(30)
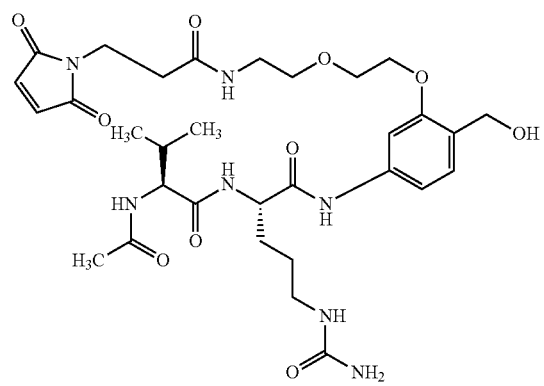
(31)
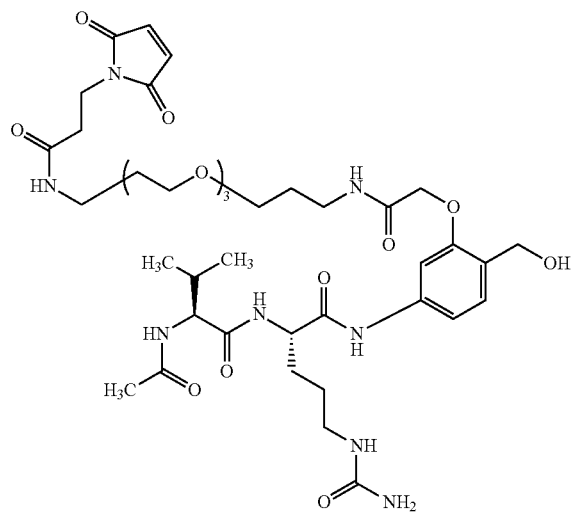
(32)
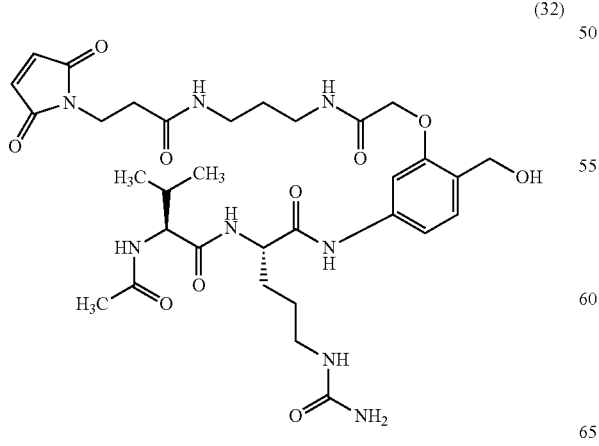
-continued
(33)
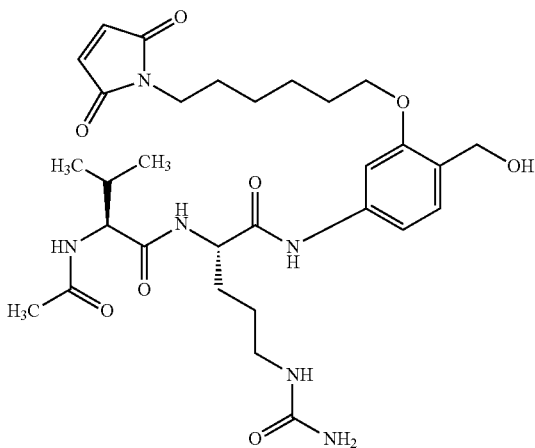
(34)
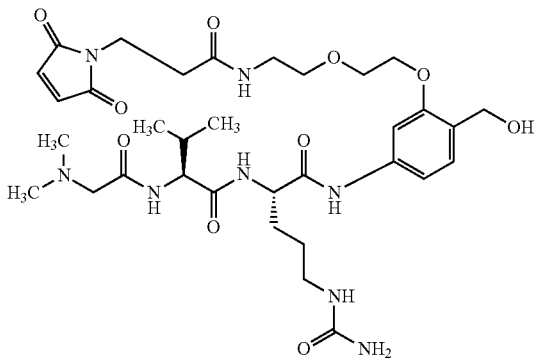
(35)
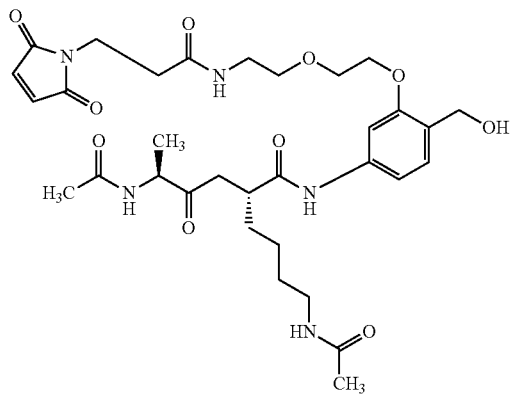

-continued (36)

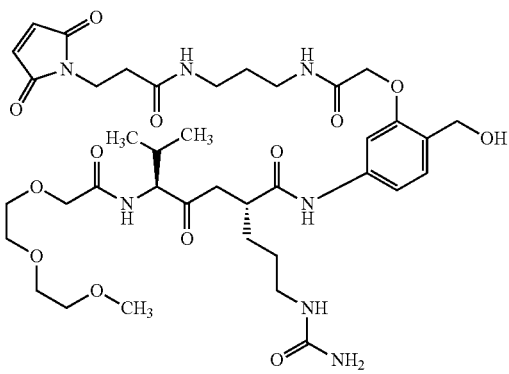

In particular, compound of formula (III0) is compound of formula (300);

(300)

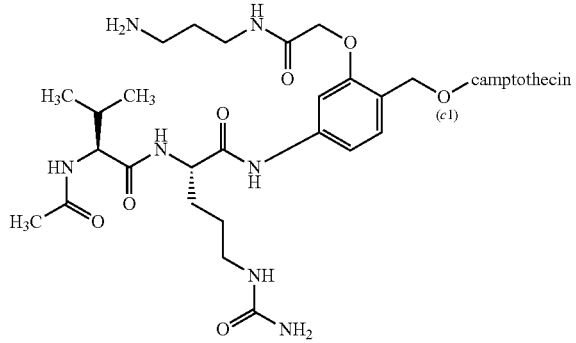

wherein
camptothecin is the compound of formula (CAMPTO), which is connected via the hydroxy group denoted with (c1) in formula (300) respectively and in formula (CAMPTO).

In particular, compound of formula (III0-I-IVa) is compound of formula (320).

(320)

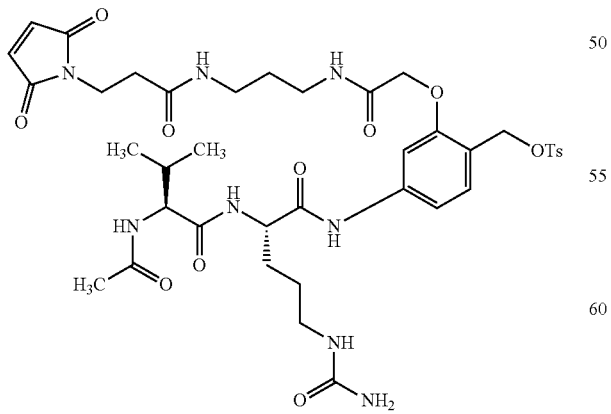

In particular, compound of formula (IV) is selected from the group consisting of compound of formula (40), compound of formula (41), compound of formula (42), compound of formula (43), compound of formula (44), compound of formula (45) and compound of formula (46).

(40)

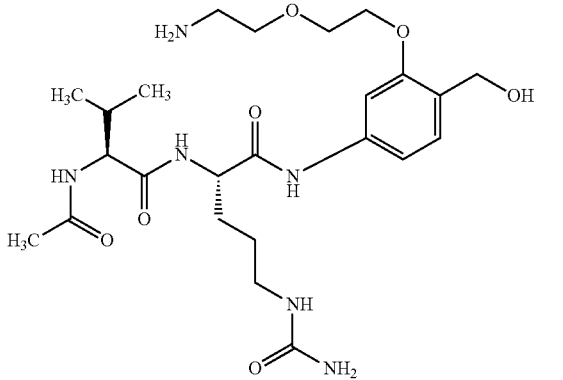

(41)

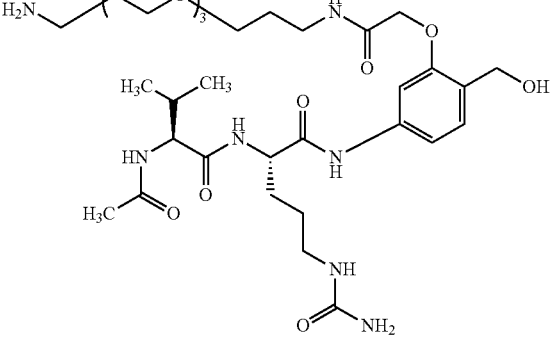

(42)

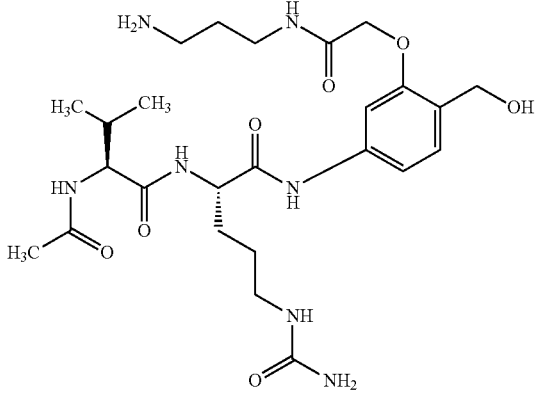

(43)
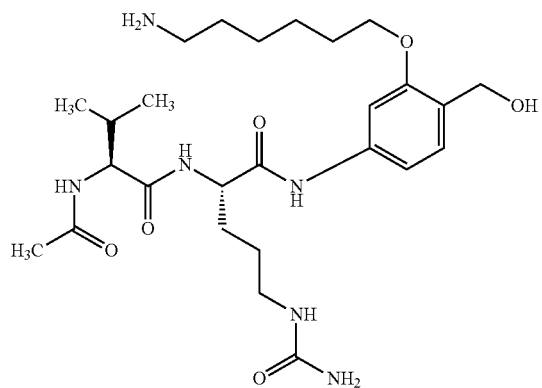

(44)
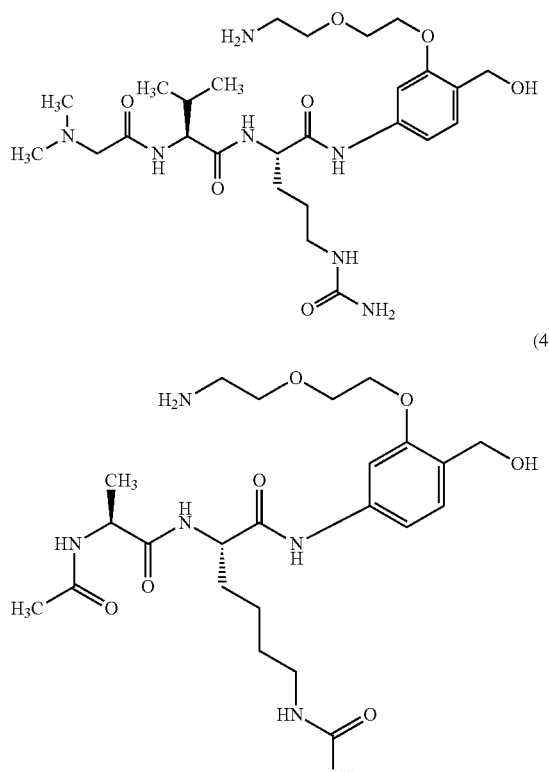

(45)

(46)
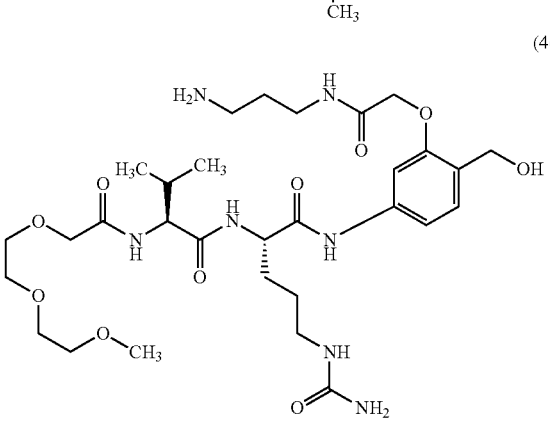

In particular, compound of formula (IV0) is compound of formula (400);

(400)
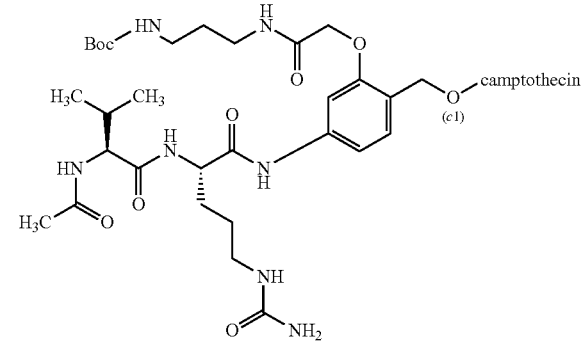

wherein
camptothecin is the compound of formula (CAMPTO), which is connected via the hydroxy group denoted with (c1) in formula (400) respectively and in formula (CAMPTO).

In particular, compound of formula (IV0a) is compound of formula (400a).

(400a)
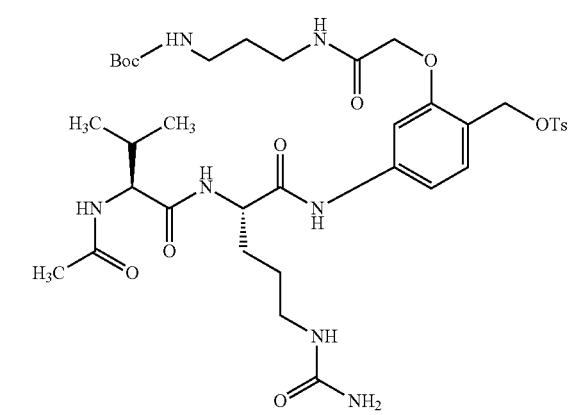

In particular, compound of formula (V) is selected from the group consisting of compound of formula (50), compound of formula (50-1), compound of formula (51), compound of formula (51-1), compound of formula (52), compound of formula (52-1), compound of formula (53), compound of formula (53-1), compound of formula (54), compound of formula (54-1), compound of formula (54-2), compound of formula (54-3), compound of formula (55), compound of formula (55-1), compound of formula (56) and compound of formula (56-1).

(50)
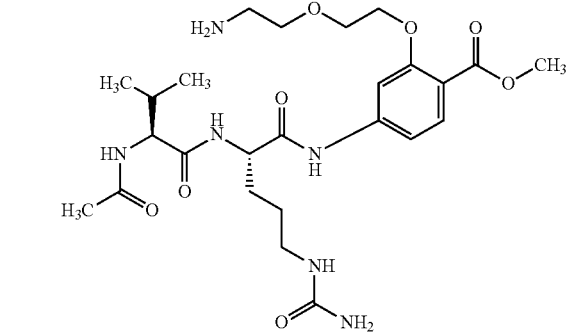

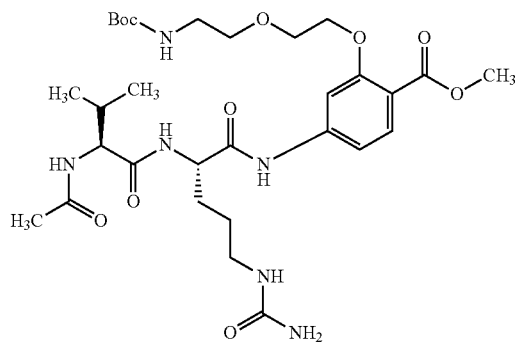
(50-1)
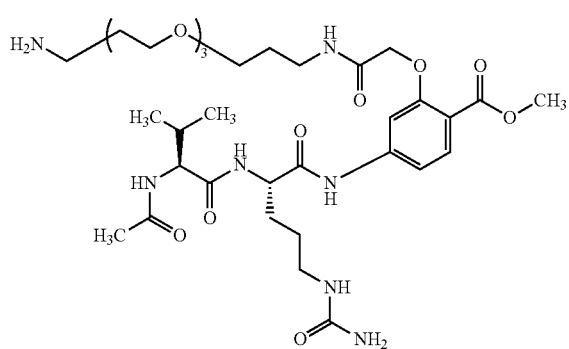
(51)
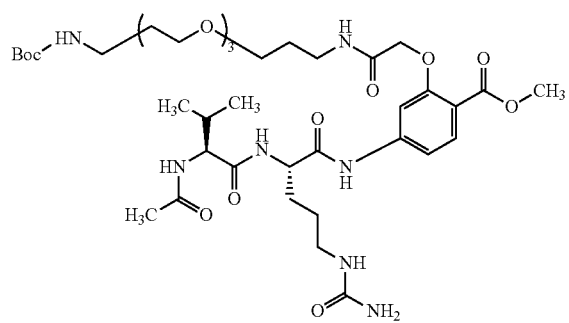
(51-1)
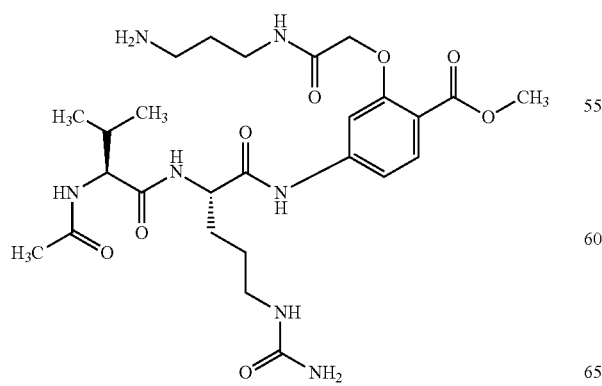
(52)
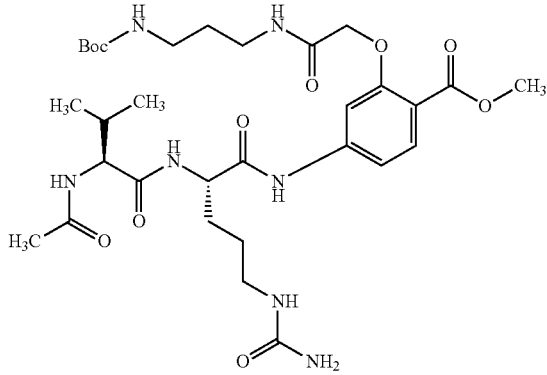
(52-1)
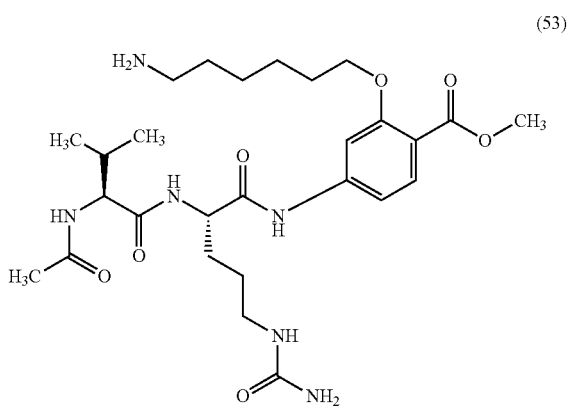
(53)
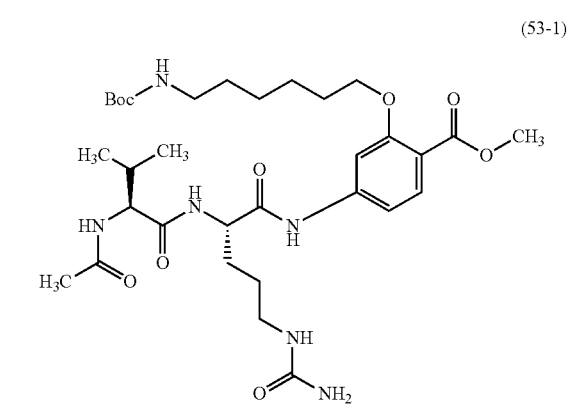
(53-1)
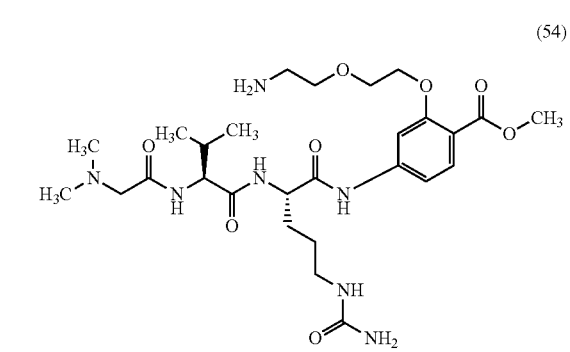
(54)

(54-1)
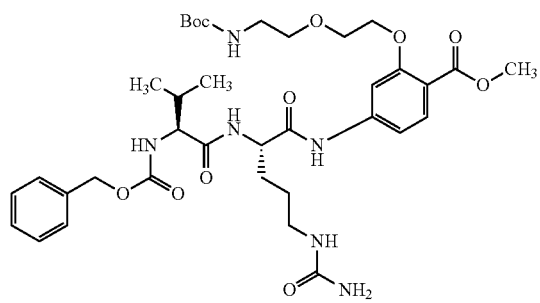
(54-2)
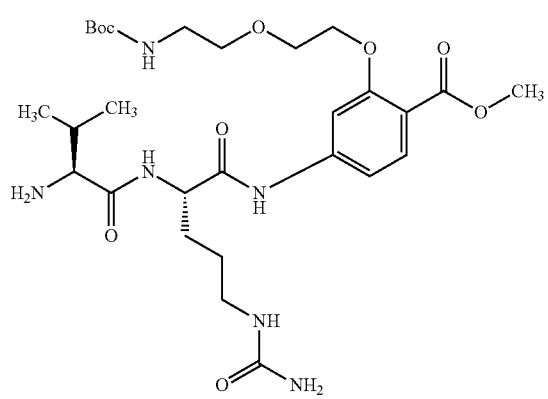
(54-3)
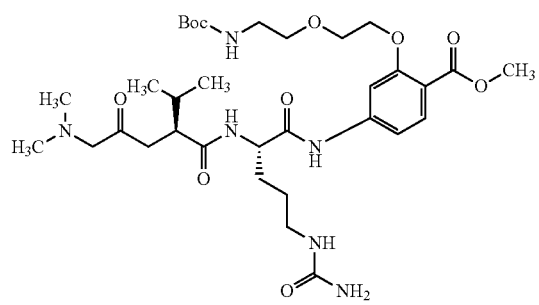
(55)
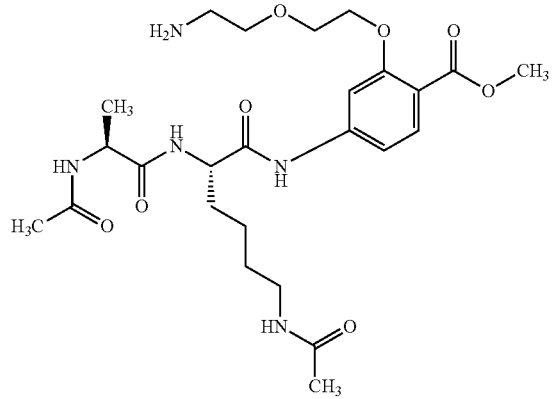
(55-1)
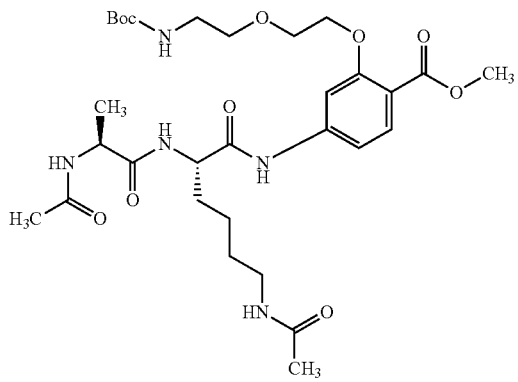
(56)
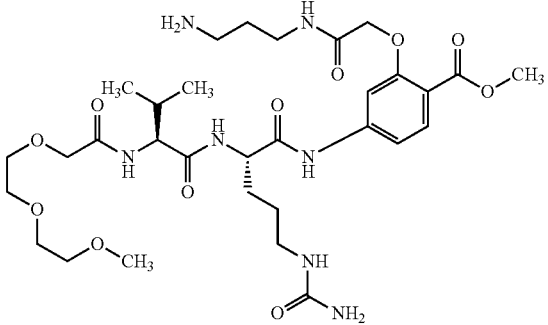
(56-1)
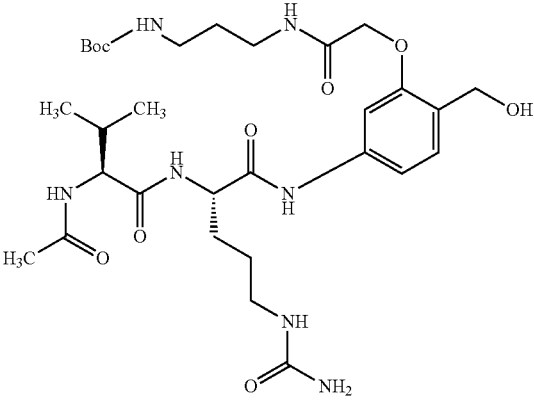
In particular, compound of formula (V0) is compound of formula (500).
(500)

In particular, compound of formula (VI) is selected from the group consisting of compound of formula (6), compound of formula (6-1), compound of formula (6-2), compound of formula (6-3), compound of formula (6-4), compound of formula (6b), compound of formula (6b-1), compound of formula (6b-2), compound of formula (6b-3), compound of formula (6b-4), compound of formula (6c) and compound of formula (6-5).
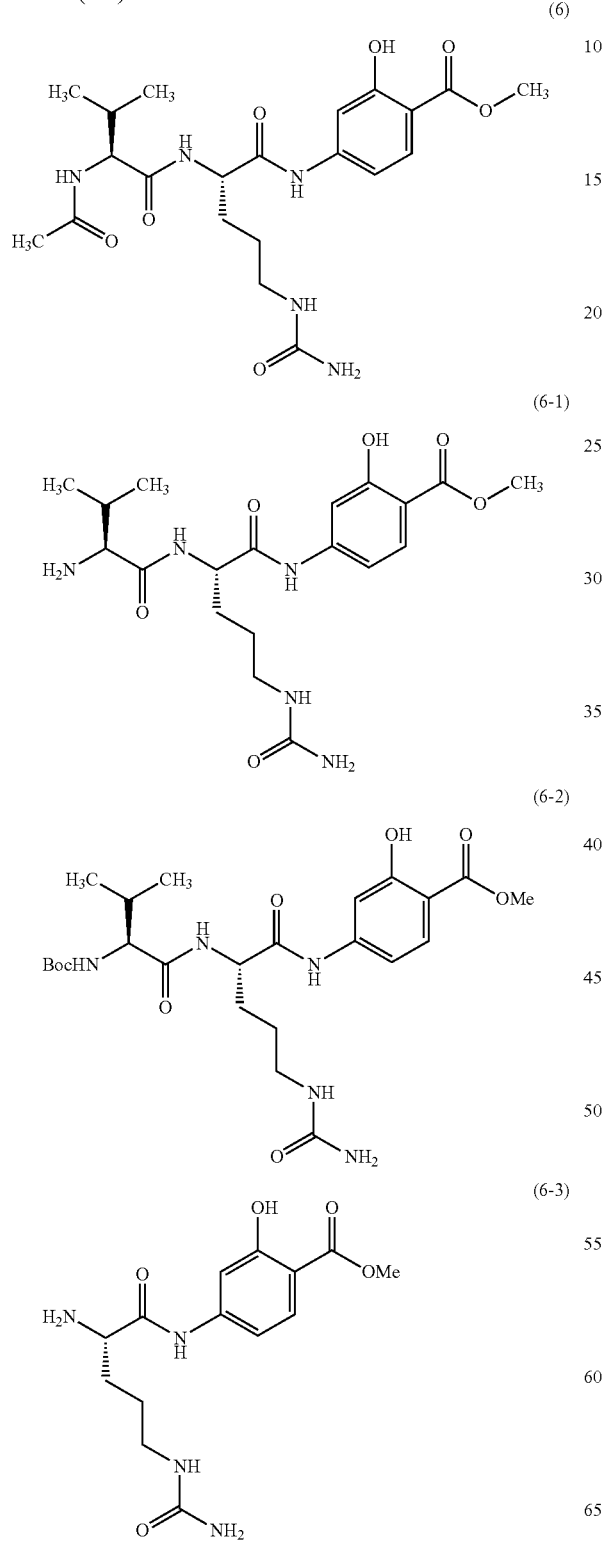
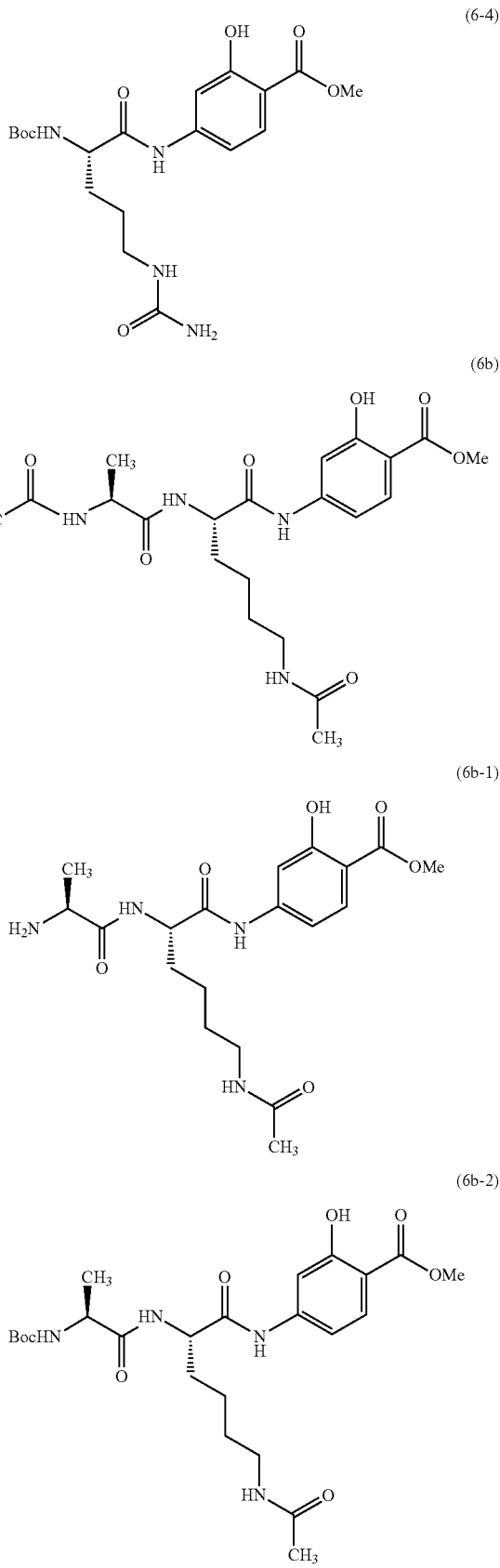

-continued (6b-3)
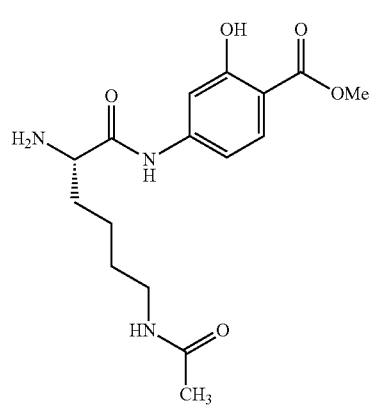

(6b-4)
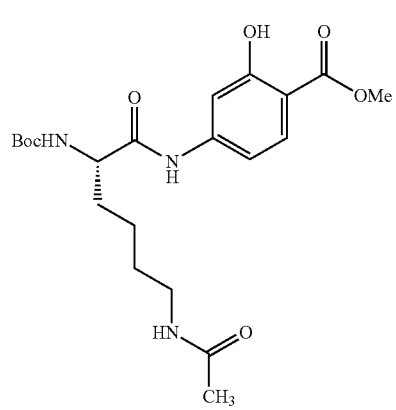

(6c)
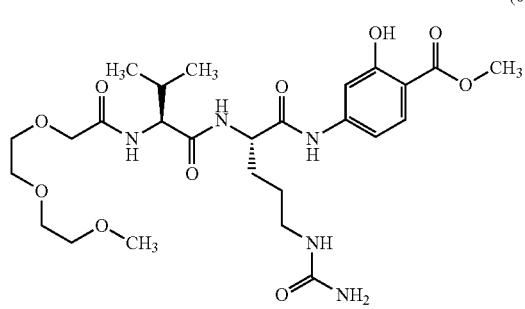

(6-5)
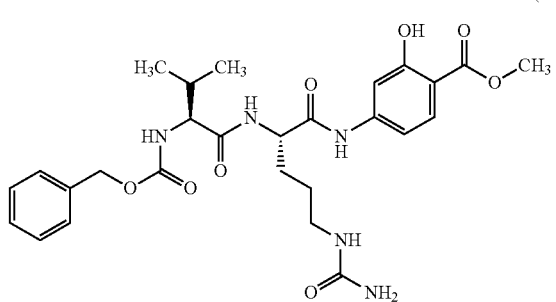

Further subject of the invention is a compound selected from the group consisting of compound of formula (I), compound of formula (II), compound of formula (IIc), compound of formula (III), compound of formula (IV), compound of formula (IV-IIa), compound of formula (V), compound of formula (Va), compound of formula (VI), compound of formula (III0-IIa), compound of formula (III0), compound of formula (IV0), compound of formula (IV0a), compound of formula (V0) and compound of formula (III0-I-IVa); with these compounds being as defined herein, also with all their preferred embodiments.

Further subject of the invention is a compound selected from the group consisting of compound of formula (10), compound of formula (II), compound of formula (12), compound of formula (12-101), compound of formula (13), compound of formula (14), compound of formula (15), compound of formula (15-102), compound of formula (16), compound of formula (20c), compound of formula (20), compound of formula (21), compound of formula (22), compound of formula (23), compound of formula (24), compound of formula (25), compound of formula (26), compound of formula (20-CAMPTO), compound of formula (21-CAMPTO), compound of formula (22-CAMPTO), compound of formula (23-CAMPTO), compound of formula (21-TAXO-t1-1), compound of formula (30), compound of formula (31), compound of formula (32), compound of formula (33), compound of formula (34), compound of formula (35), compound of formula (36), compound of formula (300), compound of formula (320), compound of formula (40), compound of formula (41), compound of formula (42), compound of formula (43), compound of formula (44), compound of formula (45), compound of formula (46), compound of formula (400), compound of formula (400a), compound of formula (50), compound of formula (50-1), compound of formula (51), compound of formula (51-1), compound of formula (52), compound of formula (52-1), compound of formula (53), compound of formula (53-1), compound of formula (54), compound of formula (54-1), compound of formula (54-2), compound of formula (54-3), compound of formula (55), compound of formula (55-1), compound of formula (56), compound of formula (56-1), compound of formula (500), compound of formula (6), compound of formula (6-1), compound of formula (6-2), compound of formula (6-3), compound of formula (6-4), compound of formula (6b), compound of formula (6b-1), compound of formula (6b-2), compound of formula (6b-3), compound of formula (6b-4), compound of formula (6c) and compound of formula (6-5); with these compounds being as defined herein.

Further subject of the invention is the use of the compound of formula (I), the compound of formula (I) being as defined herein, also in all its preferred embodiments, for the preparation of a pharmaceutical composition or of a drug.

Further subject of the invention is a pharmaceutical composition or a drug, wherein the pharmaceutical composition and the drug comprise the compound of formula (I), the compound of formula (I) being as defined herein, also in all its preferred embodiments.

Further subject of the invention is a compound of formula (I), a pharmaceutical composition or a drug, wherein the pharmaceutical composition and the drug comprise the compound of formula (I), the compound of formula (I) being as defined herein, also in all its preferred embodiments,
for use in treatment of a disease or an illness, preferably of cancer.

Compound of formula (II) can be readily covalently attached to a ligand LI. It was surprising, that the protein drug conjugates of the instant invention, which comprise a connecting group CG2, CG2 being derived from o-hydroxy-p-amino benzylic alcohol, and which comprise a linear peptide residue, in particular the compounds of formula (I), show increased plasma stability, and release the drug without the drug being chemically modified, Furthermore, they show good water solubility and low aggregation.

ABBREVIATIONS
DCM dichoromethane
DIBAL-H diisobutylaluminium hydride
DIPEA N,N-diisopropylethylamine
DMA N,N-dimethylacetamide
DMAP 4-dimethylaminopyridine
DMF N,N-dimethylformamide
EDTA ethylenediaminetetraacetic acid
EEDQ 2-ethoxy-1-ethoxycarbonyl-1,2-dihydroquinoline
ESI-MS electrospray ionisation mass spectrometry
EtOAc ethyl acetate
HIC hydrophobic interaction chromatography
MeCN acetonitrile
NAP-25 column NAP-25 columns of GE Healthcare are disposable columns prepacked with Sephadex™ G-25 DNA Grade and require only gravity to run
NMR nuclear magnetic resonance
PE petroleum ether
Rf retention factor in TLC
RP-HPLC reversed phase HPLC
RT room temperature
SAFC Sigma Aldrich Fine Chemicals
SEC-HPLC size exclusion chromatography HPLC
TBTU 2-(1H-benzotriazole-1-yl)-1,1,3,3-tetramethylaminium tetrafluoroborate
THF tetrahydrofurane
TFA Trifluoroacetic acid
TLC thin layer chromatography
Raw Materials
compound of formula (DOXO) doxorubicin, commercially available as hydrochloride salt from Beijing Zhongshuo Pharmaceutical Technology Development Co. Ltd.
daunorubicin commercially available as hydrochloride salt from Aldrich
PBS The PBS used in the experiments had the composition KH2PO4: 144 mg/L, NaCl: 9000 mg/L and Na2HPO4: 795 mg/L

EXAMPLE 1

To a mixture of p-amino salicylic acid (15.0 g) and MeOH (113.0 ml) at 0° C., conc. $H_2SO_4$ (30.0 ml) was added dropwise. The resulting mixture was heated to reflux and stirred for 2 hours to form a homogeneous solution. The reaction mixture was then cooled to RT. Water (360 ml) was added, followed by solid $NaHCO_3$ until pH 7. The resulting mixture was filtered, the wet cake was washed with water (3 times with 80 mL each) and dried under vacuum at 55° C. to afford 14.7 g of compound of formula (VII-1) as a solid (89% yield).

$^1$H NMR (400 MHz, $CDCl_3$, 20° C.) delta 3.90 (1H, s), 4.12 (2H, brs), 6.16 to 6.19 (2H, m), 7.62 to 7.65 (1H, m).
ESI-MS: 168.0 (M+H)+

EXAMPLE 2

To a mixture of H-Cit-OH (40.0 g, 1.0 eq.) and $Na_2CO_3$ (50.0 g, 2.0 eq.) in water (300 ml) and THF (150 ml), a solution of di-tert-butyl dicarbonate (60.0 g, 1.2 eq.) in THF (100 ml) was added dropwise within 1 hour. The resulting mixture was allowed to stir at RT overnight. After that, the suspension was washed with PE (2 times with 150 ml each), then the mixture was concentrated to about 300 ml under vacuum. The mixture was acidified to pH 2 with 4.0 M aqueous $KHSO_4$, then extracted with EtOAc (5 times with 150 ml each). The organic phases were combined and washed with saturated brine (100 ml), dried over anhydrous $Na_2SO_4$ and filtered. The filtrate was evaporated to dryness to afford 52.0 g of Boc-Cit-OH as white solid (83% yield).

$^1$H NMR (400 MHz, DMSO-$d_6$, 20° C.) delta 1.38 (9H, s), 1.36 to 1.43 (2H, m), 1.47 to 1.69 (2H, m), 2.93 (2H, q, J=6.3 Hz), 3.82 to 3.87 (1H, m), 5.36 (2H, brs), 5.92 (1H, t, J=5.6 Hz), 7.07 (1H, d, J=8.0 Hz), 12.44 (1H, brs).
ESI-MS: 275.8 (M+H)+, 550.8 (2M+H)+

EXAMPLE 3

Boc-Cit-OH (53.0 g, 1.0 eq.), prepared according to example 2, and EEDQ (72.0 g, 1.5 eq.) were added to THF (400 ml). To this mixture was then added compound of formula (VII-1) (49.0 g, 1.5 eq.), prepared according to example 1. The resulting mixture was stirred at RT for 14 hours. Then the reaction mixture was diluted with water (500 ml), extracted with EtOAc (3 times with 250 ml each). The organic phases were combined and washed with 1.0 M aqueous solution of citric acid (2 time with 150 ml each) and saturated brine (150 ml). After that, the organic phase was dried over anhydrous $Na_2SO_4$, then concentrated to dryness, the crude product was purified by silica gel chromatography (eluent PE:EtOAc=4:1 to 2:1 to 1:1 (v/v) to pure EtOAc) and isolated to afford 62.5 g of compound of formula (6-4) as yellow solid (76% yield).

Analysis by silica gel TLC: EtOAc as eluent (Rf=0.3, UV254)

$^1$H NMR (400 MHz, $CDCl_3$, 20° C.) delta 1.40 (9H, s), 1.57 to 1.83 (4H, m), 3.08 to 3.16 (2H, m), 3.90 (3H, s), 4.43 (1H, s), 5.26 (2H, s), 5.85 (2H, s), 7.11 (1H, d, J=8.8 Hz), 7.28 (1H, s), 7.68 (1H, d, J=8.8 Hz), 9.74 (1H, s), 10.82 (1H, brs).
ESI-MS: 325.2 (M-tBuOCO+2H)+

EXAMPLE 4

Compound of formula (6-4) (62.0 g, 1 eq.), prepared according to example 3, was suspended in a solution of 15% (w/w) HCl in 1,4-dioxane (100 ml), the resulting mixture was stirred at RT for 1 hour. The reaction mixture was then concentrated under vacuum to afford 51.6 g of compound of formula (6-3) as HCl salt, being a white solid (98% yield).

EXAMPLE 5

Compound of formula (6-3) as HCl salt (75.6 g, 1.0 eq.), prepared according to example 4, Boc-L-Val (43.0 g, 1.0 eq.) and TBTU (135.5 g, 2.0 eq.) were dissolved in DMF (250 ml). Then DIPEA (71.2 g, 2.6 eq.) was added. The resulting solution was stirred at RT for 17 h. The reaction mixture was then diluted with water (750 ml), extracted with EtOAc (5 times with 200 ml each), the organic phases were combined and washed with 1.0 M aqueous $NaHCO_3$ solution (3 times with 300 ml each) and then with saturated brine (150 ml). The organic phase was collected and concentrated to dryness, the crude product was then purified by silica gel chromatography (eluent DCM:MeOH=20:1 to 10:1 to 7:1 (v/v) and isolated to afford 62.0 g of compound of formula (6-2) as a solid (57% yield).

Analysis by silica gel TLC: DCM:MeOH=6:1 (v/v) as eluent (Rf=0.4, UV254)

$^1$H NMR (400 MHz, DMSO-$d_6$, 20° C.) delta 0.84 (6H, dd, J1=17.2 Hz, J2=6.8 Hz), 1.39 (9H, s), 1.42 to 1.51 (2H, m), 1.55 to 1.73 (2H, m), 1.93 to 1.98 (1H, m), 2.90 to 3.08 (2H, m), 3.82 to 3.84 (1H, m), 3.88 (3H, s), 4.39 to 4.45 (1H, m), 5.43 (2H, s), 6.01 (1H, t, J=5.8 Hz), 6.72 (1H, d, J=8.8

Hz), 7.09 (1H, dd, J1=8.8 Hz, J2=2.0 Hz), 7.73 (1H, d, J=8.8 Hz), 8.08 (1H, d, J=7.2 Hz), 10.34 (1H, s), 10.62 (1H, brs).
ESI-MS: 524.3 (M+H)+, 424.3 (M-tBuOCO+2H)+

EXAMPLE 6

Compound of formula (6-2) (62.0 g, 1 eq.), prepared according to example 5, was suspended in a solution of 15% (w/w) HCl in 1,4-dioxane (200 ml), the resulting mixture was stirred at RT for 1 hour. The reaction mixture was then concentrated under vacuum to afford 52.4 g of compound of formula (6-1) as HCl salt, being a white solid (97% yield).

EXAMPLE 7

Compound of formula (6-1) as HCl salt (52.4 g, 1.0 eq.), prepared according to example 6, acetic anhydride (60.0 g, 5.0 eq.), pyridine (100.0 g, 11.0 eq.) and methanol (150 ml) were mixed and stirred at RT for 7 days. The suspension was filtered and the resulting wet cake was washed with MeOH (4 times with 200 ml each), then dried under vacuum to afford 32.9 g of compound of formula (6) as a white solid (62% yield).
$^1$H NMR (400 MHz, DMSO-$d_6$, 20° C.) delta 0.86 (6H, dd, J1=12.4 Hz, J2=6.8 Hz), 1.35 to 1.50 (2H, m), 1.56 to 1.74 (2H, m), 1.87 (3H, s), 1.94 to 2.00 (1H, m), 2.93 to 3.06 (2H, m), 3.87 (3H, s), 4.20 (1H, t, J=7.6 Hz), 4.34 to 4.39 (1H, m), 5.43 (2H, s), 6.00 (1H, t, J=5.2 Hz), 7.11 (1H, dd, J1=8.8 Hz, J2=1.6 Hz), 7.41 (1H, d, J=1.6 Hz), 7.73 (1H, d, J=8.8 Hz), 7.89 (1H, d, J=8.4 Hz), 8.21 (1H, d, J=7.2 Hz), 10.24 (1H, s), 10.62 (1H, s).
ESI-MS: 466.3 (M+H)+, 931.3 (2M+H)+

EXAMPLE 8

Compound of formula (MA) (5.5 g, 1.0 eq.) and beta-alanine (5.0 g, 1.0 eq.) in DMF (30.0 ml), were stirred under nitrogen atmosphere for 2 hours. The mixture was then cooled to 0° C. Compound of formula (HOSu) (8.0 g, 1.3 eq.) and DCC (24.0 g, 2.0 eq.) were added. Then the reaction mixture was allowed to warm up to RT and stirred at RT overnight. The reaction mixture was then filtered, the resulting wet cake was washed with DMF (40.0 ml), the organic phases were combined and then diluted with water (120 ml) and extracted with DCM (3 times with 50 ml each). The organic phases were combined, washed with water (50 ml), then with 5% (w/w) aqueous NaHCO3 solution (50 ml) and then with saturated brine (50 ml). The organic phase was dried over anhydrous Na$_2$SO$_4$, then concentrated until solid started to precipitate. Then PE (20 ml) was added to the mixture and the resulting mixture was stirred at RT for 10 min. The mixture was then filtered, the wet cake was washed with PE (20 ml) and then dried under vacuum at 40° C. overnight to afford 4.0 g of compound of formula (CG1MR-IV-1) as a white solid (27% yield).

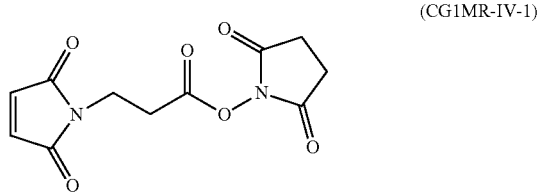 [SMILES: O=C(CCN1C(=O)C=CC1=O)ON1C(=O)CCC1=O]
(CG1MR-IV-1)

$^1$H NMR (400 MHz, CDCl$_3$, 20° C.) delta 2.84 (4H, s), 3.04 (2H, t, J=7.0 Hz), 3.95 (2H, t, J=7.0 Hz), 6.75 (2H, s).
ESI-MS: 267.2 (M+H)+, 289.4 (M+Na)+

EXAMPLE 9

To a mixture of compound of formula (HSGH-II-1) (10.0 g, 1.0 eq.), MeOH (50 ml) and Et3N (10.7 g, 1.1 eq.), a solution of Boc$_2$O in MeOH (22.8 g, 1.1 eq. Boc$_2$O in 50 ml MeOH) was added dropwise. Then the resulting mixture was stirred at RT for 15 hours and then dried under vacuum to afford 20.0 g of compound of formula (Boc-HSGH-II-1) as a slightly yellow oil (quantitative yield).

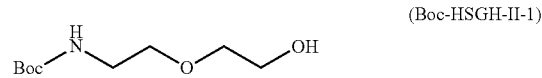 [SMILES: CC(C)(C)OC(=O)NCCOCCO]
(Boc-HSGH-II-1)

$^1$H NMR (400 MHz, CDCl$_3$, 20° C.) delta 1.44 (9H, s), 2.73 (1H, brs), 3.32 (2H, q, J=5.2 Hz), 3.54 to 3.58 (4H, m), 3.72 to 3.74 (2H, m), 5.15 (1H, brs).

EXAMPLE 10

To a mixture of compound of formula (Boc-HSGH-II-1) (6.17 g, 1 eq.), prepared according to example 9, pyridine (2.86 g, 1.2 eq) and DCM (30 ml) at 0° C., DMAP (0.366 g, 0.1 eq) were added. A mixture of tosyl chloride (6.31 g, 1.1 eq) and DCM (45 ml) was added dropwise. The resulting mixture was stirred at RT for 8 days. Then the resulting mixture was poured onto DCM (100 ml), the resulting mixture was washed with water (1 time with 100 ml), the organic phase was then dried over anhydrous Na$_2$SO$_4$. The resulting solution was further concentrated and purified by silica gel chromatography (PE:EtOAc=6:1 to PE:EtOAc=1:1 (v/v)) to afford 8.1 g of compound of formula (SGM-II-1) as a colorless oil (75% yield).
$^1$H NMR (400 MHz, DMSO-$d_6$, 20° C.) delta 0.86 (6H, dd, J1=12.4 Hz, J2=6.8 Hz), 1.35 to 1.50 (2H, m), 1.56 to 1.74 (2H, m), 1.87 (3H, s), 1.94 to 2.00 (1H, m), 2.93 to 3.06 (2H, m), 3.87 (3H, s), 4.20 (1H, t, J=7.6 Hz), 4.34 to 4.39 (1H, m), 5.43 (2H, s), 6.00 (1H, t, J=5.2 Hz), 7.11 (1H, dd, J1=8.8 Hz, J2=1.6 Hz), 7.41 (1H, d, J=1.6 Hz), 7.73 (1H, d, J=8.8 Hz), 7.89 (1H, d, J=8.4 Hz), 8.21 (1H, d, J=7.2 Hz), 10.24 (1H, s), 10.62 (1H, s).

EXAMPLE 11

A mixture of compound of formula (6) (3.00 g, 1 eq), prepared according to example 7, compound of formula (SGM-II-1) (4.65 g, 2 eq), prepared according to example 10, K$_2$CO$_3$ (1.82 g, 2 eq) and anhydrous DMF (30 ml) was heated to 50° C. and stirred under nitrogen atmosphere for 7 days. Then the reaction mixture was concentrated to dryness under vacuum. To the residue methanol (30 ml) was added, the resulting mixture was stirred for 10 min and then filtered. The wet cake was washed with methanol (3 times with 10 ml each). The organic phase were combined and then concentrated. The residue was purified by silica gel column chromatography (DCM:MeOH=7:1 (v/v)) to afford 3.40 g of compound of formula (50-1) as a slightly yellow solid (81% yield).
$^1$H NMR (400 MHz, DMSO-$d_6$, 20° C.) δ 0.86 (6H, dd, J1=12.8 Hz, J2=6.8 Hz), 1.38 to 1.51 (2H, m), 1.56 to 1.80 (2H, m), 1.89 (3H, s), 1.92 to 2.01 (1H, m), 2.92 to 3.05 (2H, m), 3.07 to 3.12 (2H, m), 3.50 (2H, t, J=6.0 Hz), 3.75 to 3.77

(5H, m), 4.08 to 4.10 (2H, m), 4.20 (1H, dd, J1=8.4 Hz, J2=6.8 Hz), 4.34 to 4.40 (1H, m), 5.42 (2H, s), 5.99 (1H, t, J=5.8 Hz), 6.74 (1H, t, J=5.6 Hz), 7.26 (1H, dd, J1=8.4 Hz, J2=1.6 Hz), 7.49 (1H, d, J=2.0 Hz), 7.68 (1H, d, J=8.8 Hz), 7.91 (1H, d, J=8.4 Hz), 8.19 (1H, d, J=7.6 Hz), 10.20 (1H, s).

ESI-MS: 653.4 (M+H)+, 675.5 (M+Na)+, 553.5 (M-tBuOCO+2H)+

EXAMPLE 12

A mixture of compound of formula (50-1) (500 mg), prepared according to example 11, and a solution of 10% (w/w) HCl in 1,4-dioxane (10 ml) was stirred at RT for 15 hours. The solvent was removed under vacuum to afford 431 mg of compound of formula (50) as HCl salt, being a slightly yellow solid (quantitative yield).

ESI-MS: 553.5 (M+H)+, 1105.2 (2M+H)+

EXAMPLE 13

To a mixture of compound of formula (50) as HCl salt (1.10 g, 1.0 eq), prepared according to example 12, and anhydrous THF (20 ml) at −30° C. was added a solution of DIBAL-H in hexanes (1 M, 11.9 ml, 6.0 eq). The resulting mixture was then heated to 0° C. and stirred under nitrogen atmosphere for 15 hours. Then methanol (2.0 mL) was added. Then saturated aqueous potassium sodium tartrate solution (10 ml) was added to the mixture and the mixture was stirred for 30 min at RT. The resulting mixture was evaporated to dryness to generate a white residue which was washed with methanol (5 times with 10 ml each). The combined organic phases were concentrated and purified by silica gel column chromatography (DCM:MeOH:Et3N=65:33:2 (v/v)) to afford 0.65 g of compound of formula (40) as a white solid (72% yield).

$^1$H NMR (400 MHz, DMSO-d$_6$, 60° C.) delta 0.86 (6H, t, J=6.6 Hz), 1.37 to 1.53 (2H, m), 1.63 to 1.79 (2H, m), 1.92 (3H, s), 1.99 to 2.07 (1H, m), 2.70 (2H, brs), 2.99 to 3.02 (2H, m), 3.47 (2H, t, J=5.6 Hz), 4.07 (2H, t, J=5.8 Hz), 4.18 (1H, t, J=7.6 Hz), 4.34 to 4.41 (1H, m), 5.25 (2H, s), 5.90 (1H, brs), 7.16 (1H, d, J=8.0 Hz), 7.26 (2H, d, J=8.0 Hz), 7.32 (1H, s), 7.76 (1H, d, J=7.6 Hz), 7.91 (1H, d, J=4.4 Hz), 9.69 (1H, s).

ESI-MS: 525.6 (M+H)+

EXAMPLE 14

To a mixture of compound of formula (40) (500.2 mg, 1.0 eq.), prepared according to example 13, compound of formula (CG1MR-IV-1) (281.0 mg, 1.1 eq) prepared according to example 8, and DMF (9.5 ml) at RT, DIPEA (140.3 mg, 1.1 eq) was added. The resulting mixture was stirred at RT for 17 hours. Then the DMF was removed under vacuum to afford a slightly yellow residue. The residue was then mixed with acetone (10 ml) and stirred at RT for 18 h. The mixture was filtered, the wet cake was washed with acetone (2 times with 5 ml each), then dried under vacuum to afford 515.0 mg of compound of formula (30) as a slightly yellow solid (80% yield).

$^1$H NMR (400 MHz, DMSO-d$_6$, 20° C.) delta 0.86 (6H, dd, J1=11.2 Hz, J2=6.8 Hz), 1.32 to 1.48 (2H, m), 1.55 to 1.76 (2H, m), 1.89 (3H, s), 1.94 to 2.02 (1H, m), 2.33 (2H, t, J=7.2 Hz), 2.93 to 3.04 (2H, m), 3.16 to 3.20 (2H, q, J=5.6 Hz), 3.46 (2H, t, J=5.8 Hz), 3.60 (2H, t, J=7.8 Hz), 3.73 (2H, t, J=4.6 Hz), 4.04 (2H, t, J=4.6 Hz), 4.18 (1H, dd, J1=8.4 Hz, J2=6.8 Hz), 4.34 to 4.39 (1H, m), 4.44 (2H, s), 4.88 (1H, brs), 5.42 (2H, s), 6.00 (1H, t, J=5.4 Hz), 7.00 (2H, s), 7.16 (1H, dd, J1=8.4 Hz, J2=2.0 Hz), 7.26 (1H, d, J=8.4 Hz), 7.32 (1H, d, J=1.6 Hz), 7.92 (1H, d, J=8.4 Hz), 8.05 (1H, t, J=5.6 Hz), 8.12 (1H, d, J=7.6 Hz), 9.88 (1H, s).

EXAMPLE 15

A mixture of compound of formula (30) (400 mg, 1.0 eq), prepared according to example 14, DIPEA (231.0 mg, 3.0 eq), 4 angstrom molecular sieves (800 mg) and dry DMF (8.0 ml) was stirred for 5 min. Then compound of formula (II-1) (361.2 mg, 2 eq) was added. The resulting mixture was stirred for 3 h at RT. Then compound of formula (DOXO) as HCl salt (342.8 mg, 1.0 eq) was added and the mixture was stirred for 4 hours. Then MeCN (40.0 ml) was added. A precipitate had formed and was filtered and washed with a mixture of MeCN and DMF (5:1 (v/v), 2 times with 5 ml each). The filtrates were combined and dried under vacuum at 45° C. to get a dark red residue. The residue was washed with MeCN (2 times with 10 ml each), then the residue was dissolved in a mixture of acetone and water (20:1 (v/v)) and purified by preparative silica gel TLC (DCM:MeOH=5:1 (v/v), Rf=0.15). The product was extracted from the silica-gel by a mixture of acetone and water (20:1 (v/v), 6 times with 20 ml each), the combined extraction solutions were dried under vacuum to afford a crude product as a red solid. The crude product was then mixed with acetonitrile (5.0 ml), the mixture was stirred at RT for 5 hours and then filtered. The presscake was mixed with acetonitrile (5.0 ml) and the mixture stirred for 3 hours at RT. The mixture was then filtered. The presscake was dried under vacuum at RT to afford 48.0 mg of compound of formula (20) as a red solid (7% yield).

$^1$H NMR (400 MHz, DMSO-d$_6$, 20° C.) delta 0.85 (6H, dd, J1=11.2 Hz, J2=6.8 Hz), 1.13 (3H, d, J=6.4 Hz), 1.34 to 1.47 (3H, m), 1.57 to 1.72 (2H, m), 1.82 to 1.90 (1H, m), 1.90 (3H, s), 1.93 to 1.98 (1H, m), 2.08 to 2.22 (2H, m), 2.29 (2H, t, J=7.2 Hz), 2.91 to 3.01 (4H, m), 3.11 to 3.16 (2H, m), 3.41 (2H, t, J=5.6 Hz), 3.45 to 3.46 (1H, m), 3.54 (2H, t, J=7.2 Hz), 3.68 to 3.74 (3H, m), 3.98 (3H, s), 4.03 (2H, t, J=4.0 Hz), 4.17 (2H, t, J=7.6 Hz), 4.32 to 4.38 (1H, m), 4.58 (2H, d, J=5.2 Hz), 4.69 (2H, d, J=5.6 Hz), 4.85 to 4.89 (2H, m), 4.94 (1H, brs), 5.22 (1H, brs), 5.40 (2H, s), 5.46 (1H, brs), 5.98 (1H, t, J=4.8 Hz), 6.80 (1H, d, J=8.0 Hz), 6.95 (2H, s), 7.12 (1H, d, J=8.4 Hz), 7.19 (1H, d, J=8.4 Hz), 7.36 (1H, s), 7.64 (1H, brs), 7.89 to 7.91 (3H, m), 7.99 (1H, t, J=5.2 Hz), 8.10 (1H, d, J=7.2 Hz), 9.92 (1H, s), 13.26 (1H, s), 14.02 (1H, s).

ESI-MS: 1245.5 (M+H)+

EXAMPLE 16

To a mixture of compound of formula (HSGH-III-1) (110.16 g, 5 eq) and dioxane (400 ml) at 0° C., a mixture of Boc$_2$O (22.10 g, 1 eq) in dioxane (200 ml) was added dropwise. The resulting mixture was then heated to RT and then stirred for 20 hours. Then the solvent was removed under vacuum. The resulting residue was added to water (300 ml), the resulting mixture was extracted with DCM (2 times with 300 ml each). The organic layer was dried over anhydrous Na$_2$SO$_4$ and then evaporated to dryness. The residue was purified by silica gel column chromatography (DCM:EtOAc=1:1 (v/v), then with DCM:MeOH:Et3N=89:9:2 (v/v)) to afford 17.7 g of compound of formula (Boc-HSGH-III-1) as a slightly yellow oil (55% yield).

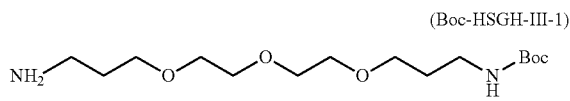
(Boc-HSGH-III-1)

1H NMR (400 MHz, CDCl3, 20° C.) δ 1.44 (9H, s), 1.64 (2H, s), 1.72-1.78 (4H, m), 2.81 (2H, t, J=6.6 Hz), 3.23 (2H, q, J=6.0 Hz), 3.55-3.62 (8H, m), 3.64-3.66 (4H, m), 5.14 (1H, brs).

EXAMPLE 17

To a mixture of compound of formula (Boc-HSGH-III-1) (5.00 g, 1.0 eq), prepared according to example 18, $K_2CO_3$ (4.30 g, 2.0 eq) and DCM (40 ml) at 0° C., a mixture of compound of formula (HSGHReac-1) (2.17 g, 1.2 eq) in DCM (20 ml) was added dropwise within 1 hour. The resulting mixture was warmed to RT and stirred for 20 hours. Then the solid was filtered, the cake was washed with DCM (2 times with 5 ml each). The filtrates were combined and evaporated to dryness. The residue was then purified by silica gel column chromatography (eluent EtOAc:PE=3:1) to afford 5.6 g of compound of formula (SGM-III-1) as a slightly yellow oil (90% yield).

$^1$H NMR (400 MHz, CDCl3, 20° C.) δ 1.44 (9H, s), 1.64 (2H, s), 1.73-1.86 (4H, m), 3.23 (2H, q, J=6.0 Hz), 3.44 (2H, q, J=6.0 Hz), 3.54 (2H, t, J=6.0 Hz), 3.58-3.66 (10H, m), 4.04 (2H, s), 4.98 (1H, brs), 7.31 (1H, brs).

EXAMPLE 18

Compound of formula (6) (5.80 g, 1.0 eq), prepared according to example 7, $K_2CO_3$ (5.18 g, 2.0 eq), compound of formula (SGM-III-1) (9.95 g, 2.0 eq), prepared according to example 17, and DMF (45 ml) were mixed. The resulting mixture was then heated to 50° C. and stirred for 7 days under nitrogen atmosphere. The resulting reaction mixture was evaporated to dryness under vacuum. Methanol (40 ml) was added to the residue, the resulting mixture was stirred for 10 min and then filtered. The wet cake was washed with methanol (3 times with 10 ml each). The organic filtrates were collected and combined and then evaporated. The residue was purified by silica gel column chromatography (DCM:MeOH=7:1 (v/v)) to afford 7.20 g of compound of formula (51-1) as a slightly yellow solid (70% yield).

$^1$H NMR (400 MHz, DMSO-$d_6$, 20° C.) delta 0.86 (6H, dd, J1=13.6 Hz, J2=6.8 Hz), 1.32 to 1.49 (2H, m), 1.37 (9H, s), 1.55 to 1.78 (6H, m), 1.89 (3H, s), 1.94 to 1.99 (1H, m), 2.93 to 3.07 (4H, m), 3.26 (2H, q, J=6.8 Hz), 3.37 (2H, t, J=6.4 Hz), 3.43 to 3.52 (10H, m), 3.81 (3H, s), 4.20 (1H, dd, J1=8.4 Hz, J2=6.8 Hz), 4.35 to 4.41 (1H, m), 4.53 (2H, s), 5.44 (2H, s), 6.03 (1H, t, J=5.6 Hz), 6.74 (1H, t, J=5.6 Hz), 7.36 (1H, dd, J1=8.4 Hz, J2=2.0 Hz), 7.41 (1H, d, J=2.0 Hz), 7.80 (1H, d, J=8.8 Hz), 7.90 (1H, d, J=8.4 Hz), 8.06 (1H, t, J=5.6 Hz), 8.21 (1H, d, J=7.2 Hz), 10.32 (1H, s).

ESI-MS: 726.6 (M-tBuOCO+2H)+, 826.3 (M+H)+, 848.5 (M+Na)+

EXAMPLE 19

Compound of formula (51-1) (1.00 g), prepared according to example 18, and a solution of 15% (v/v) HCl in 1,4-dioxane (10 ml) were mixed. The mixture was stirred at RT for 3 hours. The solvent was removed under vacuum to afford 0.99 g of compound of formula (51) as HCl salt, being a slightly yellow solid (quantitative yield).

ESI-MS: 726.6 (M+H)+

EXAMPLE 20

A mixture of compound of formula (51) as HCl salt (6.08 g, 1 eq), prepared according to example 19, water (100 ml), $CaCl_2$ (1.86 g, 2.0 eq), and $NaBH_4$ (1.27 g, 4.0 eq) was stirred at RT. Further $NaBH_4$ was added portion wise (1.27 g, 4.0 eq. after a total of 15 hours stirring; 1.27 g, 4.0 eq. after a total of 20 hours stirring; 1.27 g, 4.0 eq. after a total of 24 hours of stirring). After a total of 36 hours of stirring, MeOH (30 ml) was added to the mixture. The reaction mixture was then filtered and the wet cake was washed with MeOH (3 times with 10 ml each). The liquid phase was collected, combined and then evaporated to dryness. The residue was purified by silica gel column chromatography (eluent DCM:MeOH:Et3N=65:33:2 (v/v)) to afford 2.70 g of compound of formula (41) as a slightly yellow solid (48% yield).

$^1$H NMR (400 MHz, DMSO-$d_6$, 20° C.) delta 0.86 (6H, dd, J1=10.8 Hz, J2=6.8 Hz), 1.31 to 1.49 (2H, m), 1.55 to 1.82 (6H, m), 1.90 (3H, s), 1.93 to 2.02 (1H, m), 2.82 (2H, t, J=7.4 Hz), 2.98 to 3.05 (2H, m), 3.15 to 3.20 (2H, q, J=6.8 Hz), 3.34 to 3.51 (12H, m), 4.16 to 4.20 (1H, m), 4.34 to 4.41 (1H, m), 4.46 (2H, s), 4.50 (2H, s), 5.47 (2H, s), 6.13 (1H, t, J=5.6 Hz), 7.25 (2H, s), 7.26 (1H, s), 7.95 (1H, d, J=8.8 Hz), 8.10 (1H, t, J=5.6 Hz), 8.14 (1H, d, J=7.6 Hz), 10.01 (1H, s).

ESI-MS: 698.7 (M+H)+

EXAMPLE 21

Compound of formula (41) (2.78 g, 1.0 eq.), prepared according to example 20, compound of formula (CG1MR-IV-1) (1.18 g, 1.1 eq), prepared according to example 8, and DMF (30 ml) were mixed at RT. Then DIPEA (0.58 g, 1.1 eq) was added. The resulting mixture was stirred at RT for 16 hours. Then DMF was removed under vacuum to afford a slightly yellow residue. The residue was then mixed with acetone (30 ml) and the mixture was stirred at RT for 5 hours. Then the mixture was filtered, the wet cake was washed with acetone (2 times with 15 ml each) and then dried under vacuum to afford 2.55 g of compound of formula (31) as a slightly yellow solid (75% yield).

$^1$H NMR (400 MHz, DMSO-$d_6$, 20° C.) delta 0.86 (6H, dd, J1=11.2 Hz, J2=6.8 Hz), 1.32 to 1.48 (2H, m), 1.55 to 1.73 (2H, m), 1.89 (3H, s), 1.93 to 2.01 (1H, m), 2.31 (2H, t, J=7.2 Hz), 2.90 to 3.11 (4H, m), 3.17 (2H, q, J=6.4 Hz), 3.36 (2H, t, J=6.4 Hz), 3.44 to 3.60 (8H, m), 3.60 (2H, t, J=7.2 Hz), 4.19 (1H, dd, J1=8.4 Hz, J2=6.8 Hz), 4.35 to 4.40 (1H, m), 4.46 (2H, s), 4.51 (2H, s), 5.08 (1H, brs), 5.42 (2H, s), 6.00 (1H, t, J=5.6 Hz), 7.00 (2H, s), 7.22 (1H, s), 7.25 (1H, s), 7.89 to 7.91 (1H, m), 8.04 (1H, t, J=5.6 Hz), 8.10 (1H, d, J=7.6 Hz), 9.92 (1H, s).

ESI-MS: 831.6 (M-OH)+, 849.4 (M+H)+

EXAMPLE 22

A mixture of compound of formula (31) (500.4 mg, 1.0 eq), prepared according to example 21, DIPEA (305.7 mg, 4.0 eq), 4 angstrom molecular sieves (500.5 mg) and dry DMF (10.0 ml) was stirred for 5 min. Then compound of formula (II-1) (271.1 mg, 1.5 eq.) was added. The resulting mixture was stirred for 5 hours at RT. Then compound of formula (DOXO) as HCl salt (342.8 mg, 1.0 eq.) was added and the resulting mixture was stirred for 3.5 hours. Then MeCN (50.0 ml) was added. A precipitate had formed and was filtered and washed with a mixture of MeCN with DMF (5:1 (v/v), 3 times with 10 ml each). The filtrates were combined and dried under vacuum at 45° C. to afford a dark red residue. The residue was dissolved in a mixture of DCM with MeOH (7:1 (v/v)) and purified by preparative silica gel TLC (DCM:MeOH=7:1 (v/v), Rf=0.15). The product was extracted from the silica gel by a mixture of acetone with water (20:1 (v/v), 5 times with 50 ml each), the combined extracts were dried under vacuum to afford the crude product as a red solid. The crude product was then mixed with acetonitrile (30 ml), the mixture was stirred at RT for 18 hours and was then filtered. The cake was mixed with acetonitrile (10 ml) and the mixture was stirred for 3 hours at RT. The mixture was then filtered. The cake was dried under vacuum at RT to afford 100.3 mg of compound of formula (21) as a red solid (12% yield).

$^1$H NMR (400 MHz, DMSO-$d_6$, 20° C.) delta 0.85 (6H, dd, J1=11.8 Hz, J2=6.8 Hz), 1.13 (3H, d, J=6.4 Hz), 1.34 to 1.68 (9H, m), 1.82 to 1.90 (1H, m), 1.90 (3H, s), 1.93 to 2.00 (1H, m), 2.13 to 2.24 (2H, m), 2.30 (2H, t, J=7.2 Hz), 2.91 to 3.04 (6H, m), 3.10 to 3.15 (2H, m), 3.29 (2H, t, J=6.0 Hz), 3.37 to 3.49 (11H, m), 3.59 (2H, t, J=7.2 Hz), 3.68 to 3.76 (1H, m), 3.99 (3H, s), 4.13 to 4.19 (2H, m), 4.33 to 4.41 (3H, m), 4.58 (2H, d, J=5.6 Hz), 4.71 (1H, d, J=5.2 Hz), 4.86 (1H, t, J=5.8 Hz), 4.95 (1H, brs), 5.02 (2H, s), 5.23 (1H, brs), 5.41 (2H, s), 5.46 (1H, brs), 5.99 (1H, t, J=4.6 Hz), 6.87 (1H, d, J=7.2 Hz), 7.00 (2H, s), 7.21 to 7.25 (3H, m), 7.66 (1H, t, J=4.6 Hz), 8.11 (1H, d, J=7.2 Hz), 9.97 (1H, s), 13.28 (1H, s), 14.04 (1H, s).

ESI-MS: 1417.8 (M+H)+

EXAMPLE 23

To a mixture of compound of formula (HSGH-III-2) (84.9 g, 5.0 eq.) and CHCl$_3$ (500 ml) was added a mixture of Boc$_2$O (50.0 g, 1.0 eq.) in CHCl$_3$ (200 ml) dropwise within 2 hours at room temperature. The resulting solution was stirred for 16 hours at RT. The resulting suspension was filtered and the wet cake was washed with DCM (50 ml). The filtrate was combined and evaporated to dryness to afford a colorless oil. The oil was then dissolved in DCM (200 ml), washed with water (300 ml) and dried over anhydrous Na$_2$SO$_4$. The resulting organic phase was then evaporated to dryness and the product purified by silica gel column chromatography (eluent DCM:MeOH=20:1 to 5:1 (v/v)) to afford 13.0 g of compound of formula (Boc-HSGH-III-2) (33% yield).

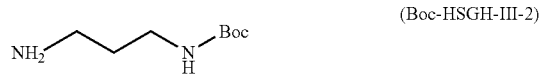 [SMILES: CC(C)(C)OC(=O)NCCCN]
(Boc-HSGH-III-2)

$^1$H NMR (400 MHz, CDCl$_3$, 20° C.) delta 1.32 (9H, s), 1.46-1.53 (4H, m), 2.64 (2H, t, J=6.4 Hz), 3.06 to 3.09 (2H, m), 5.22 (1H, brs).

EXAMPLE 24

To a mixture of compound of formula (Boc-HSGH-III-2) (11.3 g), prepared according to example 23, K$_2$CO$_3$ (18.0 g) and DCM (200 ml) at 0° C. was added a mixture of compound of formula (HSGHReac-1) with DCM (50 ml) dropwise within 40 min. The resulting mixture was then heated to RT and stirred for 2 hours. Then aqueous citric acid solution (% by weight, based on the weight of the solution, 180 ml) was added. The organic phase was separated and washed with saturated brine (100 ml), dried over anhydrous Na$_2$SO$_4$ and then evaporated to dryness. The residue was then purified by silica gel column chromatography (eluent PE:EtOAc 2:1 to 1:1 to 1:2 (v/v)) to afford 13.9 g of compound of formula (SGM-III-2) as a white solid (89% yield).

$^1$H NMR (400 MHz, CDCl$_3$, 20° C.) delta 1.46 (9H, s), 1.68 to 1.71 (2H, m), 3.20 (2H, q, J=6.2 Hz), 3.39 (2H, q, J=6.4 Hz), 4.07 (2H, s), 4.87 (1H, brs), 7.17 (1H, brs).

EXAMPLE 25

A mixture of compound of formula (6) (5.51 g, 1.0 eq.), prepared according to example 7, compound of formula (SGM-III-2) (6.02 g, 2.0 eq.), prepared according to example 24, K$_2$CO$_3$ (3.31 g, 2.0 eq.), and anhydrous DMF (30 ml) was heated to 50° C. and stirred under nitrogen atmosphere for 7 days. Then the reaction mixture was concentrated to dryness under vacuum. MeOH (40 ml) was added to the residue, the resulting mixture was stirred for 10 min and then filtered. The wet cake was washed with methanol (3 times with 10 ml each). The filtrate was collected, combined and then concentrated. The residue was purified by silica gel column chromatography (eluent DCM:MeOH=7:1 (v/v)) to afford 3.8 g of compound of formula (52-1) as a slightly yellow solid (46% yield).

$^1$H NMR (400 MHz, DMSO-$d_6$, 20° C.) delta 0.88 (6H, dd, J1=9.6 Hz, J2=6.8 Hz), 1.32 to 1.50 (2H, m), 1.52 to 1.82 (4H, m), 1.90 (3H, s), 1.92 to 1.97 (1H, m), 2.91 to 3.05 (4H, m), 3.17 to 3.22 (2H, m), 3.81 (3H, s), 4.13 (1H, t, J=7.6 Hz), 4.33 to 4.39 (1H, m), 5.42 (2H, s), 5.98 (1H, t, J=5.8 Hz), 6.80 (1H, t, J=5.4 Hz), 7.45 (1H, dd, J1=8.6 Hz, J2=1.8 Hz), 7.50 (1H, d, J=1.6 Hz), 7.80 (1H, d, J=8.6 Hz), 8.02 to 8.05 (2H, m), 8.50 (1H, d, J=11.6 Hz), 10.14 (1H, s).

ESI-MS: 580.5 (M-tBuOCO+2H)+, 680.4 (M+H)+, 1359.0 (2M+H)+

EXAMPLE 26

A mixture of compound of formula (52-1) (3.40 g), prepared according to example 25, and of a solution of 10% (w/w) HCl in 1,4-dioxane (50 ml) was stirred at RT for 15 hours. Then the reaction mixture was concentrated under vacuum to afford 3.20 g of compound of formula (52) as HCl salt, being a white solid (quantitative yield). The crude mixture was used directly in the next step.

EXAMPLE 27

A mixture of compound of formula (52) as HCl salt (3.00 g, 1 eq.), prepared according to example 26, water (60 ml), CaCl$_2$ (1.09 g, 2.0 eq.) and NaBH$_4$ (0.75 g, 4.0 eq.) was stirred at RT. Further amount of NaBH$_4$ was added portionwise (0.75 g, 4.0 eq. after a total of 15 hours of stirring; 0.74 g, 4.0 eq. after a total of 19 hours of stirring; 0.74 g, 4.0 eq. after a total of 23 hours of stirring). After a total of 40 hours of stirring, MeOH (15 ml) was added to the mixture. The reaction mixture was then filtered and the wet cake was washed with MeOH (3 times with 10 ml each). The filtrate was collected and combined and then evaporated to dryness. The residue was purified by silica gel column chromatography (eluent DCM:MeOH:Et3N=65:33:2 (v/v)) to afford 1.05 g of compound of formula (42) as a slightly yellow solid (39% yield).

$^1$H NMR (400 MHz, DMSO-$d_6$, 20° C.) delta 0.86 (6H, dd, J1=11.0 Hz, J2=6.8 Hz), 1.30 to 1.46 (2H, m), 1.48 to 1.73 (4H, m), 1.89 (3H, s), 1.93 to 2.01 (1H, m), 2.56 (1H, t, J=6.8 Hz), 2.91 to 3.06 (4H, m), 3.13 to 3.22 (2H, m), 4.16 to 4.20 (1H, m), 4.34 to 4.39 (1H, m), 4.46 (2H, s), 4.50 (2H, s), 5.45 (2H, s), 6.06 (1H, t, J=5.6 Hz), 7.22 to 7.27 (3H, m), 7.94 (1H, d, J=8.4 Hz), 8.16 to 8.19 (2H, m), 9.96 (1H, s).

ESI-MS: 534.2 (M-OH)+, 552.2 (M+H)+

EXAMPLE 28

Compound of formula (42) (940.4 mg, 1.0 eq.), prepared according to example 27, compound of formula (CG1MR-IV-1) (501.2 mg, 1.1 eq.), prepared according to example 8, and DMF (10 ml) were mixed. Then DIPEA (247.0 mg, 1.1 eq.) was added at RT. The resulting mixture was stirred at RT for 4 h. Then DMF was removed under vacuum to get a slightly yellow residue. The residue was then mixed with acetone (20 ml) and the resulting mixture was stirred at RT for 2 hours. Then the mixture was filtered, the wet cake was washed with acetone (3 times with 5 ml each) and then dried under vacuum to afford 950.0 mg of compound of formula (32) as a slightly yellow solid (79% yield).

$^1$H NMR (400 MHz, DMSO-d$_6$, 20° C.) delta 0.86 (6H, dd, J1=11.2 Hz, J2=6.8 Hz), 1.34 to 1.46 (2H, m), 1.47 to 1.73 (4H, m), 1.89 (3H, s), 1.94 to 2.01 (1H, m), 2.32 (2H, t, J=7.6 Hz), 2.92 to 3.05 (4H, m), 3.10 to 3.15 (2H, m), 3.60 (2H, t, J=7.2 Hz), 4.17 to 4.20 (1H, m), 4.34 to 4.42 (1H, m), 4.46 (2H, s), 4.52 (2H, s), 5.08 (1H, brs), 5.42 (2H, s), 5.99 (1H, t, J=5.6 Hz), 7.00 (2H, s), 7.21 (1H, s), 7.25 (2H, s), 7.90 (1H, d, J=8.4 Hz), 7.95 (1H, t, J=5.6 Hz), 8.05 (1H, t, J=5.6 Hz), 8.11 (1H, d, J=7.6 Hz), 9.92 (1H, s).

EXAMPLE 29

A mixture of compound of formula (32) (402.5 mg, 1.0 eq.), prepared according to example 28, 4 angstrom molecular sieves (800.0 mg), anhydrous DMF (8.0 ml) and compound of formula (II-1) (347.3 mg, 2.0 eq.) was stirred for 5 min. Then DIPEA (297.7 mg, 4.0 eq.) was added. The resulting mixture was stirred for 5 h at RT. Then compound of formula (DOXO) as HCl salt (332.2 mg, 1.0 eq.) was added and the mixture was then stirred for 4 hours. Then MeCN (40.0 ml) was added. A precipitate had formed and was filtered and washed with a mixture of MeCN and DMF (5:1 (v/v), 2 times with 5 ml each). The filtrate was combined and dried under vacuum at 45° C. to get a dark red residue. The residue was dissolved in a mixture of DCM and MeOH (7:1 (v/v)) and purified by preparative silica gel TLC (DCM:MeOH=7:1 (v/v), Rf=0.15). The product was extracted from the silica gel by a mixture of acetone and water (20:1 (v/v), 5 times with 50 ml each), the combined extraction solutions were dried under vacuum to afford the crude product as a red solid. The crude product was then mixed with acetonitrile (20 ml), the mixture was stirred at RT for 2 hours and then filtered. The cake was dried under vacuum at RT to afford 74.0 mg of compound of formula (22) as a red solid (10% yield).

$^1$H NMR (400 MHz, DMSO-d$_6$, 20° C.) delta 0.84 (6H, dd, J1=10.8 Hz, J2=6.8 Hz), 1.13 (3H, d, J=6.4 Hz), 1.30 to 1.49 (5H, m), 1.56 to 1.69 (2H, m), 1.81 to 1.88 (4H, m), 1.93 to 1.98 (1H, m), 2.13 to 2.25 (2H, m), 2.28 (2H, t, J=7.2 Hz), 2.92 to 3.07 (8H, m), 3.45 (1H, brs), 3.56 (2H, t, J=7.2 Hz), 3.73 (1H, brs), 3.99 (3H, s), 4.15 to 4.19 (2H, m), 4.35 to 4.38 (1H, m), 4.41 (2H, s), 4.58 (2H, d, J=5.8 Hz), 4.71 (1H, d, J=5.6 Hz), 4.85 (1H, t, J=6.0 Hz), 4.94 (1H, brs), 5.03 (2H, s), 5.22 (1H, brs), 5.42 (2H, s), 5.47 (1H, brs), 6.02 (1H, t, J=4.6 Hz), 6.87 (1H, d, J=8.0 Hz), 6.97 (2H, s), 7.22 to 7.25 (3H, m), 7.65 (1H, t, J=4.8 Hz), 7.88 to 7.90 (5H, m), 8.11 (1H, d, J=7.6 Hz), 9.98 (1H, s), 13.27 (1H, s), 14.02 (1H, s).

ESI-MS: 1271.9 (M+H)+, 1294.4 (M+Na)+

EXAME 30

To a mixture of compound of formula (HSGH-II-2) (21.24 g, 1.0 eq) and Et$_3$N (21.03 g, 1.1 eq.) in MeOH (100 mL) at 0° C., a solution of Boc$_2$O (43.83 g, 1.1 eq.) in MeOH (50 ml) was added dropwise within 1 hours. The mixture was then warmed to RT and stirred for 24 hours. The resulting mixture was then evaporated to dryness under vacuum to afford 43.05 g of compound of formula (Boc-HSGH-II-2) as a yellow oil (quantitative yield).

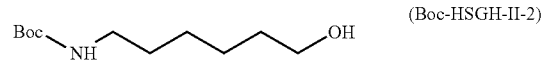

(Boc-HSGH-II-2)

$^1$H NMR (400 MHz, CDCl$_3$, 20° C.) delta 1.30 to 1.43 (4H, m), 1.45 (9H, s), 1.48 to 1.61 (4H, m), 1.70 (1H, brs), 3.12 (2H, q, J=6.8 Hz), 3.64 (2H, t, J=6.8 Hz), 4.57 (1H, brs).

EXAMPLE 31

To a mixture of compound of formula (Boc-HSGH-II-2) (20.02 g, 1.0 eq.), prepared according example 30, pyridine (8.02 g, 1.1 eq.) and dichloromethane (50 mL) at 0° C., a mixture of TsCl (19.33 g, 1.1 eq.) in dichloromethane (75 mL) dropwise within 2 hours. The resulting mixture was stirred at RT for 7 days. The solution was then evaporated to dryness. The residue was washed with a mixture solvent (PE:EtOAc=6:1 (v/v), 4 times with 100 ml each) and filtered. The filtrate was combined then evaporated to dryness. The crude product was further purified by silica gel column chromatography (PE:EtOAc=6:1 (v/v)) to afford 14.20 of compound of formula (SGM-II-2) as a white solid (41% yield).

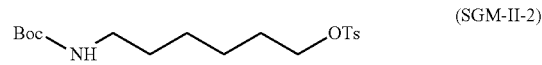 [SMILES: Cc1ccc(S(=O)(=O)OCCCCCCNC(=O)OC(C)(C)C)cc1]

(SGM-II-2)

$^1$H NMR (400 MHz, CDCl$_3$, 20° C.) delta 1.22 to 1.37 (4H, m), 1.39 to 1.47 (11H, ms), 1.62 to 1.68 (2H, m), 2.46 (3H, s), 3.07 (2H, t, J=6.6 Hz), 4.02 (2H, t, J=6.4 Hz), 4.52 (1H, brs), 7.36 (2H, d, J=8.0 Hz), 7.78 to 7.82 (2H, m).

EXAMPLE 32

A mixture of compound formula (6) (9.31 g, 1.0 eq.), prepared according to example 7, compound of formula (SGM-II-2), prepared according to example 31 (14.90 g, 2.0 eq.), K$_2$CO$_3$ (5.65 g, 2.0 eq.) and anhydrous DMF (60 mL) was heated to 50° C. and stirred for under N$_2$ atmosphere 9 days. The reaction mixture was evaporated to dryness. To this residue MeOH (40 mL) was added and, the resulting mixture was stirred for 10 min then filtered, the cake was further washed with MeOH (3 times with 15 ml each). The filtrate was combined and evaporated to dryness. The residue was purified by silica gel column chromatography to afford 6.35 g of compound of formula (53-1) as a slight yellow solid (48% yield).

¹H NMR (400 MHz, DMSO-d₆, 20° C.) delta 0.86 (6H, dd, J₁=12.0 Hz, J₂=6.8 Hz), 1.24 to 1.33 (2H, m), 1.35 to 1.48 (15H, m), 1.56 to 1.76 (4H, m), 1.89 (3H, s), 1.92 to 2.01 (1H, m), 2.89 to 3.05 (4H, m), 3.75 (3H, s), 3.97 (2H, t, J=6.2 Hz), 4.17 to 4.21 (1H, m), 4.34 to 4.39 (1H, m), 5.41 (2H, s), 5.99 (1H, t, J=5.8 Hz), 6.77 (1H, t, J=5.2 Hz), 7.24 (1H, dd, J₁=8.6 Hz, J₂=1.8 Hz), 7.47 to 7.48 (1H, m), 7.67 (1H, d, J=8.6 Hz), 7.90 (1H, d, J=8.6 Hz), 8.18 (1H, d, J=7.4 Hz), 10.17 (1H, s).

ESI-MS: 565.0 (M-$^t$BuOCO+2H)$^+$, 664.8 (M+H)$^+$, 1329.1 (2M+H)$^+$

EXAMPLE 33

Compound of formula (53-1) (8.10 g), prepared according to example 32, and a solution of 10% (w/w) HCl in 1,4-dioxane (50 ml) were mixed. The mixture was stirred at RT for 1.5 hours. The solvent was removed under vacuum to afford 9.00 g of compound of formula (53) as HCl salt, being a white solid (quantitative yield).

EXAMPLE 34

To a mixture of compound of formula (53) as HCl salt (4.01 g, 1.0 eq.), prepared according to example 33, and anhydrous THF (40 mL) at −30° C. was added a solution of DIBAL-H in hexanes (1M, 51.1 ml, 8.1 eq). The resulting mixture was then heated to 0° C. and stirred under nitrogen atmosphere for 2.5 hours then warmed to RT naturally and stirred for 16 hours. The mixture as then cooled to 0° C. Methanol (10 mL) was added. Then saturated potassium sodium tartarate (100 ml) aqueous solution was added to the mixture and the mixture was stirred for 1 hour at RT. The resulting mixture was evaporated to dryness to generate a white residue which was mixed with methanol (60 ml) and stirred for 1 hour. The resulting suspension was filtered, the cake was further washed with methanol (3 times with 30 ml each). The combined filtrate was concentrated and purified by silica gel column chromatography (DCM:Methanol: Et₃N=66:32:2 (v/v)) to afford 1.81 g of compound of formula (43) as a white solid (53% yield).

¹H NMR (400 MHz, DMSO-d₆, 20° C.) delta 0.86 (6H, dd, J₁=10.4 Hz, J₂=6.8 Hz), 1.31 to 1.46 (8H, m), 1.55 to 1.74 (4H, m), 1.90 (3H, s), 1.94 to 2.02 (1H, m), 2.60 (2H, t, J=6.8 Hz), 2.91 to 3.05 (2H, m), 3.92 (2H, t, J=6.4 Hz), 4.16 to 4.20 (1H, m), 4.34 to 4.39 (1H, m), 4.44 (2H, s), 5.43 (2H, s), 6.07 (1H, t, J=5.6 Hz), 7.14 to 7.17 (1H, m), 7.25 (1H, d, J=8.0 Hz), 7.32 (1H, d, J=2.0 Hz), 7.94 (1H, d, J=8.4 Hz), 8.13 (1H, d, J=7.6 Hz), 9.90 (1H, s).

ESI-MS: 519.9 (M-OH⁻)$^+$, 538.0 (M+H)$^+$, 1129.5 (2M+H)$^+$

EXAMPLE 35

A mixture of compound of formula (43) (1.13 g, 1.0 eq), prepared according to example 34, maleic anhydride (207.3 mg, 1.1 eq), and DMF (10 mL) was stirred at RT for 20 h. To the resulting solution was added compound of formula (HOSu) (225.1 mg, 1.0 eq) and EDC (in its mono hydrogen chloride form) (745.0 mg, 2.0 eq). The resulting mixture was further stirred at RT for 4 days. The mixture was evaporated to dryness then mixed with acetone (30 ml). The resulting mixture was stirred at RT for 20 h then filtered. The cake was further washed with acetone (3 times with 15 ml each) and then dried under vacuum to afford 1.10 g of compound of formula (33) as a slightly yellow solid (90% yield).

¹H NMR (400 MHz, DMSO-d₆, 20° C.) delta 0.86 (6H, dd, J₁=10.2 Hz, J₂=6.8 Hz), 1.26 to 1.55 (8H, m), 1.59 to 1.78 (4H, m), 1.90 (3H, s), 1.93 to 2.02 (1H, m), 2.95 to 3.06 (2H, m), 3.41 (2H, t, J=7.0 Hz), 3.89 (2H, t, J=6.2 Hz), 4.16 to 4.20 (1H, m), 4.34 to 4.40 (1H, m), 4.43 (2H, s), 5.42 (2H, brs), 6.05 (1H, brs), 7.00 (2H, s), 7.15 to 7.18 (1H, m), 7.24 to 7.29 (2H, m), 7.93 (1H, d, J=8.4 Hz), 8.11 (1H, d, J=7.6 Hz), 9.87 (1H, s).

ESI-MS: 599.6 (M-OH⁻)$^+$, 639.8 (M+Na)$^+$

EXAMPLE 36

A mixture of compound of formula (33) (50.2 mg, 1.0 eq), prepared according to example 35, 4 angstrom molecular sieves (100.0 mg), anhydrous DMF (1.0 ml) and compound of formula (II-1) (37.0 mg, 1.6 eq) was stirred at RT for 5 min. Then DIPEA (46.5 mg, 4.4 eq) was added. The resulting mixture was stirred at RT for 3.5 hours. Then compound of formula (DOXO) as HCl salt (37.8 mg, 0.86 eq) was added and the mixture was then stirred for 4.5 hours. Then MeCN (5.0 ml) was added. A precipitate had formed and was filtered and washed with a mixture of MeCN and DMF (5:1 (v/v), 2 times with 1 ml each). The filtrate was combined and dried under vacuum at 45° C. to get a dark residue. The residue was dissolved in the mixture of DCM and MeOH (10:1, v/v, 3 ml) and purified by preparative silica gel TLC (DCM:MeOH=7:1, (v/v), Rf=0.35). The product was extracted from the silica gel by a mixture of acetone and water (20:1, v/v, 6 times with 3 ml each). The combined extraction solutions were dried under vacuum to afford the crude product as a red solid. The crude product was then mixed with acetonitrile (5 ml), the mixture was stirred at RT for 2 hours and then filtered. The cake was washed with acetonitrile (2 times with 1 ml each) then dried under vacuum at 25° C. to afford 9.0 mg of compound of formula (23) as a red solid (9% yield).

¹H NMR (400 MHz, DMSO-d₆, 20° C.) delta 0.84 (6H, dd, J₁=10.2 Hz, J₂=6.8 Hz), 1.13 (3H, d, J=6.4 Hz), 1.19 to 1.23 (2H, m), 1.35 to 1.50 (7H, m), 1.56 to 1.68 (4H, m), 1.81 to 1.86 (1H, m), 1.88 (3H, s), 1.91 to 2.01 (1H, m), 2.11 to 2.23 (2H, m), 2.91 to 3.01 (4H, m), 3.32 (2H, t, J=6.8 Hz), 3.45 to 3.47 (1H, m), 3.69 to 3.74 (1H, m), 3.98 (3H, s), 4.15 to 4.19 (2H, m), 4.32 to 4.37 (1H, m), 4.58 (2H, d, J=5.8 Hz), 4.66 (2H, d, J=6.8 Hz), 4.82 to 4.93 (4H, m), 5.23 (1H, brs), 5.39 (2H, s), 5.46 (1H, brs), 5.96 (1H, t, J=5.6 Hz), 6.74 (1H, d, J=8.0 Hz), 6.93 (2H, s), 7.10 to 7.18 (2H, m), 7.31 (1H, brs), 7.62 to 7.65 (1H, m), 7.89 to 7.90 (3H, m), 8.09 (1H, d, J=7.4 Hz), 9.88 (1H, s), 13.26 (1H, s), 14.02 (1H, s).

ESI-MS: 1185.8 (M+H)$^+$, 1208.4 (M+Na)$^+$

EXAMPLE 37

A mixture of Z-L-Val (1.47 g, 0.95 eq), anhydrous DMF (15 ml), TBTU (2.97 g, 1.5 eq) and DIPEA (2.00 g, 2.5 eq) was stirred at RT for 15 min. To the resulting mixture was added compound of formula (6-3) as HCl salt (2.23 g, 1.0 eq), prepared according to example 4. The mixture was further stirred at RT for 14 hours then evaporated to dryness at 45° C. Water (150 ml) was then added, the resulting mixture was extracted with EtOAc (3 times with 200 ml each). The combined organic phase was washed with 250 ml saturated brine then dried over anhydrous Na₂SO₄. The resulting solution was concentrated then purified by silica gel column chromatography) (PE:EA=1:2 to DCM: MeOH=10:1 (v/v)) to afford 2.92 g of compound of formula (6-5) as a white solid (85%) yield.

¹H NMR (400 MHz, DMSO-d₆, 20° C.) delta 0.87 (6H, dd, J₁=17.6 Hz, J₂=6.8 Hz), 1.36 to 1.50 (2H, m), 1.58 to 1.74 (2H, m), 1.94 to 2.02 (1H, m), 2.91 to 3.08 (2H, m), 3.87 (3H, s), 3.90 to 3.96 (1H, m), 4.37 to 4.43 (1H, m), 5.04 (2H, s), 5.43 (2H, s), 5.99 (1H, t, J=5.6 Hz), 7.10 (1H, dd, J₁=8.8 Hz, J₂=2.0 Hz), 7.30 to 7.37 (6H, m), 7.41 (1H, d, J=2.0 Hz), 7.74 (1H, d, J=8.8 Hz), 8.19 (1H, d, J=7.2 Hz), 10.32 (1H, s), 10.62 (1H, s).

ESI-MS: 557.6 (M+H)⁺, 579.9 (M+Na)⁺, 1114.8 (2M+H)⁺, 1136.5 (2M+Na)⁺

EXAMPLE 38

A mixture of compound of formula (6-5) (20.00 g, 1.0 eq), prepared according to example 37, K₂CO₃ (9.91 g, 2.0 eq) and anhydrous DMF (80 ml). The resulting mixture was heated to 50° C. and stirred for 0.5 hour. Compound of formula (SGM-II-1) (25.79 g, 2.0 eq), prepared according to example 10, was added to the reaction mixture in 4 portions within 2 hours. The reaction mixture was stirred at 50° C. for 3 days then evaporated to dryness at 45° C. The residue was washed with MeOH (4 times with 20 ml each). The filtrate was combined then concentrated into dryness. The residue was further purified by silica gel column chromatography (DCM:MeOH=20:1, v/v) to afford 22.17 g of compound of formula (54-1) as a white solid (83% yield).

¹H NMR (400 MHz, DMSO-d₆, 20° C.) delta 0.87 (6H, dd, J₁=17.6 Hz, J₂=6.8 Hz), 1.36 to 1.49 (11H, m), 1.59 to 1.73 (2H, m), 1.96 to 2.03 (1H, m), 2.92 to 3.14 (4H, m), 3.50 (2H, t, J=6.0 Hz), 3.74 to 3.76 (5H, m), 3.93 to 3.97 (1H, m), 4.08 (2H, t, J=4.6 Hz), 4.39 to 4.44 (1H, m), 5.05 (2H, s), 5.42 (2H, s), 5.98 (1H, t, J=5.6 Hz), 6.73 (1H, t, J=5.4 Hz), 7.25 (1H, dd, J₁=8.6 Hz, J₂=1.56 Hz), 7.30 to 7.36 (6H, m), 7.48 (1H, s), 7.69 (1H, d, J=8.6 Hz), 8.15 (1H, d, J=7.2 Hz), 10.28 (1H, s).

ESI-MS: 745.0 (M+H)⁺, 1488.8 (2M+H)⁺, 645.3 (M-ᵗBuOCO+2H)⁺

EXAMPLE 39

A mixture of compound of formula (54-1) (4.80 g, 1.0 eq), prepared according to example 38, methanol (200 ml) and Pd/C (5%, 0.24 g) was degassed for three times then stirred under H₂ atmosphere (6 bar) at 30° C. for 18 hours. The resulting mixture was filtered, the filtrate was concentrated to dryness under vacuum to afford 3.96 g of compound of formula (54-2) as a white solid (quantitative yield.)

¹H NMR (400 MHz, DMSO-d₆, 20° C.) delta 0.81 (3H, d, J=6.8 Hz), 0.90 (3H, d, J=6.8 Hz), 1.36 to 1.49 (11H, m), 1.58 to 1.78 (2H, m), 1.91 to 1.99 (1H, m), 2.92 to 3.12 (5H, m), 3.50 (2H, t, J=6.0 Hz), 3.75 to 3.77 (5H, m), 4.09 (2H, t, J=4.8 Hz), 4.47 (1H, s), 5.45 (2H, s), 6.07 (1H, t, J=5.6 Hz), 6.72 (1H, t, J=5.2 Hz), 7.24 (1H, dd, J₁=8.6 Hz, J₂=1.6 Hz), 7.51 (1H, d, J=1.4 Hz), 7.69 (1H, d, J=8.6 Hz), 8.24 (1H, d, J=8.6 Hz), 10.42 (1H, s).

ESI-MS: 611.8 (M+H)⁺, 1221.4 (2M+Na)⁺, 512.0 (M-ᵗBuOCO+2H)⁺

EXAMPLE 40

A mixture of N,N-dimethylglycine (0.48 g, 1.0 eq), DMF (15 ml) and TBTU (3.01 g, 2.0 eq) was cooled to 0° C. The resulting mixture was then stirred for 15 min followed by addition of compound of formula (54-2) (2.86 g, 1.0 eq), prepared according to example 39. The mixture was then warmed to RT naturally and further stirred for 18 hours. The resulting mixture was then evaporated to dryness. The resulting residue was purified by silica gel column chromatography (DCM:MeOH=7:1, (v/v)) to afford 2.78 g of compound of formula (54-3) as a white solid (85% yield).

¹H NMR (400 MHz, DMSO-d₆, 20° C.) delta 0.82 (3H, d, J=6.8 Hz), 0.89 (3H, d, J=6.8 Hz), 1.36 to 1.49 (11H, m), 1.56 to 1.75 (sH, m), 1.98 to 2.06 (1H, m), 2.33 (6H, s), 2.92 to 3.04 (2H, m), 3.06 to 3.11 (4H, m), 3.50 (2H, t, J=6.0 Hz), 3.74 to 3.77 (5H, m), 4.09 (2H, t, J=4.6 Hz), 4.30 to 4.34 (1H, m), 4.36 to 4.41 (1H, m), 5.43 (2H, s), 6.01 (1H, t, J=5.8 Hz), 6.73 (1H, t, J=5.2 Hz), 7.25 (1H, dd, J₁=8.6 Hz, J₂=1.8 Hz), 7.28 to 7.32 (1H, m), 7.35 to 7.39 (1H, m), 7.46 (1H, d, J=1.6 Hz), 7.55 (1H, d, J=8.4 Hz), 7.68 (1H, d, J=8.6 Hz), 7.82 (1H, d, J=9.0 Hz), 7.85 to 7.87 (1H, m), 8.38 (1H, d, J=7.2 Hz), 10.30 (1H, s).

ESI-MS: 696.2 (M+H)⁺, 1391.1 (2M+H)⁺, 596.3 (M-ᵗBuOCO+2H)⁺

EXAMPLE 41

A mixture of compound of formula (54-3), prepared according to example 40, and a solution of 10% (w/w) HCl in 1,4-dioxane (50 ml) was stirred at RT for 18 hours. The solvent was removed under vacuum to afford 5.60 g of compound of formula (54) as di-HCl salt, being a white solid (quantitative yield).

ESI-MS: 596.4 (M+H)⁺, 1191.3 (2M+H)⁺

EXAMPLE 42

To a mixture of compound of formula (54) as di-HCl salt (1.00 g, 1.0 eq), prepared according to example 41 and anhydrous THF (15 ml) was at 0° C. was added a solution of DIBAL-H in hexanes (1 M, 10 ml, 6.7 eq). The resulting mixture was further at 0° C. for 1.5 hours. Then methanol (10 ml) was added dropwise. Then saturated potassium sodium tartarate aqueous solution (30 mL) was added and stirred at RT for 1 hour. The resulting mixture was evaporated to dryness. The resulting residue was washed with MeOH (3 times with 10 ml each). The combined filtrate was concentrated then purified by silica gel column chromatography (DCM:MeOH:Et₃N=65:33:2 (v/v)) to afford 0.43 g of compound of formula (44) as a white solid (yield 51%).

¹H NMR (400 MHz, DMSO-d₆, 60° C.) delta 0.82 (3H, d, J=6.8 Hz), 0.87 (3H, d, J=6.8 Hz), 1.32 to 1.50 (2H, m), 1.55 to 1.74 (2H, m), 1.97 to 2.06 (1H, m), 2.23 (6H, s), 2.73 (2H, t, J=5.6 Hz), 2.91 (2H, brs), 2.93 to 3.06 (2H, m), 3.50 (2H, t, J=5.6 Hz), 3.75 (2H, t, J=4.6 Hz), 4.05 to 4.07 (2H, m), 4.29 to 4.33 (1H, m), 4.35 to 4.40 (1H, m), 4.45 (2H, s), 5.41 (2H, s), 6.02 (1H, t, J=5.6 Hz), 7.15 (1H, dd, J₁=8.4 Hz, J₂=1.6 Hz), 7.26 (1H, d, J=8.0 Hz), 7.31 (1H, d, J=1.6 Hz), 7.63 (1H, d, J=9.2 Hz), 8.31 (1H, d, J=7.4 Hz), 9.97 (1H, s).

ESI-MS: 550.3 ((M-OH⁻)⁺, 568.2 (M+H)⁺, 1134.7 (2M+H)⁺

EXAMPLE 43

To a mixture of compound of formula (44) (1.10 g, 1.0 eq), prepared according to example 42, compound of formula (CG1MR-IV-1) (0.57 g, 1.1 eq), prepared according to example 8, and DMF (4.0 ml) at RT, DIPEA (0.28 g, 1.1 eq) was added. The resulting mixture was stirred at RT for 18 hours. Then the DMF was removed under vacuum to afford a slightly yellow residue which was then mixed with acetone (20 ml) and stirred at RT for 18 hours. The mixture was filtered, the cake was washed with acetone (2 times with 5 ml each), then dried under vacuum to afford 1.11 g of compound of formula (34) (80% yield).

¹H NMR (400 MHz, DMSO-d₆, 20° C.) delta 0.82 (3H, d, J=6.8 Hz), 0.88 (3H, d, J=6.8 Hz), 1.34 to 1.46 (2H, m), 1.55 to 1.73 (2H, m), 1.97 to 2.05 (1H, m), 2.25 (6H, s), 2.34 (2H, t, J=7.0 Hz), 2.95 to 3.06 (4H, m), 3.17 to 3.21 (2H, m), 3.46 (2H, t, J=5.8 Hz), 3.60 (2H, t, J=7.2 Hz), 3.73 (2H, t, J=4.4 Hz), 4.03 (2H, t, J=4.4 Hz), 4.29 to 4.33 (1H, m), 4.35 to 4.40 (1H, m), 4.45 (2H, s), 4.86 (1H, brs), 5.41 (2H, s), 5.99 (1H, t, J=5.6 Hz), 7.00 (2H, s), 7.14 to 7.16 (1H, m), 7.26 to 7.30 (2H, m), 7.67 (1H, d, J=9.2 Hz), 8.03 (1H, t, J=5.2 Hz), 8.30 (1H, d, J=7.4 Hz), 9.95 (1H, s).

ESI-MS: 701.3 (M-OH⁻)⁺, 719.2 (M+H)⁺, 1436.7 (2M+H)⁺

EXAMPLE 44

A mixture of compound of formula (II-1) (169.4 mg, 2.0 eq), anhydrous DMF (4.0 ml) and 4 angstrom molecular sieves (400.0 mg) was stirred at RT for 15 min. To the resulting mixture was added DIPEA (107.9 mg, 3.0 eq.) and compound of formula (34), (200.0 mg, 1.0 eq) prepared according to example 43. The resulting mixture was further stirred for 2.5 hours. Then compound of formula (DOXO) as HCl salt (161.8 mg, 1.0 eq) was added and further stirred for 2 hours. Then MeCN (20 ml) was added. A precipitate had formed and was filtered and washed with a mixture of MeCN and DMF (5:1 (v/v), 3 times with 3 ml each). The filtrates were combined and dried under vacuum at 48° C. The resulting residue was dissolved in a mixture of DCM and MeOH (5:1 (v/v), 5 ml) and purified by preparative silica gel TLC (DCM:MeOH=4:1 (v/v), Rf=0.5). The product was extracted from the silica-gel by a mixture of acetone and water (7:1 (v/v), 6 times with 10 ml each). The combined extraction solutions were dried under vacuum to afford a crude product as a red solid. The crude product was then mixed with acetonitrile (5 mL), stirred at RT for 2 hours then filtered. The wet cake was dried under vacuum at RT to afford 7.0 mg of compound of formula (24) as a red solid (2% yield.)

¹H NMR (400 MHz, DMSO-d₆, 20° C.) delta 0.80 (3H, d, J=6.8 Hz), 0.86 (3H, d, J=6.6 Hz), 1.13 (3H, d, J=6.4 Hz), 1.32 to 1.52 (3H, m), 1.57 to 1.69 (2H, m), 1.82 to 1.88 (1H, m), 1.95 to 2.04 (1H, m), 2.10 to 2.18 (2H, m), 2.24 (6H, s), 2.29 (2H, t, J=7.4 Hz), 2.92 to 3.02 (6H, m), 3.12 to 3.16 (2H, m), 3.41 (2H, t, J=5.6 Hz), 3.45 (1H, brs), 3.55 (2H, t, J=7.2 Hz), 3.69 to 3.74 (3H, m), 3.99 (3H, s), 4.03 (2H, brs), 4.13 to 4.17 (1H, m), 4.28 to 4.31 (1H, m), 4.33 to 4.38 (1H, m), 4.58 (2H, d, J=5.2 Hz), 4.69 (1H, d, J=5.6 Hz), 4.86 (1H, t, J=6.0 Hz), 4.90 (1H, s), 4.95 (1H, t, J=4.4 Hz), 5.23 (1H, brs), 5.40 (2H, s), 5.47 (1H, s), 6.00 (1H, t, J=5.6 Hz), 6.79 (1H, d, J=8.0 Hz), 6.95 (2H, s), 7.12 (1H, d, J=8.2 Hz), 7.19 (1H, d, J=8.2 Hz), 7.34 (1H, s), 7.64 to 7.68 (2H, m), 7.91 (2H, d, J=4.8 Hz), 7.98 (1H, t, J=5.2 Hz), 8.30 (1H, d, J=7.2 Hz), 10.02 (1H, s), 13.27 (1H, s), 14.02 (1H, s).

ESI-MS: 1288.3 (M+H)⁺

EXAMPLE 45

A mixture of compound of formula (VII-1) (26.10 g, 1.5 eq), prepared according to example 1, THF (150 ml), Boc-L-Lys(Ac)-OH (30.00 g, 1.0 eq) and EEDQ (51.45 g, 2.0 eq) was stirred at RT for 24 hours. The mixture was then evaporated to dryness. The residue was purified by silica gel column chromatography (PE:EtOAc=2:1 (v/v) to pure EtOAc) to afford 26.00 g of compound of formula (6b-4) as a slightly yellow solid (57% yield).

¹H NMR (400 MHz, DMSO-d₆, 20° C.) delta 1.21 to 1.34 (4H, m), 1.38 (9H, s), 1.58 to 1.66 (2H, m), 1.77 (3H, s), 3.00 to 3.04 (2H, m), 3.87 (3H, s), 3.99 to 4.07 (1H, m), 7.08 to 7.11 (2H, m), 7.40 (1H, d, J=2.0 Hz), 7.74 (1H, d, J=8.8 Hz), 7.78 to 7.81 (1H, m), 10.20 (1H, s), 10.62 (1H, s).

ESI-MS: 437.9 (M+H)⁺, 460.3 (M+Na)⁺, 875.1 (2M+H)⁺, 896.9 (2M+Na)⁺, 338.1 (M-ᵗBuOCO+2H)⁺

EXAMPLE 46

Compound of formula (6b-4) (26.00 g), prepared according to example 45, was suspended in a solution of 10% (w/w) HCl in 1,4-dioxane (150 ml), the resulting mixture was stirred at RT for 3 hours. The reaction mixture was then concentrated under vacuum to afford 22.05 g of compound of formula (6b-3) as HCl salt, being a yellow solid (quantitative yield).

ESI-MS: 339.2 (M+H)⁺

EXAMPLE 47

A mixture of compound of formula (6b-3) as HCl salt (25.21 g, 1.0 eq), prepared according to example 46, Boc-L-Val-OH (13.25 g, 1.0 eq), TBTU (23.66 g, 1.1 eq), DIPEA (19.05 g, 2.2 eq) and DMF (100 ml) was stirred at RT for 18 hours. The resulting mixture was evaporated to dryness then purified by silica gel chromatography (DCM:MeOH=10:1 to 7:1, (v/v)) to afford 30.80 g of compound of formula (6b-2) as a slightly yellow solid (90% yield).

¹H NMR (400 MHz, CDCl₃, 20° C.) delta 1.39 to 1.46 (14H, m), 1.49 to 1.56 (2H, m), 1.74 to 1.83 (1H, m), 1.95 to 2.02 (4H, m), 3.17 to 3.30 (2H, m), 3.92 (3H, s), 4.17 to 4.22 (1H, m), 4.54 to 4.60 (1H, m), 5.53 (1H, brs), 6.32 (1H, brs), 7.15 (1H, d, J=8.0 Hz), 7.31 (1H, brs), 7.38 (1H, s), 7.72 (1H, dd, J₁=8.8 Hz, J₂=1.0 Hz), 9.38 (1H, brs), 10.80 (1H, s).

ESI-MS: 509.3 (M+H)⁺, 1017.0 (2M+H)⁺, 1038.8 (2M+Na)⁺, 409.5 (M-ᵗBuOCO+2H)⁺

EXAMPLE 48

Compound of formula (6b-2) (30.80 g), prepared according to example 47, was suspended in a solution of 10% (w/w) HCl in 1,4-dioxane (150 ml), the resulting mixture was stirred at RT for 23 hours. The reaction mixture was then concentrated under vacuum to afford 25.90 g of compound of formula (6b-1) as HCl salt, being a white solid (96% yield).

ESI-MS: 409.0 (M+H)⁺

EXAMPLE 49

A mixture of compound of formula (6b-1) as HCl salt (15.32 g, 1.0 eq), prepared according to example 48, methanol (100 ml), pyridine (9.0 ml, 3.2 eq) and acetic anhydride (14.0 ml, 4.3 eq) was stirred at RT for 60 hours. The resulting mixture was evaporated to dryness under vacuum. The residue was purified by silica gel column chromatography (DCM:MeOH=15:1 to 7:1, (v/v)) to afford 12.51 g of compound of formula (6b) as a slightly yellow solid (80% yield).

¹H NMR (400 MHz, DMSO-d₆, 20° C.) delta 1.21 (3H, d, J=7.0 Hz), 1.29 to 1.38 (4H, m), 1.61 to 1.74 (2H, m), 1.78 (3H, s), 1.86 (3H, s), 2.99 to 3.04 (2H, m), 3.87 (3H, s), 4.27 to 4.34 (2H, m), 7.14 (1H, d, J=8.8 Hz), 7.42 (1H, brs), 7.73 (1H, d, J=8.6 Hz), 7.81 (1H, t, J=5.2 Hz), 8.09 (1H, d, J=7.0 Hz), 10.18 (1H, s), 10.62 (1H, s).

ESI-MS: 451.3 (M+H)$^+$, 473.6 (M+Na)$^+$, 900.9 (2M+H)$^+$, 923.1 (2M+Na)$^+$

EXAMPLE 50

A mixture of compound of formula (6b) (6.73 g, 1.0 eq), prepared according to example 49, compound of formula (SGM-II-1) (11.50 g, 2.1 eq), prepared according to example 10, K$_2$CO$_3$ (4.40 g, 2.1 eq.) and anhydrous DMF (60 ml) was heated to 0° C. and stirred under nitrogen atmosphere for 8 days. The resulting mixture was evaporated to dryness, the residue was washed with MeOH (3 times with 15 ml each). The filtrates were combined and evaporated to dryness. The residue was purified by silica gel column chromatography (DCM:MeOH=15:1 to 7:1, (v/v)) to afford 7.64 g of compound of formula (55-1) as a white solid (81% yield).

$^1$H NMR (400 MHz, DMSO-d$_6$, 20° C.) delta 1.21 (3H, d, J=7.2 Hz), 1.25 to 1.40 (13H, m), 1.59 to 1.74 (2H, m), 1.78 (3H, s), 1.87 (3H, s), 2.99 to 3.04 (2H, m), 3.08 to 3.12 (2H, m), 3.50 (2H, t, J=6.0 Hz), 3.75 to 3.77 (5H, m), 4.09 (2H, t, J=4.6 Hz), 4.24 to 4.34 (2H, m), 6.74 (1H, t, J=5.4 Hz), 7.28 (1H, dd, J$_1$=8.6 Hz, J$_2$=1.6 Hz), 7.51 (1H, d, J=1.6 Hz), 7.69 (1H, d, J=8.6 Hz), 7.81 (1H, t, J=5.2 Hz), 8.08 to 8.13 (2H, m), 10.14 (1H, s).

ESI-MS: 638.2 (M+H)$^+$, 660.4 (M+Na)$^+$, 1275.0 (2M+H)$^+$, 538.4 (M-$^t$BuOCO+2H)$^+$

EXAMPLE 51

Compound of formula (55-1) (7.60 g), prepared according to example 50, was suspended in 10% (w/w) HCl in 1,4-dioxane (50 ml), the resulting mixture was stirred at RT for 5 hours. The reaction mixture was then concentrated under vacuum to afford 6.72 g of compound of formula (55) as HCl salt, being a white solid (98% yield).

ESI-MS: 538.5 (M+H)$^+$, 1074.8 (2M+H)$^+$, 1097.0 (2M+Na)$^+$

EXAMPLE 52

To a mixture of compound of formula (55) as HCl salt (6.00 g, 1.0 eq.), prepared according to example 51, and anhydrous THF (50 mL) at 0° C. was added a solution of DIBAL-H in hexanes (1M, 63.0 ml, 6.0 eq). The resulting mixture was then heated to 0° C. and stirred under nitrogen atmosphere for 6 hours. Then methanol (10 mL) was added. After that, saturated potassium sodium tartarate (150 ml) aqueous solution was added to the mixture and the mixture was stirred at RT for 15 hours. The resulting mixture was evaporated to dryness to generate a white residue which was further washed with methanol (3 times with 50 ml each). The filtrates were combined then concentrated, and purified by silica gel column chromatography (DCM:Methanol: Et$_3$N=75:25:2 (v/v)) to afford 3.27 g of compound of formula (45) as a white solid (61% yield).

$^1$H NMR (400 MHz, DMSO-d$_6$, 20° C.) delta 1.22 (3H, d, J=4.4 Hz), 1.27 to 1.41 (4H, m), 1.62 to 1.78 (2H, m), 1.79 (3H, s), 1.88 (3H, s), 2.68 (2H, t, J=5.6 Hz), 2.99 to 3.03 (2H, m), 3.46 (2H, t, J=5.6 Hz), 3.73 (2H, t, J=4.4 Hz), 4.04 (2H, t, J=4.4 Hz), 4.21 to 4.38 (2H, m), 4.45 (2H, s), 5.36 (1H, s), 7.22 to 7.28 (2H, m), 7.40 (1H, s), 8.00 (1H, t, J=5.4 Hz), 8.16 (1H, d, J=8.0 Hz), 8.27 (1H, d, J=6.8 Hz), 10.05 (1H, s).

ESI-MS: 510.5 (M+H)$^+$, 1019.6 (2M+H)$^+$, 492.6 (M-OH$^-$)$^+$

EXAMPLE 53

To a mixture of compound of formula (45) (1.20 g, 1.0 eq), prepared according to example 52, compound of formula (CG1MR-IV-1) (0.69 g, 1.1 eq), prepared according to example 8, and DMF (25 ml) at RT, DIPEA (0.34 g, 1.1 eq) was added. The resulting mixture was stirred at RT for 2 hours. Then the DMF was removed under vacuum to afford a slightly yellow residue which was then mixed with acetone (50 ml) and stirred at RT for 1 hour. The mixture was filtered, the cake was washed with acetone (2 times with 10 ml each), then dried under vacuum to afford 1.12 g of compound of formula (35) (72% yield).

$^1$H NMR (400 MHz, DMSO-d$_6$, 20° C.) delta 1.20 (3H, d, J=7.2 Hz), 1.24 to 1.40 (4H, m), 1.58 to 1.75 (2H, m), 1.78 (3H, s), 1.87 (3H, s), 2.33 (2H, t, J=7.2 Hz), 2.98 to 3.03 (2H, m), 3.16 to 3.21 (2H, m), 3.46 (2H, t, J=5.8 Hz), 3.60 (2H, t, J=7.2 Hz), 3.72 to 3.75 (2H, m), 4.04 (2H, t, J=4.4 Hz), 4.24 to 4.36 (2H, m), 4.44 (2H, d, J=5.6 Hz), 4.86 (1H, t, J=5.6 Hz), 7.00 (2H, s), 7.16 to 7.18 (1H, m), 7.26 to 7.28 (1H, m), 7.34 (1H, d, J=1.4 Hz), 7.80 (1H, t, J=5.4 Hz), 7.99 (1H, d, J=8.0 Hz), 8.03 (1H, t, J=5.4 Hz), 8.10 (1H, d, J=6.8 Hz), 9.79 (1H, s).

ESI-MS: 661.5 (M+H)$^+$, 643.6 (M-OH$^-$)$^+$

EXAMPLE 54

A mixture of compound of formula (35) (400.0 mg, 1.0 eq), prepared according to example 53, 4 angstrom molecular sieves (800.0 mg), anhydrous DMF (4.0 ml) and compound of formula (II-1) (373.0 mg, 2.0 eq) was stirred at RT for 5 min. Then DIPEA (313.5 mg, 4.0 eq) was added. The resulting mixture was stirred at RT for 5 hours. Then compound of formula (DOXO) as HCl salt (328.0 mg, 0.9 eq) was added and the mixture was then stirred for 4 hours. Then MeCN (20 ml) was added. A precipitate had formed and was filtered and washed with a mixture of MeCN and DMF (5:1 (v/v), 2 times with 10 ml each). The filtrate was combined and dried under vacuum at 45° C. to get a dark residue. The residue was dissolved in the mixture of DCM and MeOH (7:1, v/v, 5 ml) and purified by preparative silica gel TLC (DCM: MeOH=7:1, (v/v), Rf=0.15). The product was extracted from the silica gel by a mixture of acetone and water (20:1, v/v, 10 times with 20 ml each). The combined extraction solutions were dried under vacuum to afford the crude product as a red solid. The crude product was then mixed with acetonitrile (10 ml), the mixture was stirred at RT for 0.5 hour and then filtered. The cake was washed with acetonitrile (5 ml) then dried under vacuum at RT to afford 100.7 mg of compound of formula (25) as a red solid (13% yield).

$^1$H NMR (400 MHz, DMSO-d$_6$, 20° C.) δ 1.13 (3H, d, J=6.4 Hz), 1.20 (3H, d, J=7.2 Hz), 1.24 to 1.38 (4H, m), 1.48 to 1.51 (1H, m), 1.59 to 1.73 (2H, m), 1.77 (3H, s), 1.82 to 1.86 (4H, m), 2.12 to 2.23 (2H, m), 2.29 (2H, t, J=7.2 Hz), 2.89 to 3.02 (4H, m), 3.11 to 3.15 (2H, m), 3.41 (2H, t, J=5.6 Hz), 3.46 (1H, brs), 3.54 (2H, t, J=7.2 Hz), 3.68 to 3.76 (3H, m), 3.98 (3H, s), 4.03 (2H, brs), 4.14 to 4.18 (1H, m), 4.22 to 4.34 (2H, m), 4.58 (2H, d, J=5.2 Hz), 4.70 (1H, d, J=5.8 Hz), 4.85 to 4.92 (4H, m), 5.22 (1H, brs), 5.46 (1H, s), 6.81 (1H, d, J=8.0 Hz), 6.95 (2H, s), 7.14 to 7.20 (2H, m), 7.39 (1H, s), 7.61 to 7.64 (1H, m), 7.82 (1H, t, J=5.2 Hz), 7.88 to 7.91 (2H, m), 7.98 to 8.03 (2H, m), 8.12 (1H, d, J=6.8 Hz), 9.89 (1H, s), 13.24 (1H, s), 14.00 (1H, s).

ESI-MS: 1252.1 (M+Na)$^+$

EXAMPLE 55

Compound of formula (6-1) as HCl salt (22.81 g, 1.0 eq.), prepared according to example 6, 2-[2-(2-Methoxyethoxy) ethoxy]acetic acid (8.00 g, 0.9 eq.), purchased from Aldrich, TBTU (24.00 g, 1.5 eq), and DIPEA (16.00 g,) were dissolved in DMF (100 ml). The resulting solution was stirred at RT for 20 h. The reaction mixture was concentrated to dryness, the residue was then purified by silica gel chromatography (eluent DCM:MeOH=10:1 to 7:1 (v/v)) to afford 12.02 g of compound of formula (6c) as a slightly yellow solid (41% yield).

$^1$H NMR (400 MHz, DMSO-d$_6$, 20° C.) delta 0.86 (6H, dd, J$_1$=24.4 Hz, J$_2$=6.8 Hz), 1.37 (9H, s), 1.39 to 1.52 (2H, m), 1.56 to 1.75 (4H, m), 1.97 to 2.06 (1H, m), 2.91 to 3.07 (4H, m), 3.19 to 3.22 (2H, m), 3.42 to 3.47 (2H, m), 3.52 to 3.64 (6H, m), 3.81 (3H, s), 3.95 (2H, brs), 4.30 to 4.34 (1H, m), 4.36 to 4.41 (1H, m), 4.53 (2H, s), 5.43 (2H, s), 6.01 (1H, t, J=5.8 Hz), 6.78 (1H, t, J=5.2 Hz), 7.34 to 7.40 (2H, m), 7.45 (1H, d, J=8.8 Hz), 7.79 (1H, d, J=8.4 Hz), 8.04 (1H, t, J=5.6 Hz), 8.38 (1H, d, J=7.2 Hz), 10.36 (1H, s).

ESI-MS: 584.7 (M+H)$^+$, 1167.2 (2M+H)$^+$

EXAMPLE 56

A mixture of compound of formula (6c) (8.01 g, 1.0 eq.), prepared according to example 55, compound of formula (SGM-III-2) (6.89 g, 2.0 eq.), prepared according to example 24, K$_2$CO$_3$ (3.80 g, 2.0 eq.), and anhydrous DMF (60 ml) was heated to 50° C. and stirred under nitrogen atmosphere for 7 days. Then the reaction mixture was concentrated to dryness under vacuum. Dichloromethane (15 ml) was added to the residue, the resulting mixture was purified by silica gel column chromatography (eluent DCM:MeOH=7:1 (v/v)) to afford 5.52 g of compound of formula (56-1) as a slightly yellow solid (50% yield).

$^1$H NMR (400 MHz, DMSO-d$_6$, 20° C.) δ 0.86 (6H, dd, J$_1$=24.4 Hz, J$_2$=6.8 Hz), 1.37 (9H, s), 1.39 to 1.52 (2H, m), 1.56 to 1.75 (4H, m), 1.97 to 2.06 (1H, m), 2.91 to 3.07 (4H, m), 3.19 to 3.22 (2H, m), 3.42 to 3.47 (2H, m), 3.52 to 3.64 (6H, m), 3.81 (3H, s), 3.95 (2H, brs), 4.30 to 4.34 (1H, m), 4.36 to 4.41 (1H, m), 4.53 (2H, s), 5.43 (2H, s), 6.01 (1H, t, J=5.8 Hz), 6.78 (1H, t, J=5.2 Hz), 7.34 to 7.40 (2H, m), 7.45 (1H, d, J=8.8 Hz), 7.79 (1H, d, J=8.4 Hz), 8.04 (1H, t, J=5.6 Hz), 8.38 (1H, d, J=7.2 Hz), 10.36 (1H, s).

ESI-MS: 698.7 (M-$^t$BuOCO+2H)$^+$, 798.3 (M+H)$^+$, 820.7 (M+Na)$^+$, 1595.7 (2M+H)$^+$

EXAMPLE 57

Compound of formula of (56-1), prepared according to example 56, was suspended in 10% (w/w) HCl in 1,4-dioxane (60 ml). The resulting mixture was stirred at RT for 8 hours then concentrated to afford 4.99 g of compound of formula (56) as a white solid (quantitative yield).

ESI-MS: 698.4 (M+H)$^+$, 1394.6 (2M+H)$^+$

EXAMPLE 58

A mixture of compound of formula (56) as HCl salt (4.91 g, 1.0 eq.), prepared according to example 57, water (45 ml), CaCl$_2$ (1.49 g, 2.0 eq.) and NaBH$_4$ (1.02 g, 4.0 eq.) was stirred at RT. Further amount of NaBH$_4$ was added portionwise (1.02 g, 4.0 eq. after a total of 2.5 hours of stirring; 1.01 g, 4.0 eq. after a total of 4 hours of stirring; 1.03 g, 4.0 eq. after a total of 6 hours of stirring). After a total of 22 hours of stirring, MeOH (20 ml) was added to the mixture. The reaction mixture was then filtered and the wet cake was washed with MeOH (3 times with 15 ml each). The filtrate was collected and combined and then evaporated to dryness. The residue was purified by silica gel column chromatography (eluent DCM:MeOH:Et$_3$N=80:20:2.5 (v/v)) to afford 1.12 g of compound of formula (46) as a slightly yellow solid (25% yield).

$^1$H NMR (400 MHz, DMSO-d$_6$, 20° C.) δ 0.86 (6H, dd, J$_1$=22.8 Hz, J$_2$=6.8 Hz), 1.32 to 1.48 (4H, m), 1.51 to 1.73 (4H, m), 1.96 to 2.06 (1H, m), 2.58 (2H, t, J=6.8 Hz), 2.91 to 3.06 (2H, m), 3.16 to 3.21 (2H, m), 3.22 (3H, s), 3.52 to 3.64 (8H, m), 3.95 (2H, brs), 4.29 to 4.33 (1H, m), 4.36 to 4.41 (2H, m), 4.46 (2H, s), 4.51 (2H, s), 5.44 (2H, s), 6.10 (1H, t, J=5.6 Hz), 7.22 to 7.27 (3H, m), 7.48 (1H, d, J=8.8 Hz), 8.19 (1H, t, J=5.4 Hz), 8.34 (1H, d, J=7.6 Hz), 10.05 (1H, s).

ESI-MS: 652.4 (M-OH$^-$)$^+$, 670.4 (M+H)$^+$, 1338.7 (2M+H)$^+$

EXAMPLE 59

To a mixture of compound of formula (46) (250.7 mg, 1.0 eq), prepared according to example 58, compound of formula (CG1MR-IV-1) (103.1 g, 1.1 eq), prepared according to example 8, and DMF (4 ml) at RT, DIPEA (53.6 mg, 1.1 eq) was added. The resulting mixture was stirred at RT for 1 hour. Then the DMF was removed under vacuum to afford a slightly yellow residue which was then mixed with acetone (5 ml) and stirred at RT for 1 hour. The mixture was filtered, the cake was washed with acetone (3 times with 3 ml each), then dried under vacuum to afford 253.7 g of compound of formula (36) (83% yield).

$^1$H NMR (400 MHz, DMSO-d$_6$, 20° C.) delta 0.85 (6H, dd, J$_1$=23.0 Hz, J$_2$=6.8 Hz), 1.36 to 1.54 (4H, m), 1.58 to 1.72 (2H, m), 1.97 to 2.05 (1H, m), 2.32 (2H, t, J=7.2 Hz), 2.92 to 3.05 (4H, m), 3.08 to 3.13 (2H, m), 3.22 (3H, s), 3.44 (2H, t, J=4.8 Hz), 3.52 to 3.62 (8H, m), 3.95 (2H, s), 4.29 to 4.33 (1H, m), 4.35 to 4.40 (1H, m), 4.46 (2H, s), 4.52 (2H, d, J=5.2 Hz), 5.08 (1H, t, J=5.6 Hz), 5.42 (2H, s), 6.01 (1H, t, J=5.2 Hz), 6.99 (2H, s), 7.20 to 7.27 (3H, m), 7.46 (1H, d, J=8.8 Hz), 7.95 (1H, t, J=5.4 Hz), 8.05 (1H, t, J=5.8 Hz), 8.31 (1H, d, J=7.6 Hz), 10.00 (1H, s).

ESI-MS: 803.4 (M-OH$^-$)$^+$, 821.1 (M+H)$^+$, 1641.1 (2M+H)$^+$

EXAMPLE 60

A mixture of compound of formula (36) (201.3 mg, 1.0 eq), prepared according to example 59, 4 angstrom molecular sieves (400.0 mg), anhydrous DMF (4.0 ml) and compound of formula (II-1) (146.9 mg, 2.0 eq) was stirred at RT for 10 min. Then DIPEA (105.7 mg, 3.3 eq) was added. The resulting mixture was stirred at RT for 4.5 hours. Then compound of formula (DOXO) as HCl salt (142.1 mg, 1.0 eq) was added and the mixture was then stirred for 2.5 hours. Then MeCN (20 ml) was added. A precipitate had formed and was filtered and washed with a mixture of MeCN and DMF (5:1 (v/v), 4 times with 4 ml each). The filtrate was combined and dried under vacuum at 45° C. to get a dark residue. The residue was dissolved in the mixture of DCM and MeOH (7:1, v/v, 3 ml) and purified by preparative silica gel TLC (DCM: MeOH=7:1, (v/v), Rf=0.3). The product was extracted from the silica gel by a mixture of acetone and water (10:1, v/v, 6 times with 10 ml each). The combined extraction solutions were dried under vacuum to afford the crude product as a red solid. The crude product was then mixed with acetonitrile (5 ml), the mixture was stirred at RT for 2 hour and then filtered. The cake was washed with acetonitrile (2 times with 2 ml each) then dried under vacuum at RT to afford 33.2 mg of compound of formula (26) as a red solid (10% yield).

$^1$H NMR (400 MHz, DMSO-d$_6$, 20° C.) delta 0.84 (6H, dd, J$_1$=23.2 Hz, J$_2$=6.8 Hz), 1.13 (3H, d, J=6.4 Hz), 1.30 to 1.70 (7H, m), 1.82 to 1.87 (4H, m), 1.97 to 2.04 (1H, m), 2.08 to 2.22 (2H, m), 2.28 (2H, t, J=7.2 Hz), 2.91 to 3.09 (8H, m), 3.22 (3H, s), 3.42 to 3.46 (3H, m), 3.52 to 3.61 (8H, m), 3.70 to 3.76 (1H, m), 3.95 (2H, s), 3.99 (3H, s), 4.13 to 4.18 (2H, m), 4.28 to 4.32 (1H, m), 4.34 to 4.41 (3H, m), 4.58 (2H, d, J=5.6 Hz), 4.70 (1H, d, J=5.2 Hz), 4.85 (1H, t, J=5.8 Hz), 4.94 (1H, brs), 5.03 (2H, s), 5.22 (1H, brs), 5.41 (2H, s), 5.46 (1H, brs), 5.99 (1H, t, J=5.4 Hz), 6.86 (1H, d, J=8.0 Hz), 6.97 (2H, s), 7.19-7.24 (3H, m), 7.44 (1H, d, J=8.8 Hz), 7.65 (1H, t, J=4.8 Hz), 7.85 to 7.91 (4H, m), 8.30 (1H, d, J=7.2 Hz), 10.04 (1H, s), 13.26 (1H, s), 14.02 (1H, s).

ESI-MS: 1390.2 (M+H)$^+$

EXAMPLE 61

A mixture of compound of formula (TAXO) (200.0 mg, 1.0 eq), 4 angstrom molecular sieves (100.0 mg), anhydrous DCM (4.0 ml) and compound of formula (II-1) (146.9 mg, 2.0 eq) at 0° C. was stirred for 10 min. To the mixture was then added pyridine (28.1 mg, 1.5 eq). The resulting mixture was further stirred for 41 hours at 0° C. under N$_2$. To the mixture was then added N,N'-Dimethyl-1,2-ethylenediamine (102.0 mg, 5.0 eq.) at 0° C. under N$_2$. After stirred for 2 hours, the mixture was filtered. The cake was washed with dichloromethane (1 mL). The filtrate was combined then evaporated to dryness to give yellow residue. The residue was further purified by preparative silica gel TLC (DCM:MeOH=7:1, (v/v)) to afford 220.0 mg of compound of formula (TAXO-t1-1) as a slightly yellow solid in 96% isolated yield.

ESI-MS: 968.5 (M+Na)$^+$

EXAMPLE 62

A mixture of compound of formula (31) (252.0 mg, 1.2 eq), prepared according to example 21, compound of formula (II-1) (136.0 mg, 1.8 eq), 4 angstrom molecular sieves (100.0 mg) and anhydrous DMF (1 ml) was stirred at RT for 10 min. Then DIPEA (80.1 mg, 2.5 eq) was added. The resulting mixture was stirred for 2 hours at RT. Then compound of formula (XXXX), prepared according to example 61, was added. The resulting mixture was stirred for 2 hours. The resulting suspension was filtered; the cake was further washed with DCM (3 times with 10 ml each). The filtrate was combined then evaporated to dryness at 35° C. The resulting residue was mixed with DCM (30 ml) and stirred for 0.5 hour. The resulting suspension was filtered, the cake was further washed with DCM (2 times with 5 ml each). The filtrate was dried under vacuum at RT. The crude product was dissolved in the mixed solvent of CH$_2$Cl$_2$-MeOH (8:1, (v/v)) and further purified by preparative silica gel TLC (DCM:MeOH=8:1, (v/v)). The product was extracted from the silica-gel by a mixture of THF-water (20:1 (v/v), 6 times with 30 ml each), dried under vacuum to afford the crude product as a white solid. The crude product was then mixed with Et$_2$O (5 ml), stirred at 25° C. for 0.5 hour then filtered. The cake was washed with Et$_2$O (3 times with 5 ml each) then dried under vacuum at RT to afford 100.0 mg of compound of formula (21-TAXO-t1-1) as a white solid in 21% isolated yield.

ESI-MS: 1842.1 (M+H)$^+$, 1864.5 (M+Na)$^+$

COMPARATIVE EXAMPLE 1

T a mixture of Boc-Cit-OH (1.00 g, 1.0 eq.), prepared according to example 2, EEDQ (1.35 g, 1.5 eq.) and THF (15 ml), p-amino benzoic acid methyl ester (0.82 g, 1.5 eq.) was added. The resulting mixture was stirred at RT for 14 hours. Then the solvent was removed under vacuum and the residue was purified by silica gel chromatography (eluent PE:EtOAc=6:1 (v/v) then DCM:MeOH=10:1 (v/v)) to afford 1.2 g of compound of formula (Comp-6-4) as a white solid (81% yield).

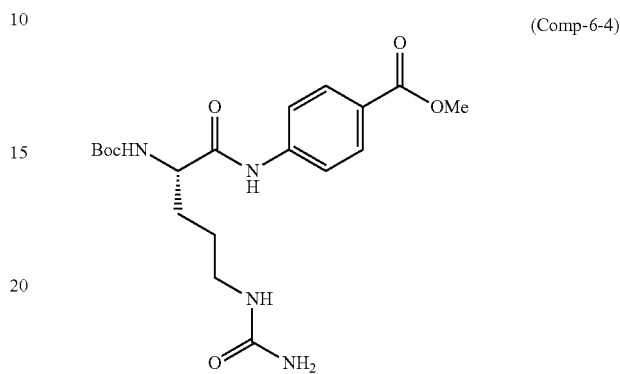
(Comp-6-4)

Analysis by silica gel TLC: eluent EtOAc (Rf=0.35, UV254)

$^1$H NMR (400 MHz, CDCl$_3$, 20° C.) delta 1.28 to 1.45 (11H, m), 1.55 to 1.65 (2H, m), 2.91 to 3.08 (2H, m), 3.83 (3H, s), 4.09 to 4.14 (1H, m), 5.43 (2H, s), 5.99 (1H, t, J=5.6 Hz), 7.10 (1H, d, J=7.6 Hz), 7.75 to 7.77 (2H, m), 7.91 to 7.93 (2H, m), 10.32 (1H, s).

ESI-MS: 309.3 (M-tBuOCO+2H)+, 409.2 (M+H)+, 817.1 (2M+H)+

COMPARATIVE EXAMPLE 2

A mixture of compound of formula (Comp-6-4) (1.66 g), prepared according to comparative example 1, and of a solution of 15% (w/w) HCl in 1,4-dioxane (10 ml) was stirred at RT for 3 hours. The reaction mixture was then concentrated under vacuum to afford 1.38 g of compound of formula (Comp-6-3) as HCl salt, being a white solid (98% yield).

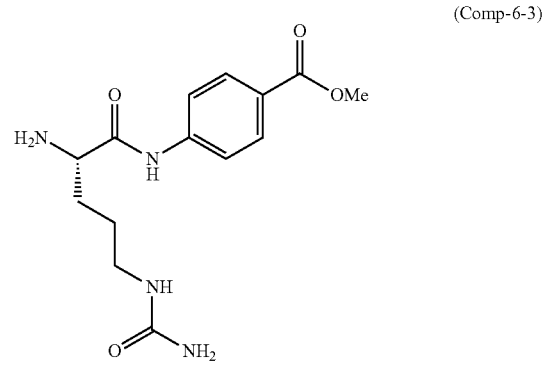 [SMILES: COC(=O)c1ccc(NC(=O)[C@@H](N)CCCNC(N)=O)cc1]
(Comp-6-3)

COMPARATIVE EXAMPLE 3

To a mixture of compound of formula (Comp-6-3) as HCl salt (14.50 g, 1.0 eq.), prepared according to comparative example 2, Boc-L-Val (10.05 g, 1.1 eq.), TBTU (27.00 g, 2.0 eq.) and DMF (80 ml) was added DIPEA (16.31 g, 3.0 eq.). The resulting mixture was stirred at RT for 16 hours. Then the mixture was diluted with water (120 ml), and then extracted with EtOAc (5 times with 100 ml each), the organic phases were combined and evaporated to dryness, the resulting residue was purified by silica gel column chromatography (eluent DCM:MeOH=20:1 to 10:1 to 7:1 (v/v)) to afford 12.9 g of compound of formula (Comp-6-2) as a solid (60% yield).

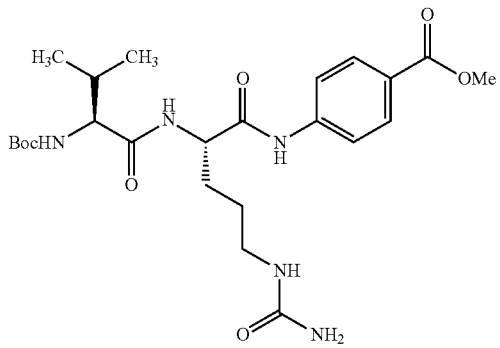
(Comp-6-2)

$^1$H NMR (400 MHz, DMSO-$d_6$, 20° C.) delta 0.85 (6H, dd, J1=17.4 Hz, J2=6.6 Hz), 1.39 (9H, s), 1.43 to 1.50 (2H, m), 1.57 to 1.76 (2H, m), 1.91 to 1.97 (1H, m), 2.91 to 3.09 (2H, m), 3.83 (3H, s), 3.85 to 3.88 (1H, m), 4.43 to 4.48 (1H, m), 5.43 (2H, s), 5.99 (1H, t, J=5.8 Hz), 6.72 (1H, d, J=8.8 Hz), 7.73 to 7.76 (2H, m), 7.90 to 7.94 (2H, m), 8.07 (1H, d, J=7.6 Hz), 10.39 (1H, s).

COMPARATIVE EXAMPLE 4

A mixture of compound of formula (Comp-6-2) (12.3 g), prepared according to comparative example 3, and of a solution of 10% (w/w) HCl in dioxane (60 ml) was stirred at RT for 3 hours. The mixture was then concentrated under vacuum to afford 10.9 g of compound of formula (Comp-6-1) as HCl salt, being a white solid (quantitative yield).

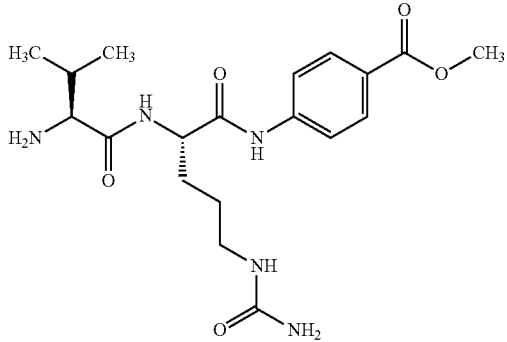
(Comp-6-1)

COMPARATIVE EXAMPLE 5

To a mixture of compound of formula (Comp-6-1) as HCl salt (10.20 g, 1.0 eq.), prepared according to comparative example 4, and anhydrous THF (150 ml) at −20° C. was added a solution of DIBAL-H in hexanes (1 M, 120.0 ml, 6.2 eq.). The mixture was warmed to RT and stirred for 14 hours. Then MeOH (20 ml) was added, followed by a saturated aqueous potassium sodium tartrate solution (180 ml) was added and the mixture was stirred for 30 min at RT. The resulting mixture was evaporated to dryness to afford a white residue which was washed with MeOH (5 times with 50 ml each). The eluents were combined, concentrated and purified by silica gel column chromatography (eluent DCM:MeOH=10:1 to 7:1 to 5:1 (v/v)) to afford 5.10 g or compound of formula (Comp-10) as a white solid (58% yield).

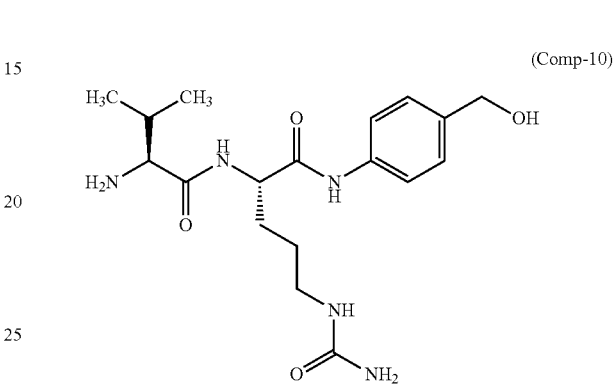
(Comp-10)

$^1$H NMR (400 MHz, DMSO-$d_6$, 20° C.) delta 0.89 (6H, dd, J1=24.0 Hz, J2=6.8 Hz), 1.33 to 1.50 (2H, m), 1.56 to 1.77 (2H, m), 1.96 to 2.04 (1H, m), 2.92 to 3.07 (2H, m), 3.30 (1H, d, J=5.2 Hz), 4.12 (2H, brs), 4.43 (2H, s), 4.47 to 4.52 (1H, m), 5.12 (1H, brs), 5.50 (2H, s), 6.10 (1H, t, J=5.6 Hz), 7.24 (2H, d, J=8.8 Hz), 7.54 to 7.57 (2H, m), 8.37 (1H, d, J=5.8 Hz), 10.11 (1H, s).

ESI-MS: 380.4 (M+H)+, 759.2 (2M+H)+

COMPARATIVE EXAMPLE 6

To a mixture of compound of formula (Comp-10) (1.02 g, 1.0 eq.), prepared according to comparative example 5, compound of formula (CG1MR-IV-2) (0.92 g, 1.1 eq.)

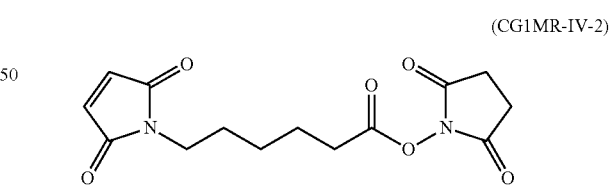
(CG1MR-IV-2)

and DMF (15 ml) at RT was added DIPEA (0.39 g, 1.1 eq.). The resulting mixture was stirred at RT for 16 hours. Then the DMF was removed under vacuum to afford a slightly yellow residue. The residue was then mixed with acetone (20 ml) and the mixture was then stirred at RT for 5 hours. The mixture was filtered, the wet cake was washed with acetone (2 times with 10 ml each) and then dried under vacuum to afford 1.05 g of compound of formula (Comp-11) as a slightly yellow solid (67% yield).

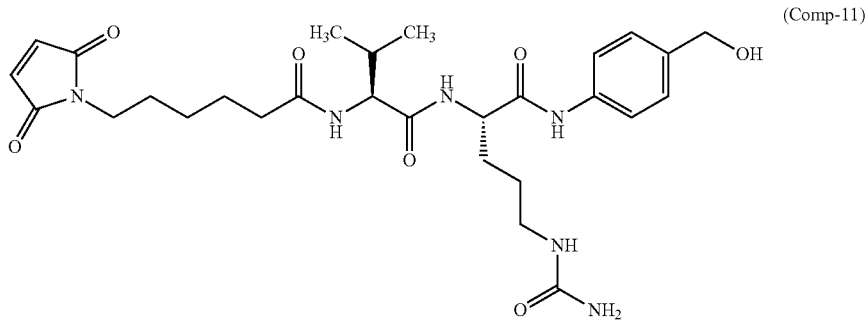 [SMILES: CC(C)[C@H](NC(=O)CCCCCN1C(=O)C=CC1=O)C(=O)N[C@@H](CCCNC(N)=O)C(=O)Nc1ccc(CO)cc1]

(Comp-11)

¹H NMR (400 MHz, DMSO-d₆, 20° C.) delta 0.84 (6H, dd, J1=12.2 Hz, J2=6.6 Hz), 1.17 to 1.31 (2H, m), 1.37 to 1.75 (8H, m), 1.95 to 2.00 (1H, m), 2.11 to 2.21 (2H, m), 2.92 to 3.06 (2H, m), 3.38 (2H, t, J=6.8 Hz), 4.18 to 4.22 (1H, m), 4.38 to 4.39 (1H, m), 4.43 (2H, d, J=4.8 Hz), 5.09 (1H, t, J=5.2 Hz), 5.41 (2H, s), 5.98 (1H, t, J=5.6 Hz), 7.00 (2H, s), 7.23 (2H, d, J=8.0 Hz), 7.55 (2H, d, J=8.2 Hz), 7.81 (2H, d, J=8.4 Hz), 8.06 (1H, d, J=7.2 Hz), 9.90 (1H, s).

COMPARATIVE EXAMPLE 7

A mixture of compound of formula (Comp-11) (350.0 mg, 1.0 eq.), prepared according to comparative example 6, DIPEA (307.0 mg, 3.9 eq.), 500.0 mg 4 angstrom molecular sieves and anhydrous DMF (5.0 ml) was stirred for 25 min. Then compound of formula (II-1) (280.0 mg, 1.5 eq.) was added. The resulting mixture was stirred at RT for 3 hours. Then compound of formula (DOXO) as HCl salt (368.8 mg, 1.0 eq.) was added and then the mixture was stirred for 12 hours. Then MeCN (25.0 ml) was added to the reaction mixture. A precipitate had formed and was filtered and washed with a mixture of MeCN and DMF (5:1 (v/v), 3 times with 5 ml each). The filtrates were combined and dried under vacuum at 45° C. to afford a dark red residue. The residue was dissolved in a mixture of DCM and MeOH (7:1 (v/v)) and purified by preparative silica gel TLC (DCM:MeOH=7:1 (v/v), Rf=0.15). The product was extracted from the silica gel by a mixture of acetone and water (20:1 (v/v), 10 times with 50 ml each), the combined extracts were dried under vacuum to afford the crude product as a red solid. The crude product was then mixed with acetonitrile (20 ml), the mixture was stirred at RT for 18 hours then filtered. The cake was mixed with acetonitrile (10 ml) and the mixture was stirred for 3 hours at RT. The mixture was then filtered. The cake was dried under vacuum at RT to afford 61.0 mg of compound of formula (Comp-12) as a red solid (8.7% yield); in formula (Comp-12) doxorubicin is the compound of formula (DOXO), which is connected via the amino group denoted with (d1) in formula (Comp-12) and in formula (DOXO).

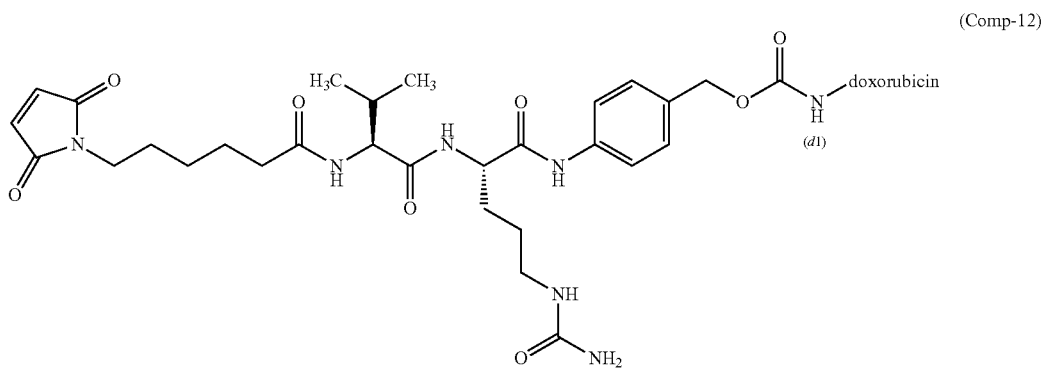

(Comp-12)

¹H NMR (400 MHz, DMSO-d₆, 20° C.) delta 0.85 (6H, dd, J1=12.0 Hz, J2=6.8 Hz), 1.12 (3H, d, J=6.4 Hz), 1.16 to 1.22 (2H, m), 1.31 to 1.50 (7H, m), 1.54 to 1.71 (2H, m), 1.82 to 1.88 (1H, m), 1.91 to 2.01 (1H, m), 2.10 to 2.22 (4H, m), 2.89 to 3.03 (4H, m), 3.38 (2H, t, J=6.8 Hz), 3.44 (1H, m), 3.71 to 3.75 (1H, m), 3.99 (3H, s), 4.16 to 4.20 (2H, m), 4.33 to 4.39 (1H, m), 4.58 (2H, d, J=5.6 Hz), 4.71 (1H, d, J=5.6 Hz), 4.86 (1H, t, J=6.0 Hz), 4.89 (2H, s), 4.95 (1H, brs), 5.22 (1H, d, J=2.8 Hz), 5.40 (2H, s), 5.47 (1H, s), 5.99 (1H, t, J=4.8 Hz), 6.84 (1H, d, J=8.0 Hz), 7.00 (2H, s), 7.24 (2H, d, J=8.4 Hz), 7.55 (2H, d, J=8.4 Hz), 7.66 (1H, t, J=4.8 Hz), 7.80 (1H, d, J=8.4 Hz), 7.92 (2H, d, J=4.8 Hz), 8.06 (1H, d, J=7.6 Hz), 9.97 (1H, s), 13.28 (1H, s), 14.04 (1H, s).

ESI-MS: 1141.7 (M+H)+

EXAMPLE 100

General Method Description for the Preparation of Compounds of Formula (I) Given in Table 1:

To a 10 mM aqueous solution of N-acetyl-cysteine (2500 μl, 5 eq.) was added a 10 mM solution of the respective compound of formula (II) in N,N-dimethylacetamide (500μl). The pH was adjusted to 7.5 with a 0.3 M sodium hydrogen phosphate solution, and the reaction mixture stirred for 2 h at 20° C. The resulting respective solution of compound of formula (I) was used/tested without further purification.

Details are given in Table (1)

TABLE 1

| Example | Compound of formula (II) | Compound of formula (I) |
|---|---|---|
| 100-1 | Compound of formula (Comp-12), prepared according to comparative example 7 | Compound of formula (Comp-13) |
| 100-2 | Compound of formula (23), prepared according to example 36 | Compound of formula (13) |
| 100-3 | Compound of formula (20), prepared according to example 15 | Compound of formula (10) |
| 100-4 | Compound of formula (21), prepared according to example 22 | Compound of formula (11) |
| 100-5 | Compound of formula (22), prepared according to example 29 | Compound of formula (12) |
| 100-6 | Compound of formula (25), prepared according to example 54 | Compound of formula (15) |
| 100-7 | Compound of formula (26), prepared according to example 60 | Compound of formula (16) |
| 100-8 | Compound of formula (24), prepared according to example 44 | Compound of formula (14) |

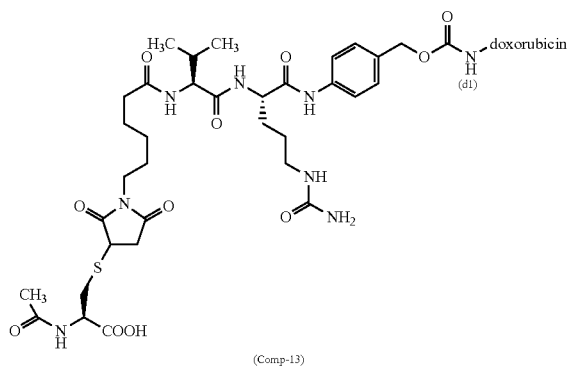

(Comp-13)

Method RP-HPLC

RP-HPLC analysis of the respective solution of compounds of formula (I), prepared according to example 100, was done with the following parameter:

Luna 5 u C18 250×4.6 mm column (purchased form Phenomenex), solvent A: 0.1% (v/v) TFA in water, solvent B: 0.1% (v/v) TFA in acetonitrile, 100% solvent A for 10 min., gradient from 0 to 70% solvent B over next 70 min., and to 100% over next 3 min., 1 ml/min., detection at 254 nm.

RT=retention time
Values are given in Table 2

TABLE 2

| | RT |
|---|---|
| compound of formula (DOXO) | 44.9 min. |
| compound of formula (Comp-13) | 54.5 min. |
| compound of formula (13) | 55.1 min. |
| compound of formula (10) | 51.2 min. |
| compound of formula (11) | 51.7 min. |
| compound of formula (12) | 50.7 min. |
| compound of formula (15) | 50.6 min. |
| compound of formula (16) | 52.2 min. |
| compound of formula (14) | 48.3 min. |

Solubility Test

The respective solution of compound of formula (I) (15, 48 and 96 µl respectively), prepared according to example 100 were mixed with water (135, 102 and 54 µl respectively) to get a total of 150 µA of the respective three diluted solutions. These three diluted solutions have a concentration of 1.5%, 5.0% and 10.0% of DMA respectively, the % being % by volume, based on the total volume of the water in the respective solutions. These diluted solutions were stirred for 1 h at 20° C. and then analysed by Method RP-HPLC.

The solubility of the compounds of formula (I) was assessed by comparison of the peak areas (relative to the most soluble conjugate, namely compound of formula (II), the peak area of which was set to 100%, denoted with (*ref) in Table 3), values are given in Table 3:

TABLE 3

| | 1.5% DMA | 5.0% DMA | 10.0% DMA |
|---|---|---|---|
| Compound of formula (Comp-13) | 8% | 41% | 77% |
| Compound of formula (13) | 17% | 53% | 82% |
| Compound of formula (10) | 15% | 47% | 84% |
| Compound of formula (11) | 19% | 58% | 100% (*ref) |
| Compound of formula (12) | 16% | 49% | 85% |
| Compound of formula (15) | 16% | 45% | 77% |
| Compound of formula (16) | 16% | 47% | 80% |
| Compound of formula (14) | 12% | 36% | 66% |

The higher solubilities, especially at the more relevant low DMA concentration, of the compound of formula (I) compared to the reference linker compound of formula (Comp-13) provide two advantages:
1) A higher yield when compound of formula (I) is synthesized, thanks to reduced aggregation
2) Superior pharmacokinetic Cathepsin B Release of Compound of Formula (DOXO)

Bovine spleen cathepsin B (SAFC C6286-10UN, 10 units) was dissolved in 1 ml of a pH 5.0 aqueous acetate buffer (25 mM acetate and 1 mM EDTA) to provide for a cathepsin B stock solution.

This cathepsin B stock solution (16 µl) was mixed with a aqueous solution of 30 mM dithiothreitol and 15 mM EDTA (32 µl) and the resulting solution was left to stand without stirring for 15 min. at 20° C. Then an aqueous solution of 25 mM acetate and 1 mM EDTA (1175 µl), the respective solution of compound of formula (I) (142 µl prepared according to example 100), N,N-dimethylacetamide (53.7 µl), and a 10 mM aqueous solution of daunorubicin as internal standard for assigning peaks based on retention time (157.7 µl) were added. The resulting solution was incubated for 2 days at 37° C. Aliquots (100 µl) were periodically removed as given in Table 4 and analysed undiluted by Method RP-HPLC. The relative percentage of released compound of formula (DOXO) relative to respective compound of formula (I) during the experiment are given in Table 4:

TABLE 4

| | 0 h | 4 h | 8 h | 24 h | 48 h |
|---|---|---|---|---|---|
| Compound of formula (13) | <0.1% | 18.0% | 24.4% | 32.2% | 33.8% |
| Compound of formula (10) | <0.1% | 15.8% | 23.5% | 35.5% | 41.4% |
| Compound of formula (11) | <0.1% | 6.4% | 8.7% | 13.5% | 15.4% |
| Compound of formula (12) | <0.1% | 3.0% | 3.8% | 5.3% | 5.0% |
| Compound of formula (15) | <0.1% | 1.3% | 1.6% | 2.3% | 4.1% |
| Compound of formula (16) | <0.1% | 0.6% | 1.0% | 2.0% | 2.2% |
| Compound of formula (14) | <0.1% | <0.1% | 1.0% | 1.7% | 2.2% |

All compounds showed drug release in the presence of Cathepsin B.

Stability in Human Serum

To human serum (SAFC H4522, 950 µl) was added the respective solution of compound of formula (I) (950 µl prepared according to example 100) and a 10 mM aqueous solution of daunorubicin as internal standard (100 µl). The resulting solution was incubated at 37° C. for 7 days. Aliquots (100 µl) were periodically removed as given in Table 4, diluted with 0 to 5° C. methanol (400 µl) filtered, and the resulting filtrate analyzed by Method RP-HPLC.

Released compound of formula (DOXO) was quantified relative to the daunorubicin (the internal standard), values are given in Table 5:

TABLE 5

|  | 0 h | 4 h | 8 h | 24 h | 48 h | 72 h |
| --- | --- | --- | --- | --- | --- | --- |
| Compound of formula (13) | <0.1% | <0.1% | <0.1% | 4.4% | 6.3% | 6.9% |
| Compound of formula (10) | <0.1% | <0.1% | <0.1% | 2.4% | 4.3% | 4.3% |
| Compound of formula (11) | <0.1% | <0.1% | <0.1% | <0.1% | <0.1% | <0.1% |
| Compound of formula (12) | <0.1% | <0.1% | <0.1% | <0.1% | <0.1% | <0.1% |
| Compound of formula (15) | <0.1% | <0.1% | 0.2% | 3.2% | 5.2% | 6.0% |
| Compound of formula (16) | <0.1% | 1.3% | 1.2% | 1.9% | 3.2% | 1.6% |
| Compound of formula (14) | <0.1% | <0.1% | <0.1% | 1.1% | 2.5% | 2.6% |

All branched linkers proved to have good stability.

EXAMPLE 101

A compound of formula (12-101), derived from compound of formula (22) and monoclonal anti-interleukin-1b antibody was prepared as follows:

Monoclonal anti-interleukin-1b antibody produced in mouse (5 mg, Sigma article No I3642) was mixed in PBS (8.0 ml).

To an aliquot of this solution (3 ml) was added a 1.0 mM aqueous solution of tris(2-carboxyethyl)phosphine hydrochloride (25 µl, 2.0 eq.) and the mixture was stirred for 90 min. at 20° C. A 1.0 mM solution of compound of formula (22), prepared according to example 29, in N,N-dimethylacetamide (64.4 µl, 5.15 eq.) was added and the resulting mixture further stirred for 30 min at 20° C. A 1.0 mM aqueous solution of N-acetyl-cysteine (64.4 µl, 5.15 eq.) was added and the resulting mixture further stirred for 36 min. at 20° C. to yield a so called conjugation mix. A NAP-25 column was rinsed with PBS (25 ml), loaded with the conjugation mix (2.5 ml) and eluted with PBS (5.0 ml). Fractions were collected and those that contained protein were pooled. The pooled protein solution, which comprised compound of formula (12-101), was analysed by Method SEC-HPLC (results are given in Table 6) and by Method HIC with the monoclonal anti-interleukin-1b antibody suspended in PBS.

EXAMPLE 102

A compound of formula (15-102), derived from compound of formula (25) and monoclonal anti-interleukin-1b antibody was prepared as follows:

Monoclonal anti-interleukin-1b antibody produced in mouse (5 mg, Sigma article No I3642, as used in example 101) was mixed in PBS (8.0 ml). To an aliquot of this solution (3 ml) was added a 1.0 mM aqueous solution of tris(2-carboxyethyl)phosphine hydrochloride (25 µl, 2.0 eq.) and the mixture was stirred for 90 min. at 20° C. A 1.0 mM solution of compound of formula (25), prepared according to example 54, in N,N-dimethylacetamide (64.4 µl, 5.15 eq.) was added and the mixture further stirred for 30 min. at 20° C. A 1.0 mM aqueous solution of N-acetyl-cysteine (64.4 µl, 5.15 eq.) was added and the mixture further stirred for 42 min. at 20° C. to yield a so called conjugation mix. A NAP-25 column was rinsed with PBS (25 ml), loaded with the conjugation mix (2.5 ml) and eluted with PBS (5.0 ml). Fractions were collected and those that contained protein were pooled. The pooled protein solution, which comprised compound of formula (15-102), was analysed by Method SEC-HPLC (results are given in Table 6) and by Method HIC with the monoclonal anti-interleukin-1b antibody suspended in PBS.

Method SEC-HPLC

SEC-HPLC analysis of respective pooled protein solution was done with the following parameters:

TSK G3000SWXL 300×7.8 mm column (Silica based column with mean pore size of 250 Angstrom and mean particle size of 5 micrometer, purchased from Tosoh Bioscience), eluent 10% (v/v) isopropanol in 0.2 M potassium phosphate buffer, 0.5 ml/min., detection at 280 nm.

RT=retention time

The peak and therewith the retention time of the respective compound of formula (I) was identified by comparison with the unmodified Monoclonal anti-interleukin-1b antibody, which was used as substrate in the examples 101 and 102.

HMW=high molecular weight fraction, not assigned
LMW=low molecular weight fraction, not assigned

TABLE 6

|  | RT | purity | HMW | LMW |
| --- | --- | --- | --- | --- |
| Monoclonal anti-interleukin-1b antibody as used in examples 101 and 102 | 15.5 min. | 92.1% | 7.6% | 0.3% |
| Compound of formula (12-101), prepared according to example 101 | 15.6 min. | 92.4% | 7.5% | 0.1% |
| Compound of formula (15-102), prepared according to example 102 | 15.6 min. | 91.5% | 8.4% | 0.1% |

Method HIC

HIC analysis of respective pooled protein solution was done with the following parameters:

TSK-gel Butyl-NPR 4.6 mm×35 mm column (NPR means non-porous resin, polymethacrylate base material with mean particle size 2.5 micrometer, purchased from Tosoh Bioscience), solvent A: 50 mM sodium phosphate buffer, solvent B: 25% (v/v) isopropanol in 50 mM sodium phosphate buffer, gradient from 100% solvent A to 100% solvent B over 12 min., 0.8 ml/min, detection at 280 nm. FIG. 1 shows the obtained chromatogram.

Legend of FIG. 1:
Continuous line ⎯ The monoclonal anti-interleukin-1b antibody used in examples 101 and 102
Dashed line _ _ _ Compound of formula (12-101), prepared according to example 101
Dotted line ....... Compound of formula (15-102), prepared according to example 102
AU absorption unit

The invention claimed is:

1. A method (MI) for connecting a ligand LI with a drug DR, the method comprising
covalently connecting the ligand LI to the drug DR using a linker LIN,
wherein the connecting step forms a ligand-linker-drug conjugate, wherein
LI is selected from the group consisting of amino acids LI-AA, mono- or polyclonal antibodies LI-Ab, antibody fragments LI-AbFrag, proteins LI-Prot and peptides LI-Pep;
DR is a pharmaceutically active drug;
LIN comprises a connecting group CG2; and
CG2 is a connecting group of formula (CG2-1)

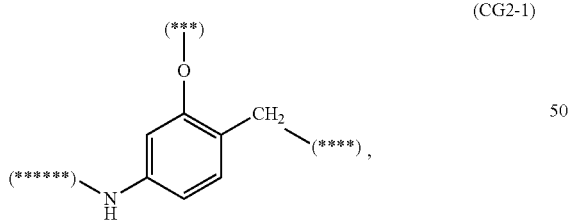

wherein
(\*\*\*) denotes the connecting site which is used to connect LI;
(\*\*\*\*) denotes the connecting site which is used to connect DR;
(\*\*\*\*\*\*) denotes the connecting, site to which a linear peptide is connected, said peptide having, 2 to 8 amino acid residues.

2. The method (MI) according to claim 1, wherein the ligand-linker-drug conjugate is in the form of a compound of formula (I),

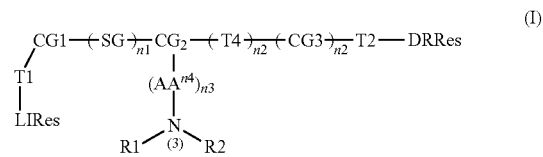

wherein
T1 is —S—, —O— or —NH—;
T2 is —N(R4)-, —O— or —S—;
R4 H or $C_{1-4}$ alkyl;
T4 —O—;
n1 is 0 or 1;
n2 is 0 or 1;
n3 is 2, 3, 4, 5, 6, 7 or 8;
n4 is an integer from 1 to n3;
CG1 is a connecting group selected from the group consisting of a connecting group of formula (CG1-I) and spacer group of formula (CG1-II), a connecting group of formula (CG1-III) and a connecting group of formula (CG1-IV);

-continued

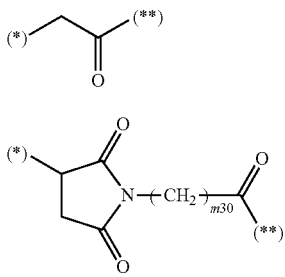
(CG1-III)

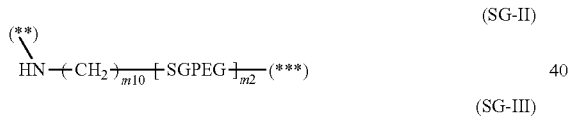
(CG1-IV)

wherein
m30 and m32 are identical or different and independently from each other 1, 2, 3, 4, 5, 6, 7, 8, 9 or 10;
(*) in the formulae of CG1 denotes the bond between T1 and CG1, the covalently connected LI forms in compound of formula (I) a ligand residue LIRes, which is covalently connected to CG1 via T1;
LI is a compound of formula (LIRes-T1-H);

LIRes-T1-H                              (LIRes-H)

LIRes is selected from the group consisting of amino acid residue LIRes-AA, mono- or polyclonal antibody residue LIRes-Ab, antibody fragment residue LIRes-Ab-Frag, protein residue LIRes-Prot and peptide residue LIRes-Pep;
LI has a functional group selected from the group consisting of SH, OH or NH$_2$, which forms in formula (I) the T1, the T1 is bonded to CG1 via the bond (*);
SG is a spacer group selected from the group consisting of a spacer group of formula (SG-II) and a spacer group of formula (SG-III);

(SG-II)
$$\overset{()}{\underset{}{\diagdown}}\text{HN}-(\text{CH}_2)_{m10}-(\text{SGPEG})_{m2}-(*)$$

(SG-III)
$$\overset{()}{\underset{}{\diagdown}}\text{HN}-(\text{CH}_2)_{m11}-(\text{SGPEG})_{m1}-(\text{CH}_2)_{m12}-\text{NH}\overset{(*)}{\underset{\text{O}}{-\text{CH}_2}}$$

wherein
m1 and m2 are identical or different and independently from each other 0 or 1;
m10, m11 and m12 are identical or different and independently from each other 0, 1, 2, 3, 4, 5, 6, 7, 8, 9 or 10;
with the proviso, that m2 and m10 are not simultaneously 0 and that m1, m11 and m12 are not simultaneously 0;
SGPEG is a connecting group of formula (SGPEG-I);

(SGPEG-I)
$$-(\text{CH}_2-\text{CH}_2-\text{O})_{m20}-\text{CH}_2-\text{CH}_2-$$

wherein
m20 is 1, 2, 3, 4, 5 or 6;

CG3 is selected from the group consisting of connecting group of formula (CG3-I) and connecting group of formula (CG3-II);

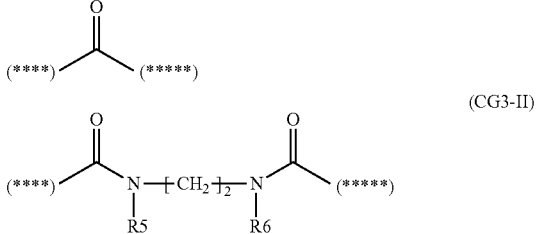

(CG3-I)

(CG3-II)

wherein
R5 and R6 are identical or different and independently from each other $C_{1-4}$ alkyl;
(******) in the formulae of CG2 denote the bond between to CG2 and AA$^{n4}$;
the covalently connected DR forms in compound of formula (I) a drug residue DRRes, which is covalently connected to CG2 via T2;
DR is a compound of formula (DDRes-T2-H);

H-T2-DRRes                              (DRRes-T2-H)

DRRes is a drug residue derived from DR;
DR has a functional group selected from the group consisting of —N(R4)H, —OH or —SH, which forms in formuls (I) the T2;
AA$^{n4}$ is an amino acid residue and (AA$^{n4}$)$_{n3}$ is a linear peptide with n3 amino acid residues wherein n4 denotes the position of the amino acid residue in the peptide starting from CG2 with AA$^1$ being the first amino acid residue in the chain and being connected to CG2 via the bond (****), with the bond (****) being an amide bond of the carboxylic acid group of AA$^1$ with the amino group of CG2, and the AA$^{n3}$ being the last amino acid residue in the chain, and with the individual amino acid residues being independently from each other identical or different, wherein the individual amino acid residures are connected to each other via a peptide bond;
(3) denotes the N-terminal amino group of said linear peptide, which is the amino group of AA$^{n3}$;
R1 and R2 are identical or different and independently from each other selected from the group consisting of hydrogen, $C_{1-4}$ alkyl, $C(O)-(CH_2-O-)_{m5}-(GRPEG)_{m4}$-R3 and PGN;
R3 $C_{1-4}$ alkyl;
m4 is 0 or 1;
m5 is 0 or 1;
PGN is a protecting group;
GRPEG is a connecting group of formula (GRPEG-I);

(GRPEG-I)
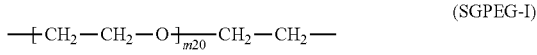

wherein
m21 is 1, 2, 3, 4, 5 or 6
wherein
if n1 being 1, the () in the formulae of CG1 and the () in the formula of SG denote the bond between CG1 and SG and the (*) in the formula of SG and the (*) in the formula of CG2 denote the bond between SG and CG2; and further wherein if n1 and CG1 is a connecting group of formula (CG1I), the nitrogen atom denoted with (**) in SG forms an endocyclic nitrogen atom thereby replacing the hydrogen atom of said nitrogen atom by an endocyclic bond;

if n1 is 0, the () in the formulae of CG1 and the (*) in the formula of CG2 denote the bond between CG1 and CG2; and further with the proviso that if n1 is 0 then CG1 is not a connecting group of formula (CG1-I);

if n2 is 1, the (**) in the formula of CG2 denotes the bond between CG2 and T4 and the () in the formula of CG3 denote the bonds between CG3 and T4; and further wherein n2 is 1, the (*) in the formula of CG3 denotes the bond between CG3 and T2; and if n2 being 0, the (**) in the formula of CG2 denotes the bond between CG2 and T2.

3. The method (MI) according to claim 2, the method comprising reacting a compound of formula (II) with a compound of formula (LIRes-T1H);

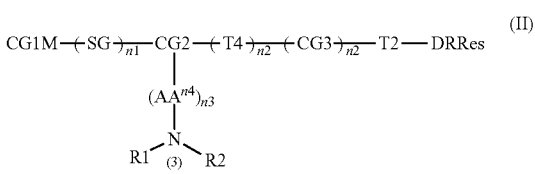

(II)

wherein
CG1M is a connecting group selected from the group consisting of connecting group of formula (CG1M-I), connecting group of formula (CG1M-II), connecting group of formula (CG1M-III) and connecting group of formula (CG1M-IV);

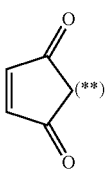

(CG1M-I)

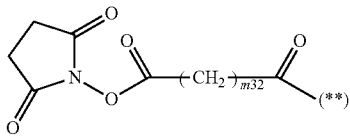

(CG1M-II)

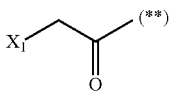

(CG1M-III)

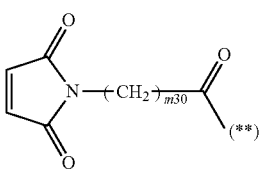

(CG1M-IV)

wherein
X1 is Cl, Br or I.

4. A method (MII) for the preparation of compound of formula (II), with the compound of formula (II) as defined in claim 3,
wherein
if n2 is 1 and CG3 is a connecting group of formula (CG3-I), then method (MII) comprises a step (MIIa) and a step (MIIb);
if n2 is 1 and CG3 is a connecting group of formula (CG3-II), then method (MII) comprises the step (MIIa), a step (MIIc), a step (MIId) and a step (MIIe);
if n2 is 0 and CG1M is a connecting group of formula (CG1M-IV) then method (MII) comprises one step, a step (MII0-IV), or two steps, a step (MII0-I-IVa) and a step (MII0-1-IVb);
if n2 is 0 and CG1M is a connecting group of formula (CG1M-III) then method (MII) comprises a step (MII0-III);
if n2 is 0 and CG1M is a connecting group of formula (CG1M-II) then method (MII) comprises two steps, a step (MII0-IIa) and a step (MII0-IIb), or one step, a step (MII0-IIc);
if n2 is 0 and CG1M is a connecting group of formula (CG1M-I) then method (MII) comprises one step, a step (MII0-I), or two steps, a step (MII0-I-IVa) and a step (MII0-I-IVb);
wherein
step (MIIa) comprises a reaction a compound of formula (III) with a compound of formula (II-I) to form a reaction product (MIIa);

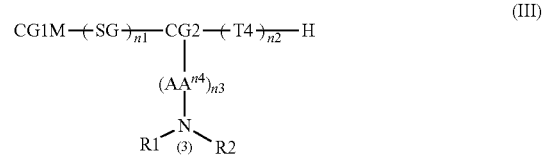

(III)

the compound of formula (II-I) is selected from the group consisting of a compound of formula (II-1), 1,1'-carbonyldiimidazole, 4-nitrophenylchloroformate, phosgene, diphosgene, triphosgene and mixtures thereof;

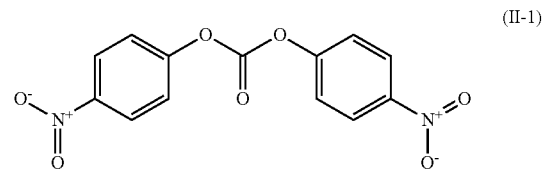 [SMILES: O=C(Oc1ccc([N+](=O)[O-])cc1)Oc1ccc([N+](=O)[O-])cc1]

(II-1)

wherein
step (MIIb) comprises a reaction product (MIIa) with a compound of formula (DRRes-T2-H);
wherein
step (MIIc) comprises a reaction (MIIa) with a compound of formula (CG3M-II) to provide a compound of formula (IIc);

(CG3M-II)

-continued

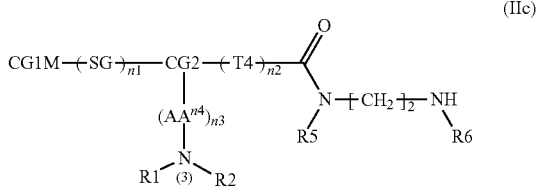
(IIc)

wherein
  step (MIId) comprises reacting compound of formula (IIc) with the compound of formula (II-I) to form a reaction product (MIId;
  step (MIIe) comprises a reaction product (MIId) with a compound of formula (DRRes-T2-H);
wherein
  step (MII0-I-IVa) comprises a reacting a compound of formula (III) with a compound (II0-I-IVa) to provide a compound of formula (III0-I-IVa);

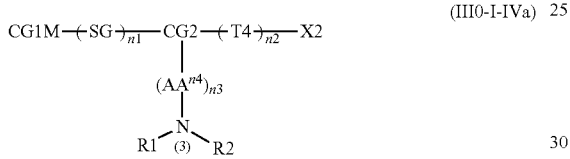
(III0-I-IVa)

wherein
  n2 is 0 in formula (III0-I-IVa);
  compound (II0-I-IVa) is selected from the group consisting of p-toluenesulfonyl chloride, p-toluenesulfonic anhydride, methanesulfonyl chloride, methanesulfonic anhydride, trifluoromethanesulfonyl chloride and trifluoromethanesulfonic anhydride and mixtures thereof;
  X2 is selected from the group consisting of —OTs, —OMs and —OTf;
wherein
  step (MII0-1-IVb) comprises a reacting the compound of formula (III0-I-IVa) with a compound of formula (DRRes-T2-H);
wherein
  step (MII0-I-IVb) comprises reacting the compound of formula (III0-I-Iva) with a compound formula (DRRes-T2-H);
  the compound of formula (III) is prepared
    in a step (MIII-IV) for the case that CG1M is a connecting group of formula (CG1M-IV); or
    in a step (MIII-III) for the case that CG1M is a connecting group of formula (CG1M-III); or
    in two steps, a step (MIII-IIa) and a step (MIII-IIb), or in one step, a step (MIII-IIc), for the case that CG1M is a connecting group of formula (CG1M-II) or a step (MIII-I) for the case that CG1 M is a connecting group of formula (CG1 M-I);
wherein
  step (MIII-IV) comprises a reaction (MIII-IV) of a compound of formula (IV),

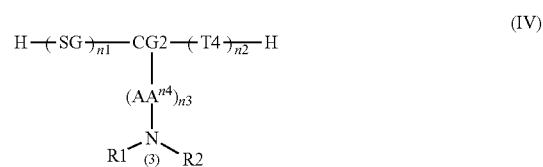
(IV)

with a compound of formula (CG1MR-IV);

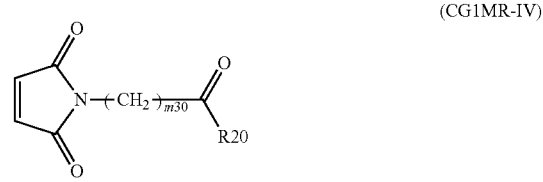
(CG1MR-IV)

wherein
  R20 is a residue of formula (R20-1);

(R20-1)

wherein
  step (MIII-III) comprises reacting a compound of formula (IV) with a compound of formula (CG1MR-III);

(CG1MR-III)

wherein
  step (MIII-IIa) comprises a reacting the compound of formula (IV) with a compound of formula (CG1MR-IIa) to provide a compound of formula (IV-IIa);

(CG1MR-IIa)

(IV-IIa)

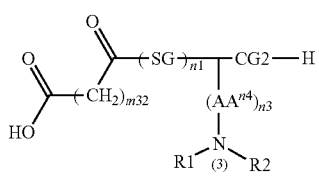

wherein
step (MIII-IIb) comprises a reacting the compound of formula (IV-IIa) with a compound of formula (HOSu);

(HOSu)

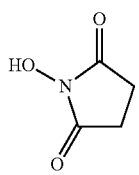

wherein
step (MIII-IIc) comprises a reacting the compound of formula (IV) with a compound of formula (CG1MR-IIc);

(CG1MR-IIc)

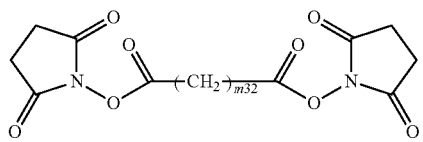

wherein
step (MIII-I) comprises a reacting a compound of formula (IV) with a compound of formula (MA);

(MA)

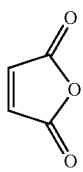

wherein
the compound of formula (IV) is prepared in a step (MIV); wherein step (MIV) comprises reducing a compound of formula (V) with a compound (IV);

(V)

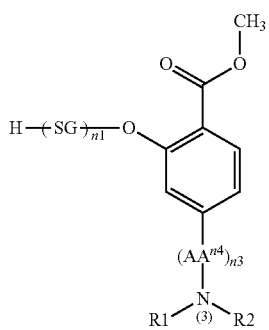

wherein
compound (IV) is selected from the group consisting of $NaBH_4$, $BH_3$, DIBAL-H, sodium bis(2-methoxyethoxy)aluminium hydride and mixtures thereof;
wherein the compound of formula (V) is prepared in a step (MVb);
wherein step (MVb) comprises cleaving R30 from a compound of formula (Va) with HCl;

(Va)

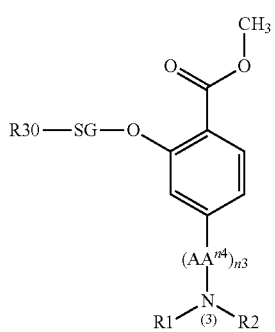

wherein
R30 is connected to SG via the bond denoted with (**) in the formulae of SG and is Boc;
wherein
step (MII0-IV) comprises a reacting a compound of formula (III0) with a compound of formula (CG1MR-IV);

(III0)

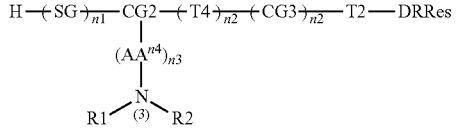

wherein
n2 is 0 in formula (III0);
wherein
step (MII0-III) comprises a reacting the compound of formula (III0) with a compound of formula (CG1MR-III);
wherein
step (MII0-IIa) comprises a reacting the compound of formula (III0) with a compound of formula (CG1MR-IIa) to provide a compound of formula (III0-IIa);

(III0-IIa)

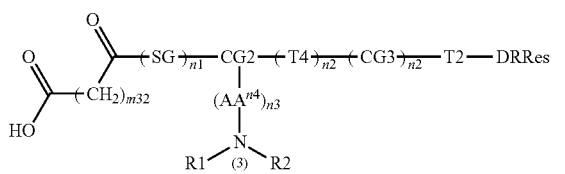

wherein
n2 is 0 in formula (III0-IIa);
wherein
step (MII0-IIb) comprises reacting the compound of formula (III0-IIa) with a compound of formula (HOSu);
wherein
step (MII0-IIc) comprises reacting the compound of formula (III0) with a compound of formula (CG1MR-IIc);
wherein
step (MII0-I) comprises reacting a compound of formula (III0) with a compound of formula (MA);
wherein
compound of formula (III0) is prepared in a step (MIII0), wherein step (MIII0) comprises cleaving R30 from compound of formula (IV0) with HCl;

(Iv0)

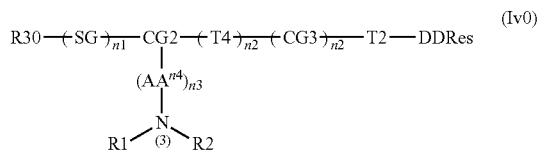

wherein
n2 is 0 in formula (IV0);
wherein
the compound of formula (IV0) is prepared in a step (MIV0a) and a step (MIV0b),
wherein
step (MIV0a) comprises a reacting a compound of formula (V0) with a compound (RIV0a) to provide a compound of formula (IV0a);
wherein
compound (RIV0a) is selected from the group consisting of p-toluenesulfonyl chloride, p-toluenesulfonic anhydride, methanesulfonyl chloride, methanesulfonic anhydride, trifluoromethanesulfonyl chloride and trifluoromethanesulfonic anhydride, $SOCl_2$, $(COCl)_2$, $POCl_3$, $PCl_3$, $PCl_5$, $POBr_3$, $PBr_3$, $PBr_5$, N-bromosuccinimide, N-iodosuccinimide, HCl, HBr, HI and mixtures thereof;

(V0)

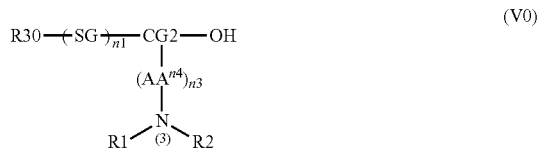

(IV0a)

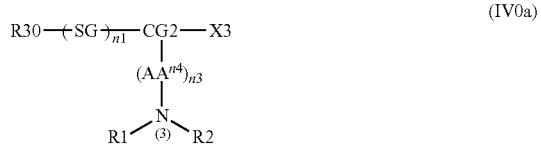

wherein
X3 is selected from the group consisting of —OTs, —OMs, —OTf, —Cl, —Br and —I;

wherein
step (MIV0b) comprises a reacting the compound of formula (IV0a), with the compound of formula (DRRes-T2-H);
wherein
the compound of formula (V0) is prepared in a step (MV0), step (MV0) comprises reducing a compound of formula (Va) with compound (IV).

5. The method (MII) according to claim 4, wherein the compound of formula (Va) is prepared in a step (MVa), wherein step (MVa) comprises reacting a compound of formula (VI) with a compound of formula (SGM);

(VI)

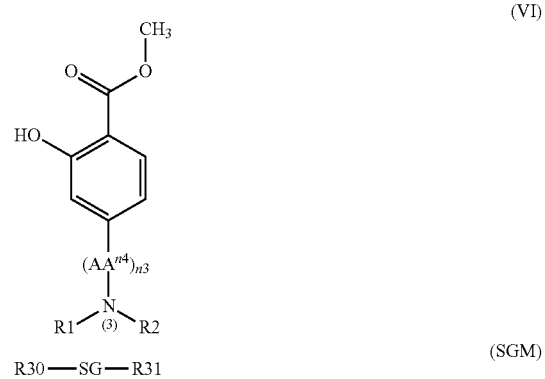

(SGM)

R30—SG—R31 wherein
R31 is connected to SG via the bond denoted with (***) in the formulae of SG and is —OTs, —OMs, —OTf, —Br, —Cl or —I.

6. The method (MII) according to claim 5, wherein the compound of formula (VI) is prepared in a step (MVIa) and optionally in a further step (MVIb);
wherein
step (MVIa) comprises coupling the n3 $AA^{n4}$ to a compound of formula (VII-1) and then to the respective products of the preceding peptide coupling reactions;

(VII-1)

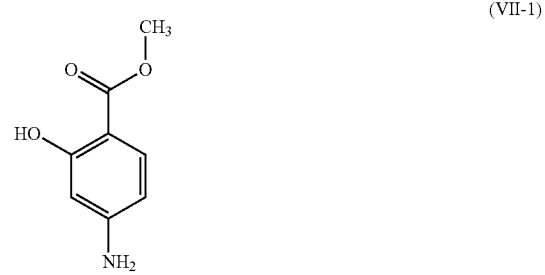

wherein
step (MVIb) comprises a reacting the N-terminal amino group of $AA^{n3}$ denoted with (3) in formula (VI) is reacted with a compound NTermProt;
wherein
NTermProt is selected from the group consisting of $C_{1-4}$ alkyl iodide, $C_{1-4}$ alkyl bromide, Cl—C(O)-(GRPEG)$_{m4}$-R3, R3-C(O)—O—C(O)—R3 and PGNPrec;
wherein
PGNPrec is a reagent which provides for the introduction of PGN on the N-terminal amino group of $AA^{n3}$ denoted with (3) in formula (VI).

7. A compound of formula (I) as defined in claim 2.
8. Compound of formula (I) according to claim 7, wherein compound of formula (I) is selected from the group consisting of a compound of formula (10), compound of formula (II), compound of formula (12), a compound of formula (12-101), compound of formula (13), compound of formula (14), a compound of formula (15), compound of formula (15-102) and compound of formula (16);
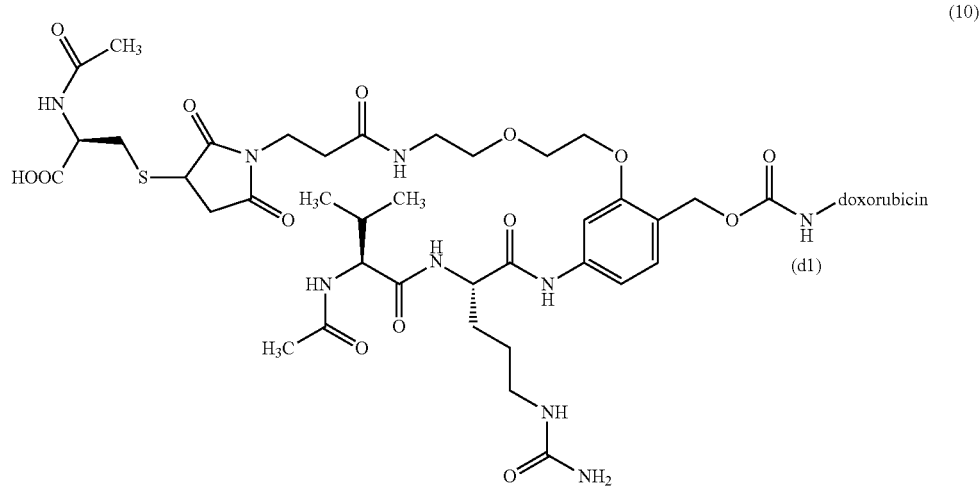
(10)
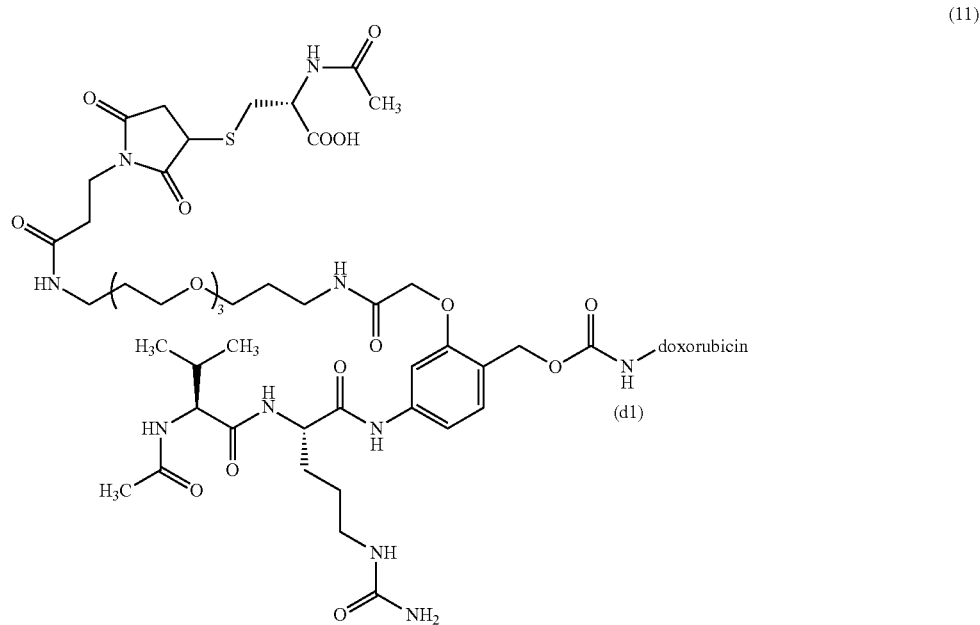
(11)

(12)
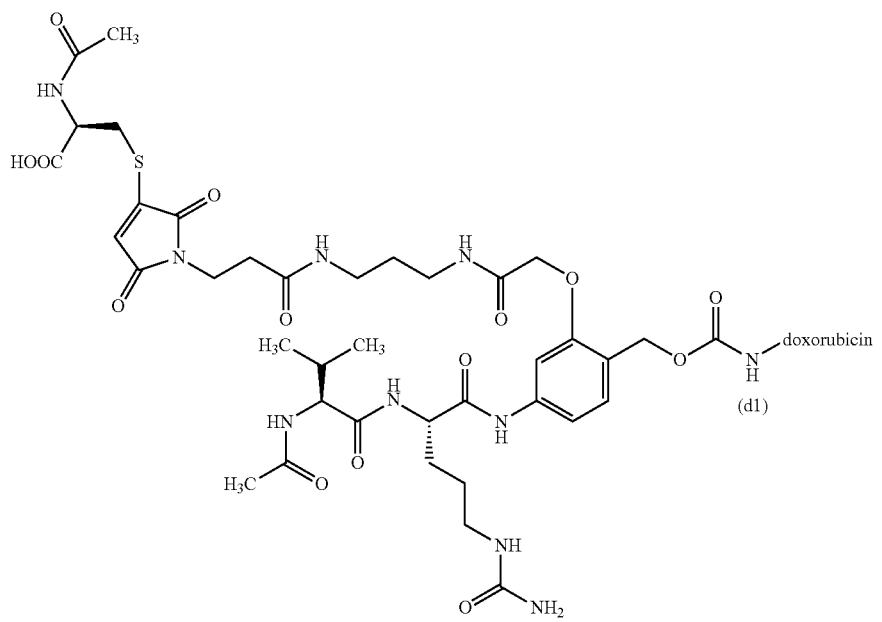
(12-101)
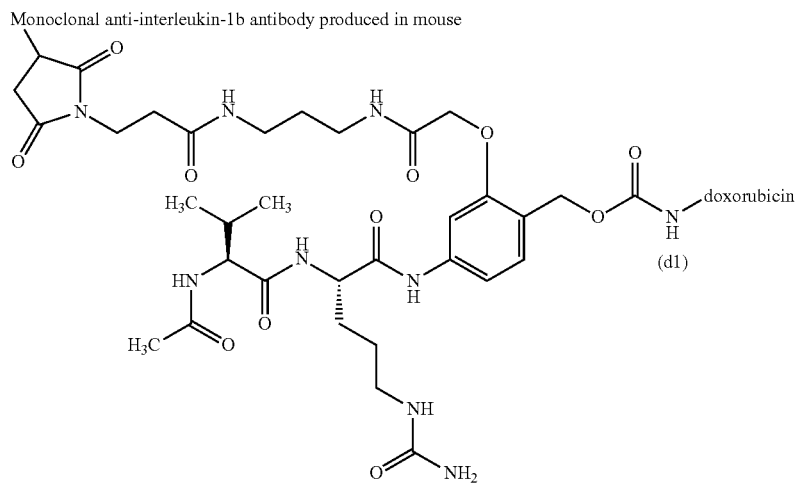

(13)
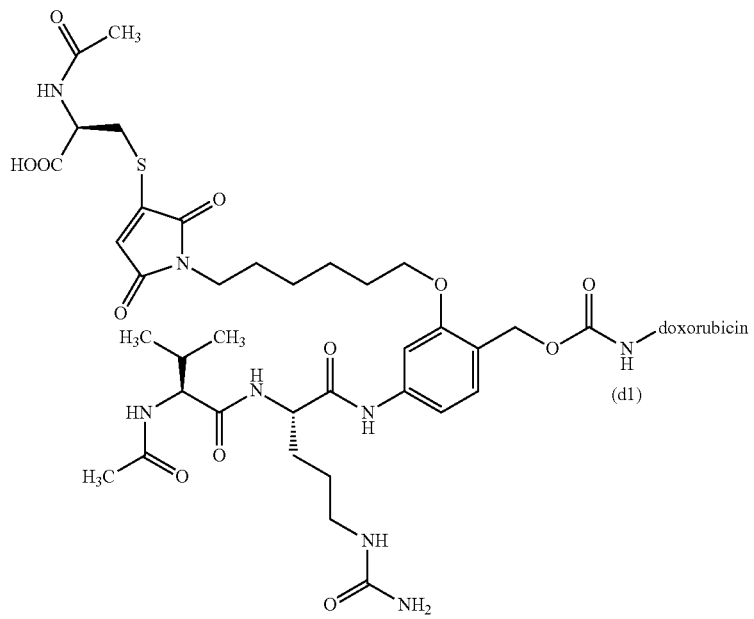
(14)
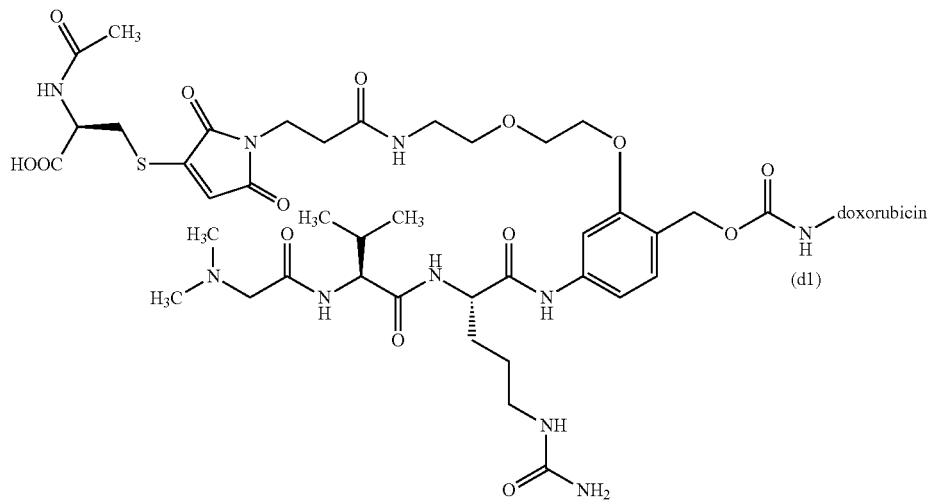
(15)
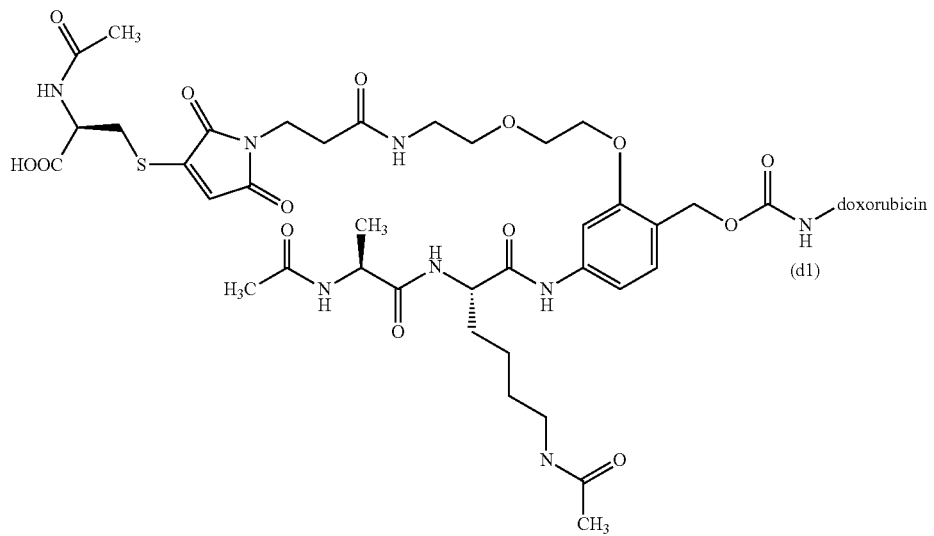

-continued

Monoclonal anti-interleukin-1b antibody produced in mouse (15-102)

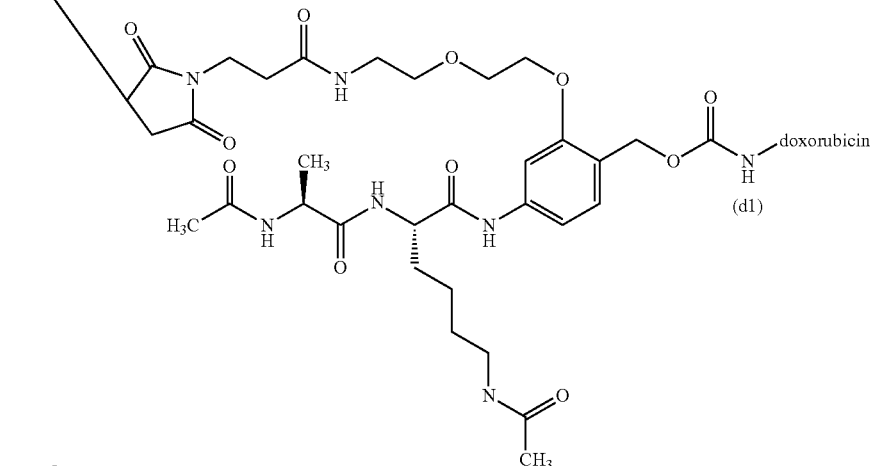

(16)

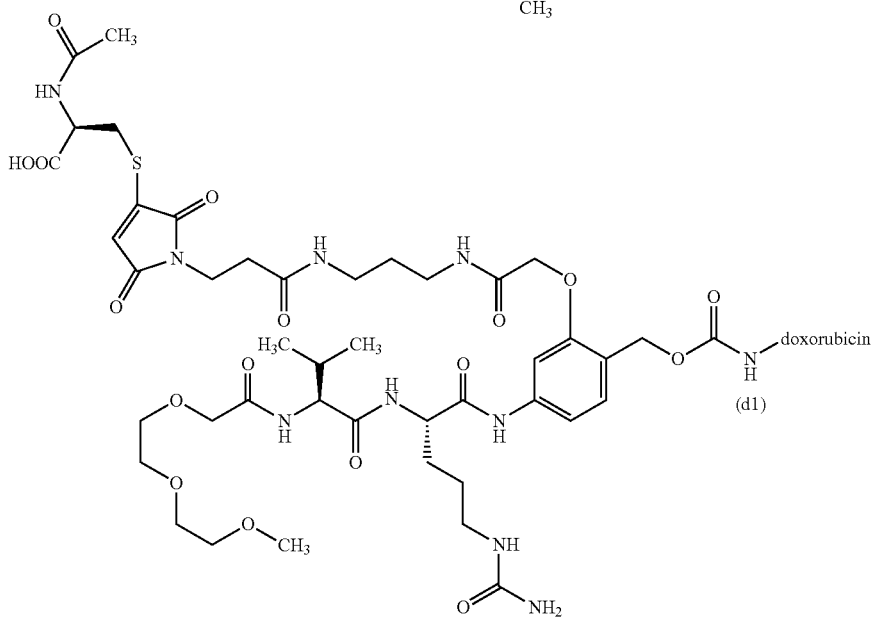

wherein
doxorubicin is the compound of formula (DOXO),

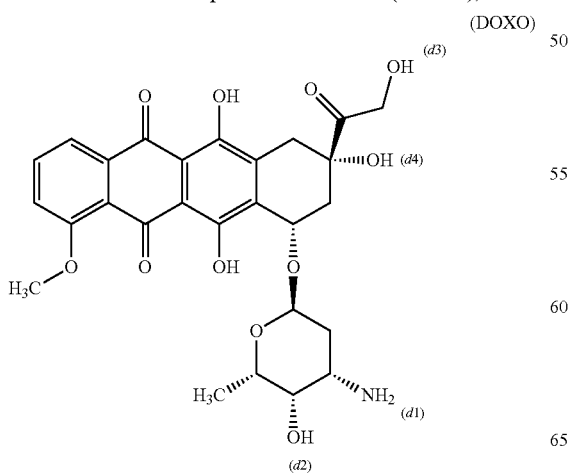

(DOXO)

wherein
(d1), (d2), (d3) and (d4) in formula (DOXO) denote functional groups;

wherein
the compound of formula (DOXO) is connected via the amino group denoted with (d1) in formulae (10), (11), (12), (12-101), (13), (14), (15), (15-102) and (16) respectively and in formula (DOXO).

9. A compound of formula (II) as defined in claim 3.

10. Compound of formula (II) according to claim 9, wherein compound of formula (II) is selected from the group consisting of a compound of formula (20), compound of formula (21), a compound of formula (22), a compound of formula (23), compound of formula (24), a compound of formula (25), a compound of formula (26), compound of formula (20-CAMPTO), a compound of formula (21-CAMPTO), a compound of formula (22-CAMPTO), a compound of formula (23-CAMPTO) and a compound of formula (21-TAXO-t1-1);

(20)
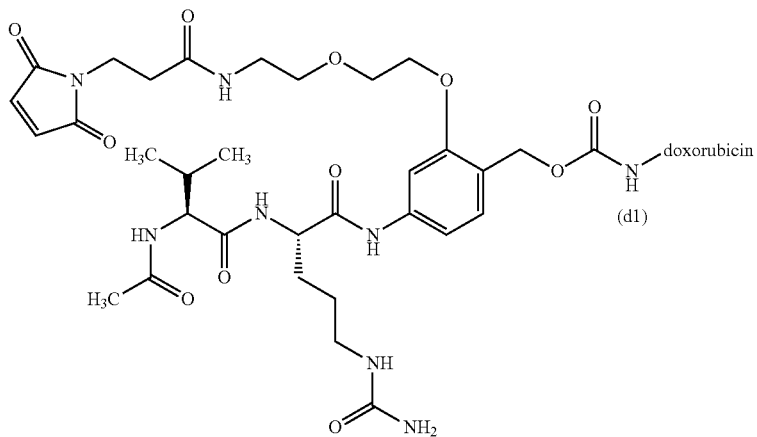
(d1)
(21)
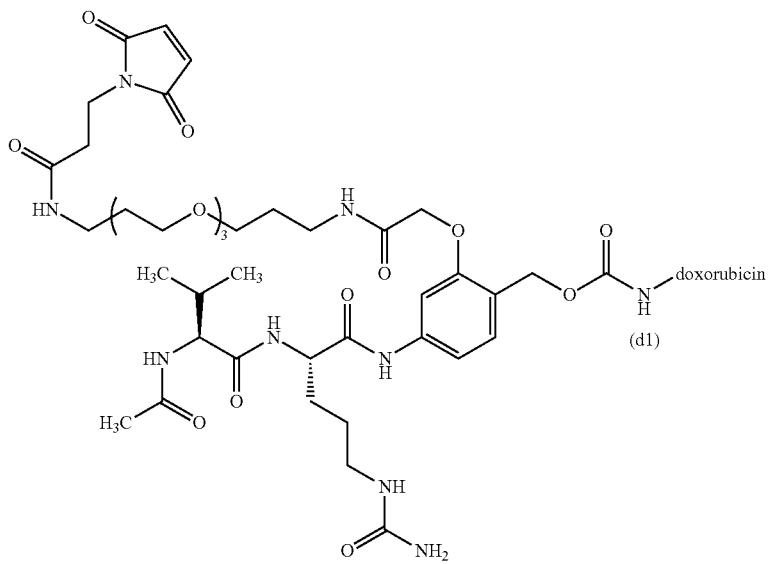
(d1)
(22)
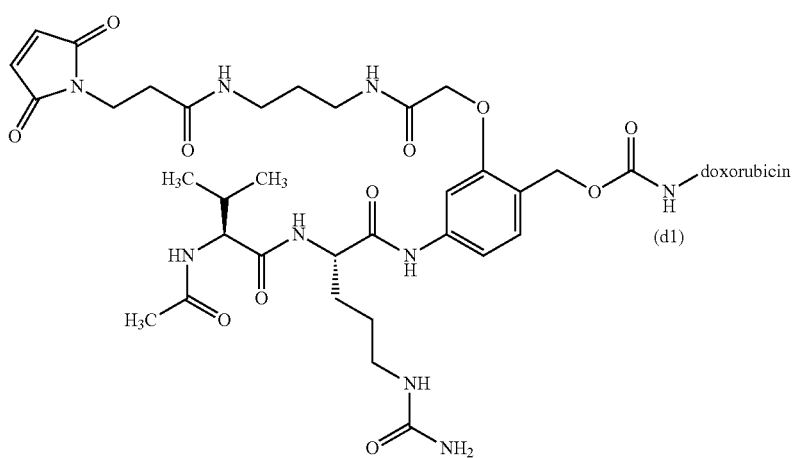
(d1)

(23)
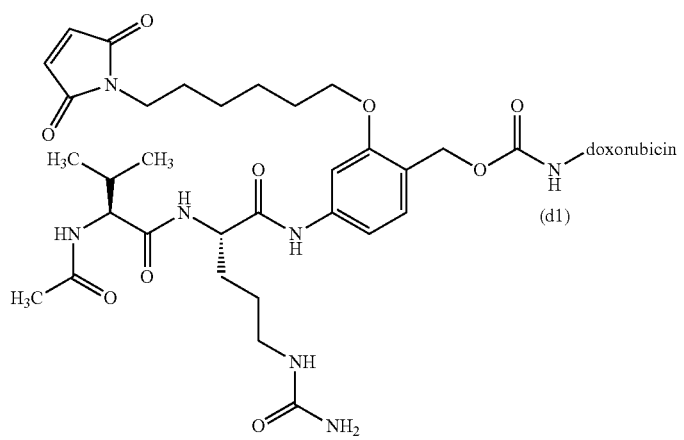
(24)
(25)
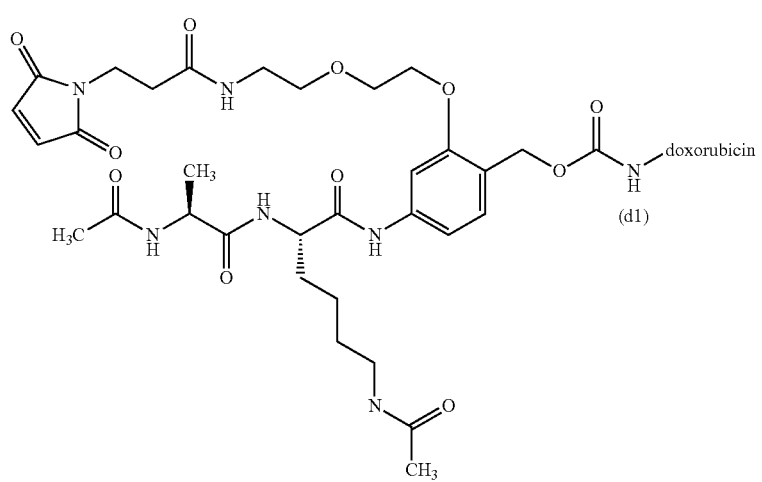

-continued
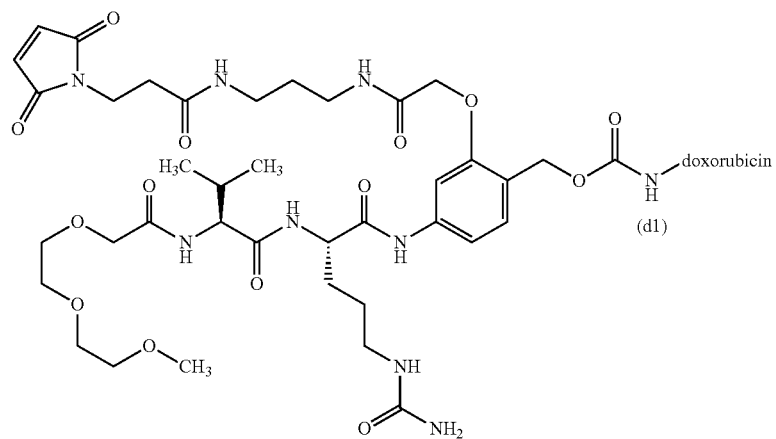
(26)
(d1)
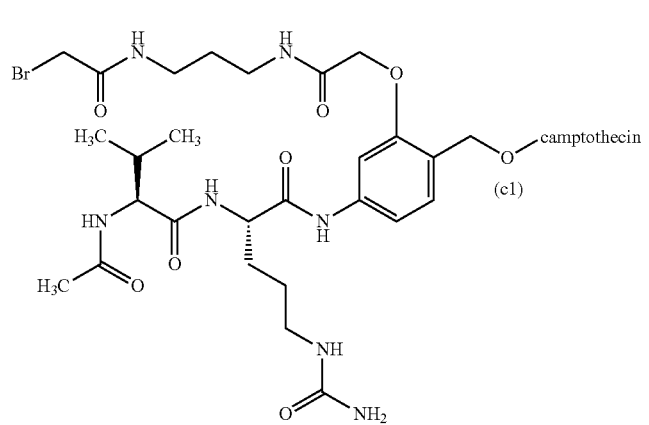
(20-CAMPTO)
(c1)
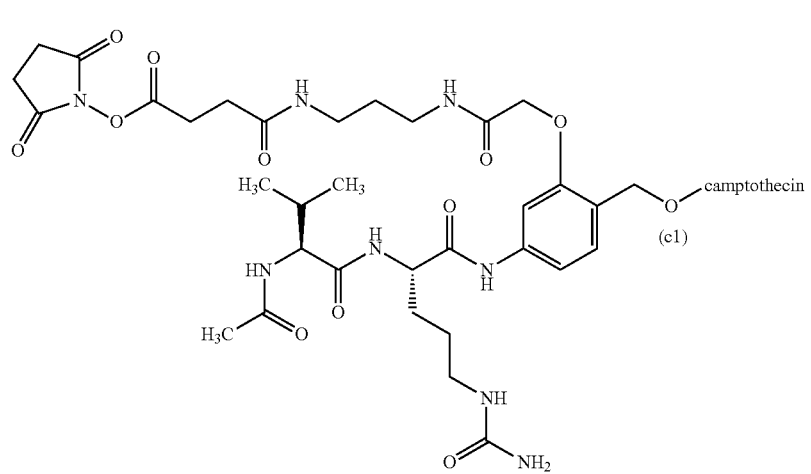
(21-CAMPTO)
(c1)

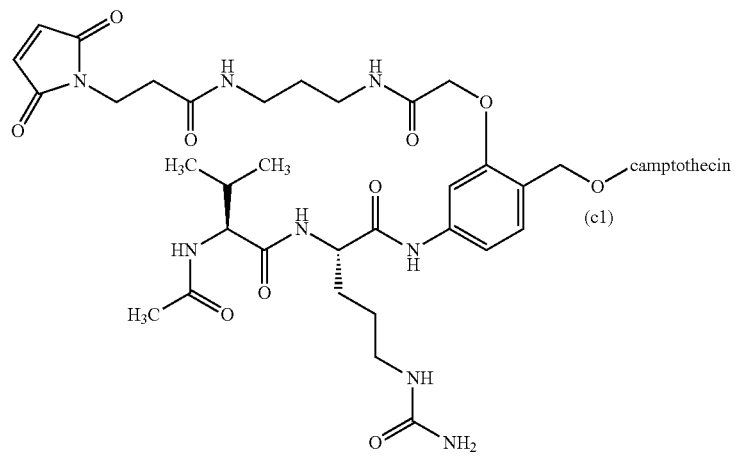
(22-CAMPTO)
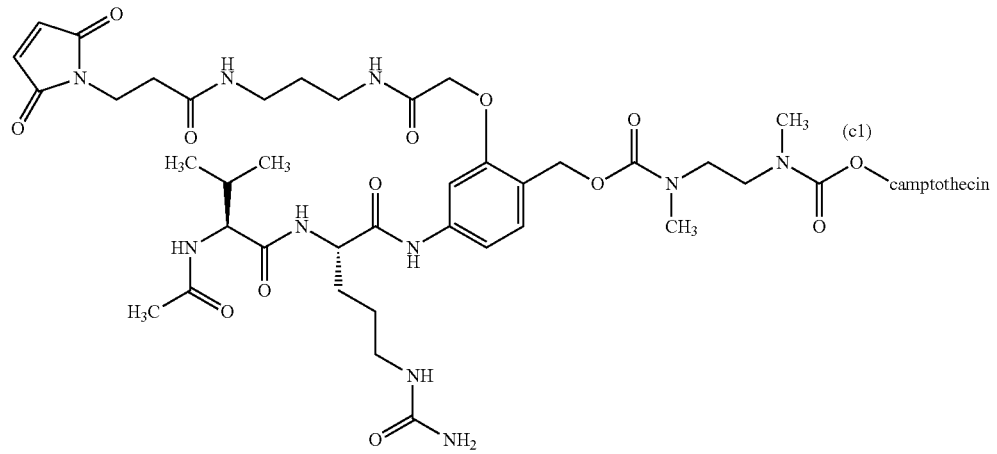
(23-CAMPTO)
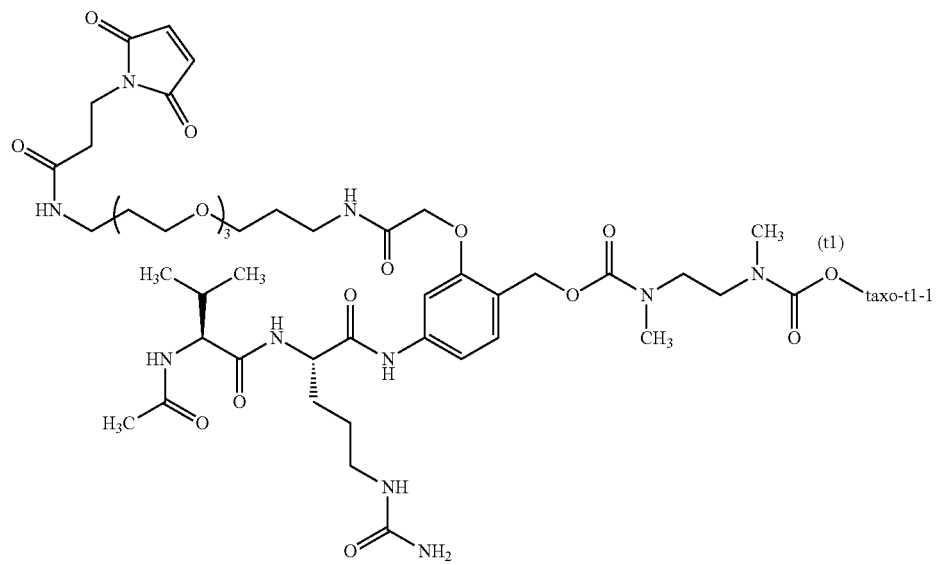
(21-TAXO-t1-1)

wherein
doxorubicin is a compound of formula (DOXO), (DOXO)

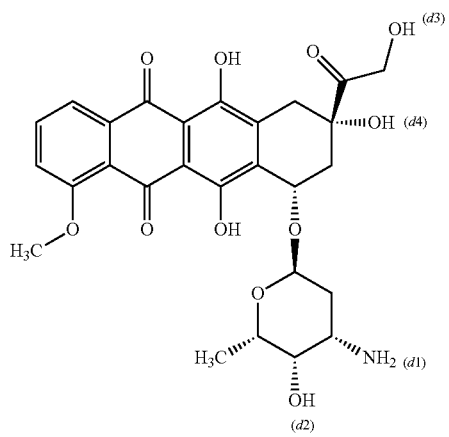

wherein
(d1), (d2), (d3) and (d4) in formula (DOXO) denote functional groups;
wherein
the compound of formula (DOXO) is connected via the amino group denoted with (d1) in formula (20), (21), (22), (23), (24), (25) and (26) respectively and in formula (DOXO);
wherein
camptothecin is the compound of formula (CAMPTO), (CAMPTO)

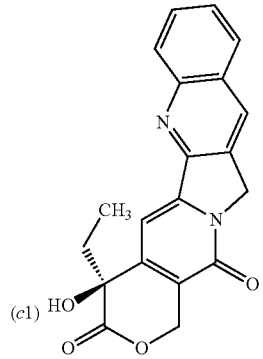

wherein
(c1) in formula (CAMPTO) denotes a functional group;
wherein
the compound of formula (CAMPTO) is connected via the hydroxy group denoted with (c1) in formula (20-CAMPTO), (21-CAMPTO), (22-CAMPTO) and (23-CAMPTO) respectively and in formula (CAMPTO);
wherein
taxo-t1-1 is the compound of formula (TAXO), (TAXO)

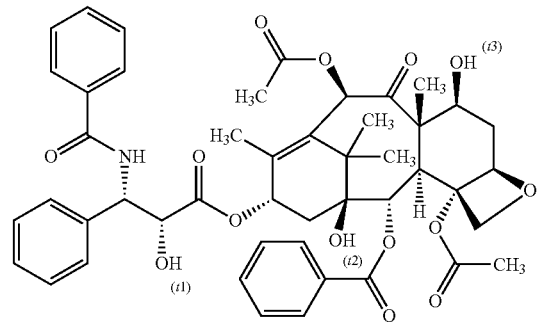

wherein
the compound of formula (TAXO) is connected via the hydroxy group denoted with (t1) in formula (21-TAXO-t1-1) and in formula (TAXO).

11. A compound selected from the group consisting of the compound of formula (IIc), the compound of formula (III), the compound of formula (IV), the compound of formula (IV-IIa), the compound of formula (V), the compound of formula (Va), the compound of formula (III0-IIa), the compound of formula (III0), the compound of formula (IV0), the compound of formula (IV0a), the compound of formula (V0) and compound of formula (III0-I-IVa) as defined in claim 4.

12. Compound according to claim 11,
wherein
compound of formula (IIc) is compound of formula (20c);

(20c)

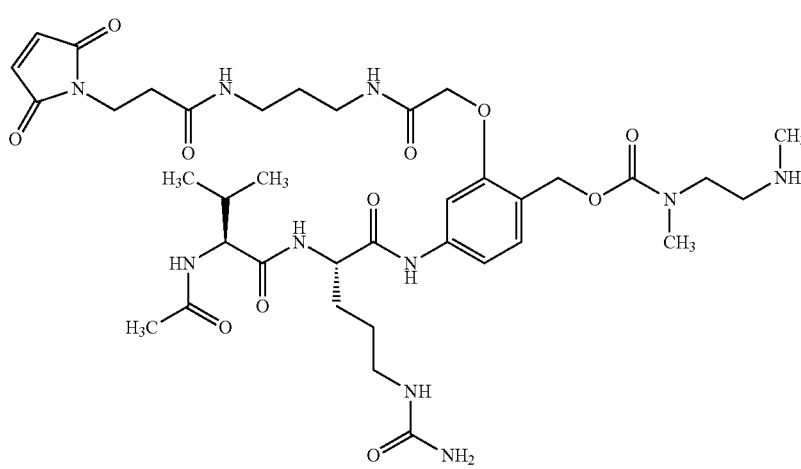

wherein
compound of formula (III) is selected from the group consisting of formula (30), a compound of formula (31), a compound of frmula (32), compound of formula (33), a compound of formula (34), a compound of formula (35) and compound of formula (36);
(30)
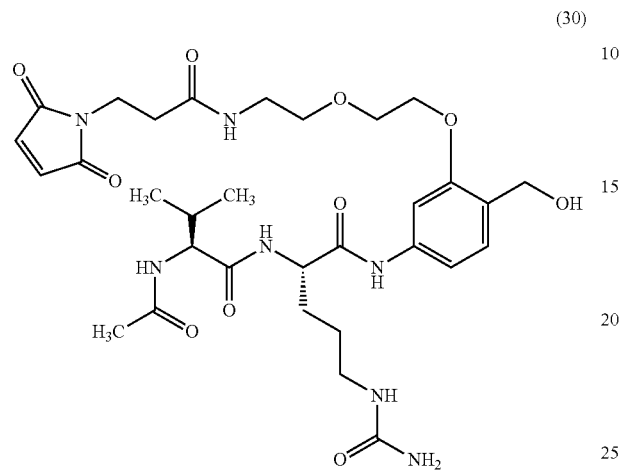
(31)
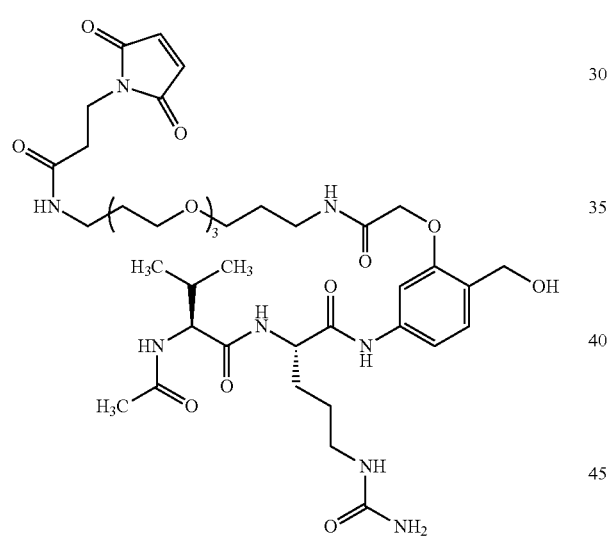
(32)
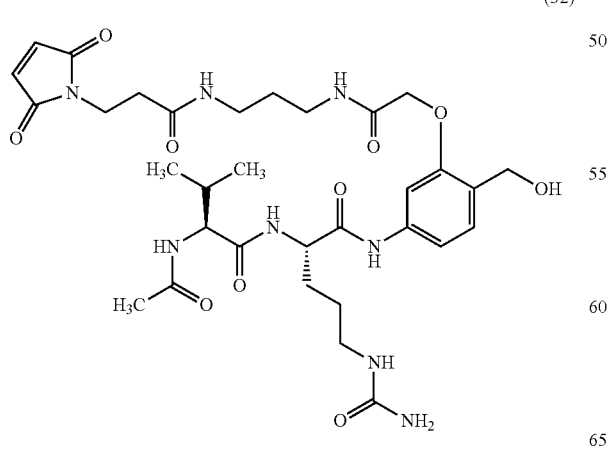
(33)
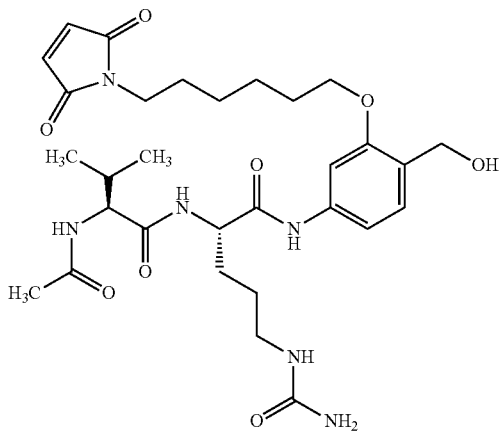
(34)
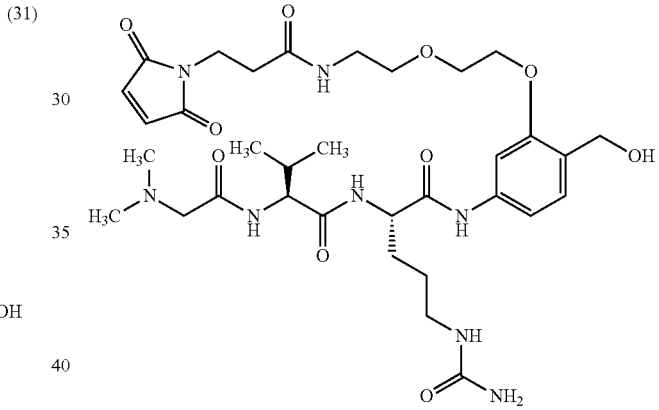
(35)
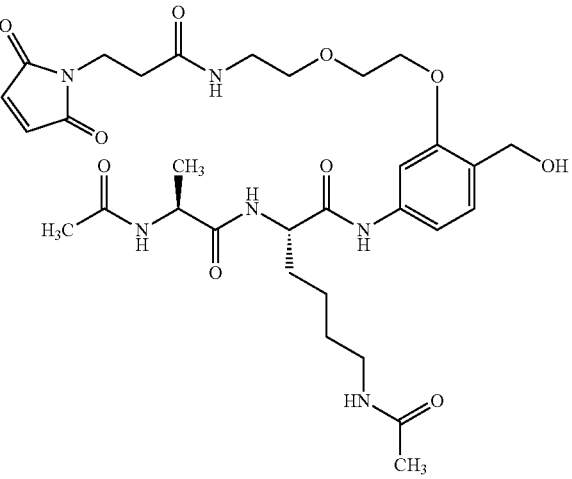

127

-continued (36)

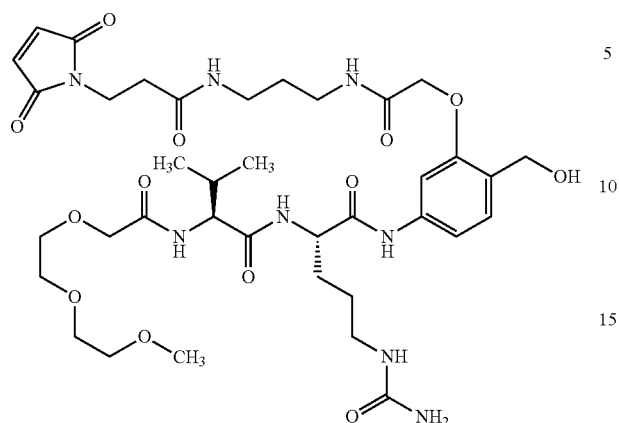

wherein
the compound of formula (III0) is compound of formula (300);

(300)

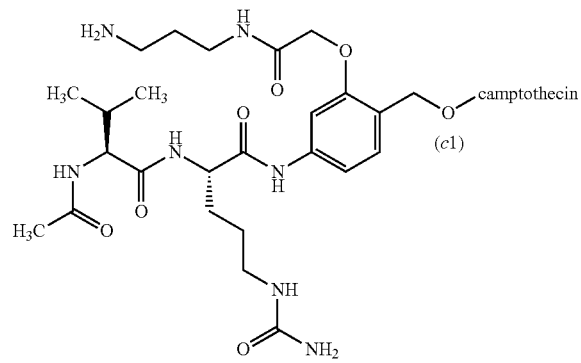

wherein
camptothecin is the compound of formula (CAMPTO), (CAMPTO)

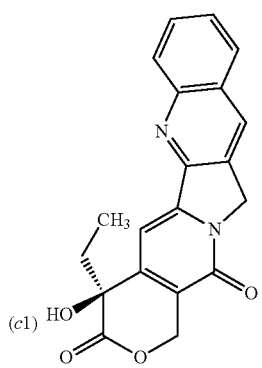

wherein
(c1) in formula (CAMPTO) denotes a functional group;

128 wherein
the compound of formula (CAMPTO) is connected via the hydroxy group denoted with (c1) in formula (300) respectively and in formula (CAMPTO);

wherein
compound of formula (III0-I-IVa) is compound of formula (320);

(320)

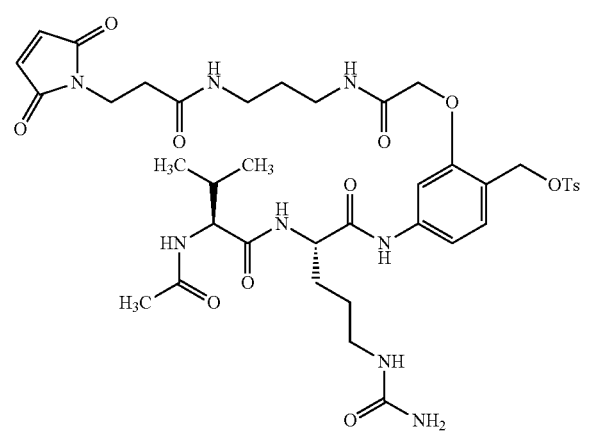

wherein
the compound of formula (IV) is selected from the group consisting of compound of formula (40), a compound of formula (41), a compound of formula (42), a compound of formula (43), a compound of formula (44), a compound of formula (45) and compound of formula (46);

(40)

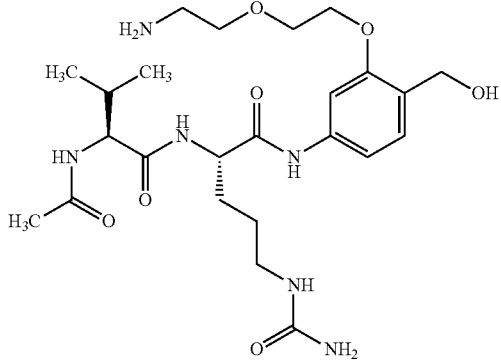

(41)
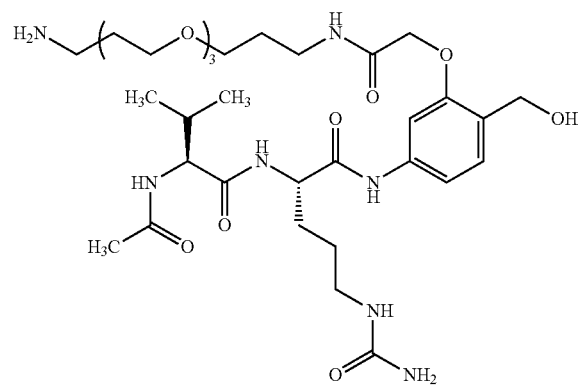
(42)
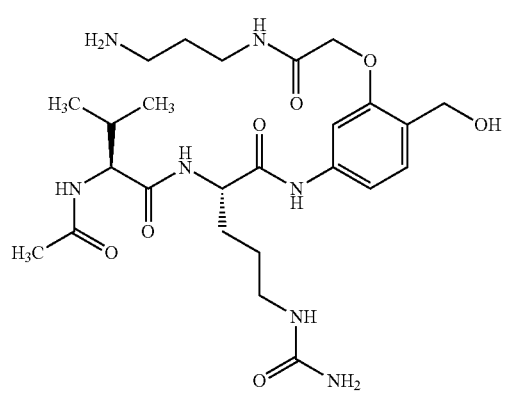
(43)
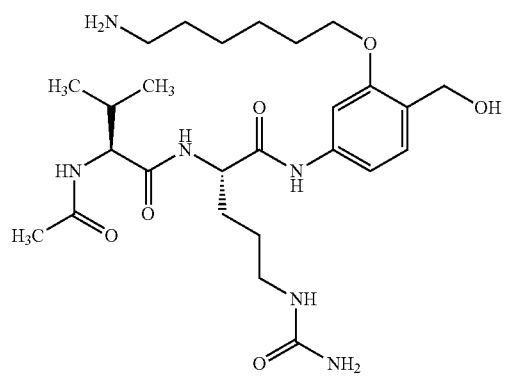
(44)
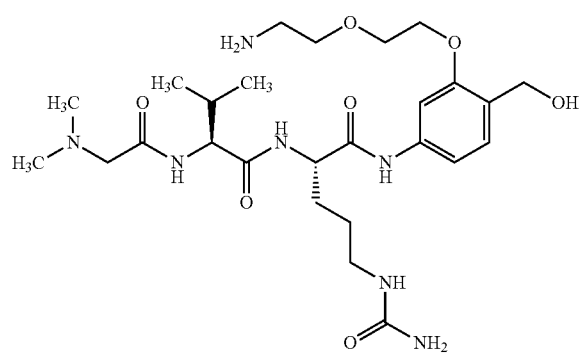
(45)
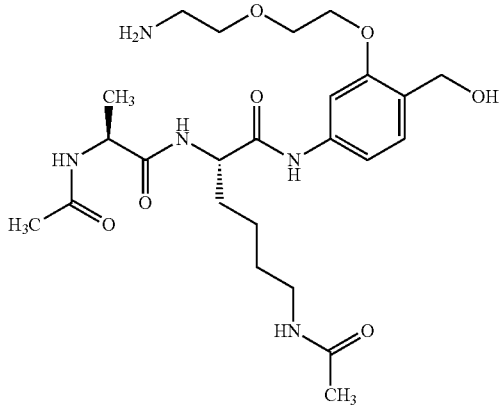
(46)
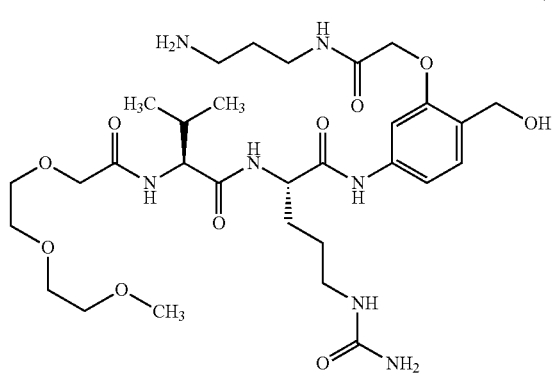
wherein
the compound of formula (IV0) is compound of formula (400);
(400)
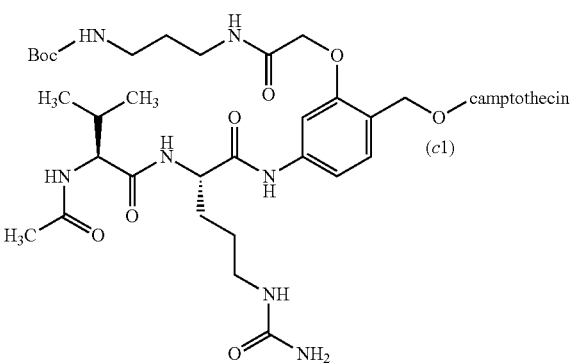
wherein
camptothecin is the compound of formula (CAMPTO),
wherein
compound of formula (IV0a) is compound of formula (400a);

(400a)

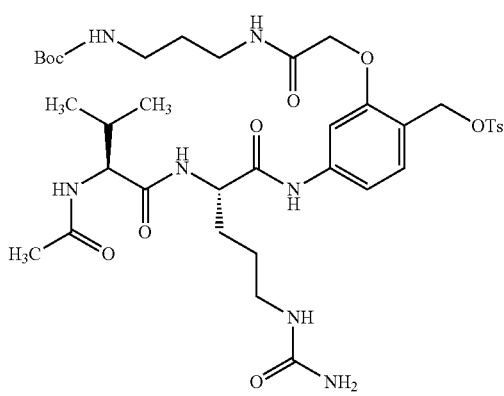

wherein
compound of formula (V) is selected from the group consisting of compound of formula (50), a compound of formula (50-1), a compound of formula (51), a compound of formula (51-1), a compound of formula (52), a compound of formula (52-1), a compound of formula (53), a compound of formula (53-1), a compound of formula (54), a compound of formula (54-1), a compound of formula (54-2), a compound of formula (54-3), a compound of formula (55), a compound of formula (55-1), a compound of formula (56) and a compound of formula (56-1);

(50)

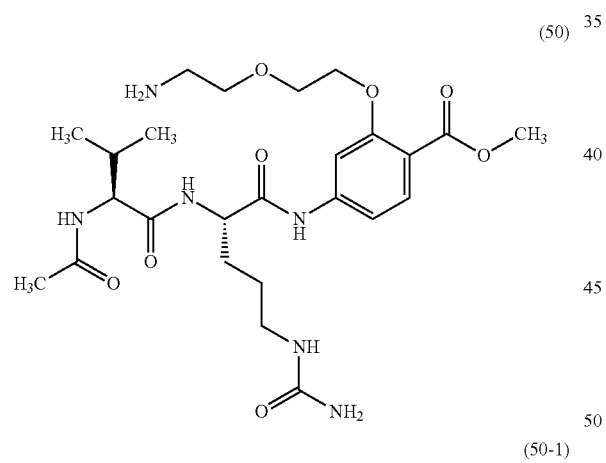

(50-1)

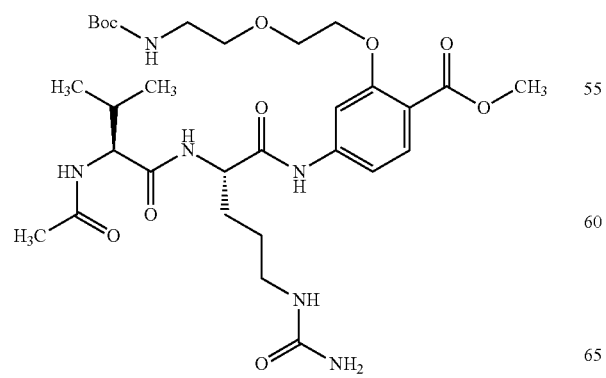

-continued (51)

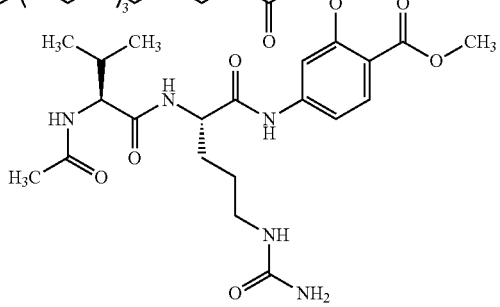

(51-1)

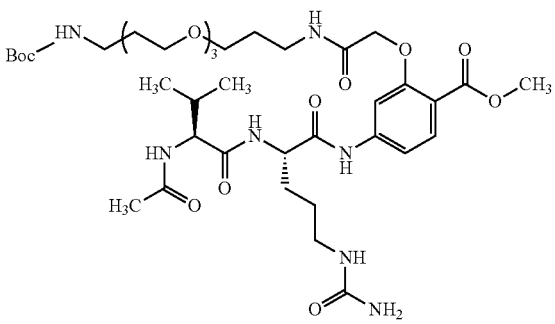

(52)

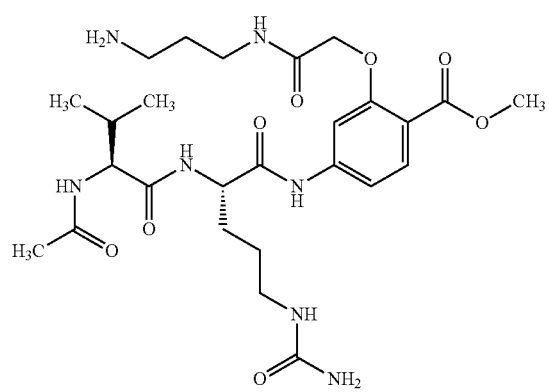

(52-1)

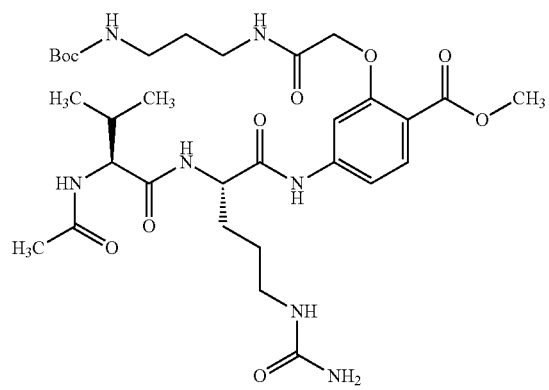

133
-continued
(53)
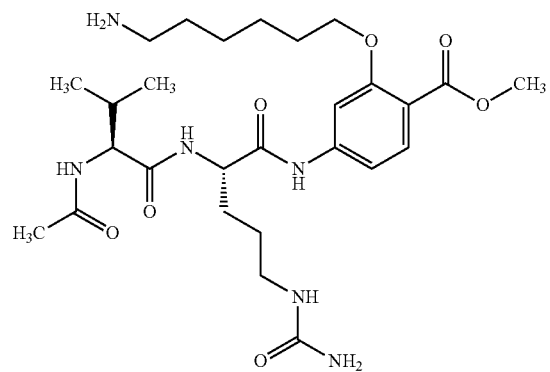
(53-1)
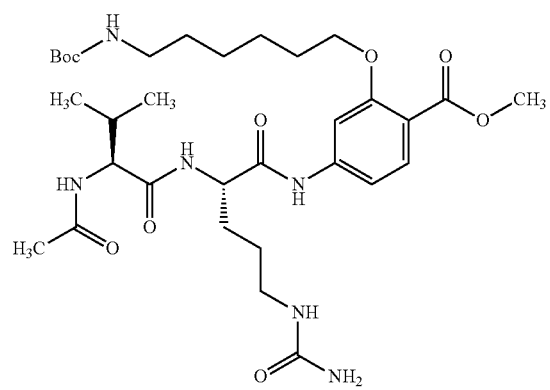
(54)
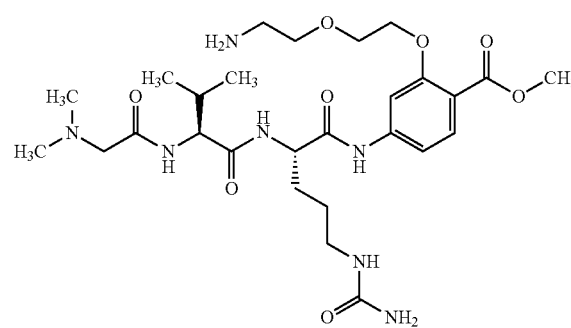
(54-1)
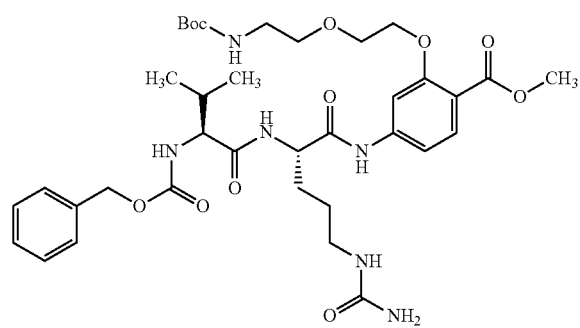
134
-continued
(54-2)
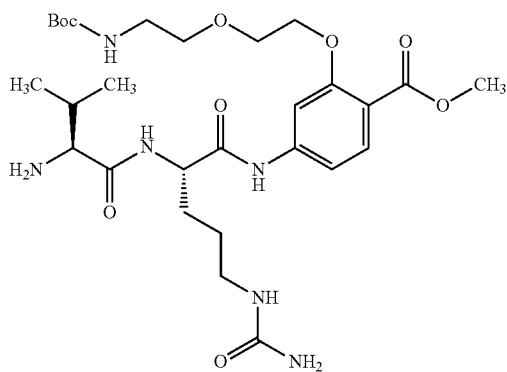
(54-3)
(55)
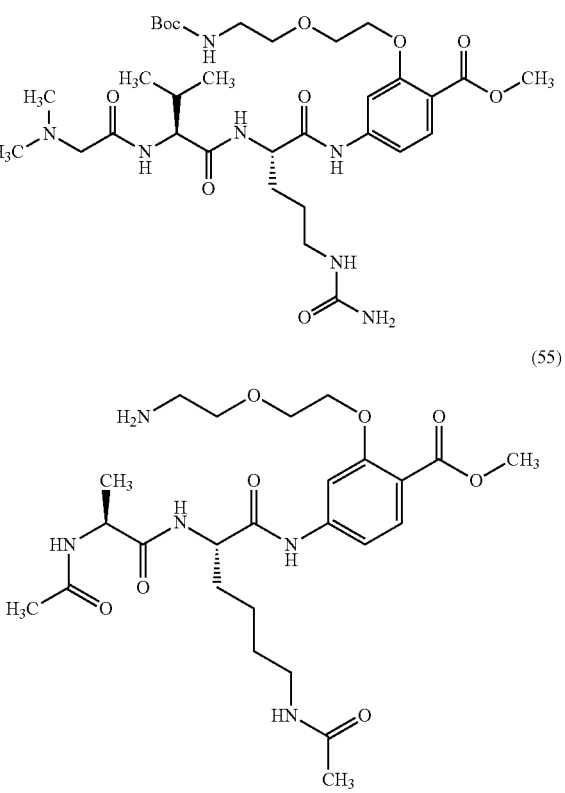
(55-1)
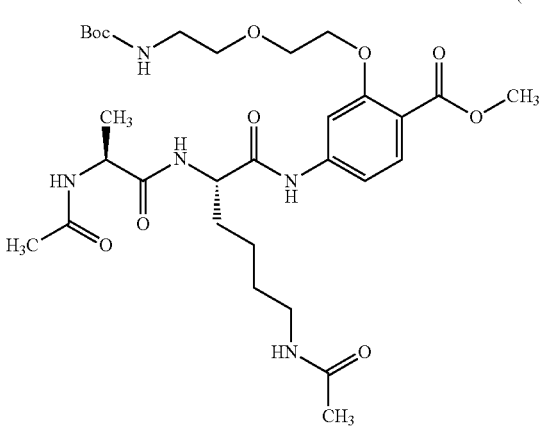

(56)

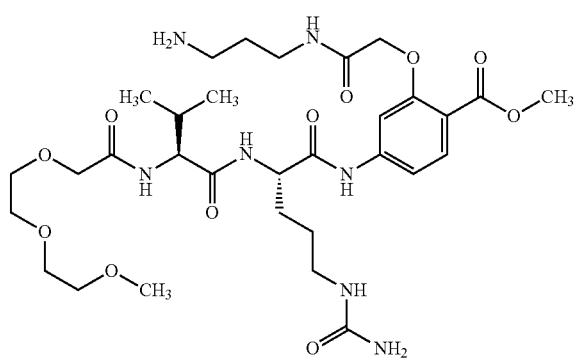

(56-1)

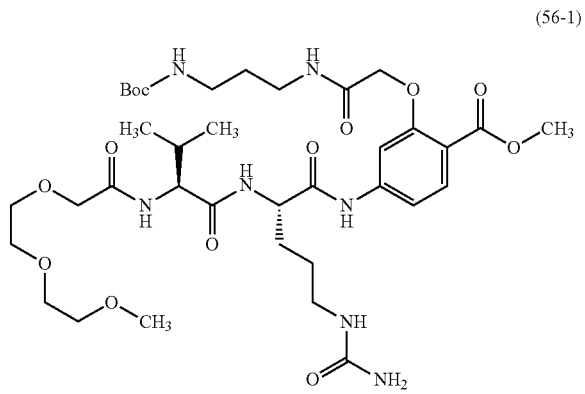

wherein
the compound of formula (V0) is compound of formula (500);

(500)

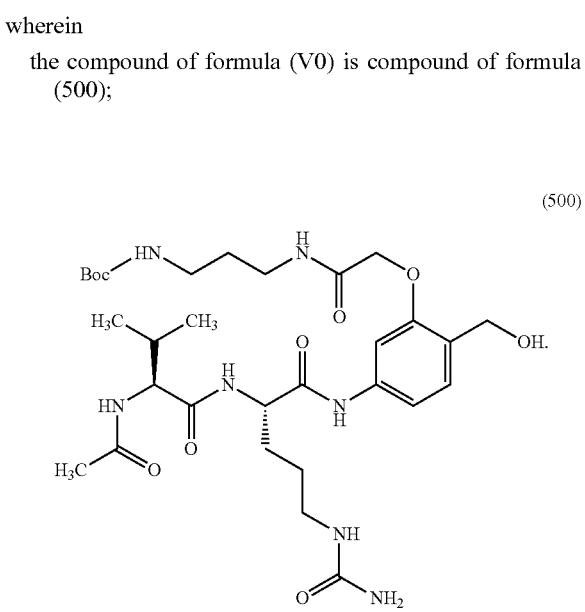

13. A compound of formula (VI) as defined in claim 5.

14. The compound of formula (VI) according to claim 13, wherein the compound of formula (VI) is selected from the group consisting of a compound of formula (6), a compound of formula (6-1), a compound of formula (6-2), a compound of formula (6b), a compound of formula (6b-1), a compound of formula (6b-2), a compound of formula (6c) and compound of formula (6-5);

(6)

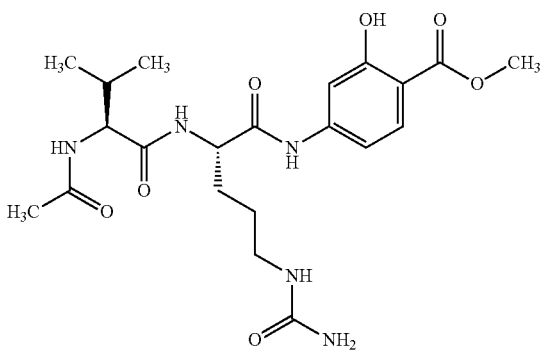

(6-1)

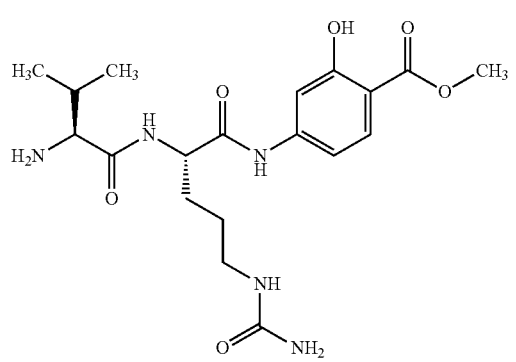

(6-2)

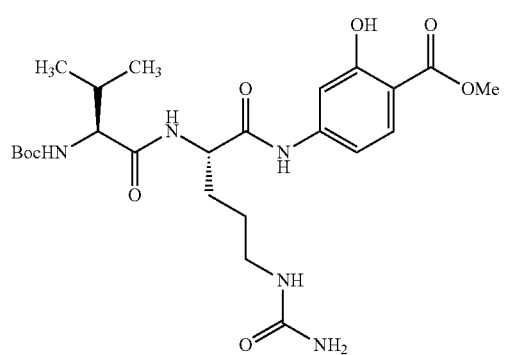

(6b)

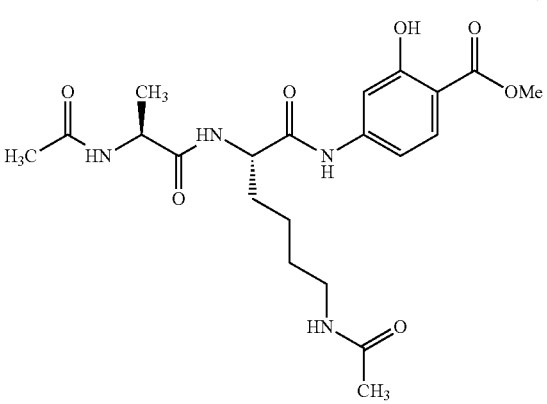

137
-continued (6b-1)

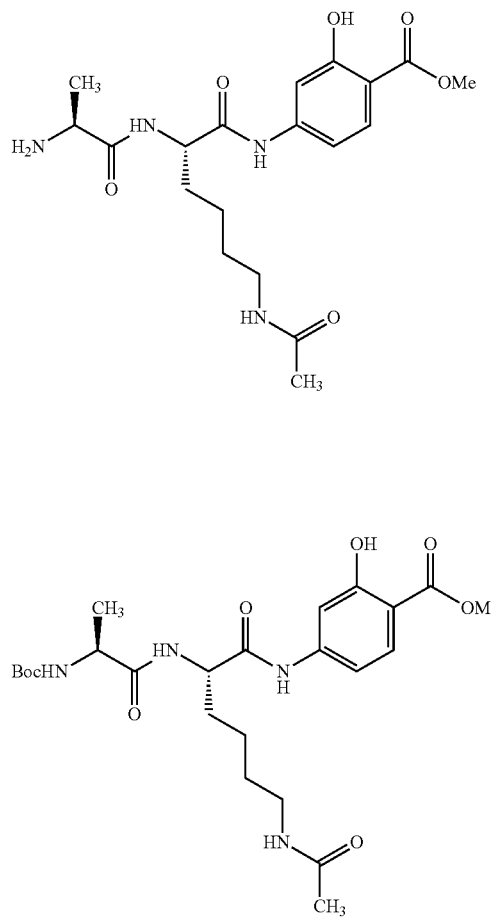

(6b-2)

(6c)

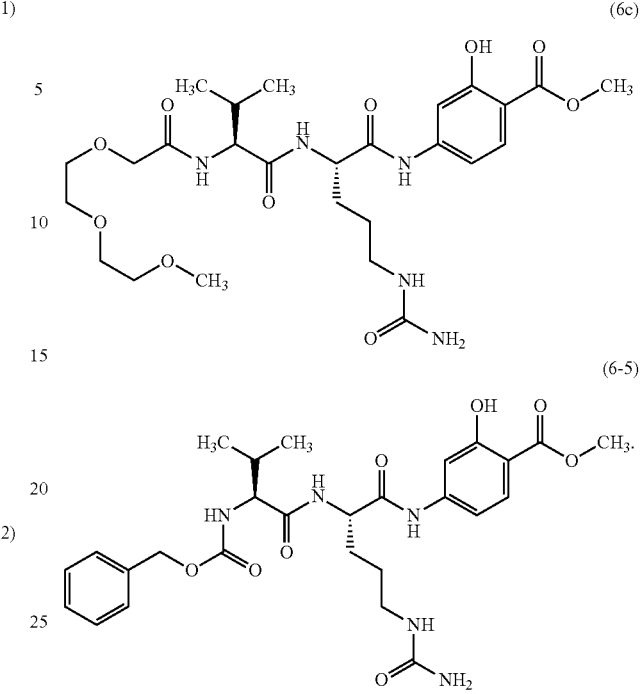

(6-5)

15. A pharmaceutical composition or of a drug, wherein the pharmaceutical composition and the drug comprise the compound of formula (I) as defined in claim 2.

16. The method (MI) according to claim 2, wherein the compound of formula (I) is selected from the group consisting of a compound of formula (10), a compound of formula (11), a compound of formula (12), a compound of formula (12-101), a compound of formula (13), a compound of formula (14), a compound of formula (15). A compound of formula (15-102) and a compound of formula (16);

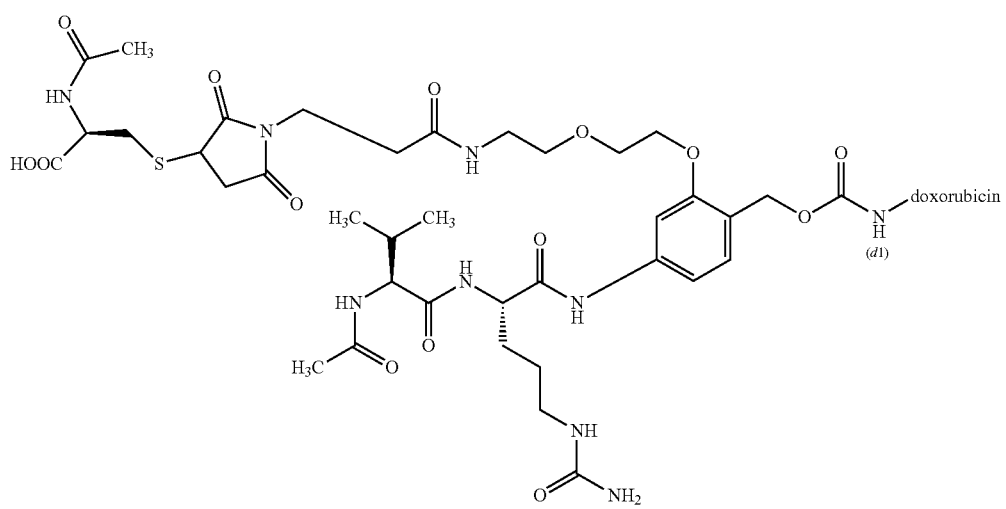

(10)

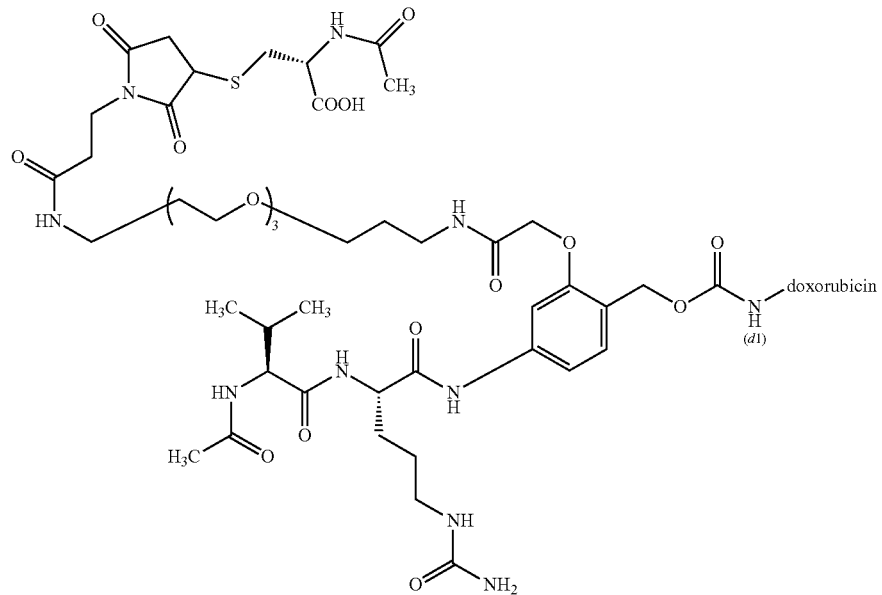
(11)
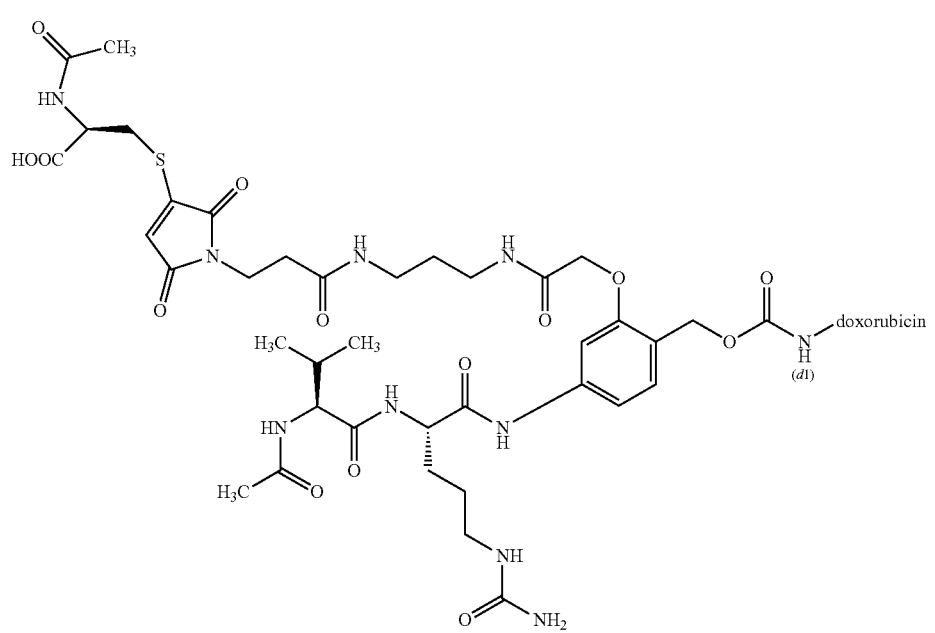
(12)

(12-101)
Monoclonal anti-interleukin-1b antibody produced in mouse
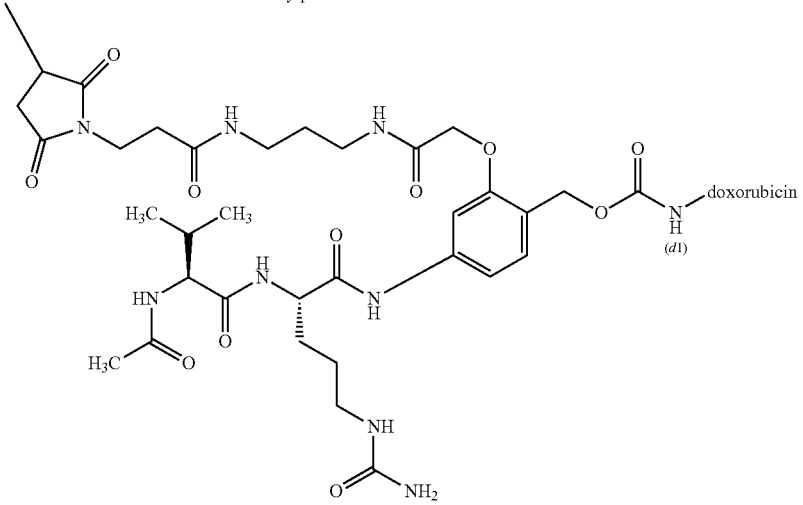
(13)
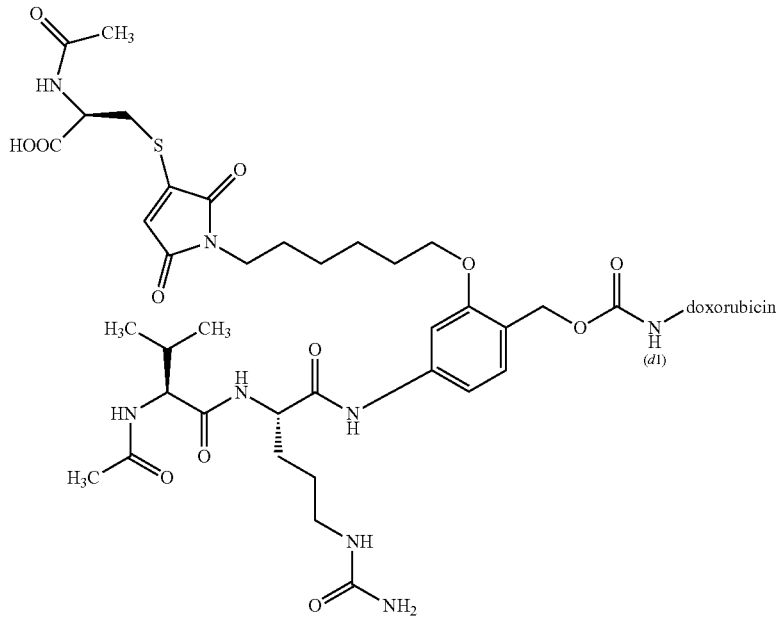
(14)
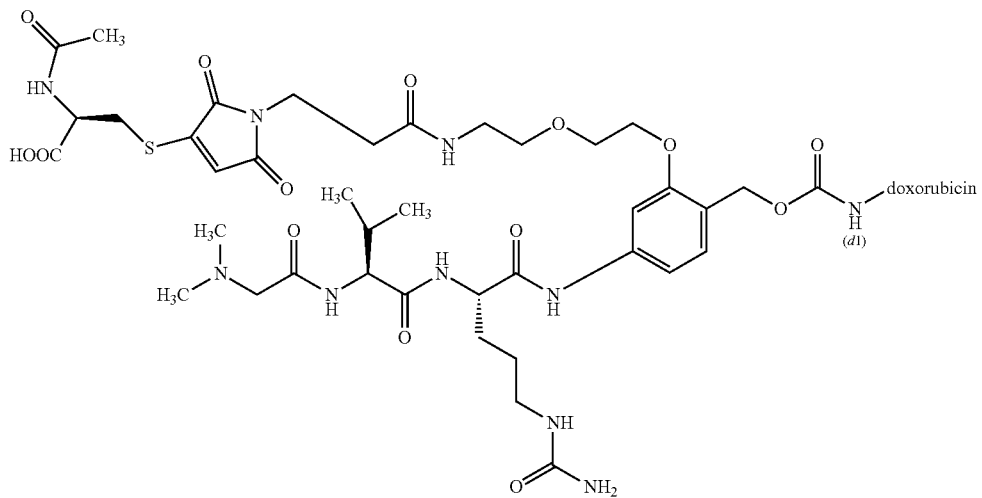

(15)
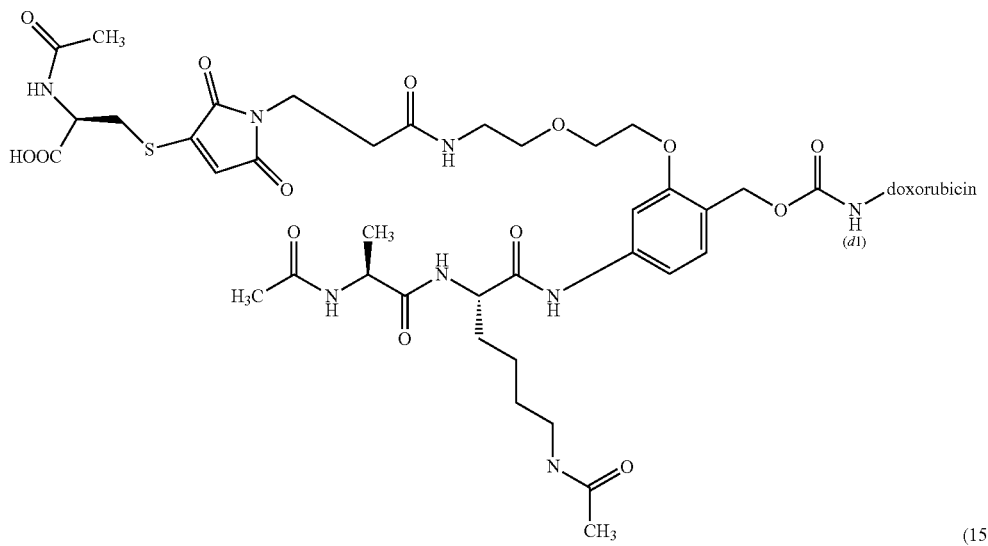
(15-102)
Monoclonal anti-interleukin-1b antibody produced in mouse
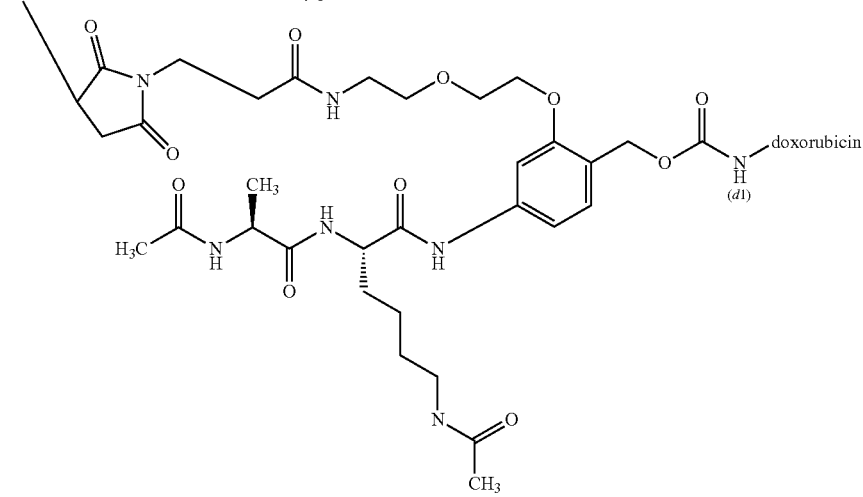
(16)
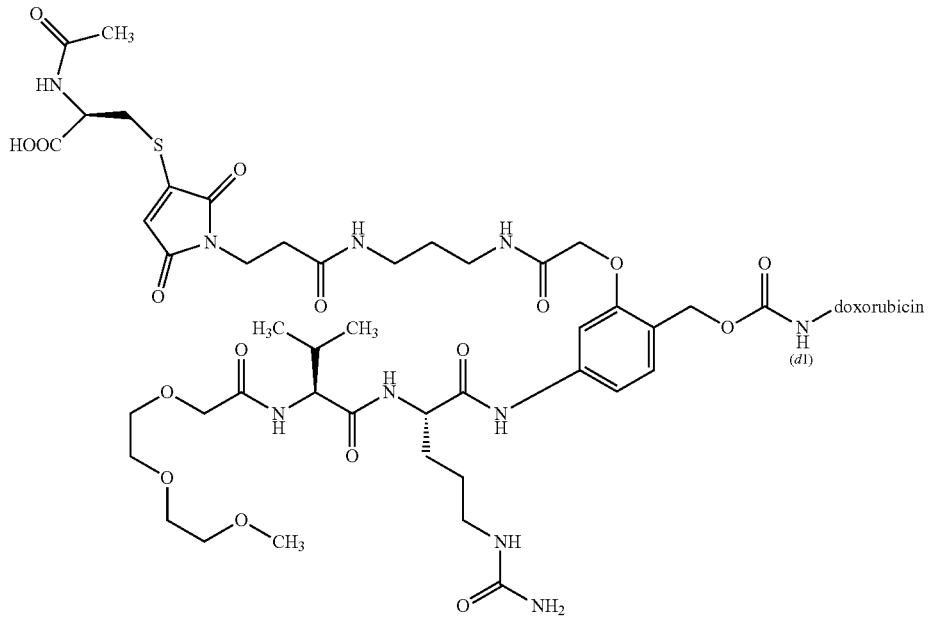

wherein
doxorubicin is a compound of formula. (DOXO), (DOXO)

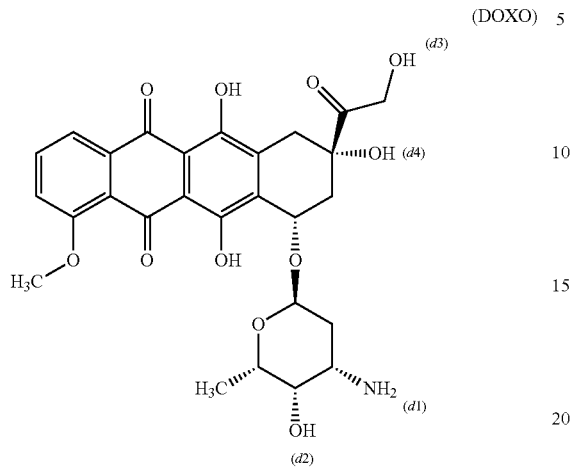

wherein
(d1), (d2), (d3) and (d4) in formula (DOXO) denote functional groups;
wherein
the compound of formula (DOXO) is connected via the amino group denoted with (d1) in formulae (10), (11), (12), (12-101), (13), (14), (15), (15-102) and (16) respectively and in formula. (DOXO).

17. The method (MI) according to claim 3, wherein the compound of formula (II) is selected from the group consisting of a compound of formula (20), a compound of formula (21), a compound of formula (22), a compound of formula (23), a compound of formula (24), a compound of formula (25), a compound of formula (26), a compound of formula (20-CAMPTO), a compound of formula (21-CAMPTO), a compound of formula (22-CAMPTO), a compound of formula (23-CAMPTO) and a compound of formula (21-TAXO-t1-1);

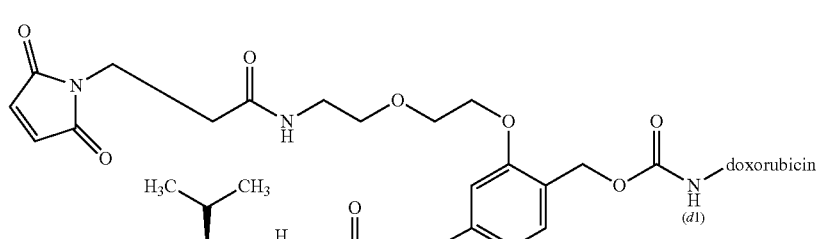
(20)

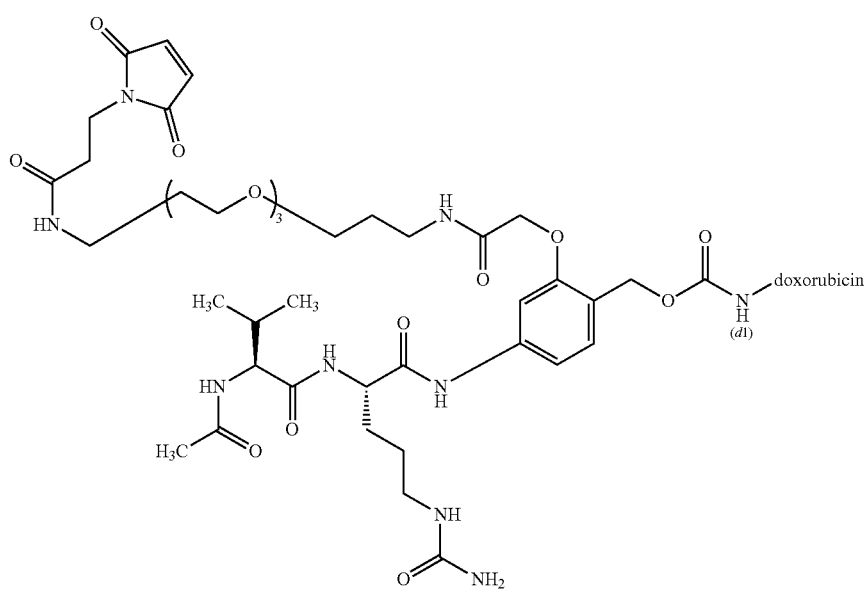
(21)

(22)
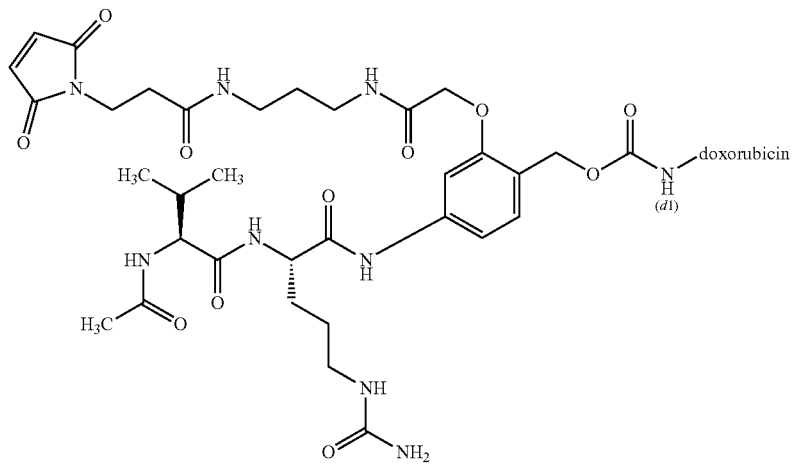
(23)
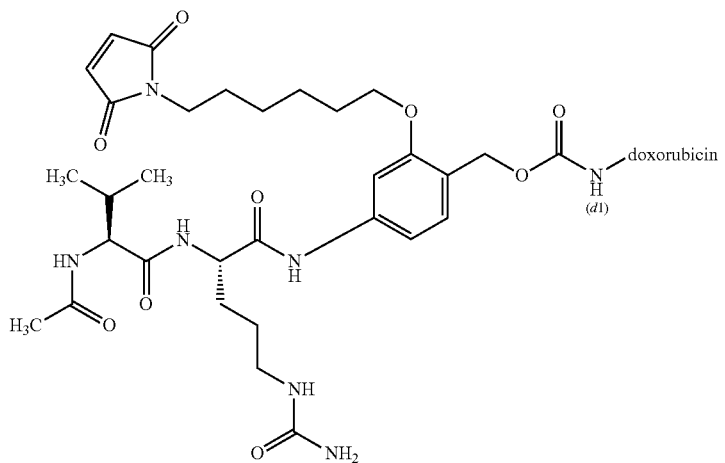
(24)
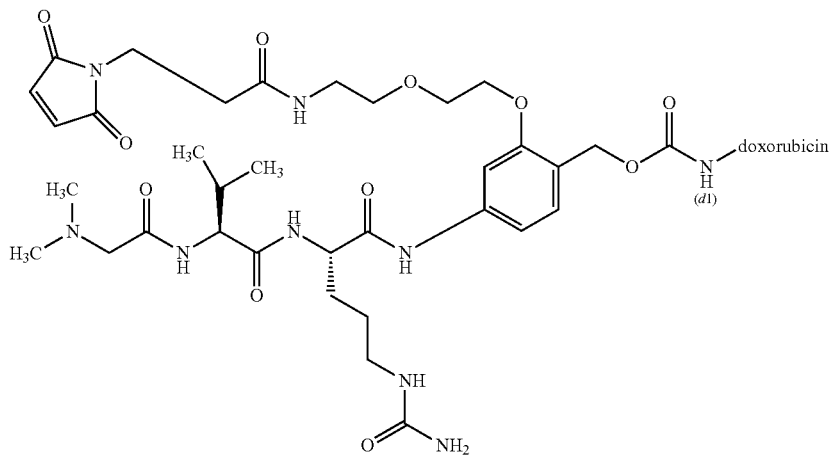

(25)
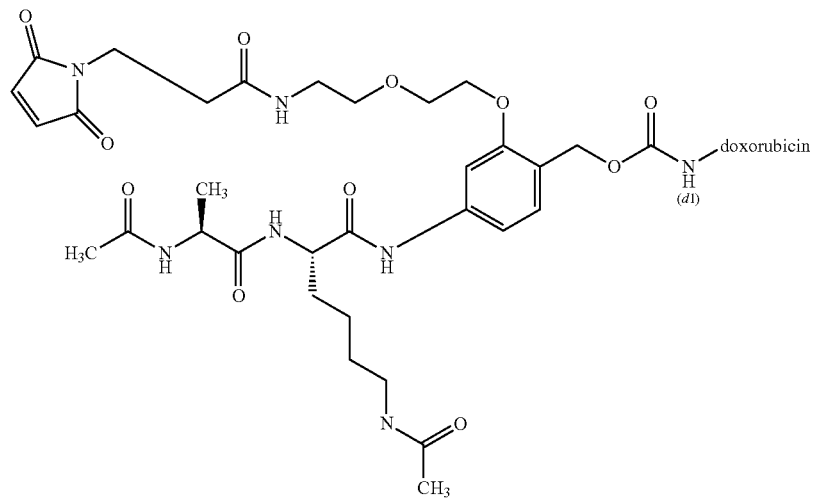
(26)
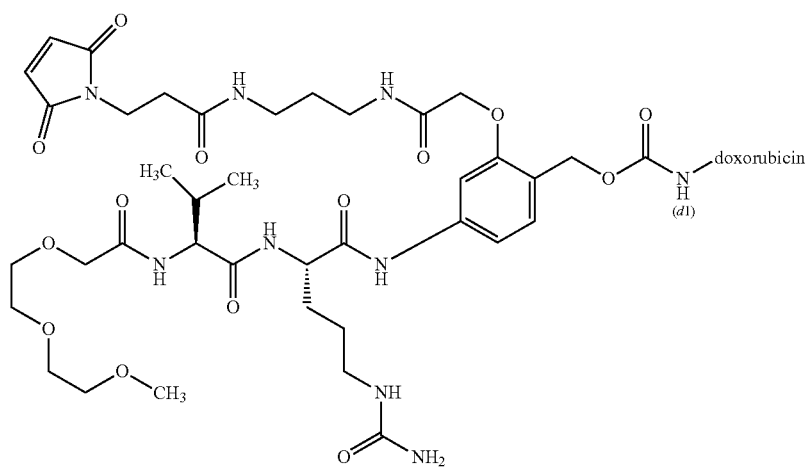
(20-CAMPTO)
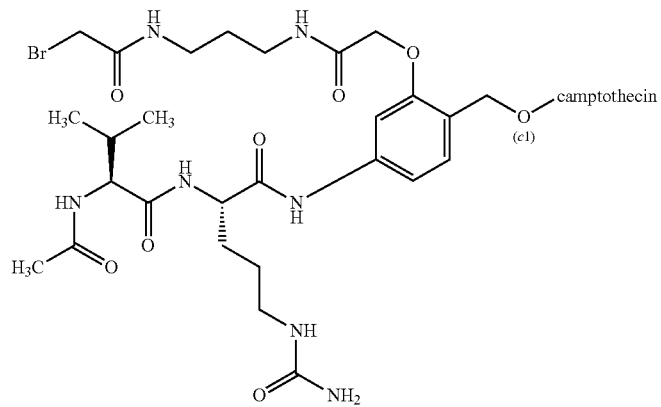

(21-CAMPTO)
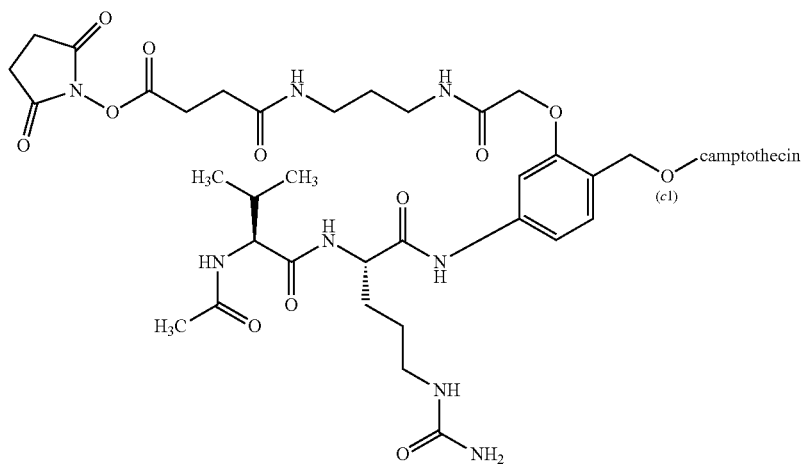
(22-CAMPTO)
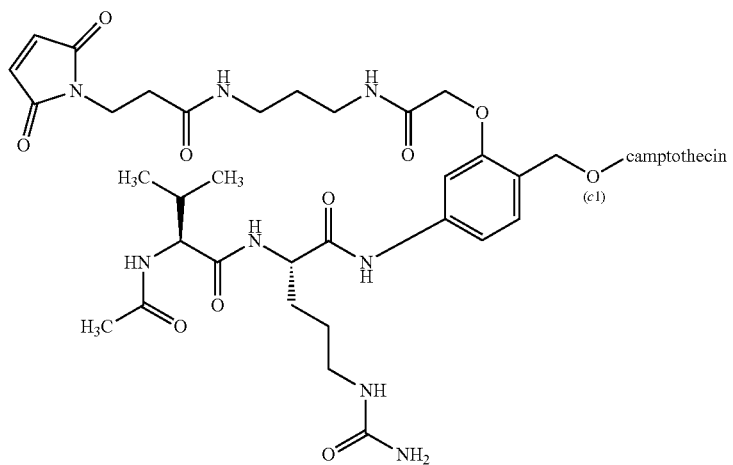
(23-CAMPTO)
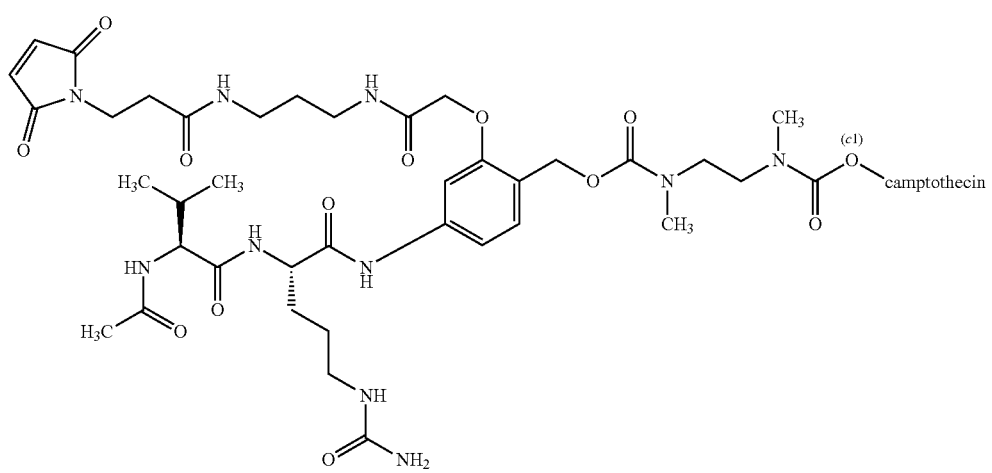

(21-TAXO-t1-1)

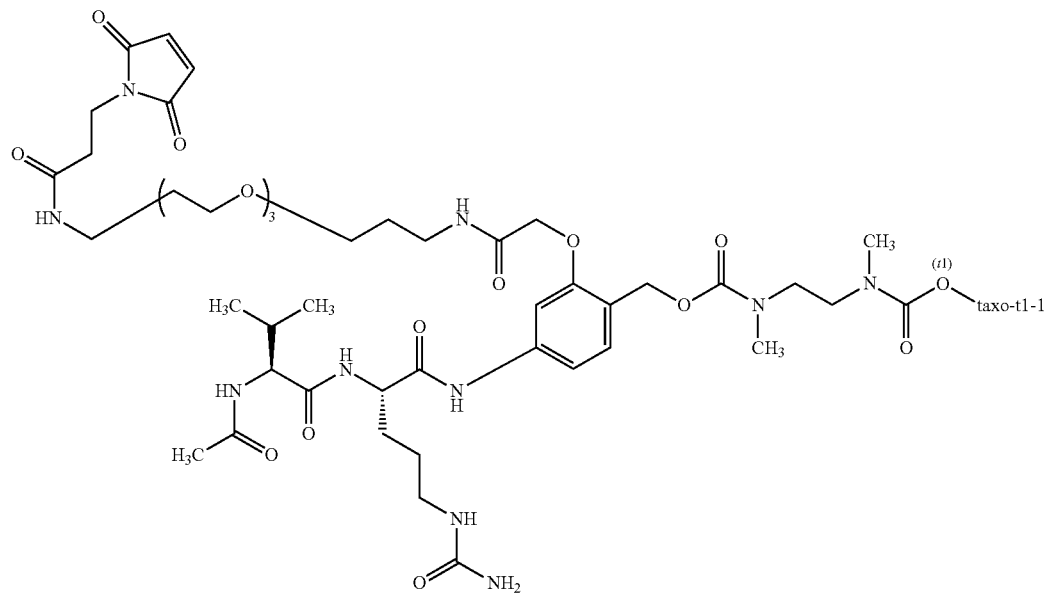

wherein
doxorubicin is a compound of formula (DOXO),

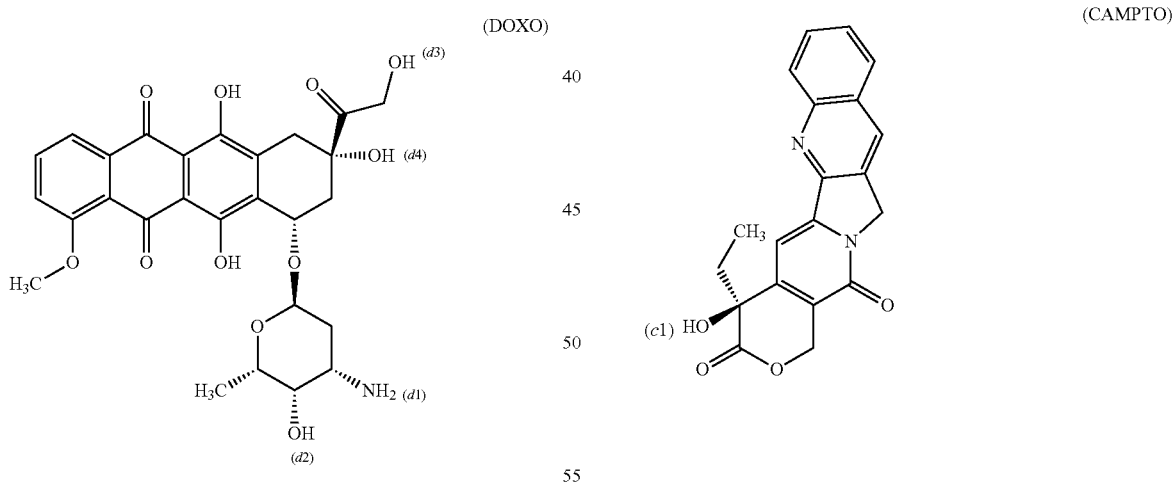

wherein
(d1), (d2), (d3) and (d4) in formula (DOXO) denote functional groups;
wherein
the compound of formula (DOXO) is connected via the amino group denoted with (d1) in formula (20), (21), (22), (23), (24), (25) and (26) respectively and in formula (DOXO);

wherein
camptothecin is a compound of formula (CAMPTO), wherein
(c1) in formula (CAMPTO) denotes a functional group;
wherein
the compound of formula (CAMPTO) is connected via the hydroxy group denoted with (c1) in formulae (20-CAMPTO), (21-CAMPTO), (22-CAMPTO) and (23-CAMPTO) respectively and in formula (CAMPTO);
wherein
taxo-t1-1 is a compound of formula (TAXO), (TAXO)

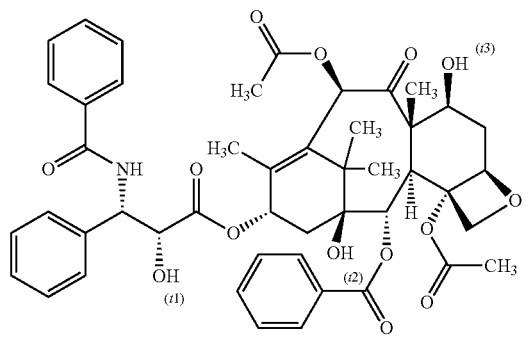

wherein
the compound of formula (TAXO) is connected via the hydroxy group denoted with (t1) in formula (21-TAXO-t1-1) and in formula (TAXO).

18. The method (MII) for the preparation of the compound of formula (II) according to claim 4,
wherein
the compound of formula (IIc) is a compound of formula (20c);

(31)

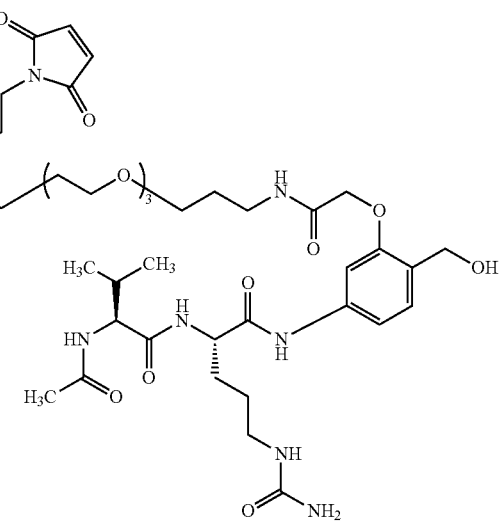

(20c)

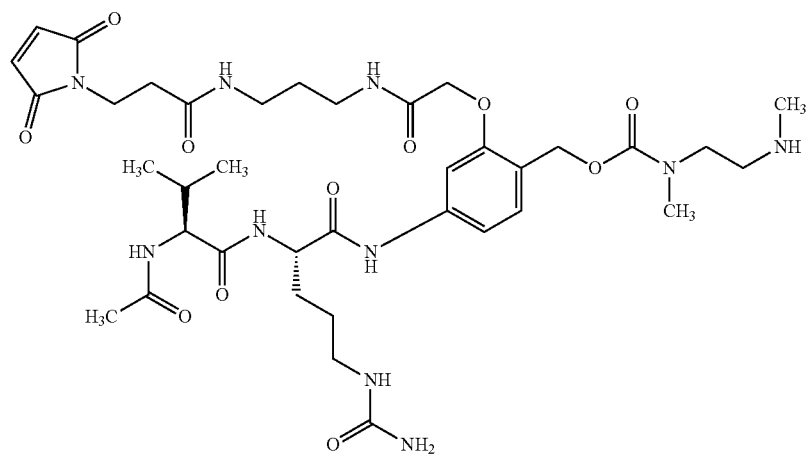

wherein
the compound of formula (III) is selected from the group consisting of a compound of formula (30), a compound of formula (31), a compound of formula (32), a compound of formula (33), a compound of formula (34), a compound of formula (35) and a compound of formula (36);

(30)

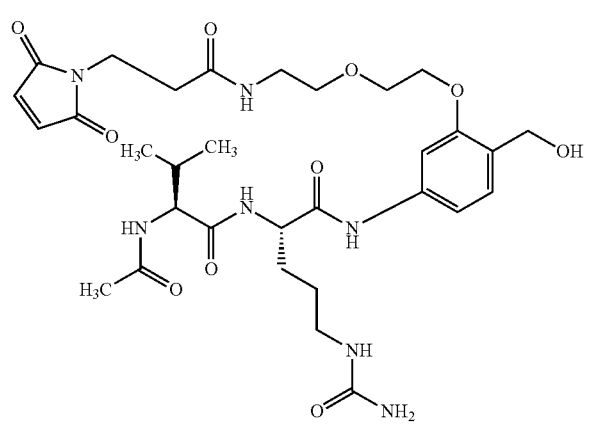

(32)

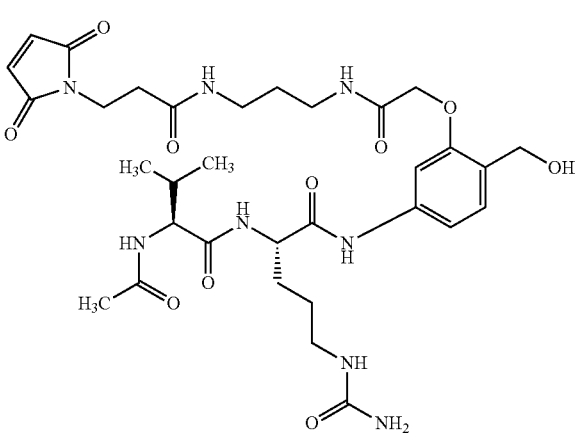

(33)
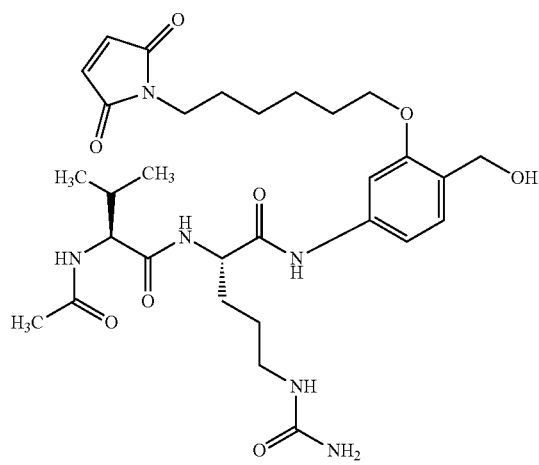
(34)
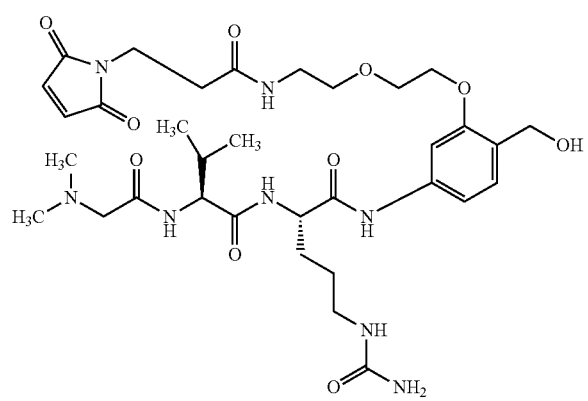
(35)
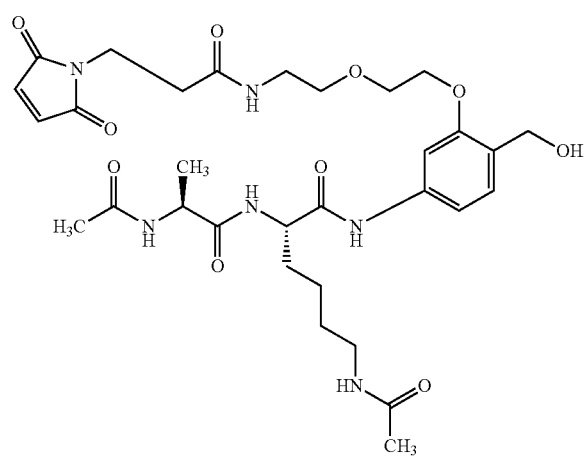
(36)
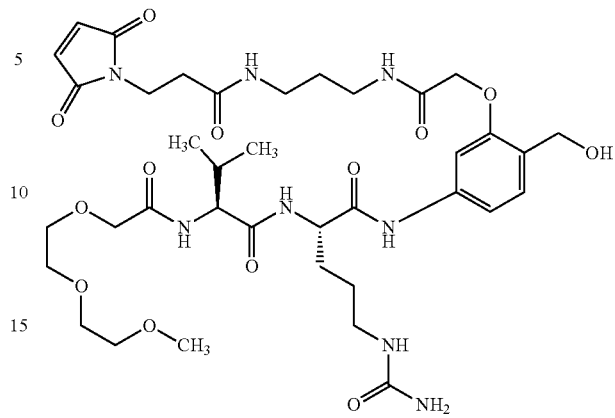
wherein
the compound of formula (III0) is a compound of formula (300);
(300)
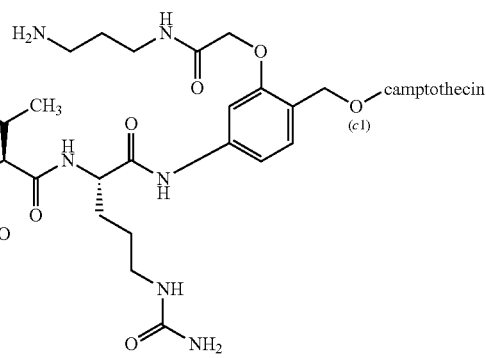
wherein
camptothecin is a compound of formula (CAMPTO),
(CAMPTO)
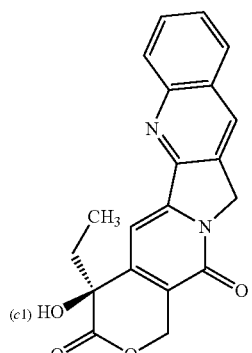
wherein
(c1) in formula (CAMPTO) denotes a functional group;
wherein
the compound of formula (CAMPTO) is connected via the hydroxy group denoted with (c1) in formula (300) respectively and in formula (CAMPTO);

wherein
the compound of formula (III0-I-IVa) is a compound of formula (320);
(320)
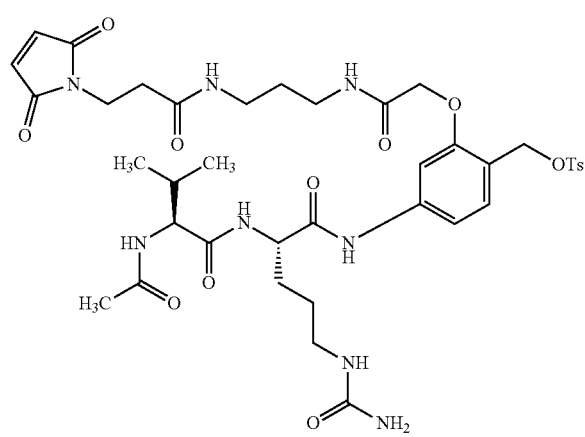
wherein
the compound of formula (IV) is selected from the group consisting of a compound of formula (40), a compound of formula (41), a compound of formula (42), a compound of formula (43), a compound of formula (44), a compound of formula (45) and a compound of formula (46);
(40)
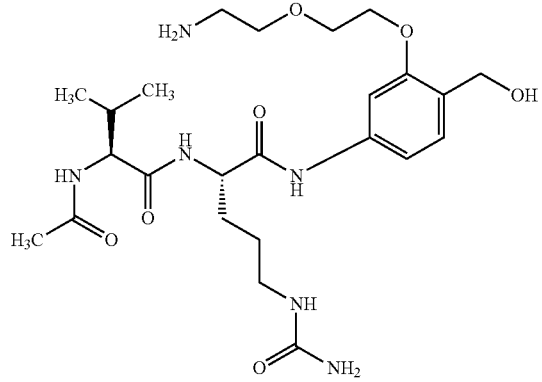
(41)
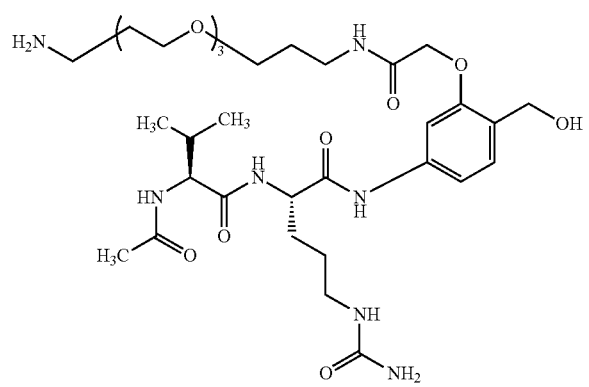
(42)
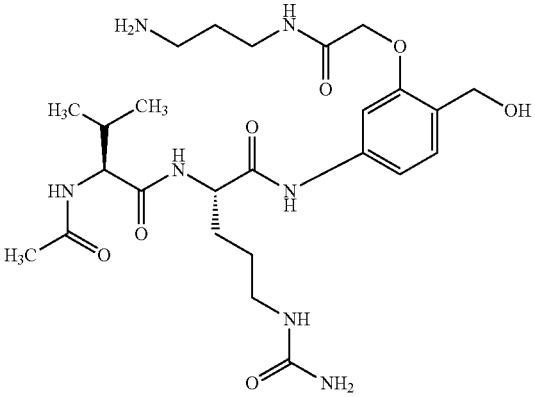
(43)
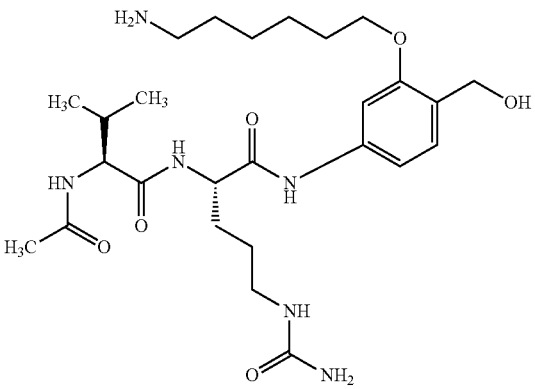
(44)
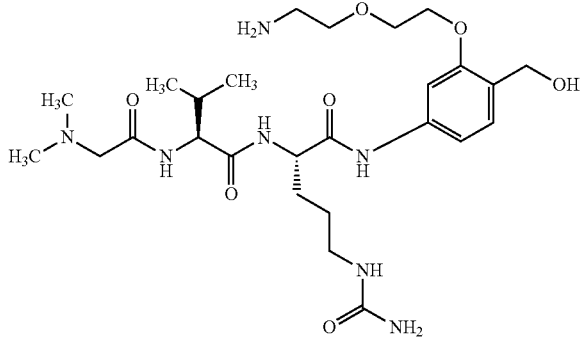
(45)
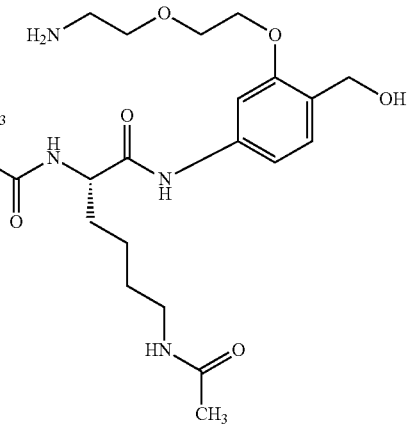

(46)

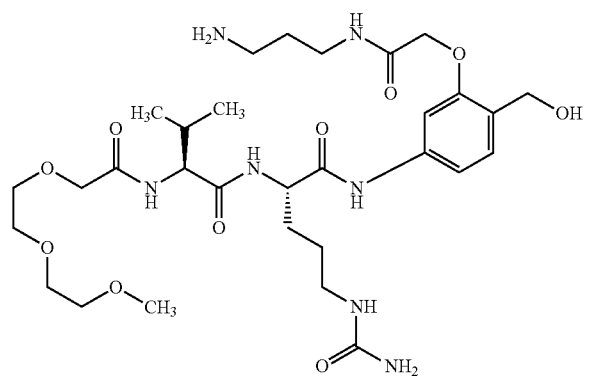

wherein
the compound of formula (IV0) is a compound of formula (400);

(400)

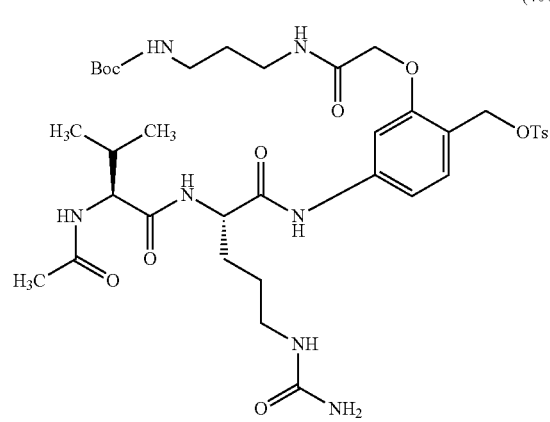

wherein
camptothecin is the compound of formula (CAMPTO);
wherein
the compound of formula (IV0a) is a compound of formula (400a);

(400a)

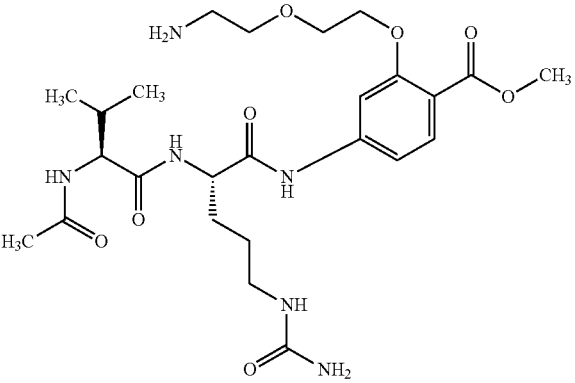

wherein
the compound of formula (V) is selected from the group consisting of a compound of formula (50), a compound of formula (50-1), a compound of formula (51), a compound of formula (51-1), a compound of formula (52), a compound of formula (52-1), a compound of formula (53), a compound of formula (53-1), a compound of formula (54), a compound of formula (54-1), a compound of formula (54-2), a compound of formula (54-3), a compound of formula (55), a compound of formula (55-1), a compound of formula (56) and a compound of formula (56-1);

(50)

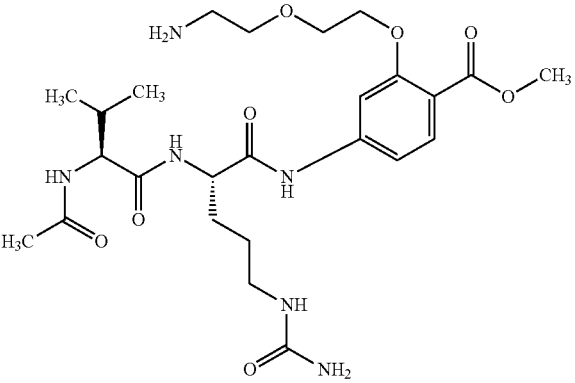

(50-1)

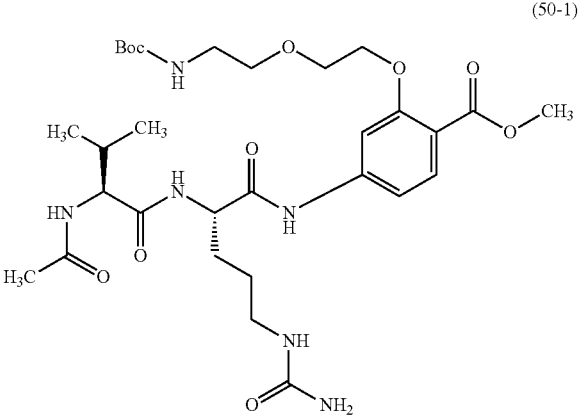

(51)

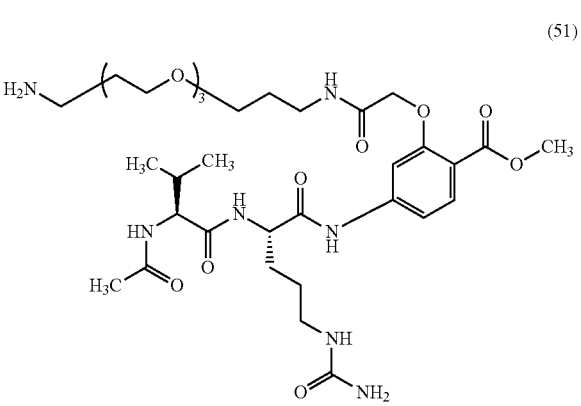

(51-1)
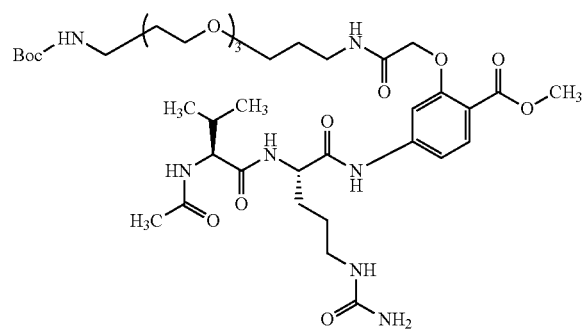
(52)
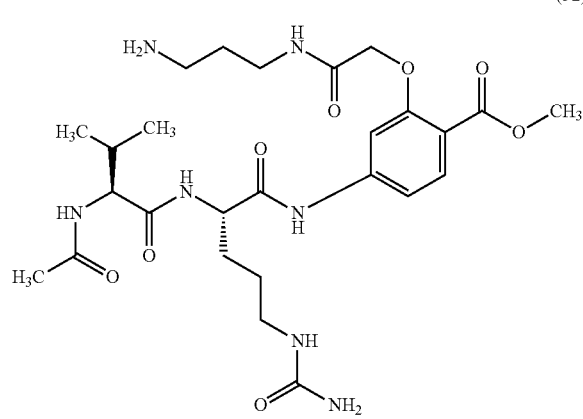
(52-1)
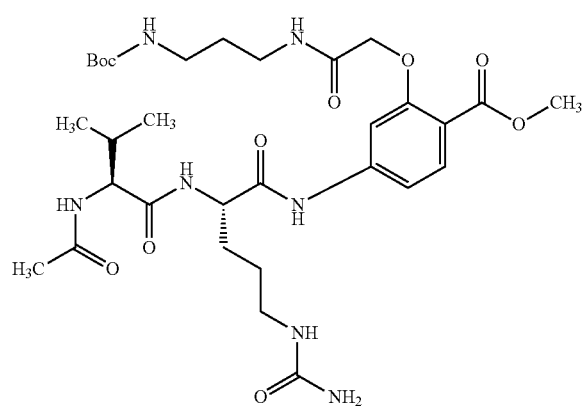
(53)
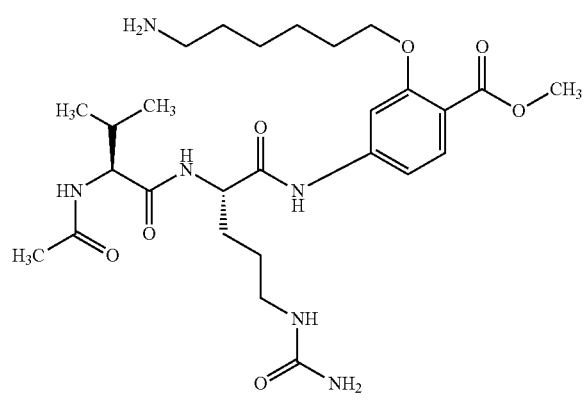
(53-1)
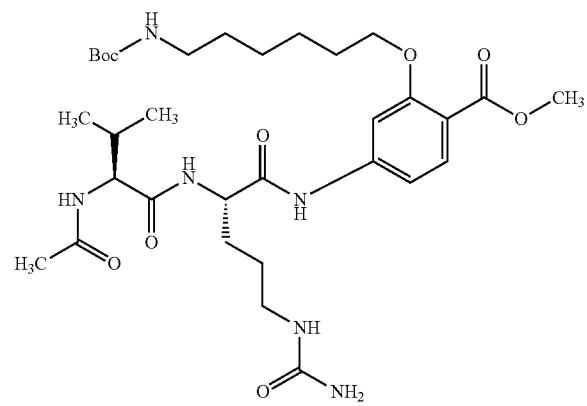
(54)
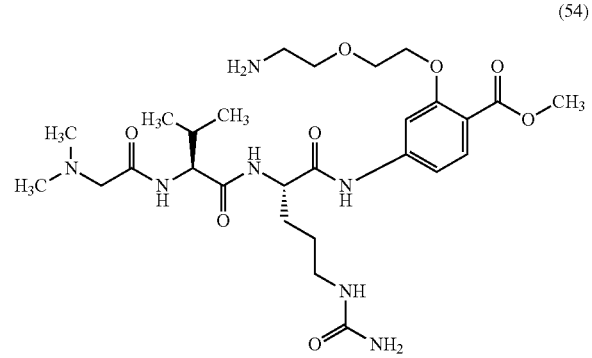
(54-1)
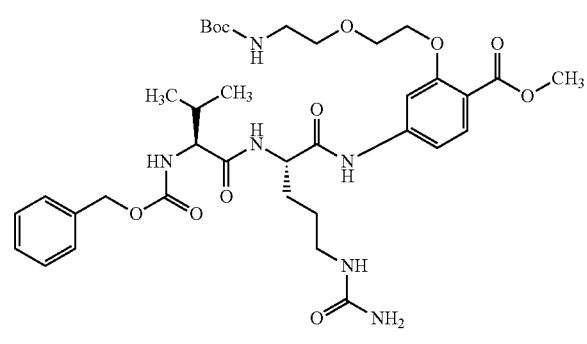
(54-2)
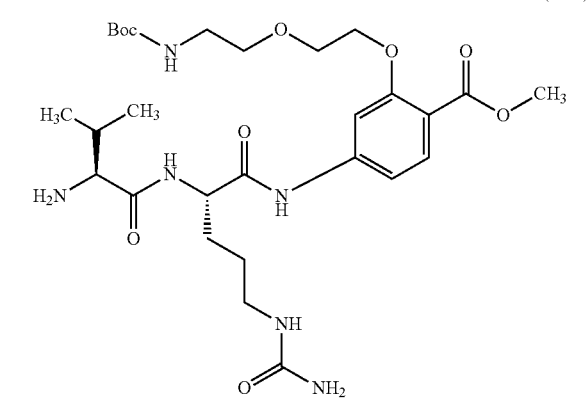

-continued (54-3)
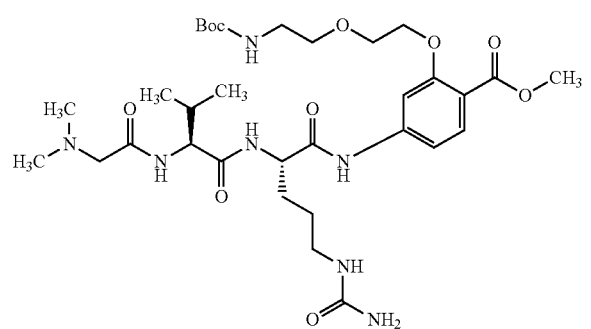

(55)
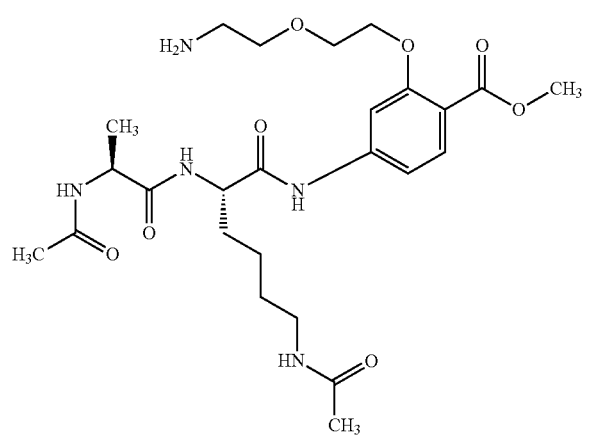

(55-1)
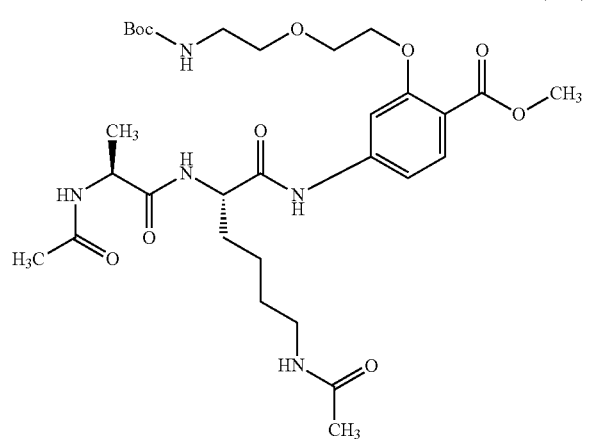

(56)
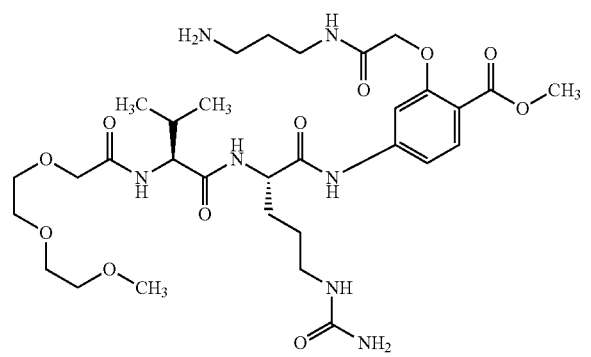

-continued (56-1)
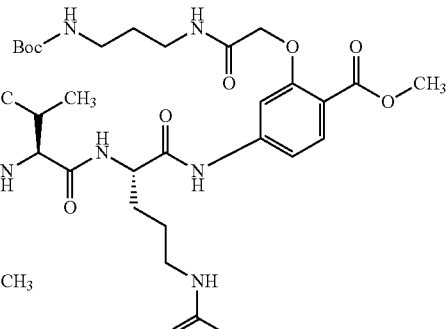

wherein
the compound of formula (V0) is a compound of formula (500);

(500)
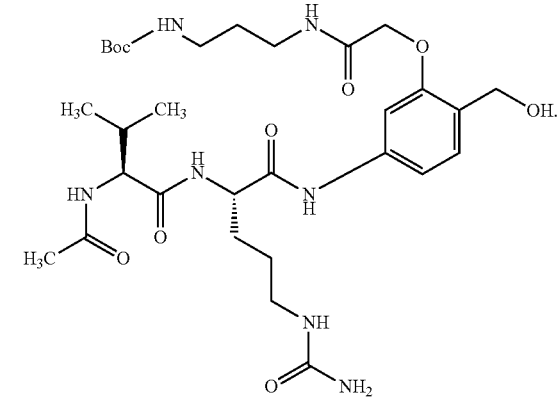

19. The method (MII) according to claim 5, wherein the compound of formula (VI) is selected from the group consisting of a compound of formula (6), a compound of formula (6-1), a compound of formula (6-2), a compound of formula (6-3), a compound of formula (6-4), a compound of formula (6b), a compound of formula (6b-1), a compound of formula (6b-2), a compound of formula (6b-3), a compound of formula (6 b-4), a compound of formula (6c) and a compound of formula (6-5);

(6)
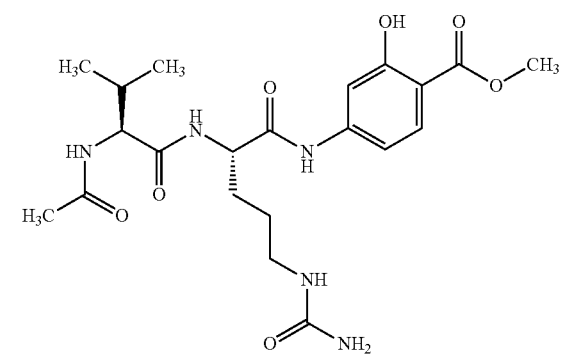

(6-1)
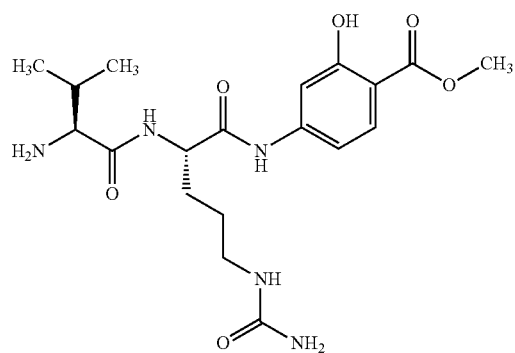
(6-2)
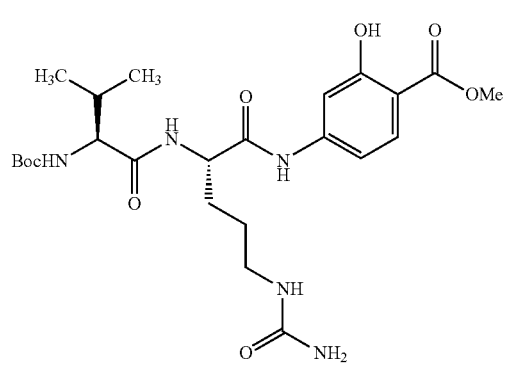
(6-3)
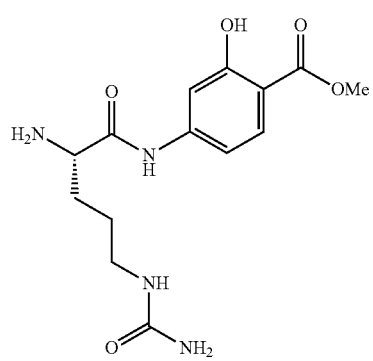
(6-4)
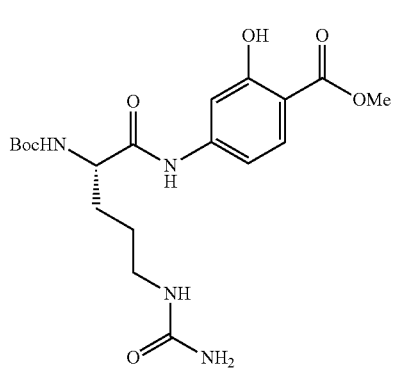
(6b)
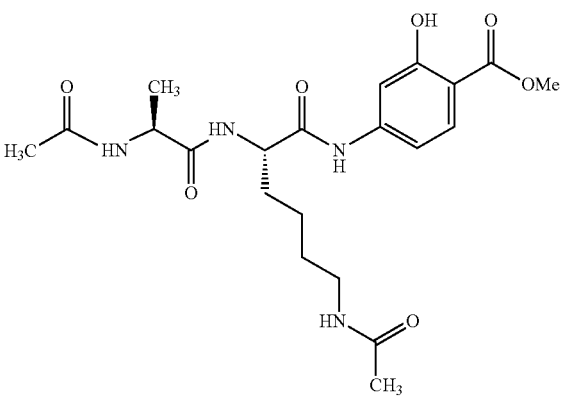
(6b-1)
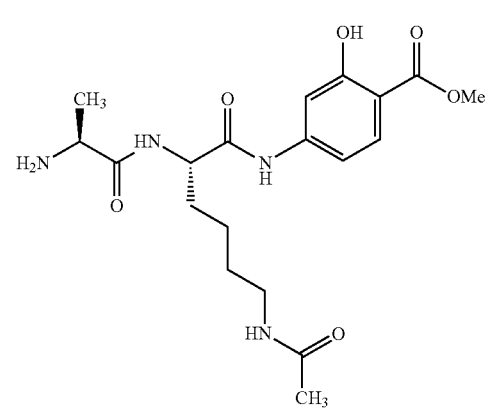
(6b-2)
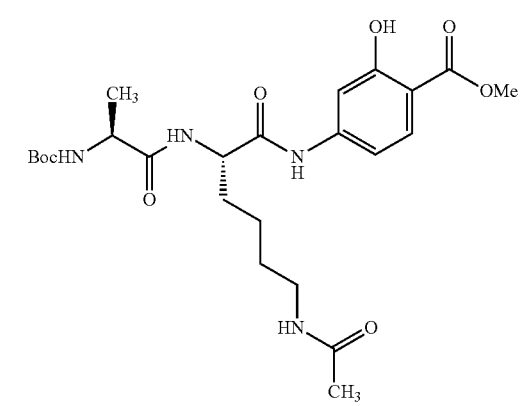

(6b-3)
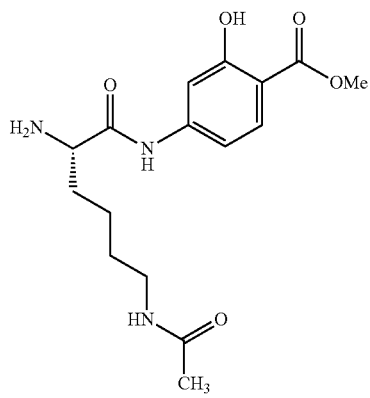
(6c)
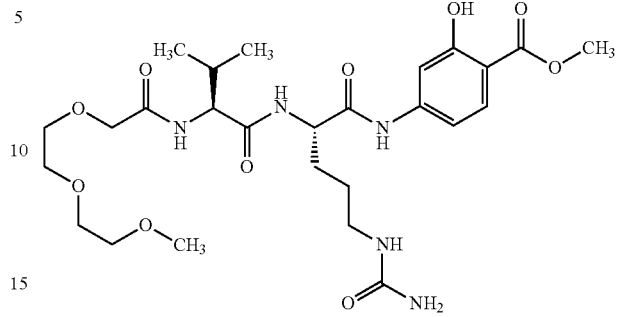
(6b-4)
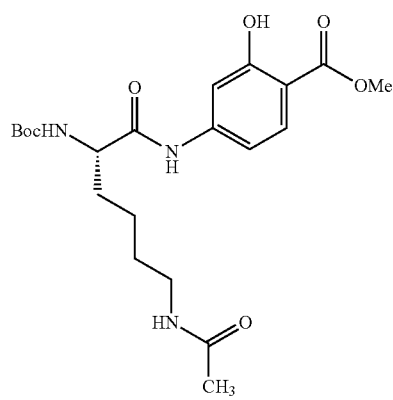
(6-5)
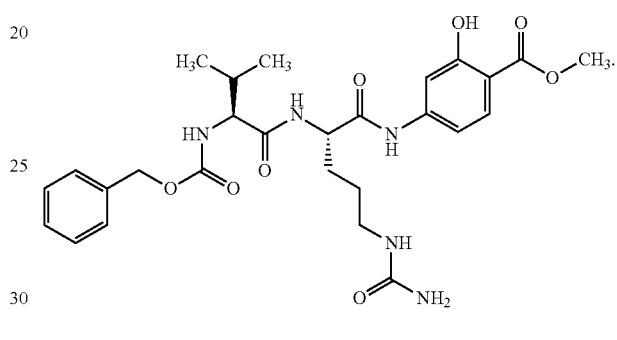
* * * * *